United States Patent
Frickel et al.

(10) Patent No.: US 9,732,063 B2
(45) Date of Patent: Aug. 15, 2017

(54) KINASE INHIBITORS

(71) Applicants: RESPIVERT LIMITED, High Wycombe, Buckinghamshire (GB); TOPIVERT PHARMA LIMITED, London (GB)

(72) Inventors: Fritz-Frieder Frickel, Deidensheim (DE); Matthew Colin Thor Fyfe, London (GB); Premji Meghani, Nottingham (GB); Stephen Malcolm Thom, Nottingham (GB)

(73) Assignees: RESPIVERT LIMITED, High Wycombe, Buckinghamshire (GB); TOPIVERT PHARMA LIMITED, London (GB)

( * ) Notice: Subject to any disclaimer, the term of this patent is extended or adjusted under 35 U.S.C. 154(b) by 0 days.

(21) Appl. No.: 14/443,351

(22) PCT Filed: Nov. 15, 2013

(86) PCT No.: PCT/GB2013/053011
§ 371 (c)(1),
(2) Date: May 15, 2015

(87) PCT Pub. No.: WO2014/076484
PCT Pub. Date: May 22, 2014

(65) Prior Publication Data
US 2015/0329523 A1    Nov. 19, 2015

(30) Foreign Application Priority Data

Nov. 16, 2012 (GB) .................................. 1220684.3
Mar. 15, 2013 (GB) .................................. 1304782.4

(51) Int. Cl.
| | | |
|---|---|---|
| *C07D 401/12* | (2006.01) | |
| *C07D 403/12* | (2006.01) | |
| *A61K 31/506* | (2006.01) | |
| *C07D 401/14* | (2006.01) | |
| *A61K 31/5377* | (2006.01) | |
| *C07D 403/02* | (2006.01) | |

(52) U.S. Cl.
CPC .......... *C07D 401/14* (2013.01); *A61K 31/506* (2013.01); *A61K 31/5377* (2013.01); *C07D 401/12* (2013.01); *C07D 403/02* (2013.01); *C07D 403/12* (2013.01)

(58) Field of Classification Search
CPC .. C07D 401/12; C07D 401/14; C07D 403/02; C07D 403/12; A61K 31/506; A61K 31/5377
USPC ............ 544/122, 321; 546/275.4; 514/235.8, 514/274, 341
See application file for complete search history.

(56) References Cited

U.S. PATENT DOCUMENTS

| | | |
|---|---|---|
| 6,492,393 B1 | 12/2002 | Breitfelder et al. |
| 6,852,717 B2 | 2/2005 | Cirillo et al. |
| 6,894,173 B2 | 5/2005 | Zhang et al. |
| 7,241,758 B2 | 7/2007 | Hao et al. |
| 7,838,541 B2 | 11/2010 | Dumas et al. |
| 8,293,748 B2 | 10/2012 | Ito et al. |
| 8,293,771 B2 | 10/2012 | Ito et al. |
| 8,299,073 B2 | 10/2012 | Ito et al. |
| 8,299,074 B2 | 10/2012 | Ito et al. |
| 8,618,140 B2 | 12/2013 | Ito et al. |
| 8,642,773 B2 | 2/2014 | Ito et al. |

(Continued)

FOREIGN PATENT DOCUMENTS

| | | |
|---|---|---|
| AU | 2006/201959 A1 | 6/2006 |
| WO | WO 01/04115 | 1/2001 |

(Continued)

OTHER PUBLICATIONS

Boehm et al., New Inhibitors of p38 kinase, Expert Opinion in Therapeutic Patents, 10(1), pp. 25-37, (2000).*
Dodeller et al., The p38 mitogen-activated protein kinase signalling cascade in CD4 T cells, Arthritis Research & Therapy, vol. 8, No. 2, (2006). Online at http://arthritis-research.com/content/8/2/205.*
U.S. Appl. No. 14/349,356, filed Apr. 3, 2014, Ito.
U.S. Appl. No. 14/422,158, filed Feb. 17, 2015, Cariou et al.
U.S. Appl. No. 14/424,240, filed Feb. 26, 2015, Fyfe et al.

(Continued)

*Primary Examiner* — Deepak Rao
(74) *Attorney, Agent, or Firm* — Knobbe, Martens, Olson & Bear, LLP

(57) ABSTRACT

In compounds of formula I:

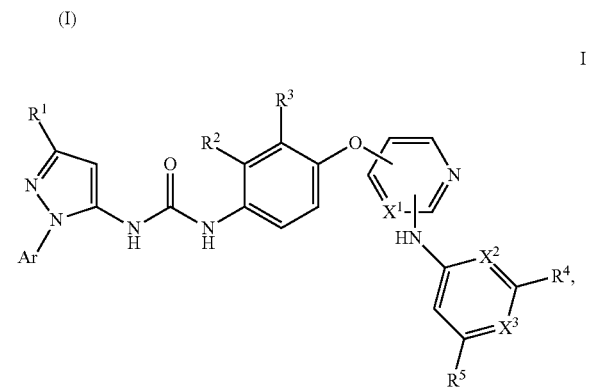

$R^1$ to $R^5$, Ar and $X^1$ to $X^3$ have defined meanings. The compounds have anti-inflammatory activity (e.g., through inhibition of one or more of members of: the family of p38 mitogen-activated protein kinase enzymes; Syk kinase; and members of the Src family of tyrosine kinases) and have use in therapy, including in pharmaceutical combinations, especially in the treatment of inflammatory diseases, including inflammatory diseases of the lung, eye and intestines.

21 Claims, No Drawings

(56) References Cited

U.S. PATENT DOCUMENTS

| | | |
|---|---|---|
| 8,927,563 B2 | 1/2015 | Fyfe et al. |
| 8,933,228 B2 | 1/2015 | Murray et al. |
| 8,975,285 B2 | 3/2015 | Ito et al. |
| 9,024,041 B2 | 5/2015 | King-Underwood |
| 9,079,893 B2 | 7/2015 | Cass |
| 9,108,950 B2 | 8/2015 | Ito et al. |
| 9,242,960 B2 | 1/2016 | Ito et al. |
| 9,249,125 B2 | 2/2016 | Duffy et al. |
| 9,481,648 B2 | 11/2016 | Baker et al. |
| 2003/0232865 A1 | 12/2003 | Cirillo et al. |
| 2012/0244120 A1 | 9/2012 | Charron et al. |
| 2013/0029990 A1 | 1/2013 | King-Underwood et al. |
| 2013/0040962 A1 | 2/2013 | King-Underwood et al. |
| 2013/0040995 A1 | 2/2013 | King-Underwood et al. |
| 2013/0102607 A1 | 4/2013 | Cass et al. |
| 2013/0123260 A1 | 5/2013 | Charron et al. |
| 2013/0150343 A1 | 6/2013 | Van Niel et al. |
| 2013/0156826 A1 | 6/2013 | Murray et al. |
| 2014/0057915 A1 | 2/2014 | Cariou et al. |
| 2014/0114061 A1 | 4/2014 | Kugimoto et al. |
| 2014/0114064 A1 | 4/2014 | Ito et al. |
| 2014/0228410 A1 | 8/2014 | Ito et al. |
| 2014/0249169 A1 | 9/2014 | Ito et al. |
| 2014/0296208 A1 | 10/2014 | Baker et al. |
| 2015/0166483 A1 | 6/2015 | Fyfe |
| 2015/0203475 A1 | 7/2015 | Duffy et al. |
| 2015/0210722 A1 | 7/2015 | Fyfe et al. |
| 2015/0218137 A1 | 8/2015 | Cariou et al. |
| 2015/0225373 A1 | 8/2015 | Fyfe et al. |
| 2015/0225427 A1 | 8/2015 | Fyfe et al. |
| 2015/0232450 A1 | 8/2015 | Longshaw et al. |
| 2015/0252024 A1 | 9/2015 | Ito et al. |
| 2016/0009695 A1 | 1/2016 | Ito et al. |
| 2016/0016934 A1 | 1/2016 | Fyfe |
| 2016/0039797 A1 | 2/2016 | Fyfe |
| 2016/0045482 A1 | 2/2016 | Charron |
| 2016/0045512 A1 | 2/2016 | Charron |
| 2016/0096805 A1 | 4/2016 | Fyfe |
| 2016/0102059 A1 | 4/2016 | Baker et al. |
| 2016/0115152 A1 | 4/2016 | King-Underwood et al. |
| 2016/0130256 A1 | 5/2016 | King-Underwood et al. |
| 2016/0318909 A1 | 11/2016 | Fyfe |
| 2016/0340343 A1 | 11/2016 | Fyfe et al. |
| 2016/0340375 A1 | 11/2016 | Fyfe et al. |

FOREIGN PATENT DOCUMENTS

| | | |
|---|---|---|
| WO | WO 01/36403 | 5/2001 |
| WO | WO 02/092576 | 11/2002 |
| WO | WO 03/068228 | 8/2003 |
| WO | WO 03/072569 | 9/2003 |
| WO | WO 2004/113352 | 12/2004 |
| WO | WO 2007/053394 | 5/2007 |
| WO | WO 2010/038085 | 4/2010 |
| WO | WO 2010/038086 | 4/2010 |
| WO | WO 2010/067130 | 6/2010 |
| WO | WO 2010/067131 | 6/2010 |
| WO | WO 2010/112936 | 10/2010 |
| WO | WO 2011/070368 | 6/2011 |
| WO | WO 2011/070369 | 6/2011 |
| WO | WO 2011/121366 | 10/2011 |
| WO | WO 2011/124923 | 10/2011 |
| WO | WO 2011/124930 | 10/2011 |
| WO | WO 2011/158039 | 12/2011 |
| WO | WO 2011/158042 | 12/2011 |
| WO | WO 2011/158044 | 12/2011 |
| WO | WO 2013/050756 | 4/2013 |
| WO | WO 2013/050757 | 4/2013 |
| WO | WO 2013/083604 A1 | 6/2013 |
| WO | WO 2014/027209 | 2/2014 |
| WO | WO 2014/033446 | 3/2014 |
| WO | WO 2014/033447 | 3/2014 |
| WO | WO 2014/033448 | 3/2014 |
| WO | WO 2014/033449 | 3/2014 |
| WO | WO 2014/140582 A1 | 9/2014 |
| WO | WO 2014/162121 A1 | 10/2014 |
| WO | WO 2015/121444 A1 | 8/2015 |
| WO | WO 2016/051187 A1 | 4/2016 |
| WO | WO 2016/051188 A1 | 4/2016 |

OTHER PUBLICATIONS

U.S. Appl. No. 14/424,627, filed Feb. 26, 2015, Fyfe et al.
U.S. Appl. No. 14/424,361, filed Feb. 27, 2015, Duffy et al.
U.S. Appl. No. 14/424,967, filed Feb. 27, 2015, Fyfe et al.
U.S. Appl. No. 14/561,290, filed Dec. 5, 2014, Murray
U.S. Appl. No. 14/622,368, filed Feb. 13, 2015, Alistair Ian Longshaw, et al.
U.S. Appl. No. 14/626,548, filed Feb. 19, 2015, Fyfe.
Barnes, et al. 2007 "Trimethylsilylpyrazoles as novel inhibitors of p38 MAP kinase: A new use of silicon bioisosteres in medicinal chemistry" *Bioorganic & Medicinal Chemistry* 17; 354-357.
Bühler, et al. 2014 "p38 MAPK inhibitors: a patent review (2012-2013)" *Expert Opinion on Therapeutic Patents* 24(5): 535-554.
Dumas, et al. 2004 "Recent developments in the discovery of protein kinase inhibitors from the urea class" *Current Opinion in Drug Discovery & Development* 7(5); 600-616.
Fischer, et al. 2011 "p38α mitogen-activated protein kinase inhibitors, a patent review (2005-2011)" *Expert Opinion on Therapeutic Patents* 21(12): 1843-1866.
Lee, et al. 2005 "MAP kinase p38 inhibitors: Clinical results and an intimate look at their interactions with p38α protein" *Current Medicinal Chemistry* 12: 2979-2994.
Pettus, et al. 2008 "Small Molecule p38 MAP Kinase Inhibitors for the Treatment of Inflammatory Diseases: Novel Structures and Developments During 2006-2008" *Current Topics in Medicinal Chemistry* 8; 1452-1467.
CAS Registry No. 1379397-83-7, 2012 American Chemical Society.
CAS Registry No. 1384608-34-7, 2012 American Chemical Society.
Biancheri, et al. 2016 "Effect of narrow spectrum versus selective kinase inhibitors on the intestinal proinflammatory immune response in ulcerative colitis" *Inflamm Bowel Dis* 22(6): 1306-1315.
Boehm, et al. 2000 "New inhibitors of p38 kinase" *Expert Opinion on Therapeutic Patents* 10(1): 25-37.
CAS Registry No. 1379397-83-7, Jun. 2012 American Chemical Society.
CAS Registry No. 1384608-34-7, Jul. 2012 American Chemical Society.
Dodeller, et al. 2006 "The p38 mitogen-activated protein kinase signaling cascade in CD4 T cells" *Arthritis Research & Therapy* 8(2): 1-11.
Onions, et al. 2016 "Discovery of narrow spectrum kinase inhibitors: new therapeutic agents for the treatment of COPD and steroid-resistant asthma" *Journal of Medicinal Chemistry* 59: 1727-1746.
To, et al. 2015 "Potent anti-inflammatory effects of the narrow spectrum kinase inhibitor RV1088 on rheumatoid arthritis synovial membrane cells" *British Journal of Pharmacology* 172: 3805-3816.
U.S. Appl. No. 15/261,174, filed Sep. 9, 2016, Thom.
Brinkmann, et al. 2010 "Fingolimod (FTY720): discovery and development of an oral drug to treat multiple sclerosis" *Nature Reviews Drug Discovery* 9: 883-897.
Coughlin, et al. 2010 "Approaches and limitations of phosphatidylinositol-3-kinase pathway activation status as a predictive biomarker in the clinical development of targeted therapy" *Breast Cancer Res Treat* 124: 1-11.
Jope, et al. 2007 "Glycogen synthase kinase-3 (GSK3): Inflammation, diseases, and therapeutics" *Neurochem Res* 32: 577-595.
Judge, et al. 2006 "Potassium channel blockers in multiple sclerosis: Neuronal $K_v$ channels and effects of symptomatic treatment" *Pharmacology & Therapeutics* 111: 224-259.
Kim, et al 2009 "Src family kinases as mediators of endothelial permeability: effects on inflammation and metastasis" *Cell Tissue Res* 335: 249-259.
Kuster "Kinase inhibitors, Methods and Protocols" *Methods in Molecular Biology* 795 Chapters 1 and 2 (in 46 pages).

(56) References Cited

OTHER PUBLICATIONS

Lima, et al. 2011 "Anti-inflammatory effects of LASSBio-998, a new drug candidate designed to be a p38 MAPK inhibitor, in an experimental model of acute lung inflammation" *Pharmacological Reports* 63: 1029-1039.
Liu, et al. 2011 "Src phosphorylation of endothelial cell surface intercellular adhesion molecule-1 mediates neutrophil adhesion and contributes to the mechanism of lung inflammation" *Arterioscler Thromb Vasc Biol* 31: 1342-1350.
Masuda, et al. 2008 "Syk inhibitors as treatment for allergic rhinitis" *Pulmonary Pharmacology & Therapeutics* 21: 461-467.
McDermott, et al. 2009 "Personalized cancer therapy with selective kinase inhibitors: An emerging paradigm in medical oncology" *Journal of Clinical Oncology* 27(33): 5650-5659.
Sawyers 2008 "The cancer biomarker problem" *Nature* 452: 548-552.
Singh, et al. 2007 "Spleen tyrosine kinase (Syk) biology, inhibitors and therapeutic applications" *Annual Reports in Medicinal Chemistry* 42: 379-391.
Singh, et al. 2010 "A randomized, placebo-controlled study of the effects of the p38 MAPK inhibitor SB-681323 on blood biomarkers of inflammation in COPD patients" *J Clin Pharmacol* 50: 94-100.
Sutherland, et al. 2004 "Management of chronic obstructive pulmonary disease" *The New England Journal of Medicine* 350: 2689-2697.
Weinblatt, et al. 2010 "An oral spleen tyrosine kinase (Syk) inhibitor for rheumatoid arthritis" *The New England Journal of Medicine* 363(14): 1303-1312.
Yamamoto, et al. 2003 "The orally available spleen tyrosine kinase inhibitor 2-[7-(3,4-Dimethoxyphenyl)-imidazo[1,2-c]pyrimidin-5-ylamino]-nicotinamide dihydrochloride (BAY 61-3606) blocks antigen-induced airway inflammation in rodents" *The Journal of Pharmacology and Experimental Therapeutics* 306(3): 1174-1181.

\* cited by examiner

KINASE INHIBITORS

FIELD OF THE INVENTION

This invention relates, inter alia, to compounds which are antiinflammatory agents (e.g. through inhibition of one or more of members of: the family of p38 mitogen-activated protein kinase enzymes (referred to herein as p38 MAP kinase inhibitors), for example the alpha kinase sub-type thereof; Syk kinase; and the Src family of tyrosine kinases). The invention also relates to the use of such compounds in therapy, including in mono- and combination therapies, especially in the treatment of inflammatory diseases, including inflammatory diseases of the lung (such as asthma and chronic obstructive pulmonary disease (COPD)), eye (such as uveitis) and gastrointestinal tract (such as Crohn's disease and ulcerative colitis).

BACKGROUND OF THE INVENTION

The listing or discussion of an apparently prior-published document in this specification should not necessarily be taken as an acknowledgement that the document is part of the state of the art or is common general knowledge.

Four p38 MAPK isoforms (alpha, beta, gamma and delta respectively) have been identified, each displaying different patterns of tissue expression. The p38 MAPK alpha and beta isoforms are found ubiquitously throughout the body; are present in many different cell types and are inhibited by a number of previously described small molecular weight compounds. Early classes of inhibitors were highly toxic due to the broad tissue distribution of these isoforms which resulted in off-target effects of the compounds. Some of the more recently identified inhibitors show improved selectivity for p38 MAPK alpha and beta isoforms and have wider safety margins.

p38 MAP kinase is believed to play a pivotal role in many of the signalling pathways that are involved in initiating and maintaining chronic, persistent inflammation in human disease, for example, in severe asthma, COPD and inflammatory bowel disease (IBD). There is now an abundant literature which demonstrates that p38 MAP kinase is activated by a range of pro-inflammatory cytokines and that its activation results in the recruitment and release of further pro-inflammatory cytokines. Indeed, data from some clinical studies demonstrate beneficial changes in disease activity in patients during treatment with p38 MAP kinase inhibitors. For instance Smith describes the inhibitory effect of p38 MAP kinase inhibitors on TNFα (but not IL-8) release from human PBMCs (Smith, S. J., *Br. J. Pharmacol.*, 2006, 149:393-404).

The use of inhibitors of p38 MAP kinase in the treatment of COPD and IBD has also been proposed. Small molecule inhibitors targeted to p38 MAPKα/β have proved to be effective in reducing various parameters of inflammation in:
- cells and tissues obtained from patients with COPD, who are generally corticosteroid insensitive (Smith, S. J., Br. J. Pharmacol., 2006, 149:393-404);
- biopsies from IBD patients (Docena, G. et al., *J. of Trans. Immunol.*, 2010, 162:108-115); and
- in vivo animal models (Underwood, D. C. et al., *Am. J. Physiol.*, 2000, 279:L895-902; Nath, P. et al., *Eur. J. Pharmacol.*, 2006, 544:160-167).

Irusen and colleagues also suggested the possibility of involvement of p38 MAPKα/β on corticosteroid insensitivity via the reduction of binding affinity of the glucocorticoid receptor (GR) in nuclei (Irusen, E. et al., *J. Allergy Clin. Immunol.*, 2002, 109:649-657). Clinical investigations in inflammatory diseases with a range of p38 MAP kinase inhibitors, including AMG548, BIRB 796, VX702, SCIO469 and SCIO323, has been described (Lee, M. R. and Dominguez, C., *Current Med. Chem.*, 2005, 12:2979-2994). However, the major obstacle hindering the utility of p38 MAP kinase inhibitors in the treatment of human chronic inflammatory diseases has been the toxicity observed in patients. This has been sufficiently severe to result in the withdrawal from clinical development of many of the compounds progressed, including all those specifically mentioned above.

COPD is a condition in which the underlying inflammation is reported to be substantially resistant to the anti-inflammatory effects of inhaled corticosteroids. Consequently, a superior strategy for treating COPD would be to develop an intervention which has both inherent anti-inflammatory effects and the ability to increase the sensitivity of the lung tissues of COPD patients to inhaled corticosteroids. The recent publication of Mercado et al. (2007; *American Thoracic Society Abstract A56*) demonstrates that silencing p38 MAPK γ has the potential to restore sensitivity to corticosteroids. Thus, there may be a dual benefit for patients in the use of a p38 MAP kinase inhibitor for the treatment of COPD.

Many patients diagnosed with asthma or with COPD continue to suffer from uncontrolled symptoms and from exacerbations of their medical condition that can result in hospitalisation. This occurs despite the use of the most advanced, currently available treatment regimens, comprising of combination products of an inhaled corticosteroid and a long acting β-agonist. Data accumulated over the last decade indicates that a failure to manage effectively the underlying inflammatory component of the disease in the lung is the most likely reason that exacerbations occur. Given the established efficacy of corticosteroids as anti-inflammatory agents and, in particular, of inhaled corticosteroids in the treatment of asthma, these findings have provoked intense investigation. Resulting studies have identified that some environmental insults invoke corticosteroid-insensitive inflammatory changes in patients' lungs. An example is the response arising from virally-mediated upper respiratory tract infections (URTI), which have particular significance in increasing morbidity associated with asthma and COPD.

It has been disclosed previously that compounds that inhibit the activity of both the c-Src and Syk kinases are effective agents against rhinovirus replication (Charron, C. E. et al., WO 2011/158042) and that compounds that inhibit p59-HCK are effective against influenza virus replication (Charron, C. E. et al., WO 2011/070369). Taken together with inhibition of p38 MAPK, these are particularly attractive properties for compounds to possess that are intended to treat patients with chronic respiratory diseases.

Certain p38 MAPK inhibitors have also been described as inhibitors of replication of respiratory syncitial virus (Cass L. et al., WO 2011/158039).

The precise etiology of IBD is uncertain, but is believed to be governed by genetic and environmental factors that interact to promote an excessive and poorly controlled mucosal inflammatory response directed against components of the luminal microflora. This response is mediated through infiltration of inflammatory neutrophils, dendritic cells and T-cells from the periphery. Due to the ubiquitous expression of p38 in inflammatory cells it has become an obvious target for investigation in IBD models. Studies investigating the efficacy of p38 inhibitors in animal models of IBD and human biopsies from IBD patients indicated that p38 could be a target for the treatment of IBD (Hove, T. ten et al., *Gut*, 2002, 50:507-512, Docena, G. et al., *J. of Trans. Immunol.*, 2010, 162:108-115). However, these findings are not completely consistent with other groups reporting no effect with p38 inhibitors (Malamut G. et al., *Dig. Dis. Sci*, 2006, 51:1443-1453). A clinical study in Crohn's patients using the p38 alpha inhibitor BIRB796 demonstrated potential clinical benefit with an improvement in C-reactive protein levels. However this improvement was transient, returning to baseline by week 8 (Schreiber, S. et al., *Clin. Gastro. Hepatology*, 2006, 4:325-334). A small clinical study investigating the efficacy of CNI-1493, a P38 and Jnk inhibitor, in patients with severe Crohn's disease showed significant improvement in clinical score over 8 weeks (Hommes, D. et al. *Gastroenterology*. 2002 122:7-14).

T cells are known to play key role in mediating inflammation of the gastrointestinal tract. Pioneering work by Powrie and colleagues demonstrated that transfer of naive CD4+ cells into severly compromised immunodeficient (SCID) animals results in the development of colitis which is dependent on the presence of commensal bacteria (Powrie F. et al. *Int Immunol*. 1993 5:1461-71). Furthermore, investigation of mucosal membranes from IBD patients showed an upregulation of CD4+ cells which were either Th1 (IFNg/IL-2) or Th2 (IL5/TGFb) biased depending on whether the patient had Crohn's disease or ulcerative colitis (Fuss I J. et al. *J Immunol*. 1996 157:1261-70). Similarly, T cells are known to play a key role in inflammatory disorders of the eye with several studies reporting increased levels of T cell associated cytokines (IL-17 and IL-23) in sera of Bechets patients (Chi W. et al. *Invest Ophthalmol Vis Sci*. 2008 49:3058-64). In support, Direskeneli and colleagues demonstrated that Behcets patients have increased Th17 cells and decreased Treg cells in their peripheral blood (Direskeneli H. et al. J Allergy Clin Immunol. 2011 128: 665-6).

One approach to inhibit T cell activation is to target kinases which are involved in activation of the T cell receptor signalling complex. Syk and Src family kinases are known to play a key role in this pathway, where Src family kinases, Fyn and Lck, are the first signalling molecules to be activated downstream of the T cell receptor (Barber E K. et al. *PNAS* 1989 86:3277-81). They initiate the tyrosine phosphorylation of the T cell receptor leading to the recruitment of the Syk family kinase, ZAP-70. Animal studies have shown that ZAP-70 knockout results in a SCID phenotype (Chan A C. et al. *Science*. 1994 10; 264(5165):1599-601).

A clinical trial in rheumatoid arthritis patients with the Syk inhibitor Fostamatinib demonstrated the potential of Syk as an anti-inflammatory target with patients showing improved clinical outcome and reduced serum levels of IL-6 and MMP-3 (Weinblatt M E. et al. *Arthritis Rheum*. 2008 58:3309-18). Syk kinase is widely expressed in cells of the hematopoietic system, most notably in B cells and mature T cells. Through interaction with immunoreceptor tyrosine-based activation (ITAM) motifs it plays an important role in regulating T cell and B cell expansion as well as mediating immune-receptor signalling in inflammatory cells. Syk activation leads to IL-6 and MMP release inflammatory mediators commonly found upregulated in inflammatory disorders including IBD and rheumatoid arthritis (Wang Y D. et at *World I Gastroenterol* 2007; 13: 5926-5932, Litinsky I et al. *Cytokine*. 2006 January 33:106-10).

In addition to playing key roles in cell signalling events which control the activity of pro-inflammatory pathways, kinase enzymes are now also recognised to regulate the activity of a range of cellular functions, including the maintenance of DNA integrity (Shilo, Y. *Nature Reviews Cancer*, 2003, 3: 155-168) and co-ordination of the complex processes of cell division. Indeed, certain kinase inhibitors (the so-called "Olaharsky kinases") have been found to alter the frequency of micronucleus formation in vitro (Olaharsky, A. J. et al., *PLoS Comput. Biol.*, 2009, 5(7)). Micronucleus formation is implicated in, or associated with, disruption of mitotic processes and is therefore undesirable. Inhibition of glycogen synthase kinase 3α (GSK3α) was found to be a particularly significant factor that increases the likelihood of a kinase inhibitor promoting micronucleus formation. Also, inhibition of the kinase GSK3β with RNAi has been reported to promote micronucleus formation (Tighe, A. et al., *BMC Cell Biology*, 2007, 8:34).

Whilst it may be possible to attenuate the adverse effects of inhibition of Olaharsky kinases such as GSK3α by optimisation of the dose and/or by changing the route of administration of a molecule, it would be advantageous to identify further therapeutically useful molecules with low or negligible inhibition of Olaharsky kinases, such as GSK 3α and/or have low or negligible disruption of mitotic processes (e.g. as measured in a mitosis assay).

Various urea derivatives are disclosed as having anti-inflammatory properties (see, for example, WO 01/36403, WO 01/4115, WO 02/092576, WO 2003/068228, WO 2003/072569, WO 2004/113352, WO 2007/053394 and *Bioorg. Med. Chem. Lett.* 2007, 17, 354-357). Nevertheless, there remains a need to identify and develop alternative p38 MAP kinase inhibitors, and particularly inhibitors that have improved therapeutic potential over currently available treatments or, in particular, that exhibit a superior therapeutic index (e.g. inhibitors that are at least equally efficacious and, in one or more respects, are less toxic at the relevant therapeutic dose than previous agents).

SUMMARY OF THE INVENTION

We have now discovered, surprisingly, that certain aniline-substituted diaryl ureas inhibit one or more of p38 MAP kinase, Syk and Src family kinases and therefore possess good anti-inflammatory properties.

Thus, according to a first aspect of the invention, there is provided a compound of formula I,

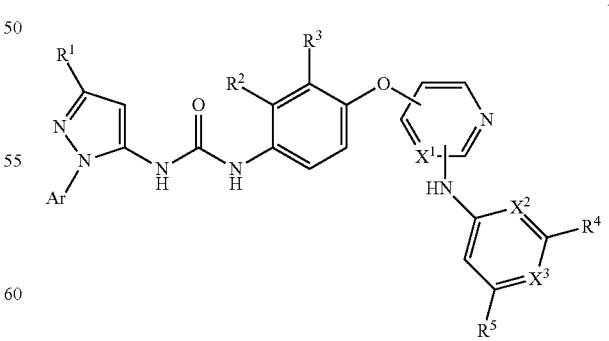

wherein
R$^1$ represents
C$_{1-6}$ alkyl optionally substituted by one or more substituents selected from halo and hydroxy, ($C_{1-2}$ alkylene)$_{0-1}$-$C_{3-8}$ cycloalkyl, which latter group is optionally substituted by one or more substituents selected from $C_{1-3}$ alkyl and $C_{1-3}$ haloalkyl or Het$^1$;

Het$^1$ represents a 4- or 5-membered heterocyclic group that is fully saturated, partially unsaturated or fully aromatic, which group contains one or more heteroatoms selected from N, O and S, and which group is optionally substituted by one or more substituents selected from halo, $C_{1-3}$ alkyl and $C_{1-3}$ haloalkyl;

Ar represents phenyl or a 5- or 6-membered heteroaryl group containing one or more heteroatoms selected from N, O and S, wherein Ar is optionally substituted by one to three substituents selected from hydroxy, halo, $C_{1-6}$ alkyl, $C_{1-6}$ alkoxy, which latter two groups are optionally substituted by one or more substituents selected from halo and hydroxy, $NH_2$, $N(H)$—$C_{1-6}$ alkyl, $N(C_{1-6}$ alkyl)$_2$, ($C_{1-6}$ alkylene)$_{0-1}$-Het$^2$ and ($C_{1-3}$ alkylene)$_{0-1}$-O—($C_{1-6}$ alkylene)$_{0-1}$-Het$^2$;

Het$^2$ represents a 5- to 10-membered heterocyclic group that is fully saturated, partially unsaturated or fully aromatic, which group is monocyclic or bicyclic and contains one or more heteroatoms selected from N, O and S, and which group is optionally substituted by one or more substituents selected from halo, hydroxy, oxo, $C_{1-3}$ alkyl, $C_{1-3}$ haloalkyl, $C_{1-3}$ alkoxy and $C_{1-3}$ haloalkoxy;

$R^2$ and $R^3$, together with the C-atoms to which they are attached, form a fused phenyl or pyridyl ring, which latter two rings are optionally substituted by one or more substituents selected from $C_{1-3}$ alkyl, $C_{1-3}$ haloalkyl, cyano and halo, or one of $R^2$ and $R^3$ represents H, halo, cyano, $C_{1-3}$ alkyl or $C_{1-3}$ haloalkyl and the other independently represents halo, cyano, $C_{1-3}$ alkyl or $C_{1-3}$ haloalkyl, or $R^2$ and $R^3$ together combine to form $C_{3-5}$ alkylene or $C_{3-5}$ alkenylene, which latter two groups are optionally substituted by one or more substituents selected from $C_{1-3}$ alkyl, $C_{1-3}$ haloalkyl, cyano and halo;

$X^1$ represents N or CH;

$X^2$ and $X^3$ both represent $C(R^X)$ or one of $X^2$ and $X^3$ represents N and the other represents $C(R^X)$;

$R^X$ represents H, halo, cyano, $C_{1-3}$ alkyl or $C_{1-3}$ alkoxy, which latter two groups are optionally substituted by one or more halo atoms;

$R^4$ represents

-$Q^1$-[$CH_2(CH_2)_{0-1}CH_2$—O]$_{1-12}$—$CH_2(CH_2)_{0-1}CH_2$—$R^{6a}$,

—$S(O)_nR^{6b}$,

-$Q^2$-$CH_2$-[$C_{1-5}$ alkylene]-$N(R^{6c})R^{6d}$

—$OS(O)_2R^{6e}$,

—$C\equiv C$—$R^{6f}$,

—$N=S(O)R^{6g}R^{6b}$ or

—$OC(O)NH_2$;

$R^5$ represents $C_{1-3}$ alkoxy or $C_{1-3}$ alkyl, which latter two groups are optionally substituted by one or more halo atoms, or $R^5$ represents H, $NH_2$, $N(H)$—$C_{1-6}$ alkyl, $N(C_{1-6}$ alkyl)$_2$, cyano, halo or $C_{2-3}$ alkynyl;

$R^{6a}$ represents $OR^{7a}$ or $N(R^{7b})R^{7c}$;

$R^{6b}$ represents $CH_2(CH_2)_{0-1}CH_2$—$OR^{7d}$ or $C_{3-8}$ cycloalkyl, which latter group is optionally substituted by one or more $C_{1-3}$ alkyl substituents;

$R^{7a}$ to $R^{7d}$ independently represent H or $C_{1-4}$ alkyl optionally substituted by one or more halo atoms, or $R^{7b}$ and $R^{7c}$ together with the N-atom to which they are attached, form a 4- to 7-membered heterocyclic group that is fully saturated, partially unsaturated or fully aromatic and which heterocyclic group contains one N atom (the atom to which $R^{7b}$ and $R^{7c}$ are attached) and, optionally, one or more further heteroatoms selected from 0, S and N, and which heterocyclic group is optionally substituted by one or more substituents selected from halo, hydroxy, oxo, $C_{1-4}$ alkyl and $C_{1-4}$ alkoxy;

$R^{6c}$ and $R^{6d}$, together with the N-atom to which they are attached, form a 4- to 7-membered heterocyclic group that is fully saturated, partially unsaturated or fully aromatic and which heterocyclic group contains one N atom (the atom to which $R^{6c}$ and $R^{6d}$ are attached) and, optionally, one or more further heteroatoms selected from O, S and N, and which heterocyclic group is optionally substituted by one or more substituents selected from halo, hydroxy, oxo, $C_{1-4}$ alkyl and $C_{1-4}$ alkoxy;

$R^{6e}$, $R^{6f}$, $R^{6g}$, and $R^{6h}$ independently represent $C_{1-4}$ alkyl optionally substituted by one or more halo atoms, or $R^{6f}$ represents H;

$Q^1$ and $Q^2$ independently represent O, $S(O)_p$ or $N(R^{6i})$;

$R^{6i}$ represents H or $C_{1-4}$ alkyl; and n and p independently represent 0, 1 or 2, or a pharmaceutically acceptable salt, solvate or isotopic derivative thereof, which compounds may be referred to hereinafter as "the compounds of the invention".

DETAILED DESCRIPTION OF THE PREFERRED EMBODIMENT

Pharmaceutically acceptable salts that may be mentioned include acid addition salts and base addition salts. Such salts may be formed by conventional means, for example by reaction of a free acid or a free base form of a compound of formula I with one or more equivalents of an appropriate acid or base, optionally in a solvent, or in a medium in which the salt is insoluble, followed by removal of said solvent, or said medium, using standard techniques (e.g. in vacuo, by freeze-drying or by filtration). Salts may also be prepared by exchanging a counter-ion of a compound of formula I in the form of a salt with another counter-ion, for example using a suitable ion exchange resin.

Examples of pharmaceutically acceptable salts include acid addition salts derived from mineral acids and organic acids, and salts derived from metals.

For the avoidance of doubt, compounds of formula I may contain the stated atoms in any of their natural or non-natural isotopic forms. In this respect, embodiments of the invention that may be mentioned include those in which:

(a) the compound of formula I is not isotopically enriched or labelled with respect to any atoms of the compound; and (b) the compound of formula I is isotopically enriched or labelled with respect to one or more atoms of the compound.

References herein to an "isotopic derivative" relate to the second of these two embodiments. In particular embodiments of the invention, the compound of formula I is isotopically enriched or labelled (with respect to one or more atoms of the compound) with one or more stable isotopes. Thus, the compounds of the invention that may be mentioned include, for example, compounds of formula I that are isotopically enriched or labelled with one or more atoms such as deuterium or the like.

Compounds of formula I may exhibit tautomerism. All tautomeric forms and mixtures thereof are included within the scope of the invention. In particular, the invention includes the keto-enol tautomerism existing between indolin-2-one and 2-hydroxyindole.

Unless otherwise specified, alkyl groups and alkoxy groups as defined herein may be straight-chain or, when there is a sufficient number (i.e. a minimum of three) of carbon atoms, be branched. Particular alkyl groups that may be mentioned include, for example, methyl, ethyl, n-propyl, iso-propyl, butyl, n-butyl and tert-butyl. Particular alkoxy groups that may be mentioned include, for example, methoxy, ethoxy, propoxy, and butoxy.

Unless otherwise specified, cycloalkyl groups as defined herein may, when there is a sufficient number (i.e. a minimum of four) of carbon atoms, be part cyclic/acyclic.

Unless otherwise specified, alkylene groups as defined herein may be straight-chain or, when there is a sufficient number (i.e. a minimum of two) of carbon atoms, be branched. In particular embodiments of the invention, alkylene refers to straight-chain alkylene.

Unless otherwise stated, the point of attachment of aryl groups may be via any atom of the ring system. However, when aryl groups are bicyclic or tricyclic, they are linked to the rest of the molecule via an aromatic ring. $C_{6-14}$ aryl groups include phenyl, naphthyl and the like. Embodiments of the invention that may be mentioned include those in which aryl is phenyl.

For the avoidance of doubt, oxo substituents that may be present on heterocyclic groups represented by $Het^2$ or $N(R^{6c})R^{6d}$ may be attached to any appropriate atoms in the heterocyclic ring including, where valencies allow, to C-, N- and/or S-atoms within the ring (thereby forming keto, N-oxide, S(O) and/or S(O)$_2$ groups).

Values of $Het^1$ that may be mentioned include oxetanyl (e.g. oxetan-3-yl) and tetrahydrofuranyl (e.g. tetrahydrofuran-2-yl or tetrahydrofuran-3-yl).

Unless otherwise specified, the term "halo" includes references to fluoro, chloro, bromo or iodo, in particular to fluoro, chloro or bromo, especially fluoro or chloro.

Embodiments of the invention that may be mentioned include those in which the compound of formula I is a compound of formula Ia or Ib,

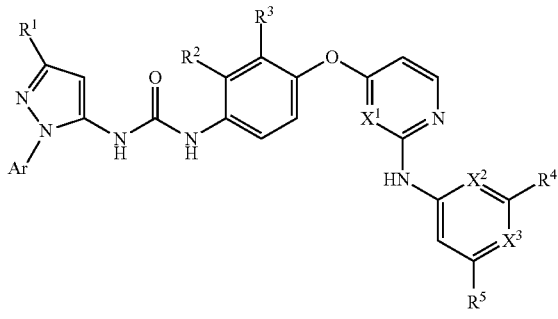

Ia

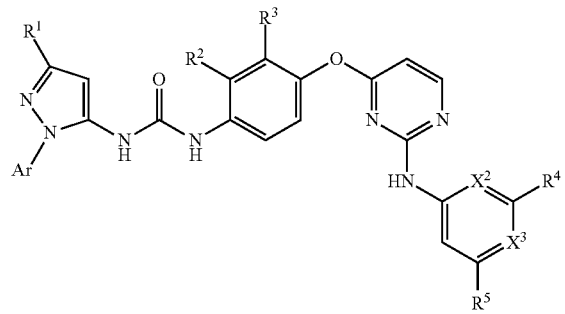

Ib or a pharmaceutically acceptable salt, solvate or isotopic derivative thereof, wherein $R^1$ to $R^5$, Ar and $X^1$ are as hereinbefore defined.

Embodiments of the invention that may be mentioned include those in which one or more of the following definitions apply to the compounds of formula I, Ia and Ib:

(a) $R^1$ represents
$C_{1-5}$ alkyl optionally substituted by one or more halo atoms or by hydroxy,
$(CH_2)_{0-1}$—$C_{3-5}$ cycloalkyl, which latter group is optionally substituted by one to three $C_{1-3}$ alkyl (e.g. methyl) substituents or
a heterocyclic group selected from oxetanyl and tetrahydrofuranyl, which group is optionally substituted by one to three $C_{1-3}$ alkyl (e.g. methyl) substituents;

(b) Ar represents an aromatic group selected from phenyl and pyridyl, which group is optionally substituted (e.g. in the 4-position relative to the point of attachment of Ar to the pyrazole N-atom) by one or two substituents selected from
halo,
$C_{1-3}$ alkyl, $C_{1-3}$ alkoxy, which latter two groups are optionally substituted by one or more halo atoms,
$N(C_{1-3}$ alkyl$)_2$,
$C_{1-3}$ alkylene-$Het^2$ and
—O—$CH_2$—($C_{1-2}$ alkylene)-$Het^2$
(e.g. which group is optionally substituted (e.g. in the 4-position relative to the point of attachment of Ar to the pyrazole N-atom) by one or two substituents selected from halo, $C_{1-3}$ alkylene-$Het^2$, —O—$CH_2$—($C_{1-2}$ alkylene)-$Het^2$, $C_{1-3}$ alkyl and $C_{1-3}$ alkoxy, which latter two groups are optionally substituted by one or more halo atoms);

(c) $R^2$ and $R^3$ either
independently represent Cl or F, or
together with the C-atoms to which they are attached, form a fused phenyl or pyridyl ring, which latter two rings are optionally substituted by one or more substituents selected from $C_{1-3}$ alkyl, $C_{1-3}$ haloalkyl, cyano and halo;

(d) $X^1$ represents CH or, particularly, N;

(e) $X^2$ and $X^3$ both represent CH or $X^2$ represents CH and $X^3$ represents N or $C(R^X)$ (e.g. $X^2$ and $X^3$ both represent CH);

(f) $R^X$ represents H or halo (e.g. chloro);

(g) $R^4$ represents
-$Q^1$-[$CH_2CH_2$—O]$_{1-10}$—$CH_2CH_2$—$R^{6a}$,
—S(O)$_n$$CH_2CH_2$—$OR^{7d}$,
—S(O)$_n$$C_{3-6}$ cycloalkyl,
-$Q^2$-$CH_2(CH_2)_{0-1}CH_2$—$N(R^{6c})R^{6d}$,
—OS(O)$_2R^{6e}$,
—C≡C—$R^{6f}$, —N=S(O)(CH$_3$)$_2$ or
—OC(O)NH$_2$;

(h) R$^5$ represents H, cyano, chloro, fluoro, C$_{2-3}$ alkynyl, C$_{1-2}$ alkyl or C$_{1-2}$ alkoxy, which latter two groups are optionally substituted by one or more fluoro atoms;

(i) Q$^1$ represents S(O)$_2$, S(O) or, particularly, S or O;
Q$^2$ represents S or, particularly, O;

(k) R$^{6a}$ represents NH$_2$, N(CH$_3$)$_2$, morpholin-4-yl or, particularly, OH or O—C$_{1-3}$ alkyl such as OCH$_3$;

(l) R$^{6e}$ represents C$_{1-4}$ alkyl optionally substituted by one or more fluoro atoms;

(m) R$^{6f}$ represents H or methyl;

(n) R$^{7d}$ represents C$_{1-3}$ alkyl or, particularly, H;

(o) R$^{6c}$ and R$^{6d}$, together with the N-atom to which they are attached, form a 5- to 7-membered heterocyclic group that is fully saturated, which heterocyclic group contains one N atom (the atom to which R$^{6c}$ and R$^{6d}$ are attached) and, optionally, one further heteroatom selected from O, S and N, and which heterocyclic group is optionally substituted by one or more substituents selected from halo, hydroxy, oxo, C$_{1-4}$ alkyl and C$_{1-4}$ alkoxy.

Further embodiments of the invention that may be mentioned include those in which the compound of formula I, Ia or Ib is a compound of formula Ic,

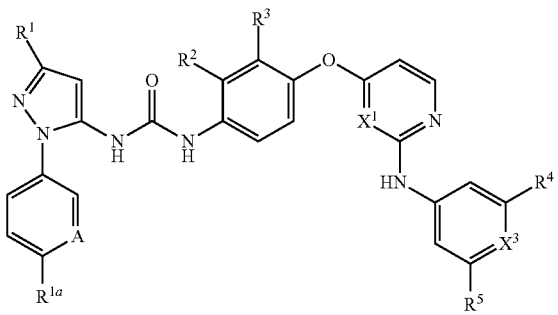

Ic or a pharmaceutically acceptable salt, solvate or isotopic derivative thereof, wherein:

R$^{1a}$ represents
halo,
C$_{1-3}$ alkyl, C$_{1-3}$ alkoxy, which latter two groups are optionally substituted by one or more halo atoms,
N(C$_{1-3}$ alkyl)$_2$ (e.g. N(CH$_3$)$_2$),
C$_{1-3}$ alkylene-Het$^2$ or
—O—CH$_2$—(C$_{1-2}$ alkylene)-Het$^2$
(e.g. R$^{1a}$ represents halo, C$_{1-3}$ alkylene-Het$^2$, —O—CH$_2$—(C$_{1-2}$ alkylene)-Het$^2$, C$_{1-3}$ alkyl or C$_{1-3}$ alkoxy, which latter two groups are optionally substituted by one or more halo atoms, or, particularly, C$_{1-3}$ alkyl or C$_{1-3}$ alkoxy, which latter two groups are optionally substituted by one or more fluoro atoms);

A represents CH or N;
X$^1$ represents CH or, particularly, N;
X$^3$ represents N or C(R$^X$) (e.g. X$^3$ represents CH); and
R$^1$ to R$^5$, R$^X$ and Het$^2$ are as hereinbefore defined.

In particular such embodiments of the invention the compound of formula I, Ia or Ib is a compound of formula Ic, or a pharmaceutically acceptable salt, solvate or isotopic derivative thereof, wherein:

R$^{1a}$ represents
halo,
C$_{1-3}$ alkyl, C$_{1-3}$ alkoxy, which latter two groups are optionally substituted by one or more halo atoms,
C$_{1-3}$ alkylene-Het$^2$ or
—O—CH$_2$—(C$_{1-2}$ alkylene)-Het$^2$
(e.g. R$^{1a}$ C$_{1-3}$ alkyl or C$_{1-3}$ alkoxy, which latter two groups are optionally substituted by one or more fluoro atoms);

A represents CH or N;
X$^1$ represents N;
X$^3$ represents CH; and
R$^1$ to R$^5$ and Het$^2$ are as hereinbefore defined.

Embodiments of the invention that may be mentioned include those in which one or more of the following definitions apply to the compounds of formula I, Ia, Ib and Ic:

(a) R$^1$ represents
C$_{1-4}$ alkyl optionally substituted by one or more halo atoms (e.g. pentafluoroethyl, 1,1,1-trifluoro-2-methylpropan-2-yl, isopropyl or, particularly, tert-butyl),
C$_{3-4}$ cycloalkyl optionally substituted by methyl (e.g. cyclopropyl or 1-methylcyclopropyl) or
a heterocyclic group selected from oxetanyl and tetrahydrofuranyl, which group is optionally substituted by methyl (e.g. tetrahydrofuranyl, oxetanyl or (methyl) oxetanyl, such as oxetan-3-yl or 3-methyl-oxetan-3-yl);

(b) R$^2$ and R$^3$ either
independently represent Cl or F, or
together with the C-atoms to which they are attached, form a fused phenyl or pyridyl ring;

(c) R$^4$ represents
—O—[CH$_2$CH$_2$—O]$_{1-7}$—CH$_2$CH$_2$—OR$^{7a}$,
—S—CH$_2$CH$_2$—OR$^{7d}$,
—S(O)$_n$C$_{3-6}$ cycloalkyl,
-Q$^2$-CH$_2$(CH$_2$)$_{0-1}$CH$_2$—N(R$^{6c}$)R$^{6d}$,
—OS(O)$_2$CH$_3$,
—S—[CH$_2$CH$_2$—O]$_{2-8}$—R$^{6a}$,
—C≡C—H,
—N=S(O)(CH$_3$)$_2$ or
—OC(O)NH$_2$;

(d) Q$^2$ represents S or, particularly, O;

(e) R$^5$ represents H, ethynyl, methyl or methoxy, which latter two groups are optionally substituted by one or more fluoro atoms (e.g. R$^5$ represents H, methyl, methoxy, trifluoromethyl or trifluoromethoxy);

(f) R$^{7a}$ represents H or, particularly, CH$_3$;

(g) R$^{7d}$ represents methyl or, particularly, H;

(h) n represents 0, 1 or, particularly, 2;

(i) R$^{6c}$ and R$^{6d}$, together with the N-atom to which they are attached, form a 5- to 7-membered heterocyclic group that is fully saturated, which heterocyclic group contains one N atom (the atom to which R$^{6c}$ and R$^{6d}$ are attached) and, optionally, one further heteroatom selected from O, S and N, and which heterocyclic group is optionally substituted by one or more substituents selected from oxo and C$_{1-3}$ alkyl (e.g. N(R$^{6c}$)R$^{6d}$ represents piperazin-1-yl or, particularly, morpholin-4-yl).

Further embodiments of the invention that may be mentioned relate to compounds of formula I, Ia, Ib and Ic in which R$^1$ represents C$_{2-4}$ alkyl optionally substituted by one or more fluoro atoms.

Certain embodiments of the invention relate to compounds of formula Ic in which:
A represents N;
R$^{1a}$ represents C$_{1-3}$ alkyl or C$_{1-3}$ alkoxy (e.g. methoxy); and
R$^1$ to R$^5$ are as defined in respect of any of the embodiments of the invention mentioned above.

Certain other embodiments of the invention relate to compounds of formula Ic in which:

A represents CH;

$R^{1a}$ represents $N(C_{1-3}$ alkyl$)_2$, $C_{1-3}$ alkyl or $C_{1-3}$ alkoxy (e.g. dimethylamino, methoxy or methyl)

(for example, $R^{1a}$ represents $C_{1-3}$ alkyl or $C_{1-3}$ alkoxy (such as methyl); and $R^1$ to $R^5$ are as defined in respect of any of the embodiments of the invention mentioned above.

Particular embodiments of the invention that may be mentioned include compounds of formula Ic in which one or more of the following apply:

$R^1$ represents $C_{2-4}$ alkyl optionally substituted by one or more fluoro atoms (e.g. pentafluoroethyl, 1,1,1-trifluoro-2-methylpropan-2-yl, isopropyl or, particularly, tert-butyl);

A represents CH or N;

when A represents CH or N, $R^{1a}$ represents methyl or methoxy or, when A represents CH, $R^{1a}$ alternatively represents dimethylamino (e.g. $R^{1a}$ represents methyl or methoxy);

$R^2$ and $R^3$ either both represent Cl or, together with the C-atoms to which they are attached, form a fused phenyl ring;

$R^4$ represents

—O—[CH$_2$CH$_2$—O]$_{2-8}$—R$^{7a}$ (e.g. O—[CH$_2$CH$_2$—O]$_{3-7}$—R$^{7a}$, such as O—[CH$_2$CH$_2$—O]$_3$—R$^{7a}$),

—S—CH$_2$CH$_2$—OH,

—S(O)$_2$-cyclopropyl,

-Q$^2$-CH$_2$(CH$_2$)$_{0-1}$CH$_2$-(morpholin-1-yl),

—OS(O)$_2$CH$_3$,

—S—[CH$_2$CH$_2$—O]$_{2-8}$—CH$_3$ (e.g. S—[CH$_2$CH$_2$—O]$_{3-7}$—CH$_3$) or

—C≡C—H;

$R^{7a}$ represents H or, particularly, CH$_3$;

$Q^2$ represents S or, particularly, O;

$R^5$ represents methyl, ethynyl or, particularly, H, methoxy, trifluoromethyl or trifluoromethoxy (e.g. H or methoxy);

$X^3$ represents N or C(R$^X$) (e.g. $X^3$ represents CH);

CR$^X$ represents H or chloro.

Examples of these particular embodiments relate to compounds of formula Ic in which one or more of the following apply:

$R^1$ represents $C_{2-4}$ alkyl optionally substituted by one or more fluoro atoms (e.g. pentafluoroethyl, 1,1,1-trifluoro-2-methylpropan-2-yl, isopropyl or, particularly, tert-butyl);

A represents CH or N;

$R^{1a}$ represents methyl or methoxy;

$R^2$ and $R^3$ either both represent Cl or, together with the C-atoms to which they are attached, form a fused phenyl ring;

$R^4$ represents

—O—[CH$_2$CH$_2$—O]$_{2-8}$—CH$_3$ (e.g. O—[CH$_2$CH$_2$—O]$_{3-7}$—CH$_3$, such as O—[CH$_2$CH$_2$—O]$_3$—CH$_3$),

—S—CH$_2$CH$_2$—OH,

—S(O)$_2$-cyclopropyl,

-Q$^2$-CH$_2$(CH$_2$)$_{0-1}$CH$_2$-(morpholin-1-yl),

—OS(O)$_2$CH$_3$,

—S—[CH$_2$CH$_2$—O]$_{2-8}$—CH$_3$ (e.g. S—[CH$_2$CH$_2$—O]$_{3-7}$—CH$_3$) or

—C≡C—H;

$Q^2$ represents S or, particularly, O;

$R^5$ represents methyl, ethynyl or, particularly, H, methoxy, trifluoromethyl or trifluoromethoxy (e.g. H or methoxy);

$X^3$ represents CH.

More particular embodiments of the invention that may be mentioned include compounds of formula I, Ia, Ib or Ic as defined in any of the embodiments mentioned above, but in which:

$R^5$ represents methyl, methoxy, trifluoromethyl or trifluoromethoxy or, when $R^4$ represents -Q$^1$-[CH$_2$(CH$_2$)$_{0-1}$CH$_2$—O]$_{1-12}$—CH$_2$(CH$_2$)$_{0-1}$CH$_2$—R$^{6a}$, —OS(O)$_2$R$^{6e}$ or —C≡C—R$^{6f}$ (e.g. when $R^4$ represents —OS(O)$_2$R$^{6e}$), then $R^5$ may alternatively represent H.

Other embodiments of the invention that may be mentioned include compounds of formula I, Ia, Ib or Ic as defined in any of the embodiments mentioned above, wherein:

Ar represents phenyl or a 5- or 6-membered heteroaryl group containing one or more heteroatoms selected from N, O and S, wherein Ar is optionally substituted by one to three substituents selected from hydroxy, halo, $C_{1-6}$ alkyl, $C_{1-6}$ alkoxy, which latter two groups are optionally substituted by one or more substituents selected from halo and hydroxy, (C$_{1-6}$ alkylene)$_{0-1}$-Het$^2$ and (C$_{1-3}$ alkylene)$_{0-1}$-O—(C$_{1-6}$ alkylene)$_{0-1}$-Het$^2$;

$X^2$ and $X^3$ both represent CH or one of $X^2$ and $X^3$ represents N and the other represents CH;

$R^5$ represents $C_{1-3}$ alkoxy or $C_{1-3}$ alkyl, which latter two groups are optionally substituted by one or more halo atoms, or $R^5$ represents H, cyano, halo or $C_{2-3}$ alkynyl; and $Q^1$ and $Q^2$ independently represent O or S(O)$_p$.

Alternative embodiments of the invention that may be mentioned include compounds of formula I, Ia, Ib or Ic as defined in any of the embodiments mentioned above, wherein:

Ar represents phenyl or a 5- or 6-membered heteroaryl group containing one or more heteroatoms selected from N, O and S, wherein Ar is substituted by NH$_2$, N(H)—C$_{1-6}$ alkyl or N(C$_{1-6}$ alkyl)$_2$ and is optionally further substituted by one or two substituents selected from hydroxy, halo, $C_{1-6}$ alkyl, $C_{1-6}$ alkoxy, which latter two groups are optionally substituted by one or more substituents selected from halo and hydroxy, NH$_2$, N(H)—C$_{1-6}$ alkyl, N(C$_{1-6}$ alkyl)$_2$, (C$_{1-6}$ alkylene)$_{0-1}$-Het$^2$ and (C$_{1-3}$ alkylene)$_{0-1}$-O—(C$_{1-6}$ alkylene)$_{0-1}$-Het$^2$;

one or both of $X^2$ and $X^3$ represent C(R$^X$), provided that at least one of $X^2$ and $X^3$ represents C(R$^X$) in which R$^X$ is halo, cyano, $C_{1-3}$ alkyl or $C_{1-3}$ alkoxy, which latter two groups are optionally substituted by one or more halo atoms;

$R^5$ represents NH$_2$, N(H)—C$_{1-6}$ alkyl or N(C$_{1-6}$ alkyl)$_2$; and/or $Q^1$ or $Q^2$ represents N(R$^{6i}$).

Other compounds of formula I, Ia, Ib or Ic that may be mentioned include the compounds of the examples described hereinafter. Thus, embodiments of the invention that may be mentioned include those in which the compound of formula I, Ia, Ib or Ic is a compound selected from the list:

1-(3-(tert-butyl)-1-(6-methoxypyridin-3-yl)-1H-pyrazol-5-yl)-3-(4-((2-((3-ethynylphenyl)-amino)pyrimidin-4-yl)oxy)naphthalen-1-yl)urea;

S,S-dimethyl-N-(4-((4-(4-(3-(3-(tert-butyl)-1-(6-methoxypyridin-3-yl)-1H-pyrazol-5-yl)-ureido)naphthalen-1-yl)oxy)pyrimidin-2-yl)amino)phenyl sulfoximine;

3-((4-((4-(3-(3-(tert-butyl)-1-(6-methoxypyridin-3-yl)-1H-pyrazol-5-yl)ureido)naphthalen-1-yl)oxy)pyrimidin-2-yl)amino)phenyl methanesulfonate;

1-(3-(tert-butyl)-1-(6-methoxypyridin-3-yl)-1H-pyrazol-5-yl)-3-(4-((2-((3-(2-(2-(2-methoxy-ethoxy)ethoxy)ethoxy)phenyl)amino)pyrimidin-4-yl)oxy)naphthalen-1-yl)urea;

3-((4-((4-(3-(3-(tert-butyl)-1-(6-methoxypyridin-3-yl)-1H-pyrazol-5-yl)ureido)naphthalen-1-yl)oxy)pyrimidin-2-yl)amino)phenyl carbamate;

1-(3-(tert-butyl)-1-(6-methoxypyridin-3-yl)-1H-pyrazol-5-yl)-3-(4-((2-((3-((2-hydroxyethyl)-thio)phenyl)amino)pyrimidin-4-yl)oxy)naphthalen-1-yl)urea;

1-(3-(tert-butyl)-1-(6-methoxypyridin-3-yl)-1H-pyrazol-5-yl)-3-(4-((2-((3-(cyclopropylsulfinyl)phenyl)amino)pyrimidin-4-yl)oxy)naphthalen-1-yl)urea;

1-(3-(tert-butyl)-1-(6-methoxypyridin-3-yl)-1H-pyrazol-5-yl)-3-(4-((2-((3-(cyclopropylsulfonyl)phenyl)amino)pyrimidin-4-yl)oxy)naphthalen-1-yl)urea;

1-(3-isopropyl-1-(p-tolyl)-1H-pyrazol-5-yl)-3-(4-((2-((3-(2-(2-(2-methoxyethoxyl)ethoxy)-ethoxy)phenyl)amino)pyrimidin-4-yl)oxy)naphthalen-1-yl)urea;

1-(4-((2-((3-ethynylphenyl)amino)pyrimidin-4-yl)oxy)naphthalen-1-yl)-3-(3-isopropyl-1-(p-tolyl)-1H-pyrazol-5-yl)urea;

3-((4-((4-(3-(3-isopropyl-1-(p-tolyl)-1H-pyrazol-5-yl)ureido)naphthalen-1-yl)oxy)pyrimidin-2-yl)amino)phenyl methanesulfonate;

3-((4-((4-(3-(3-isopropyl-1-(p-tolyl)-1H-pyrazol-5-yl)ureido)naphthalen-1-yl)oxy)pyrimidin-2-yl)amino)-5-methoxyphenyl methanesulfonate;

1-(3-isopropyl-1-(p-tolyl)-1H-pyrazol-5-yl)-3-(4-((2-((3-methoxy-5-(2-(2-(2-methoxy-ethoxy)ethoxy)ethoxy)phenyl)amino)pyrimidin-4-yl)oxy)naphthalen-1-yl)urea;

3-((4-((4-(3-(3-isopropyl-1-(p-tolyl)-1H-pyrazol-5-yl)ureido)naphthalen-1-yl)oxy)pyrimidin-2-yl)amino)phenyl-S,S-dimethyl-N-phenyl sulfoximine;

1-(4-((2-((3-ethynyl-5-methoxyphenyl)amino)pyrimidin-4-yl)oxy)naphthalen-1-yl)-3-(3-isopropyl-1-(p-tolyl)-1H-pyrazol-5-yl)urea;

3-(5-methoxy((4-((4-(3-(3-isopropyl-1-(p-tolyl)-1H-pyrazol-5-yl)ureido)naphthalen-1-yl)oxy)pyrimidin-2-yl)amino))phenyl-S,S-dimethyl-N-phenyl sulfoximine;

1-(3-isopropyl-1-(p-tolyl)-1H-pyrazol-5-yl)-3-(4-((2-((3-methoxy-5-(2-morpholinoethoxy)-phenyl)amino)pyrimidin-4-yl)oxy)naphthalen-1-yl)urea;

1-(4-((2-((3-(cyclopropylsulfonyl)-5-methoxyphenyl)amino)pyrimidin-4-yl)oxy)naphthalen-1-yl)-3-(3-isopropyl-1-(p-tolyl)-1H-pyrazol-5-yl)urea;

1-(4-((2-((3-(2-(2-(2-hydroxyethoxyl)ethoxy)ethoxy)phenyl)amino)pyrimidin-4-yl)oxy)-naphthalen-1-yl)-3-(3-isopropyl-1-(p-tolyl)-1H-pyrazol-5-yl)urea;

1-(4-((2-((3-(2-(2-(2-hydroxyethoxyl)ethoxy)ethoxy)-5-methoxyphenyl)amino)pyrimidin-4-yl)oxy)naphthalen-1-yl)-3-(3-isopropyl-1-(p-tolyl)-1H-pyrazol-5-yl)urea;

1-(2,3-dichloro-4-((2-((3-methoxy-5-(2-morpholinoethoxyl)phenyl)amino)pyrimidin-4-yl)oxy)phenyl)-3-(3-isopropyl-1-(p-tolyl)-1H-pyrazol-5-yl)urea;

1-(4-((2-((3-(2-hydroxyethyl)thio)-5-methoxyphenyl)amino)pyrimidin-4-yl)oxy)-naphthalen-1-yl)-3-(3-isopropyl-1-(p-tolyl)-1H-pyrazol-5-yl)urea;

1-(2,3-dichloro-4-((2-((3-(cyclopropylsulfonyl)-5-methoxyphenyl)amino)pyrimidin-4-yl)oxy)phenyl)-3-(3-isopropyl-1-(p-tolyl)-1H-pyrazol-5-yl)urea;

1-(2,3-dichloro-4-((2-((3-(cyclopropylsulfonyl)phenyl)amino)pyrimidin-4-yl)oxy)phenyl)-3-(3-isopropyl-1-(p-tolyl)-1H-pyrazol-5-yl)urea;

1-(2,3-difluoro-4-((2-((3-methoxy-5-(2-morpholinoethoxyl)phenyl)amino)pyrimidin-4-yl)oxy)phenyl)-3-(3-isopropyl-1-(p-tolyl)-1H-pyrazol-5-yl)urea;

S,S-dimethyl-N-(3-(4-(2,3-dichloro-4-(3-(3-isopropyl-1-(p-tolyl)-1H-pyrazol-5-yl)ureido) phenoxy)pyrimidin-2-yl)amino)-5-methoxyphenyl)-sulfoximine;

1-(3-isopropyl-1-(p-tolyl)-1H-pyrazol-5-yl)-3-(5-((2-((3-methoxy-5-(2-(2-(2-methoxy-ethoxy)ethoxy)ethoxy)phenyl)amino)pyrimidin-4-yl)oxy)quinolin-8-yl)urea;

1-(3-isopropyl-1-(p-tolyl)-1H-pyrazol-5-yl)-3-(5-((2-((3-methoxy-5-(2-morpholinoethoxy)-phenyl)amino)pyrimidin-4-yl)oxy)quinolin-8-yl)urea;

1-(4-((2-((3-(2,5,8,11-tetraoxatridecan-13-yloxy)-5-methoxyphenyl)amino)pyrimidin-4-yl)oxy)naphthalen-1-yl)-3-(3-isopropyl-1-(p-tolyl)-1H-pyrazol-5-yl)urea;

1-(4-((2-((3-(2,5,8,11,14-pentaoxahexadecan-16-yloxy)-5-methoxyphenyl)amino)-pyrimidin-4-yl)oxy)naphthalen-1-yl)-3-(3-isopropyl-1-(p-tolyl)-1H-pyrazol-5-yl)urea;

1-(3-isopropyl-1-(p-tolyl)-1H-pyrazol-5-yl)-3-(4-((2-((3-methoxy-5-((2-(2-(2-methoxy-ethoxy)ethoxy)ethyl)thio)phenyl)amino)pyrimidin-4-yl)oxy)naphthalen-1-yl)urea;

1-(4-((2-((3-(2,5,8,11,14,17,20-heptaoxadocosan-22-yloxy)-5-methoxyphenyl)amino)-pyrimidin-4-yl)oxy)naphthalen-1-yl)-3-(3-isopropyl-1-(p-tolyl)-1H-pyrazol-5-yl)urea; 1-(3-isopropyl-1-(p-tolyl)-1H-pyrazol-5-yl)-3-(4-((2-((3-(2-(2-(2-methoxyethoxyl)ethoxy)-ethoxy)-5-(trifluoromethoxy)phenyl)amino)pyrimidin-4-yl)oxy)naphthalen-1-yl)urea;

1-(3-isopropyl-1-(p-tolyl)-1H-pyrazol-5-yl)-3-(4-((2-((3-(2-(2-(2-methoxyethoxyl)ethoxy)-ethoxy)-5-(trifluoromethyl)phenyl)amino)pyrimidin-4-yl)oxy)naphthalen-1-yl)urea;

1-(2,3-dichloro-4-((2-((3-methoxy-5-(2-(2-(2-methoxy-ethoxyl)ethoxy)ethoxy)phenyl)-amino)pyrimidin-4-yl)oxy)phenyl)-3-(3-isopropyl-1-(p-tolyl)-1H-pyrazol-5-yl)urea;

1-(3-isopropyl-1-(p-tolyl)-1H-pyrazol-5-yl)-3-(4-((2-((3-methoxy-5-((2-(2-(2-methoxy-ethoxy)ethoxy)ethyl)sulfonyl)phenyl)amino)pyrimidin-4-yl)oxy)naphthalen-1-yl)urea, 1-(3-(tert-Butyl)-1-(p-tolyl)-1H-pyrazol-5-yl)-3-(4-((2-((3-methoxy-5-(2-(2-(2-methoxy-ethoxy)ethoxy)ethoxy)phenyl)amino)pyrimidin-4-yl)oxy)naphthalen-1-yl)urea;

1-(3-(tert-Butyl)-1-(6-methoxypyridin-3-yl)-1H-pyrazol-5-yl)-3-(4-((2-((3-methoxy-5-(2-(2-(2-methoxyethoxyl)ethoxy)ethoxy)phenyl)amino)pyrimidin-4-yl)oxy)naphthalen-1-yl)urea;

1-(4-((2-((3-Methoxy-5-(2-(2-(2-methoxyethoxyl)ethoxy)ethoxy)phenyl)amino)pyrimidin-4-yl)oxy)naphthalen-1-yl)-3-(3-(perfluoroethyl)-1-(p-tolyl)-1H-pyrazol-5-yl)urea;

1-(4-((2-((3-Methoxy-5-(2-(2-(2-methoxyethoxyl)ethoxy)ethoxy)phenyl)amino)pyrimidin-4-yl)oxy)naphthalen-1-yl)-3-(1-(p-tolyl)-3-(1,1,1-trifluoro-2-methylpropan-2-yl)-1H-pyrazol-5-yl)urea;

1-(3-(tert-Butyl)-1-(p-tolyl)-1H-pyrazol-5-yl)-3-(4-((2-((3-methoxy-5-((2-morpholinoethyl)-thio)phenyl)amino)pyrimidin-4-yl)oxy)naphthalen-1-yl)urea;

1-(3-(tert-Butyl)-1-(p-tolyl)-1H-pyrazol-5-yl)-3-(4-((2-((3-methoxy-5-((3-morpholinopropyl)-thio)phenyl)amino)pyrimidin-4-yl)oxy)naphthalen-1-yl)urea;

1-(3-(tert-Butyl)-1-(p-tolyl)-1H-pyrazol-5-yl)-3-(4-((2-((3-methoxy-5-((3-morpholinopropyl)-sulfonyl)phenyl)amino)pyrimidin-4-yl)oxy)naphthalen-1-yl)urea;

1-(3-(tert-Butyl)-1-(4-methoxyphenyl)-1H-pyrazol-5-yl)-3-(4-((2-((3-methoxy-5-(2-(2-(2-methoxyethoxyl)ethoxy)ethoxy)phenyl)amino)pyrimidin-4-yl)oxy)naphthalen-1-yl)urea;

1-(3-(tert-Butyl)-1-(p-tolyl)-1H-pyrazol-5-yl)-3-(4-((2-((3-methoxy-5-(2-morpholinoethoxy)-phenyl)amino)pyrimidin-4-yl)oxy)naphthalen-1-yl)urea;

1-(3-(tert-Butyl)-1-(p-tolyl)-1H-pyrazol-5-yl)-3-(4-((2-((3-(cyclopropylsulfonyl)phenyl)-amino)pyrimidin-4-yl)oxy)naphthalen-1-yl)urea;

1-(3-(tert-Butyl)-1-(p-tolyl)-1H-pyrazol-5-yl)-3-(4-((2-((3-(cyclopropylsulfonyl)-5-methoxy-phenyl)amino)pyrimidin-4-yl)oxy)naphthalen-1-yl)urea;

1-(3-(tert-Butyl)-1-(p-tolyl)-1H-pyrazol-5-yl)-3-(4-((2-((3-(3-hydroxypropyl)thio)-5-methoxyphenyl)amino)pyrimidin-4-yl)oxy)naphthalen-1-yl)urea; 1-(3-(tert-Butyl)-1-(p-tolyl)-1H-pyrazol-5-yl)-3-(4-((2-((3-methoxy-5-(3-morpholino-propoxy)phenyl)amino)pyrimidin-4-yl)oxy)naphthalen-1-yl)urea;

1-(3-(tert-Butyl)-1-(p-tolyl)-1H-pyrazol-5-yl)-3-(4-((2-((3-fluoro-5-(2-(2-(2-methoxyethoxy)-ethoxy)ethoxy)phenyl)amino)pyrimidin-4-yl)oxy)naphthalen-1-yl)urea 1-(4-((2-((3-(2,5,8,11,14,17,20-Heptaoxadocosan-22-yloxy)-5-methoxyphenyl)amino)pyrimidin-4-yl)oxy)naphthalen-1-yl)-3-(3-(tert-butyl)-1-(p-tolyl)-1H-pyrazol-5-yl)urea;

1-(3-(tert-Butyl)-1-(p-tolyl)-1H-pyrazol-5-yl)-3-(4-((2-((3-cyano-5-(2-(2-(2-methoxyethoxy)-ethoxy)ethoxy)phenyl)amino)pyrimidin-4-yl)oxy)naphthalen-1-yl)urea;

1-(3-(tert-Butyl)-1-(p-tolyl)-1H-pyrazol-5-yl)-3-(2,3-dichloro-4-((2-((3-methoxy-5-(2-(2-(2-methoxyethoxyl)ethoxy)ethoxy)phenyl)amino)pyrimidin-4-yl)oxy)phenyl)urea;

1-(3-(tert-Butyl)-1-(p-tolyl)-1H-pyrazol-5-yl)-3-(4-((2-((3-ethynyl-5-(2-(2-(2-methoxyethoxyl)ethoxy)ethoxy)phenyl)amino)pyrimidin-4-yl)oxy)naphthalen-1-yl)urea;

1-(3-(tert-Butyl)-1-(p-tolyl)-1H-pyrazol-5-yl)-3-(4-((2-((3-(2-hydroxyethyl)thio)-5-methoxyphenyl)amino)pyrimidin-4-yl)oxy)naphthalen-1-yl)urea;

1-(3-(tert-Butyl)-1-(p-tolyl)-1H-pyrazol-5-yl)-3-(4-((2-((3-methoxy-5-(2-(2-(2-methoxyethoxyl)ethoxy)ethoxy)phenyl)amino)pyridin-4-yl)oxy)naphthalen-1-yl)urea;

1-(3-(tert-Butyl)-1-(p-tolyl)-1H-pyrazol-5-yl)-3-(4-((2-((3-(2-(2-(2-(dimethylamino)ethoxy)-ethoxy)ethoxy)-5-methoxyphenyl)amino)pyrimidin-4-yl)oxy)naphthalen-1-yl)urea;

1-(3-(tert-Butyl)-1-(p-tolyl)-1H-pyrazol-5-yl)-3-(4-((2-((3-methoxy-5-(2-(2-(2-morpholinoethoxyl)ethoxy)ethoxy)phenyl)amino)pyrimidin-4-yl)oxy)naphthalen-1-yl)urea;

1-(3-(tert-Butyl)-1-(p-tolyl)-1H-pyrazol-5-yl)-3-(2,3-dichloro-4-((2-((3-methoxy-5-(2-morpholinoethoxyl)phenyl)amino)pyrimidin-4-yl)oxy)phenyl)urea;

1-(3-(tert-Butyl)-1-(p-tolyl)-1H-pyrazol-5-yl)-3-(4-((2-((3-methoxy-5-(2-(2-methoxyethoxyl)ethoxy)phenyl)amino)pyrimidin-4-yl)oxy)naphthalen-1-yl)urea;

1-(3-(tert-Butyl)-1-(6-methoxypyridin-3-yl)-1H-pyrazol-5-yl)-3-(4-((2-((3-(cyclopropylsulfonyl)-5-methoxyphenyl)amino)pyrimidin-4-yl)oxy)naphthalen-1-yl)urea;

1-(3-(tert-Butyl)-1-(p-tolyl)-1H-pyrazol-5-yl)-3-(4-((2-((3-(2-(2-(2-hydroxyethoxyl)ethoxy)ethoxy)-5-methoxyphenyl)amino)pyrimidin-4-yl)oxy)naphthalen-1-yl)urea;

1-(3-(tert-Butyl)-1-(4-(dimethylamino)phenyl)-1H-pyrazol-5-yl)-3-(4-((2-((3-methoxy-5-(2-(2-(2-methoxyethoxyl)ethoxy)ethoxy)phenyl)amino)pyrimidin-4-yl)oxy)naphthalen-1-yl)urea;

1-(3-(tert-Butyl)-1-(p-tolyl)-1H-pyrazol-5-yl)-3-(4-((2-((3-chloro-5-(2-(2-(2-methoxyethoxy)-ethoxy)ethoxy)phenyl)amino)pyrimidin-4-yl)oxy)naphthalen-1-yl)urea;

1-(3-(tert-Butyl)-1-(p-tolyl)-1H-pyrazol-5-yl)-3-(2,3-dichloro-4-((2-((3-methoxy-5-(3-morpholinopropoxyl)phenyl)amino)pyrimidin-4-yl)oxy)phenyl)urea;

1-(3-(tert-Butyl)-1-(p-tolyl)-1H-pyrazol-5-yl)-3-(4-((2-((3-(dimethylamino)-5-(2-(2-(2-methoxyethoxyl)ethoxy)ethoxy)phenyl)amino)pyrimidin-4-yl)oxy)naphthalen-1-yl)urea;

1-(3-(tert-Butyl)-1-(p-tolyl)-1H-pyrazol-5-yl)-3-(4-((2-((3-methoxy-5-((2-(2-(2-methoxy ethoxy)ethoxy)ethyl)(methyl)amino)phenyl)amino)pyrimidin-4-yl)oxy)naphthalen-1-yl)urea;

1-(3-(tert-Butyl)-1-(p-tolyl)-1H-pyrazol-5-yl)-3-(2,3-dichloro-4-((2-((3-(cyclopropylsulfonyl)-5-methoxyphenyl)amino)pyrimidin-4-yl)oxy)phenyl)urea;

1-(3-(tert-Butyl)-1-(p-tolyl)-1H-pyrazol-5-yl)-3-(4-((2-((2-methoxy-6-(2-(2-(2-methoxyethoxyl)ethoxy)ethoxy)pyridin-4-yl)amino)pyrimidin-4-yl)oxy)naphthalen-1-yl)urea;

1-(3-(tert-Butyl)-1-(4-methoxyphenyl)-1H-pyrazol-5-yl)-3-(4-((2-((3-(cyclopropylsulfonyl)-5-methoxyphenyl)amino)pyrimidin-4-yl)oxy)naphthalen-1-yl)urea;

1-(3-(tert-Butyl)-1-(p-tolyl)-1H-pyrazol-5-yl)-3-(2,3-dichloro-4-((2-((3-(2-(2-(2-hydroxyethoxy)ethoxy)ethoxy)-5-methoxyphenyl)amino)pyrimidin-4-yl)oxy)phenyl)urea; and 1-(3-(tert-Butyl)-1-(p-tolyl)-1H-pyrazol-5-yl)-3-(4-((2-((4-chloro-3-methoxy-5-(2-(2-(2-methoxyethoxyl)ethoxy)ethoxy)phenyl)amino)pyrimidin-4-yl)oxy)naphthalen-1-yl)urea, or a pharmaceutically acceptable salt, solvate or isotopic derivative thereof.

Examples of salts of compounds of formula I, Ia, Ib or Ic include all pharmaceutically acceptable salts, such as, without limitation, acid addition salts of strong mineral acids such as HCl and HBr salts and addition salts of strong organic acids such as methanesulfonic acid.

References herein to a compound of the invention (a compounds of formula I, Ia, Ib or Ic) are intended to include references to the compound and to all pharmaceutically acceptable salts, solvates and/or tautomers of said compound, unless the context specifically indicates otherwise. In this respect, solvates that may be mentioned include hydrates.

The compounds of the invention (compounds of formula I, Ia, Ib or Ic) are p38 MAP kinase inhibitors (especially of the alpha subtype) and are therefore useful in medicine, in particular for the treatment of inflammatory diseases. Further aspects of the invention that may be mentioned therefore include the following.

(a) A pharmaceutical formulation comprising compound of formula I, Ia, Ib or Ic, as hereinbefore defined, or pharmaceutically acceptable salt, solvate or isotopic derivative thereof, in admixture with a pharmaceutically acceptable adjuvant, diluent or carrier.

(b) A combination product comprising
   (A) a compound of formula I, Ia, Ib or Ic, as hereinbefore defined, or pharmaceutically acceptable salt, solvate or isotopic derivative thereof, and
   (B) another therapeutic agent,
   wherein each of components (A) and (B) is formulated in admixture with a pharmaceutically-acceptable adjuvant, diluent or carrier.

In this aspect of the invention, the combination product may be either a single (combination) pharmaceutical formulation or a kit-of-parts.

Thus, this aspect of the invention encompasses a pharmaceutical formulation including a compound of formula I, Ia, Ib or Ic, as hereinbefore defined, or pharmaceutically acceptable salt, solvate or isotopic derivative thereof, and another therapeutic agent, in admixture with a pharmaceutically acceptable adjuvant, diluent or carrier (which formulation is hereinafter referred to as a "combined preparation").

It also encompasses a kit of parts comprising components:
(i) a pharmaceutical formulation including a compound of formula I, Ia, Ib or Ic, as hereinbefore defined, or pharmaceutically acceptable salt, solvate or isotopic derivative thereof, in admixture with a pharmaceutically acceptable adjuvant, diluent or carrier; and
(ii) a pharmaceutical formulation including another therapeutic agent, in admixture with a pharmaceutically-acceptable adjuvant, diluent or carrier, which components (i) and (ii) are each provided in a form that is suitable for administration in conjunction with the other.

Component (i) of the kit of parts is thus component (A) above in admixture with a pharmaceutically acceptable adjuvant, diluent or carrier. Similarly, component (ii) is component (B) above in admixture with a pharmaceutically acceptable adjuvant, diluent or carrier.

(c) A process for preparing the pharmaceutical formulation of aspect (a) above, sad process comprising the step of admixing the compound of formula I, Ia, Ib or Ic, as hereinbefore defined, or pharmaceutically acceptable salt, solvate or isotopic derivative thereof, with a pharmaceutically acceptable adjuvant, diluent or carrier.

Embodiments of this aspect of the invention that may be mentioned include those in which the pharmaceutically acceptable adjuvant, diluent or carrier is a topically acceptable adjuvant, diluent or carrier (and/or wherein the process is for preparing a topical pharmaceutical formulation, i.e. a pharmaceutical formulation that is adapted for topical administration).

(d) A compound of formula I, Ia, Ib or Ic, as hereinbefore defined, or pharmaceutically acceptable salt, solvate or isotopic derivative thereof, for use in medicine (or for use as a medicament or as a pharmaceutical).

(e) A compound of formula I, Ia, Ib or Ic, as hereinbefore defined, or pharmaceutically acceptable salt, solvate or isotopic derivative thereof, or a pharmaceutical formulation or combination product as defined in connection with aspect (a) or (b) of the invention, for use in the treatment or prevention of an inflammatory disease.

(f) The use of
a compound of formula I, Ia, Ib or Ic, as hereinbefore defined, or pharmaceutically acceptable salt, solvate or isotopic derivative thereof, or
a pharmaceutical formulation or combination product as defined in connection with aspect (a) or (b) of the invention, for the preparation of a medicament for the treatment or prevention of an inflammatory disease.

(g) A method of treating or preventing an inflammatory disease, said method comprising administering to a subject an effective amount of
a compound of formula I, Ia, Ib or Ic, as hereinbefore defined, or pharmaceutically acceptable salt, solvate or isotopic derivative thereof, or
a pharmaceutical formulation or combination product as defined in connection with aspect (a) or (b) of the invention.

(h) A method of sensitizing a subject to the anti-inflammatory effects of a corticosteroid, said method comprising administering to the subject an effective amount of
a compound of formula I, Ia, Ib or Ic, as hereinbefore defined, or pharmaceutically acceptable salt, solvate or isotopic derivative thereof, or
a pharmaceutical formulation or combination product as defined in connection with aspect (a) or (b) of the invention.

Embodiments of this aspect of the invention that may be mentioned include those in which the subject is one who has become refractory to the anti-inflammatory effects of a corticosteroid.

Formulations

In relation to aspects (a) and (b) above, diluents and carriers that may be mentioned include those suitable for parenteral, oral, topical, mucosal and rectal administration.

The pharmaceutical formulations and combination products of aspects (a) and (b) above may be prepared e.g. for parenteral, subcutaneous, intramuscular, intravenous, intra-articular, intravitreous, periocular, retrobulbar, subconjunctival, sub-Tenon, topical ocular or peri-articular administration, particularly in the form of liquid solutions, emulsions or suspensions; for oral administration, particularly in the form of tablets or capsules, and especially involving technologies aimed at furnishing colon-targeted drug release (Patel, M. M. *Expert Opin. Drug Deliv.* 2011, 8 (10), 1247-1258); for topical e.g. pulmonary or intranasal administration, particularly in the form of powders, nasal drops or aerosols and transdermal administration; for topical ocular administration, particularly in the form of solutions, emulsions, suspensions, ointments, implants/inserts, gels, jellies or liposomal microparticle formulations (Ghate, D.; Edelhauser, H. F. *Expert Opin. Drug Deliv.* 2006, 3 (2), 275-287); for ocular administration, particularly in the form of biodegradable and non-biodegradable implants, liposomes and nanoparticles (Thrimawithana, T. R. et al. *Drug Discov. Today* 2011, 16 (5/6), 270-277); for mucosal administration e.g. to buccal, sublingual or vaginal mucosa, and for rectal administration e.g. in the form of a suppository or enema.

The pharmaceutical formulations and combination products of aspects (a) and (b) above may conveniently be administered in unit dosage form and may be prepared by any of the methods well-known in the pharmaceutical art, for example as described in Remington's Pharmaceutical Sciences, 17th ed., Mack Publishing Company, Easton, Pa., (1985). Formulations for parenteral administration may contain as excipients sterile water or saline, alkylene glycols such as propylene glycol, polyalkylene glycols such as polyethylene glycol, oils of vegetable origin, hydrogenated naphthalenes and the like. Formulations for nasal administration may be solid and may contain excipients, for example, lactose or dextran, or may be aqueous or oily solutions for use in the form of nasal drops or metered sprays. For buccal administration typical excipients include sugars, calcium stearate, magnesium stearate, pregelatinated starch, and the like.

Pharmaceutical formulations and combination products suitable for oral administration may comprise one or more physiologically compatible carriers and/or excipients and may be in solid or liquid form. Tablets and capsules may be prepared with binding agents, for example, syrup, acacia, gelatin, sorbitol, tragacanth, or poly-vinylpyrollidone; fillers, such as lactose, sucrose, corn starch, calcium phosphate, sorbitol, or glycine; lubricants, such as magnesium stearate, talc, polyethylene glycol, or silica; and surfactants, such as sodium lauryl sulfate. Liquid compositions may contain conventional additives such as suspending agents, for example sorbitol syrup, methyl cellulose, sugar syrup, gelatin, carboxymethyl-cellulose, or edible fats; emulsifying agents such as lecithin, or acacia; vegetable oils such as almond oil, coconut oil, cod liver oil, or peanut oil; preservatives such as butylated hydroxyanisole (BHA) and butylated hydroxytoluene (BHT). Liquid compositions may be encapsulated in, for example, gelatin to provide a unit dosage form.

Solid oral dosage forms include tablets, two-piece hard shell capsules and soft elastic gelatin (SEG) capsules. Such two-piece hard shell capsules may be made from, for example, gelatin or hydroxylpropyl methylcellulose (HPMC).

A dry shell formulation typically comprises of about 40% to 60% w/w concentration of gelatin, about a 20% to 30% concentration of plasticizer (such as glycerin, sorbitol or propylene glycol) and about a 30% to 40% concentration of water. Other materials such as preservatives, dyes, opacifiers and flavours also may be present. The liquid fill material comprises a solid drug that has been dissolved, solubilized or dispersed (with suspending agents such as beeswax, hydrogenated castor oil or polyethylene glycol 4000) or a liquid drug in vehicles or combinations of vehicles such as mineral oil, vegetable oils, triglycerides, glycols, polyols and surface-active agents.

A compound of the invention may be administered topically (e.g. to the lung, eye or intestines). Thus, embodiments of aspects (a) and (b) above that may be mentioned include pharmaceutical formulations and combination products that are adapted for topical administration. Such formulations include those in which the excipients (including any adjuvant, diluent and/or carrier) are topically acceptable.

Topical administration to the lung may be achieved by use of an aerosol formulation. Aerosol formulations typically comprise the active ingredient suspended or dissolved in a suitable aerosol propellant, such as a chlorofluorocarbon (CFC) or a hydrofluorocarbon (HFC). Suitable CFC propellants include trichloromonofluoromethane (propellant 11), dichlorotetrafluoro methane (propellant 114), and dichlorodifluoromethane (propellant 12). Suitable HFC propellants include tetrafluoroethane (HFC-134a) and heptafluoropropane (HFC-227). The propellant typically comprises 40% to 99.5% e.g. 40% to 90% by weight of the total inhalation composition. The formulation may comprise excipients including co-solvents (e.g. ethanol) and surfactants (e.g. lecithin, sorbitan trioleate and the like). Other possible excipients include polyethylene glycol, polyvinylpyrrolidone, glycerine and the like. Aerosol formulations are packaged in canisters and a suitable dose is delivered by means of a metering valve (e.g. as supplied by Bespak, Valois or 3M or alternatively by Aptar, Coster or Vari).

Topical administration to the lung may also be achieved by use of a non-pressurised formulation such as an aqueous solution or suspension. This may be administered by means of a nebuliser e.g. one that can be hand-held and portable or for home or hospital use (i.e. non-portable). The formulation may comprise excipients such as water, buffers, tonicity adjusting agents, pH adjusting agents, surfactants and co-solvents. Suspension liquid and aerosol formulations (whether pressurised or unpressurised) will typically contain the compound of the invention in finely divided form, for example with a $D_{50}$ of 0.5-10 µm e.g. around 1-5 µm. Particle size distributions may be represented using $D_{10}$, $D_{50}$ and $D_{90}$ values. The $D_{50}$ median value of particle size distributions is defined as the particle size in microns that divides the distribution in half. The measurement derived from laser diffraction is more accurately described as a volume distribution, and consequently the $D_{50}$ value obtained using this procedure is more meaningfully referred to as a $Dv_{50}$ value (median for a volume distribution). As used herein Dv values refer to particle size distributions measured using laser diffraction. Similarly, $D_{10}$ and $D_{90}$ values, used in the context of laser diffraction, are taken to mean $Dv_{10}$ and $Dv_{90}$ values and refer to the particle size whereby 10% of the distribution lies below the $D_{10}$ value, and 90% of the distribution lies below the $D_{90}$ value, respectively.

Topical administration to the lung may also be achieved by use of a dry-powder formulation. A dry powder formulation will contain the compound of the disclosure in finely divided form, typically with a mass mean aerodynamic diameter (MMAD) of 1-10 µm or a $D_{50}$ of 0.5-10 µm e.g. around 1-5 µm. Powders of the compound of the invention in finely divided form may be prepared by a micronization process or similar size reduction process. Micronization may be performed using a jet mill such as those manufactured by Hosokawa Alpine. The resultant particle size distribution may be measured using laser diffraction (e.g. with a Malvern Mastersizer 2000S instrument). The formulation will typically contain a topically acceptable diluent such as lactose glucose or mannitol (preferably lactose), usually of large particle size e.g. an MMAD of 50 µm or more, e.g. 100 µm or more or a $D_{50}$ of 40-150 µm. As used herein, the term "lactose" refers to a lactose-containing component, including α-lactose monohydrate, R-lactose monohydrate, α-lactose anhydrous, β-lactose anhydrous and amorphous lactose. Lactose components may be processed by micronization, sieving, milling, compression, agglomeration or spray drying. Commercially available forms of lactose in various forms are also encompassed, for example Lactohale® (inhalation grade lactose; DFE Pharma), InhaLac®70 (sieved lactose for dry powder inhaler; Meggle), Pharmatose® (DFE Pharma) and Respitose® (sieved inhalation grade lactose; DFE Pharma) products. In one embodiment, the lactose component is selected from the group consisting of α-lactose monohydrate, α-lactose anhydrous and amorphous lactose. Preferably, the lactose is α-lactose monohydrate.

Dry powder formulations may also contain other excipients such as sodium stearate, calcium stearate or magnesium stearate.

A dry powder formulation is typically delivered using a dry powder inhaler (DPI) device. Examples of dry powder delivery systems include SPINHALER, DISKHALER, TURBOHALER, DISKUS and CLICKHALER. Further examples of dry powder delivery systems include ECLIPSE, NEXT, ROTAHALER, HANDIHALER, AEROLISER, CYCLOHALER, BREEZHALER/NEOHALER, MONODOSE, FLOWCAPS, TWINCAPS, X-CAPS, TURBOSPIN, ELPENHALER, MIATHALER, TWISTHALER, NOVOLIZER, PRESSAIR, ELLIPTA, ORIEL dry powder inhaler, MICRODOSE, PULVINAL, EASYHALER, ULTRAHALER, TAIFUN, PULMOJET, OMNIHALER, GYROHALER, TAPER, CONIX, XCELOVAIR and PROHALER.

In one embodiment a compound of the present invention is provided in a micronized dry powder formulation, for example further comprising lactose of a suitable grade optionally together with magnesium stearate, filled into a single dose device such as AEROLISER or filed into a multi dose device such as DISKUS.

The compounds of the present invention may also be administered rectally, for example in the form of suppositories or enemas, which include aqueous or oily solutions as well as suspensions and emulsions. Such compositions are prepared following standard procedures, well known by those skilled in the art. For example, suppositories can be prepared by mixing the active ingredient with a conventional suppository base such as cocoa butter or other glycerides. In this case, the drug is mixed with a suitable non-irritating excipient which is solid at ordinary temperatures but liquid at the rectal temperature and will therefore melt in the rectum to release the drug. Such materials are cocoa butter and polyethylene glycols.

Generally, for compositions intended to be administered topically to the eye in the form of eye drops or eye ointments, the total amount of the inhibitor will be about 0.0001 to less than 4.0% (w/w).

Preferably, for topical ocular administration, the compositions administered according to the present invention will be formulated as solutions, suspensions, emulsions and other dosage forms. Aqueous solutions are generally preferred, based on ease of formulation, as well as a patient's ability to administer such compositions easily by means of instilling one to two drops of the solutions in the affected eyes. However, the compositions may also be suspensions, viscous or semi-viscous gels, or other types of solid or semi-solid compositions. Suspensions may be preferred for compounds that are sparingly soluble in water.

The compositions administered according to the present invention may also include various other ingredients, including, but not limited to, tonicity agents, buffers, surfactants, stabilizing polymer, preservatives, co-solvents and viscosity building agents. Preferred pharmaceutical compositions of the present invention include the inhibitor with a tonicity agent and a buffer. The pharmaceutical compositions of the present invention may further optionally include a surfactant and/or a palliative agent and/or a stabilizing polymer.

Various tonicity agents may be employed to adjust the tonicity of the composition, preferably to that of natural tears for ophthalmic compositions. For example, sodium chloride, potassium chloride, magnesium chloride, calcium chloride, simple sugars such as dextrose, fructose, galactose, and/or simply polyols such as the sugar alcohols mannitol, sorbitol, xylitol, lactitol, isomaltitol, maltitol, and hydrogenated starch hydrolysates may be added to the composition to approximate physiological tonicity. Such an amount of tonicity agent will vary, depending on the particular agent to be added. In general, however, the compositions will have a tonicity agent in an amount sufficient to cause the final composition to have an ophthalmically acceptable osmolality (generally about 150-450 mOsm, preferably 250-350 mOsm and most preferably at approximately 290 mOsm). In general, the tonicity agents of the invention will be present in the range of 2 to 4% w/w. Preferred tonicity agents of the invention include the simple sugars or the sugar alcohols, such as D-mannitol.

An appropriate buffer system (e.g., sodium phosphate, sodium acetate, sodium citrate, sodium borate or boric acid) may be added to the compositions to prevent pH drift under storage conditions. The particular concentration will vary, depending on the agent employed. Preferably however, the buffer will be chosen to maintain a target pH within the range of pH 5 to 8, and more preferably to a target pH of pH 5 to 7.

Surfactants may optionally be employed to deliver higher concentrations of inhibitor. The surfactants function to solubilise the inhibitor and stabilise colloid dispersion, such as micellar solution, microemulsion, emulsion and suspension. Examples of surfactants which may optionally be used include polysorbate, poloxamer, polyosyl 40 stearate, polyoxyl castor oil, tyloxapol, triton, and sorbitan monolaurate. Preferred surfactants to be employed in the invention have a hydrophile/lipophile/balance "HLB" in the range of 12.4 to 13.2 and are acceptable for ophthalmic use, such as TritonX114 and tyloxapol.

Additional agents that may be added to the ophthalmic compositions of the present invention are demulcents which function as a stabilising polymer. The stabilizing polymer should be an ionic/charged example with precedence for topical ocular use, more specifically, a polymer that carries negative charge on its surface that can exhibit a zeta-potential of (−)10-50 mV for physical stability and capable of making a dispersion in water (i.e. water soluble). A preferred stabilising polymer of the invention would be polyelectrolyte, or polyelectrolytes if more than one, from the family of cross-linked polyacrylates, such as carbomers and Pemulen(R), specifically Carbomer 974p (polyacrylic acid), at 0.1-0.5% w/w.

Other compounds may also be added to the ophthalmic compositions of the present invention to increase the viscosity of the carrier. Examples of viscosity enhancing agents include, but are not limited to: polysaccharides, such as hyaluronic acid and its salts, chondroitin sulfate and its salts, dextrans, various polymers of the cellulose family; vinyl polymers; and acrylic acid polymers.

Topical ophthalmic products are typically packaged in multidose form. Preservatives are thus required to prevent microbial contamination during use. Suitable preservatives include: benzalkonium chloride, chlorobutanol, benzododecinium bromide, methyl paraben, propyl paraben, phenylethyl alcohol, edentate disodium, sorbic acid, polyquaternium-1, or other agents known to those skilled in the art. Such preservatives are typically employed at a level of from 0.001 to 1.0% w/v. Unit dose compositions of the present invention will be sterile, but typically unpreserved. Such compositions, therefore, generally will not contain preservatives.

The medical practitioner, or other skilled person, will be able to determine a suitable dosage for the compounds of the invention, and hence the amount of the compound of the invention that should be included in any particular pharmaceutical formulation (whether in unit dosage form or otherwise).

Embodiments of the invention that may be mentioned in connection with the combination products described at (b) above include those in which the other therapeutic agent is one or more therapeutic agents that are known by those skilled in the art to be suitable for treating inflammatory diseases (e.g. the specific diseases mentioned below).

For example, for the treatment of respiratory disorders (such as COPD or asthma), the other therapeutic agent is one or more agents selected from the list comprising:
  steroids (e.g. budesonide, beclomethasone dipropionate, fluticasone propionate, mometasone furoate, fluticasone furoate; a further example is ciclesonide);
  beta agonists, particularly beta2 agonists (e.g. terbutaline, salbutamol, salmeterol, formoterol; further examples are vilanterol, olodaterol, reproterol and fenoterol); and
  xanthines (e.g. theophylline).

For example, for the treatment of respiratory disorders (such as COPD or asthma), the other therapeutic agent is one or more agents selected from the list comprising:
  muscarinic antagonists (e.g. tiotropium, umeclidinium, glycopyrronium, aclidinium and daratropium, any of these for example as the bromide salt); and
  phosphodiesterase inhibitors.

Further, for the treatment of gastrointestinal disorders (such as Crohn's disease or ulcerative colitis), the other therapeutic agent may be, for example, one or more agents selected from the list comprising:
  5-aminosalicylic acid, or a prodrug thereof (such as sulfasalazine, olsalazine or bisalazide);

corticosteroids (e.g. prednisolone, methylprednisolone, or budesonide);
immunosuppressants (e.g. cyclosporin, tacrolimus, methotrexate, azathioprine or 6-mercaptopurine);
anti-TNFα antibodies (e.g., infliximab, adalimumab, certolizumab pegol or golimumab);
anti-IL12/IL23 antibodies (e.g., ustekinumab) or small molecule IL12/IL23 inhibitors (e.g., apilimod);
Anti-α4β7 antibodies (e.g., vedolizumab);
MAdCAM-1 blockers (e.g., PF-00547659);
antibodies against the cell adhesion molecule α4-integrin (e.g., natalizumab);
antibodies against the IL2 receptor a subunit (e.g., daclizumab or basiliximab);
JAK3 inhibitors (e.g., tofacitinib or R348);
Syk inhibitors and prodrugs thereof (e.g., fostamatinib and R-406);
Phosphodiesterase-4 inhibitors (e.g., tetomilast);
HMPL-004;
probiotics;
Dersalazine;
semapimod/CPSI-2364; and
protein kinase C inhibitors (e.g. AEB-071).

For the treatment of eye disorders (such as uveitis), the other therapeutic agent may be, for example, one or more agents selected from the list comprising:
corticosteroids (e.g. dexamethasone, prednisolone, triamcinolone acetonide, difluprednate or fluocinolone acetonide);
immunosuppressants (e.g. cyclosporin, voclosporin, azathioprine, methotrexate, mycophenolate mofetil or tacrolimus);
anti-TNFα antibodies (e.g., infliximab, adalimumab, certolizumab pegol, ESBA-105 or golimumab);
anti-IL-17A antibodies (e.g., secukinumab);
mTOR inhibitors (e.g., sirolimus);
VGX-1027;
JAK3 inhibitors (e.g., tofacitinib or R348); and
protein kinase C inhibitors (e.g. AEB-071).

Medical Uses

The compounds of the invention may be used as monotherapies for inflammatory diseases, or in combination therapies for such diseases.

Thus, embodiments of aspects (e) to (g) above that may be mentioned include those in which the compound of formula I, Ia, Ib or Ic (or pharmaceutically acceptable salt, solvate or isotopic derivative thereof) is the sole pharmacologically active ingredient utilised in the treatment.

However, in other embodiments of aspects (e) to (g) above, the compound of formula I, Ia, Ib or Ic (or pharmaceutically acceptable salt, solvate or isotopic derivative thereof) is administered to a subject who is also administered one or more other therapeutic agents (e.g. wherein the one or more other therapeutic agents are as defined above in connection with combination products).

When used herein, the term "inflammatory disease" specifically includes references to any one or more of the following:
(i) lung diseases or disorders having an inflammatory component, such as cystic fibrosis, pulmonary hypertension, lung sarcoidosis, idiopathic pulmonary fibrosis or, particularly, COPD (including chronic bronchitis and emphysema), asthma or paediatric asthma;
(ii) skin diseases or disorders having an inflammatory component, such as atopic dermatitis, allergic dermatitis, contact dermatitis or psoriasis;
(iii) nasal diseases or disorders having an inflammatory component, such as allergic rhinitis, rhinitis or sinusitis;
(iv) eye diseases or disorders having an inflammatory component, such as conjunctivitis, allergic conjunctivitis, keratoconjunctivitis sicca (dry eye), glaucoma, diabetic retinopathy, macular oedema (including diabetic macular oedema), central retinal vein occlusion (CRVO), dry and/or wet age related macular degeneration (AMD), post-operative cataract inflammation, or, particularly, uveitis (including posterior, anterior and pan uveitis), corneal graft and limbal cell transplant rejection; and
(v) gastrointestinal diseases or disorders having an inflammatory component, such as gluten sensitive enteropathy (coeliac disease), eosinophilic eosophagitis, intestinal graft versus host disease or, particularly, Crohn's disease or ulcerative colitis.

References herein to diseases having an inflammatory component include references to diseases that involve inflammation, whether or not there are other (non-inflammatory) symptoms or consequences of the disease.

According to a further aspect of the invention there is provided a process for the preparation of a compound of formula I which process comprises:

(a) reaction of a compound of formula II.

with a compound of formula III,

wherein one of $Z^1$ and $Z^2$ is a structural fragment of formula IV

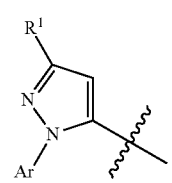

and the other of $Z^1$ and $Z^2$ is a structural fragment of formula V (d) reaction of a compound of formula VI,

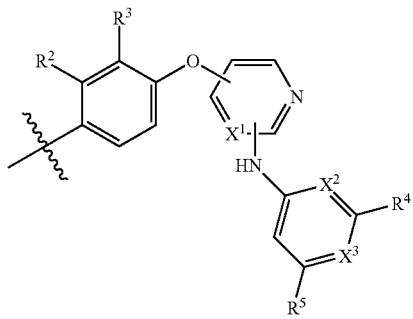

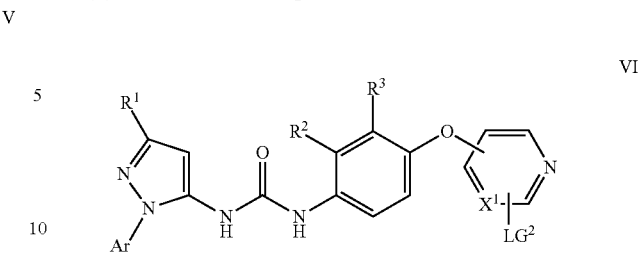

where $R^1$ to $R^5$, Ar and $X^1$ to $X^3$ are as hereinbefore defined, for example under conditions known to those skilled in the art, for example at a temperature from ambient (e.g. 15 to 30° C.) to about 110° C. in the presence of a suitable organic solvent (e.g. a polar aprotic solvent such as DMF, THF, 1,4-dioxane, or mixtures thereof);

(b) reaction of a compound of formula IIa,

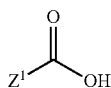

wherein $LG^2$ represents a suitable leaving group (e.g. a halo group such as chloro or bromo) and $R^1$ to $R^3$, Ar and $X^1$ are as hereinbefore defined with a compound of formula VII,

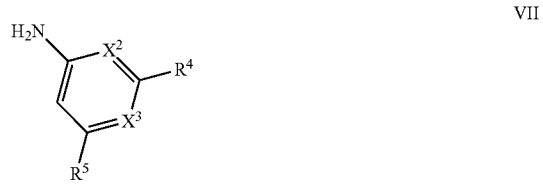

wherein $R^4$, $R^5$, $X^2$ and $X^3$ are as hereinbefore defined, for example under conditions known to those skilled in the art (e.g. as described in *J. Am. Chem. Soc.* 2011, 133, 15686-15696), such as at elevated temperature (e.g. from 50 to 110° C.) in the presence of a suitable organic solvent (e.g. a polar aprotic solvent such as DMF, THF, 1,4-dioxane, or mixtures thereof) and, optionally, an acidic catalyst (e.g. a sulfonic acid such as para-toluenesulfonic acid); or wherein $Z^1$ is as defined above, with a suitable azide-forming agent (i.e. a suitable source of a leaving group and activated azide ion, such as diphenyl phosphorazidate; see, for example, *Tetrahedron* 1974, 30, 2151-2157) under conditions known to those skilled in the art, such as at sub-ambient to ambient temperature (e.g. from an initial temperature of about −5 to 5° C. to ambient temperature post-reaction) in the presence of an amine base (e.g. triethylamine or a sterically hindered base such as N,N-diisopropylethylamine) and a suitable organic solvent (e.g. a polar aprotic solvent such as DMF, THF, 1,4-dioxane, or mixtures thereof), which reaction is followed, without isolation, by thermal rearrangement (e.g. under heating) of the intermediate acyl azide (of formula $Z^1$—C(O)—$N_3$) e.g. at ambient temperature (such as from 15 to 30° C.) to provide, in situ, a compound of formula II, which compound is then reacted with a compound of formula III, as defined above, to provide the compound of formula I;

(e) for compounds of formula I in which $R^4$ represents
—$S(O)_{1-2}$4  $CH_2(CH_2)_{0-1}CH_2$—O]$_{1-12}$—$CH_2(CH_2)_{0-1}$ $CH_2$—$R^{6a}$,
—$S(O)_{1-2}R^{6b}$,
—$S(O)_{1-2}$—$CH_2$-[$C_{1-5}$ alkylene]-N($R^{6c}$)$R^{6d}$,
oxidation of a corresponding compound of formula I in which, respectively, $R^4$ represents
—S—[$CH_2(CH_2)_{0-1}CH_2$—O]$_{1-12}$—$CH_2(CH_2)_{0-1}CH_2$— $R^{6a}$,
—S—$R^{6b}$,
—S—$CH_2$—[$C_{1-5}$ alkylene]-N($R^{6c}$)$R^{6d}$,
wherein $R^{6a}$ to $R^{6d}$ are as hereinbefore defined, for example under conditions known to those skilled in the art (e.g. at 0 to 25° C. in the presence of a suitable solvent (such as dichloromethane, methanol or a mixture thereof) and a peracid, such as meta-chloroperbenzoic acid);

(c) reaction of a compound of formula IIb,

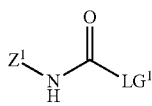

(f) deprotection of an protected derivative of a compound of formula I, under conditions known to those skilled in the art, wherein the protected derivative bears a protecting group on an O- or N-atom of the compound of formula I (and, for the avoidance of doubt, a protected derivative of one compound of formula I may or may not represent another compound of formula I).

wherein $LG^1$ represents a suitable leaving group (e.g. imidazolyl, chloro, or aryloxy) and $Z^1$ is as defined above, with a compound of formula III, as defined above, for example under conditions known to those skilled in the art, such as at ambient temperature (e.g. from ambient to 80° C.), optionally in the presence of an amine base (e.g. a sterically hindered base like N,N-diisopropylethylamine) and a suitable organic solvent (e.g. an aprotic solvent, such as dichloromethane);

Compounds of formula II may be prepared according to or by analogy with methods known to those skilled in the art, for example by reaction of a compound of formula IIa, as defined above, with an azide-forming agent, followed by rearrangement of the intermediate acyl azide (as described at (b) above; see, for example, *Tetrahedron* 1974, 30, 2151-2157).

Compounds of formula IIb may be prepared reaction of a compound of formula VIII,

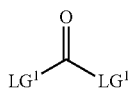

wherein LG$^1$ is as hereinbefore defined, with a compound of formula IX,

wherein Z$^1$ is as hereinbefore defined, for example under conditions known to those skilled in the art.

Amines of formula IX may be prepared from carboxylic acids of formula IIa through the route described in (b) above, where the intermediate isocyanate II is hydrolysed with water to give a carbamic acid that loses carbon dioxide to furnish IX. By the same token, the intermediate isocyanate II can be reacted with an alcohol, such as t-butanol, to generate a protected version of IX.

Certain compounds of formula III in which Z$^2$ represents a structural fragment of formula V, or compounds of formula IX in which Z$^1$ represents a structural fragment of formula V, may be synthesised employing the route outlined in Scheme 1 (see, for example: WO 2003/072569; and WO 2008/046216), wherein R$^2$, R$^3$ and X$^1$ to X$^3$ are as hereinbefore defined, LG$^3$ and LG$^4$ represent leaving groups, e.g., halogen or methanesulfonyl, and FG represents a real or latent NH$_2$ group, i.e., a group that is readily transformed into an NH$_2$ group, such as nitro or a protected variant NHPG$^2$, where PG$^2$ is a typical protecting group (see, for example: Greene, T. W.; Wuts, P. G. M. *Protective Groups in Organic Synthesis*; Wiley, 4th revised edition, 2006; ISBN-10: 0471697540), e.g., a carbamate ester or carboxamide. The sequence starts with the base-mediated S$_N$Ar displacement of LG$^3$ in XI by the aroxides formed when X is treated with base to generate ethers XII. The remaining halogen or methanesulfonyl substituents (LG$^4$) of the ether XII is then displaced i) by an amine of formula VII in a second S$_N$Ar reaction or (ii) via a Buchwald coupling (see, for example, WO 2009/017838) with an amine of formula VII to furnish the desired compound (when FG is NH$_2$), or XIII (when FG is nitro or NH PG$^2$). When FG is nitro in XIII, the NH$_2$ group may be revealed by a reduction reaction, typically done through hydrogenation employing a suitable catalyst, e.g., palladium on carbon, or employing dissolving metal conditions, such as with iron in glacial acetic acid.

Alternatively, when FG is a protecting group, the NH$_2$ group may be revealed by a deprotection reaction. Although only depicted as taking place in the final step of the sequence, it should be noted that the unmasking of the latent NH$_2$ group represented by FG can take place at any stage in the synthetic route shown in Scheme 1.

Scheme 1

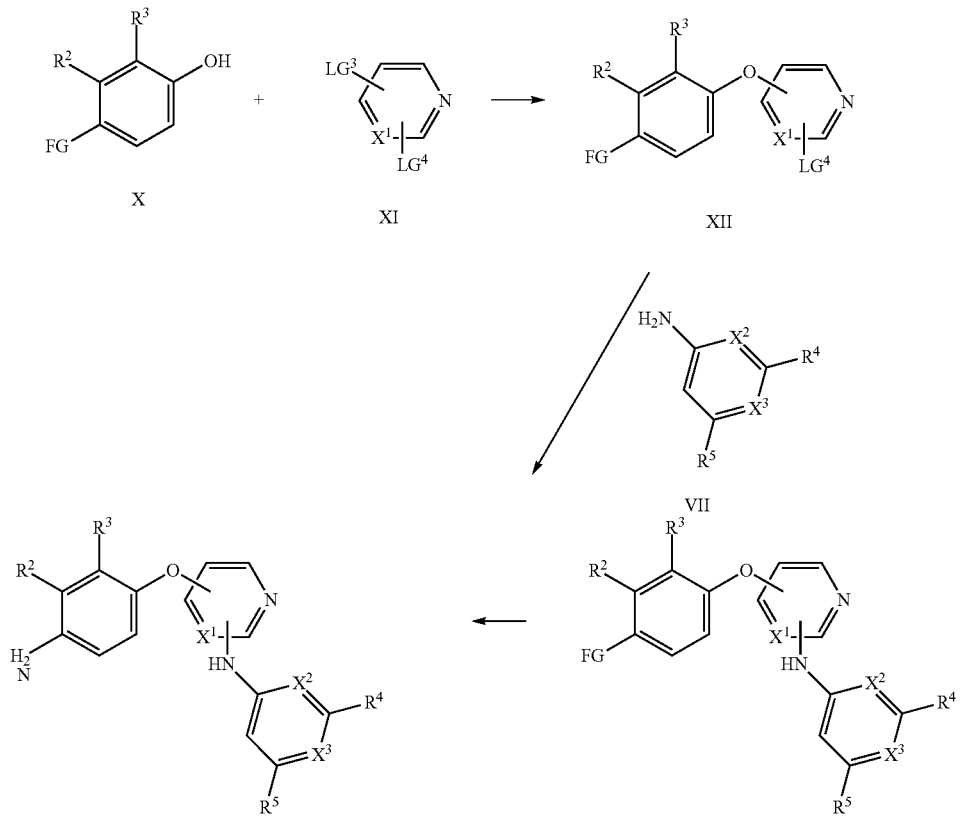

Compounds of formula IIa in which $Z^1$ represents a structural fragment of formula IV and Ar is substituted by $(C_{1-3}$ alkylene$)_{0-1}$-O—$C_{1-6}$ alkylene-Het$^2$ may be synthesised employing the route highlighted in Scheme 2. In this route, compounds of formula XIV (in which Ak represents an alkyl group, such as $C_{1-6}$ alkyl) are alkylated with alkyl halides XV, where Hal is chloro, bromo or iodo, under basic conditions in Williamson ether syntheses (see, for example: Eur. J. Med. Chem. 2010, 45, 5965-5978). Compounds of formula IIa are then synthesised by saponification of the alkyl ester (e.g. by alkaline hydrolysis under conditions known to those skilled in the art).

Scheme 2

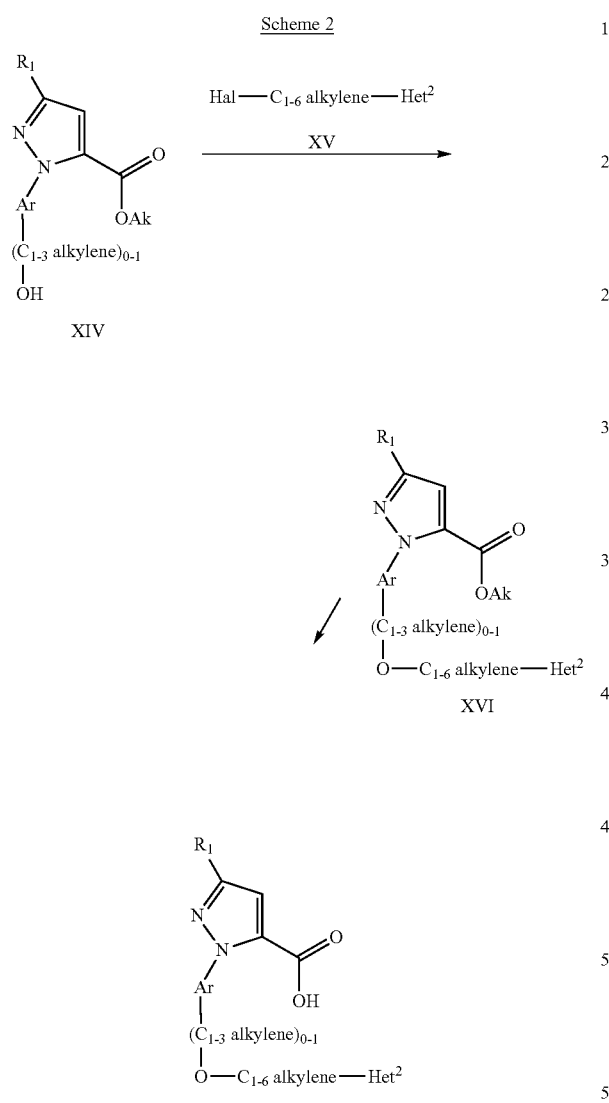

Compounds of formula VI may be synthesised by analogy with the compounds of formula I (see, for example, alternative processes (a) to (c) above). For example, compounds of formula VI can be prepared by reaction of a compound of formula IIx with a compound of formula IIIx, wherein the compounds of formulae IIx and IIIx take the same definitions as the compounds of formulae II and III, with the exception that one of $Z^1$ and $Z^2$ represents a structural fragment of formula IV, as hereinbefore defined, and the other of $Z^1$ and $Z^2$ represents a structural fragment of formula Va,

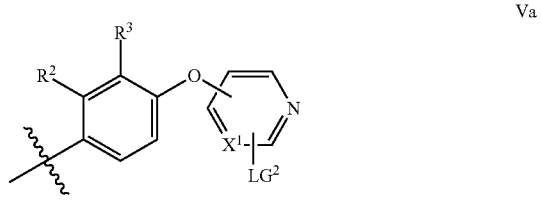

Compounds of formula VII may be prepared according to or by analogy with procedures known to those skilled in the art, for example as described below.

(i) For compounds of formula VII in which $R^4$ represents
—O—[CH$_2$(CH$_2$)$_{0-1}$CH$_2$—O]$_{1-12}$—CH$_2$(CH$_2$)$_{0-1}$CH$_2$—R$^{6a}$,
—O—CH$_2$—[C$_{1-5}$ alkylene]-N(R$^{6c}$)R$^{6d}$,
—OS(O)$_2$R$^{6e}$ or
—OC(O)NH$_2$,
reaction of a compound of formula XVII.

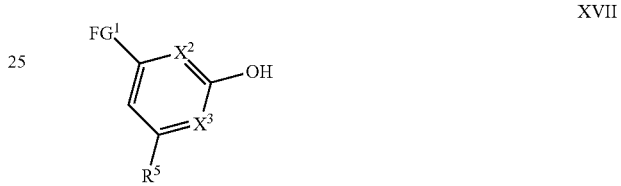

wherein FG$^1$ either represents FG or C(O)O—(C$_{1-6}$ alkyl), and FG, R$^5$, X$^2$ and X$^3$ are as hereinbefore defined, with a compound of formula XVIIIa, XVIIIb, XVIIIc or XVIIId

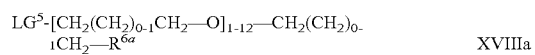   XVIIIa

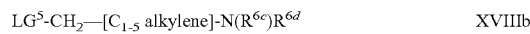   XVIIIb

   XVIIIc

   XVIIId wherein M$^+$ represents a monovalent metal cation (e.g. an alkali metal cation, such as a potassium cation) and LG$^5$ represents a suitable leaving group such as halo, (perfluoro)alkanesulfonate or arylsulfonate (e.g. methanesulfonate or p-toluenesulfonate), R$^{6a}$, R$^{6c}$ and R$^{6d}$ are as hereinbefore defined, under conditions known to those skilled in the art (e.g. in the presence of an organic solvent and either a suitable base or, in the case of reaction with the compound of formula XVIIId, a suitable acid, such as trifluoroacetic acid), followed by when FG$^1$ represents NH-PG$^2$, removal of the PG$^2$ protecting group,
when FG$^1$ represents NO$_2$, reduction of NO$_2$ to NH$_2$ or
when FG$^1$ represents C(O)O—(C$_{1-6}$ alkyl), saponification to provide the corresponding carboxylic acid and then reaction with a suitable azide-forming agent and thermal rearrangement of the resulting acyl azide (see, for example, process (b) above).

(ii) For compounds of formula VII in which $R^4$ represents
—O—[CH$_2$(CH$_2$)$_{0-1}$CH$_2$—O]$_{1-12}$—CH$_2$(CH$_2$)$_{0-1}$CH$_2$—R$^{6a}$ or
—O—CH$_2$—[C$_{1-5}$ alkylene]-N(R$^{6c}$)R$^{6d}$
reaction of a compound of formula XVII, as hereinbefore defined, with a compound of formula XIXa or XIXb

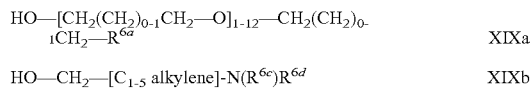

XIXa

HO—CH$_2$—[C$_{1-5}$ alkylene]-N(R$^{6c}$)R$^{6d}$        XIXb wherein R$^{6a}$, R$^{6c}$ and R$^{6d}$ are as hereinbefore defined, under conditions known to those skilled in the art (e.g. under Mitsunobu conditions, i.e. in the presence of using triphenylphosphine and an azodicarboxylate, such as diethyl azodicarboxylate or diisopropyl azodicarboxylate), followed by when FG$^1$ represents NH-PG$^2$, removal of the PG$^2$ protecting group, when FG$^1$ represents NO$_2$, reduction of NO$_2$ to NH$_2$ or when FG$^1$ represents C(O)O—(C$_{1-6}$ alkyl), saponification to provide the corresponding carboxylic acid and then reaction with a suitable azide-forming agent and thermal rearrangement of the resulting acyl azide (see, for example, process (b) above).

(iii) For compounds of formula VII in which R$^4$ represents
—S—[CH$_2$(CH$_2$)$_{0-1}$CH$_2$—O]$_{1-12}$—CH$_2$(CH$_2$)$_{0-1}$CH$_2$—R$^{6a}$,
—S—CH$_2$—[C$_{1-5}$ alkylene]-N(R$^{6c}$)R$^{6d}$ or
—S—R$^{6b}$,
reaction of a compound of formula XX,

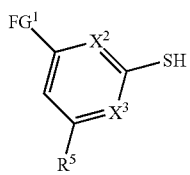

XX wherein FG$^1$, R$^5$, X$^2$ and X$^3$ are as hereinbefore defined, with a compound of formula XVIIIa or XVIIIb, as hereinbefore defined, or a compound of formula XXI LG$^5$-R$^{6b}$        XXI wherein LG$^5$ and R$^{6b}$ are as hereinbefore defined, under conditions known to those skilled in the art (e.g. in the presence of a suitable base and an organic solvent), followed by when FG$^1$ represents NH-PG$^2$, removal of the PG$^2$ protecting group, when FG$^1$ represents NO$_2$, reduction of NO$_2$ to NH$_2$ or when FG$^1$ represents C(O)O—(C$_{1-6}$ alkyl), saponification to provide the corresponding carboxylic acid and then reaction with a suitable azide-forming agent and thermal rearrangement of the resulting acyl azide (see, for example, process (b) above).

(iv) For compounds of formula VII in which X$^2$ and X$^3$ both represent CH and R$^4$ represents
—S(O)$_{1-2}$[CH$_2$(CH$_2$)$_{0-1}$CH$_2$—O]$_{1-12}$—CH$_2$(CH$_2$)$_{0-1}$CH$_2$—R$^{6a}$,
—S(O)$_{1-2}$—CH$_2$—[C$_{1-5}$ alkylene]-N(R$^{6c}$)R$^{6d}$ or
—S(O)$_{1-2}$—R$^{6b}$,
oxidation of a compound of formula XXII,

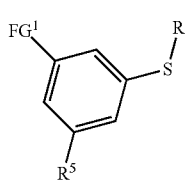

XXII wherein R represents
—[CH$_2$(CH$_2$)$_{0-1}$CH$_2$—O]$_{1-12}$—CH$_2$(CH$_2$)$_{0-1}$CH$_2$—R$^{6a}$,
—CH$_2$—[C$_{1-5}$ alkylene]-N(R$^{6c}$)R$^{6d}$ or
—R$^{6b}$,
and FG$^1$ and R$^5$ are as hereinbefore defined, under conditions known to those skilled in the art (e.g. in the presence of a peracid, such as meta-chloroperbenzoic acid), followed by when FG$^1$ represents NH-PG$^2$, removal of the PG$^2$ protecting group, when FG$^1$ represents NO$_2$, reduction of NO$_2$ to NH$_2$ or when FG$^1$ represents C(O)O—(C$_{1-6}$ alkyl), saponification to provide the corresponding carboxylic acid and then reaction with a suitable azide-forming agent and thermal rearrangement of the resulting acyl azide (see, for example, process (b) above).

(v) For compounds of formula VII in which R$^4$ represents
—S—R$^{6b}$,
—S(O)$_2$R$^{6b}$ or
—C≡C—R$^{6f}$,
coupling of a compound of formula XXIII

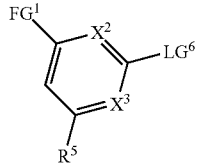

XXIII wherein LG$^6$ represents a suitable leaving group such as halo or trifluoromethanesulfonate, FG$^1$, R$^5$, X$^2$ and X$^3$ are as hereinbefore defined, with a compound of formula XXIVa, XXIVb or XXIVc, H—S—R$^{6b}$        XXIVa M$^+$O$^-$—S(O)—R$^{6b}$        XXIVb H—C≡C—R$^{6x}$        XXIVc wherein R$^{6x}$ represents (R$^a$)(R$^b$)(R$^c$)Si or C$_{1-4}$ alkyl optionally substituted by one or more halo atoms, R$^a$ to R$^c$ are C$_{1-6}$ alkyl groups (such as isopropyl) and R$^{6b}$, R$^{6f}$ and M$^+$ are as hereinbefore defined, under conditions known to those skilled in the art (e.g. in the presence of a Pd(0) catalyst, Cu(I) iodide and a suitable base), followed by when FG$^1$ represents NH-PG$^2$, removal of the PG$^2$ protecting group, when FG$^1$ represents NO$_2$, reduction of NO$_2$ to NH$_2$ or when FG$^1$ represents C(O)O—(C$_{1-6}$ alkyl), saponification to provide the corresponding carboxylic acid and then reaction with a suitable azide-forming agent and thermal rearrangement of the resulting acyl azide (see, for example, process (b) above).

(vi) For compounds of formula VII in which R$^4$ represents
—N=S(O)R$^{6g}$R$^{6h}$, reaction of a compound of formula XXV

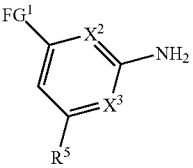

XXV wherein FG¹, R⁵, X² and X³ are as hereinbefore defined, with a compound of formula XXVI, S(O)R$^{6g}$R$^{6h}$  XXVI wherein R$^{6g}$ and R$^{6h}$ are as hereinbefore defined, under conditions known to those skilled in the art (e.g. in the presence of an oxidant such as a $C_{1-6}$ alkyl hypohalite (e.g. tert-butyl hypochlorite)), followed by
when FG¹ represents NH-PG², removal of the PG² protecting group,
when FG¹ represents NO₂, reduction of NO₂ to NH₂ or when FG¹ represents C(O)O—($C_{1-6}$ alkyl), saponification to provide the corresponding carboxylic acid and then reaction with a suitable azide-forming agent and thermal rearrangement of the resulting acyl azide (see, for example, process (b) above).

(vii) For compounds of formula VII in which R⁴ represents
-Q¹-[CH₂(CH₂)$_{0-1}$CH₂—O]$_{1-12}$—CH₂(CH₂)$_{0-1}$CH₂—R$^{6a}$
wherein Q¹ and R$^{6a}$ are as hereinbefore defined, reaction of a compound of formula XXVII

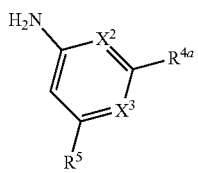

XXVII in which R$^{4a}$ represents
-Q¹-[CH₂(CH₂)$_{0-1}$CH₂—O]$_x$—CH₂(CH₂)$_{0-1}$CH₂—OH
with a compound of formula XXVIII, LG⁵-[CH₂(CH₂)$_{0-1}$CH₂—O]—CH₂(CH₂)$_{0-1}$CH₂—R$^{6a}$  XXVIII wherein x and y are integers from 0 to 11, the sum of x and y being from 0 to 11, and Q¹, LG⁵ and R$^{6a}$ are as hereinbefore defined, under conditions known to those skilled in the art (e.g. at ambient temperature in the presence of a base such as sodium hydride and a polar organic solvent such as DMF).

(viii) For compounds of formula VII in which X² and X³ both represent CH and R⁴ represents
—S—CH₂—[$C_{1-5}$ alkylene]-N(R$^{6c}$)R$^{6d}$
reaction of a compound of formula XXIX,

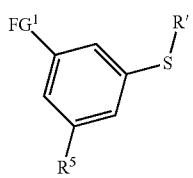

XXIX wherein R' represents
—CH₂—[$C_{1-5}$ alkylene]-LG⁶
with a compound of formula HN(R$^{6c}$)R$^{6d}$, wherein FG¹, R⁵, R$^{6c}$, R$^{6d}$ and LG⁶ are as hereinbefore defined, under conditions known to those skilled in the art (for example in the presence of a suitable organic solvent (e.g. acetone) and, optionally, catalyst for nucleophilic displacement, such as an iodide salt (e.g. sodium iodide)), followed by
when FG¹ represents NH-PG², removal of the PG² protecting group,
when FG¹ represents NO₂, reduction of NO₂ to NH₂ or when FG¹ represents C(O)O—($C_{1-6}$ alkyl), saponification to provide the corresponding carboxylic acid and then reaction with a suitable azide-forming agent and thermal rearrangement of the resulting acyl azide (see, for example, process (b) above).

Compounds of formula XXIX in which LG⁶ represents halo can be prepared according to or by analogy with procedures known to those skilled in the art, for example by reaction of a compound of formula XXX,

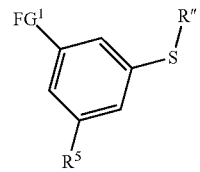

XXX wherein R" represents —CH₂—[$C_{1-5}$ alkylene]-OH, with a halogenating agent (e.g. a mixture of 2,4,6-trichloro,1,3,5-triazine and dimethylformamide).

It will be understood by persons skilled in the art that compounds represented by formulae II and IIb are generally reactive intermediates. These intermediates may be formed in situ and reacted directly, without isolation, with compounds of formula III to provide compounds of formula I. Furthermore, it will be understood by those skilled in the art that the use of appropriate protective groups may be required during the processes described above for any of the groups Z¹ and Z² which possess chemically-sensitive functional groups, for example, a hydroxyl group or an amino function.

Many of the compounds illustrated in the Schemes are either commercially available, or can be obtained using the cited procedures, or can be readily prepared by conventional methods by those skilled in the art. See for example Regan, J. et al.; *J. Med. Chem.* 2003, 46, 4676-4686, WO 2000/043384, WO 2007/053346, WO 2007/087448, WO 2007/089512 and WO 2009/117080.

The aspects of the invention described herein (e.g. the above-mentioned compounds, combinations, methods and uses) may have the advantage that, in the treatment of the conditions described herein, they may be more convenient for the physician and/or patient than, be more efficacious than, be less toxic than, have better selectivity over, have a broader range of activity than, be more potent than, produce fewer side effects than, have a better pharmacokinetic and/or pharmacodynamic profile than, have more suitable solid state morphology than, have better long term stability than, or may have other useful pharmacological properties over, similar compounds, combinations, methods (treatments) or uses known in the prior art for use in the treatment of those conditions or otherwise.

The compounds of the invention may additionally (or alternatively):
exhibit a long duration of action and/or persistence of action (e.g. in comparison to other previously disclosed p38 MAP kinase inhibitors such as, for example, BIRB796);
not strongly inhibit GSK 3α (e.g. they may have an IC$_{50}$ against GSK 3α of 1500 nM or greater; such as 2,000, 3,000, 4,000, 5,000, 6,000, 7,000, 8,000, 9,000 or 10,000 nM or greater);

maintain a relatively high drug concentration between doses (e.g. a high concentration relative to to other previously disclosed p38 MAP kinase inhibitors such as, for example, BIRB796); and/or establish and maintain a relatively high drug concentration in a target tissue following (e.g. topical) administration (e.g. a high concentration relative to to other previously disclosed p38 MAP kinase inhibitors such as, for example, BIRB796).

EXPERIMENTAL METHODS

General Procedures

All starting materials and solvents were obtained either from commercial sources or prepared according to the literature citation. Unless otherwise stated all reactions were stirred. Organic solutions were routinely dried over anhydrous magnesium sulfate. Hydrogenations were performed on a Thales H-cube flow reactor under the conditions stated or under a balloon of hydrogen. Microwave reactions were performed in a CEM Discover and Smithcreator microwave reactor, heating to a constant temperature using variable power microwave irradiation.

Normal phase column chromatography was routinely carried out on an automated flash chromatography system such as CombiFlash Companion or CombiFlash RF system using pre-packed silica (230-400 mesh, 40-63 μm) cartridges. SCX was purchased from Supelco and treated with 1M hydrochloric acid prior to use. Unless stated otherwise the reaction mixture to be purified was first diluted with MeOH and made acidic with a few drops of AcOH. This solution was loaded directly onto the SCX and washed with MeOH. The desired material was then eluted by washing with 1% $NH_3$ in MeOH.

Analytical Methods

Analytical HPLC was carried out using an Agilent Zorbax Extend C18, Rapid Resolution HT 1.8 μm column eluting with a gradient of either 0.1% formic acid in MeCN in 0.1% aqueous formic acid or a gradient of MeCN in 10 mM Ammonium Bicarbonate; a Waters Xselect CSH C18 3.5 μm eluting with a gradient of 0.1% formic acid in MeCN in 0.1% aqueous formic acid. UV spectra of the eluted peaks were measured using either a diode array or variable wavelength detector on an Agilent 1100 system.

Analytical LCMS was carried out using an Agilent Zorbax Extend C18, Rapid Resolution HT 1.8 μm column eluting with a gradient of either 0.1% formic acid in MeCN in 0.1% aqueous formic acid or a gradient of MeCN in 10 mM Ammonium Bicarbonate; a Waters Xselect CSH C18 3.5 μm eluting with a gradient of 0.1% formic acid in MeCN in 0.1% aqueous formic acid. UV and mass spectra of the eluted peaks were measured using a variable wavelength detector on either an Agilent 1100 with or an Agilent Infinity 1260 LC with 6120 quadrupole mass spectrometer with positive and negative ion electrospray.

Preparative HPLC was carried out using an Agilent Prep-C18 5 μm Preparative Cartridge using either a gradient of either 0.1% formic acid in MeCN in 0.1% aqueous formic acid or a gradient of MeCN in 10 mM Ammonium Bicarbonate; or a Waters Xselect CSH C18 5 μm column using a gradient 0.1% MeCN in 0.1% aqueous formic acid. Fractions were collected following detection by UV at 254 nm.

$^1$H NMR Spectroscopy: $^1$H NMR spectra were acquired on a Bruker Avance III spectrometer at 400 MHz. Either the central peaks of chloroform-d, dimethylsulfoxide-$d_6$ or an internal standard of tetramethylsilane were used as references.

Preparation of Compounds of the Invention

Example 1

1-(3-(tert-Butyl)-1-(6-methoxypyridin-3-yl)-1H-pyrazol-5-yl)-3-(4-((2-((3-ethynylphenyl)-amino)pyrimidin-4-yl)oxy)naphthalen-1-yl)urea

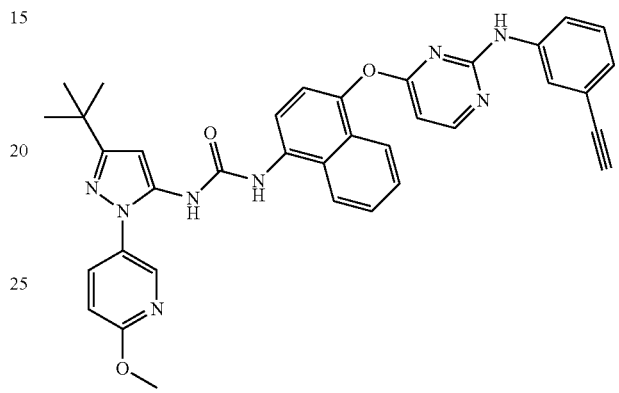

(i) Phenyl (4-((2-chloropyrimidin-4-yl)oxy)naphthalen-1-yl)carbamate

Phenyl chloroformate (2.65 mL, 21.06 mmol) was added to a stirred mixture of 4-((2-chloropyrimidin-4-yl)oxy)naphthalen-1-amine (see, for example, Cirillo, P. F. et al., WO 2002/92576, 21 Nov. 2000; 5.45 g, 20.06 mmol) and sodium bicarbonate (3.37 g, 40.1 mmol) in DCM (50 mL) and THF (20 mL) at rt. The mixture was stirred for 18 h then a further portion of phenyl chloroformate added (0.5 mL) and left for 2 h. The mixture was partitioned between DCM (300 mL) and brine (200 mL), the organic phase separated, dried ($MgSO_4$) and evaporated under reduced pressure. The residue was triturated with ether/isohexane to afford the sub-title compound (7.38 g) as a light pink solid.

1H NMR (DMSO-d6) 400 MHz, δ: 10.28 (s, 1H), 8.68 (d, 1H), 8.29 (d, 1H), 7.84 (d, 1H), 7.76 (d, 1H), 7.72-7.68 (m, 1H), 7.64-7.60 (m, 1H), 7.51-7.44 (m, 3H), 7.33-7.26 (m, 4H).

(ii) 1-(3-(tert-Butyl)-1-(6-methoxypyridin-3-yl)-1H-pyrazol-5-yl)-3-(4-((2-chloropyrimidin-4-yl)oxy)naphthalen-1-yl)urea DMAP (0.099 g, 0.812 mmol) was added to a stirred solution of 3-(tert-butyl)-1-(6-methoxypyridin-3-yl)-1H-pyrazol-5-amine (see, for example, Abraham, S. et al., WO 2009/117080, 24 Sep. 2009; 2 g, 8.12 mmol) and the product from step (i) above (3.34 g, 8.53 mmol) in THF (30 mL) at rt under $N_2$. The mixture was stirred at rt for 72 h then heated at 40° C. for 18 h. The mixture was partitioned between EtOAc (200 mL) and water (100 mL), the organic layer separated, dried ($MgSO_4$) and evaporated under reduced pressure. The crude product was purified by chromatography on silica gel (120 g column, 0-60% EtOAc/isohexane) to afford the sub-title compound (2.583 g) as a tan solid.

1H NMR (DMSO-d6) 400 MHz, δ: 9.12 (s, 1H), 8.84 (s, 1H), 8.66 (d, 1H), 8.40 (d, 1H), 8.08 (d, 1H), 7.93-7.90 (m, 2H), 7.80 (d, 1H), 7.68-7.57 (m, 2H), 7.43 (d, 1H), 7.28 (d, 1H), 7.04 (d, 1H), 6.44 (s, 1H), 3.95 (s, 3H), 1.29 (s, 9H).
LCMS m/z 544/6 (M+H)$^+$ (ES$^+$); 542/4 (M–H)$^-$ (ES$^-$)

(iii) 1-(3-(tert-Butyl)-1-(6-methoxypyridin-3-yl)-1H-pyrazol-5-yl)-3-(4-((2-((3-ethynylphenyl)amino)pyrimidin-4-yl)oxy)naphthalen-1-yl)urea The product from step (ii) above (150 mg, 0.276 mmol) was dissolved in DMF (1.5 mL) and added to p-TSA monohydrate (26.2 mg, 0.138 mmol) and 3-ethynylaniline (64.6 mg, 0.551 mmol). Stirred at 70° C. (block temperature) for 4 h then poured into saturated NaHCO$_3$ solution (10 mL). The solid was filtered off and washed with water (2 mL). The crude product was purified by chromatography on the Companion (40 g column, 20% EtOAc:isohexane to 100%) to afford product as a pale tan solid. Triturated with MeCN (4 mL) to give the title compound (163 mg) as a colourless solid.
1H NMR (400 MHz, DMSO-d6) δ 9.63 (s, 1H), 9.10 (s, 1H), 8.81 (s, 1H), 8.42 (m, 2H), 8.06 (m, 1H), 7.92 (m, 2H), 7.82 (m, 1H), 7.59 (m, 3H), 7.41 (m, 2H), 7.03 (dd, 1H), 6.94 (m, 2H), 6.61 (d, 1H), 6.44 (s, 1H), 4.02 (s, 1H), 3.95 (s, 3H), 1.30 (s, 9H).
LCMS m/z 625 (M+H)$^+$ (ES$^+$)

Example 2

S,S-Dimethyl-N-(4-((4-((4-(3-(3-(tert-butyl)-1-(6-methoxypyridin-3-yl)-1H-pyrazol-5-yl)-ureido)naphthalen-1-yl)oxy)pyrimidin-2-yl)amino)phenyl sulfoximine

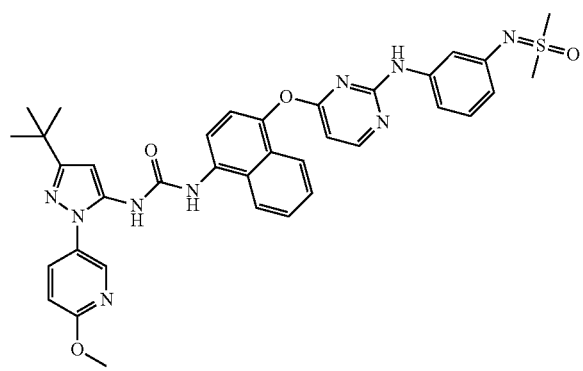 [SMILES: COc1ccc(-n2nc(C(C)(C)C)cc2NC(=O)Nc2ccc(Oc3ccnc(Nc4cccc(N=S(C)(C)=O)c4)n3)c3ccccc23)cn1]

(i) S,S-Dimethyl-N-(3-nitrophenyl)-sulfoximine

A solution of DMSO (5 mL, 70.5 mmol) in DCM (15 mL) was added slowly to a stirred solution of tert-butyl hypochlorite (2.61 g, 24 mmol) in DCM (40 mL) at −60° C. under N$_2$. The mixture was stirred for 1 h then a mixture of 3-nitroaniline (2.76 g, 20 mmol) in DCM (80 mL) was added. After stirring for 6 h at −50° C., a solution of Et$_3$N (5 mL, 35.9 mmol) in DCM (10 mL) was added and the mixture allowed to warm to rt. The solvent was evaporated under reduced pressure and the residue partitioned between EtOAc (200 mL) and water (200 mL). The organic layer was separated, washed with brine, dried (MgSO$_4$) and evaporated under reduced pressure. The crude product was purified by chromatography on silica gel (80 g column, 10-80% EtOAc/isohexane) to afford the sub-title compound (1.237 g) as a yellow solid.
1H NMR (400 MHz; CDCl$_3$) δ 7.89-7.88 (m, 1H), 7.83-7.81 (m, 1H), 7.41-7.35 (m, 2H), 3.21 (s, 6H).
LCMS m/z 215 (M+H)$^+$ (ES$^+$)

(ii) S,S-Dimethyl-N-(3-aminophenyl)-sulfoximine

A stirred mixture of the product from step (i) above (1.23 g, 5.74 mmol) and 10% Pd/C (200 mg) in EtOH (25 mL) was hydrogenated under a balloon of hydrogen for 5 h. The mixture was flushed with nitrogen, filtered and evaporated under reduced pressure to afford the sub-title compound (1.006 g) as solid.
1H NMR (DMSO-d6) 400 MHz, δ: 6.80 (t, 1H), 6.22 (s, 1H), 6.12-6.09 (m, 2H), 4.86 (s, 2H), 3.15 (s, 6H).

(iii) S,S-Dimethyl-N-(4-((4-((4-(3-(3-(tert-butyl)-1-(6-methoxypyridin-3-yl)-1H-pyrazol-5-yl)ureido)naphthalen-1-yl)oxy)pyrimidin-2-yl)amino)phenyl sulfoximine A mixture of 1-(3-(tert-butyl)-1-(6-methoxypyridin-3-yl)-1H-pyrazol-5-yl)-3-(4-((2-chloro pyrimidin-4-yl)oxy)naphthalen-1-yl)urea (see Example 1(ii) above; 150 mg, 0.276 mmol), the product from step (ii) above (102 mg, 0.551 mmol) and p-TSA monohydrate (26.2 mg, 0.138 mmol) in THF (1 mL) and DMF (1 mL) was heated at 70° C. (bath temperature) for 18 h. The mixture was diluted with water (4 mL) and saturated NaHCO$_3$ solution (4 mL) was added. The solvents were decanted to leave a sticky solid. The solid was purified by chromatography on the Companion (40 g column, 0-8% CH$_3$OH:CH$_2$Cl$_2$) to afford a solid. The solid was triturated in acetonitrile then purified by preparative HPLC (Gilson, Acidic (0.1% Formic acid), Agilent Prep C-18, 5 μm, 21.2×50 mm column, 5-95% MeCN in Water) to afford the title compound (49 mg) as a pale pink solid.
1H NMR (400 MHz; DMSO-d6) δ 9.35 (s, 1H), 9.12 (s, 1H), 8.82 (s, 1H), 8.40 (d, 1H), 8.35 (d, 1H), 8.05 (d, 1H), 9.92 (dd, 1H), 7.90 (d, 1H), 7.81 (d, 1H), 7.62 (t, 1H), 7.56 (t, 1H), 7.39 (d, 1H), 7.07 (s, 1H), 7.01 (d, 1H), 6.97-6.85 (m, 1H), 6.75 (t, 1H), 6.48 (d, 1H), 6.46-6.41 (m, 2H), 3.94 (s, 3H), 3.16 (s, 6H), 1.29 (s, 9H).
LCMS m/z 692 (M+H)$^+$ (ES$^+$); 690 (M–H)$^-$ (ES$^-$)

Example 3

3-(4-((4-(3-(3-(tert-Butyl)-1-(6-methoxypyridin-3-yl)-1H-pyrazol-5-yl)ureido)naphthalen-1-yl)oxy)pyrimidin-2-yl)amino)phenyl methanesulfonate

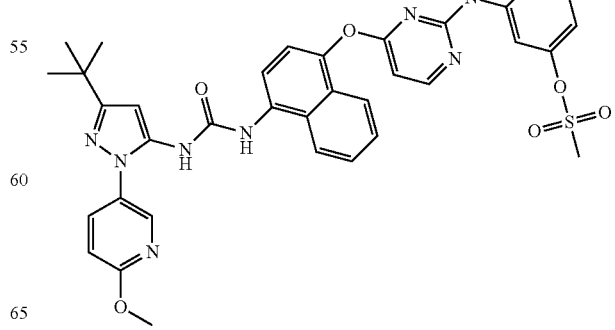

(i) 3-Aminophenyl methanesulfonate

3-Nitrophenyl methanesulfonate (3.09 g, 14.23 mmol) and 10% Pd/C (1.514 g, 1.423 mmol) were stirred in ethanol under a balloon of hydrogen overnight. Fresh catalyst was added and the mixture was left to stir for a further 6 h. The catalyst was removed by filtration and the filtrate was stirred overnight with fresh catalyst and hydrogen. The catalyst was removed by filtration and the filtrate was concentrated to yield a yellow solid. The solid was recrystallised in isopropanol to afford the sub-title compound (1350 mg) as a cream solid.

1H NMR (400 MHz; DMSO-d6) δ 7.07 (dd, 1H), 6.53 (ddd, 1H), 6.49 (dd, 1H), 6.42 (ddd, 1H), 5.45 (s, 2H), 3.31 (s, 3H).

LCMS m/z 188 (M+H)$^+$ (ES$^+$)

(ii) 3-(4-((4-(3-(3-(tert-Butyl)-1-(6-methoxypyridin-3-yl)-1H-pyrazol-5-yl)ureido)-naphthalen-1-yl)oxy)pyrimidin-2-yl)amino)phenyl methanesulfonate 1-(3-(tert-Butyl)-1-(6-methoxypyridin-3-yl)-1H-pyrazol-5-yl)-3-(4-((2-chloropyrimidin-4-yl)-oxy)naphthalen-1-yl)urea (see Example 1(ii) above; 150 mg, 0.276 mmol) was dissolved in DMF (1.5 mL) and added to p-TSA monohydrate (26.2 mg, 0.138 mmol) and the product from step (i) above (103 mg, 0.551 mmol). Stirred at 70° C. (block temperature) for 4 h then poured into saturated NaHCO$_3$ solution (10 mL). The solid was filtered off and washed with water (2 mL). The crude product was purified by chromatography on the Companion (40 g column, 50% EtOAc/ isohexane to 100%) to afford the title compound (60 mg) as a pale tan solid.

1H NMR (400 MHz, DMSO-d6) δ 9.76 (s, 1H), 9.10 (s, 1H), 8.81 (s, 1H), 8.42 (m, 2H), 8.06 (d, 1H), 7.92 (m, 2H), 7.81 (m, 1H), 7.60 (m, 2H), 7.51 (s, 1H), 7.42 (d, 1H), 7.33 (d, 1H), 7.04 (m, 2H), 6.82 (m, 1H), 6.64 (d, 1H), 6.44 (s, 1H), 3.94 (s, 3H), 3.29 (s, 3H), 1.29 (s, 9H).

LCMS m/z 695 (M+H)$^+$ (ES$^+$)

Example 4

1-(3-(tert-Butyl)-1-(6-methoxypyridin-3-yl)-1H-pyrazol-5-yl)-3-(4-((2-((3-(2-(2-(2-methoxy- ethoxy)ethoxy)ethoxy)phenyl)amino)pyrimidin-4-yl)oxy)naphthalen-1-yl)urea

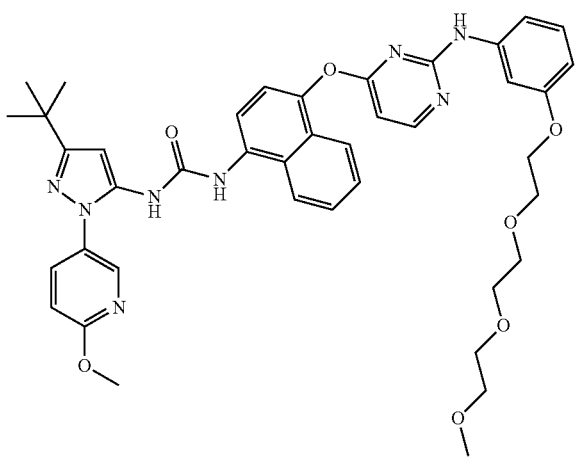 [SMILES: COCCOCCOCCOc1cccc(Nc2nccc(Oc3ccc(NC(=O)Nc4cc(C(C)(C)C)nn4-c4ccc(OC)nc4)c4ccccc34)n2)c1]

(i) 1-(2-(2-(2-Methoxyethoxy)ethoxy)ethoxy)-3-nitrobenzene

1-Bromo-2-(2-(2-methoxyethoxyl)ethoxy)ethane (1.371 mL, 7.91 mmol) was added to a vigorously stirred suspension of K$_2$CO$_3$ (2.98 g, 21.57 mmol) and 3-nitrophenol (1 g, 7.19 mmol) in acetone (20 mL). Heated at reflux overnight then filtered and solvents evaporated to a yellow oil. Redissolved in diethyl ether (20 mL) and solids filtered off. Solvents evaporated to afford the sub-title compound (2 g) as a yellow oil.

1H NMR (400 MHz, CDCl$_3$) δ 7.82 (ddd, 1H), 7.76 (t, 1H), 7.42 (t, 1H), 7.26 (m, 1H), 4.21 (m, 2H), 3.90 (m, 2H), 3.75 (m, 2H), 3.68 (m, 4H), 3.55 (m, 2H), 3.38 (s, 3H).

LCMS m/z 286 (M+H)$^+$ (ES$^+$)

(ii) 3-(2-(2-(2-Methoxyethoxyl)ethoxy)ethoxy)aniline

The product from step (i) above (2 g, 7.01 mmol) was dissolved in ethanol (40 mL) and iron powder (3.91 g, 70.1 mmol) added, followed by ammonium chloride (3.75 g, 70.1 mmol) in water (20 mL). Sonicated at 60° C. (bath temperature) for 1 h before the mixture was filtered on Celite and the solvents evaporated. The residue was then partitioned between 1N HCl (20 mL) and ethyl acetate (20 mL), and the aqueous layer was separated and basified to pH 8 with NaHCO$_3$. The aqueous layer was then extracted with ethyl acetate (2×20 mL). The combined organic layers from the extraction were then dried (MgSO$_4$), filtered then the solvent evaporated to afford the sub-title compound (1.8 g)

1H NMR (400 MHz, DMSO-d6) δ 6.89 (t, 1H), 6.14 (m, 2H), 6.07 (ddd, 1H), 5.02 (s, 2H), 3.96 (m, 2H), 3.70 (m, 2H), 3.54 (m, 6H), 3.43 (m, 2H), 3.24 (s, 3H).

LCMS m/z 256 (M+H)$^+$ (ES$^+$)

(iii) 1-(3-(tert-Butyl)-1-(6-methoxypyridin-3-yl)-1H-pyrazol-5-yl)-3-(4-((2-((3-(2-(2-(2-methoxyethoxyl)ethoxy)ethoxy)phenyl)amino)pyrimidin-4-yl)oxy)naphthalen-1-yl)urea 1-(3-(tert-Butyl)-1-(6-methoxypyridin-3-yl)-1H-pyrazol-5-yl)-3-(4-((2-chloropyrimidin-4-yl)-oxy)naphthalen-1-yl)urea (see Example 1(ii) above; 150 mg, 0.276 mmol) was dissolved in DMF (1.5 mL) and added to p-TSA monohydrate (26.2 mg, 0.138 mmol) and the product from step (ii) above (141 mg, 0.551 mmol). Stirred at 70° C. (block temperature) for 4 h then poured into saturated NaHCO$_3$ solution (10 mL). The solid was filtered off and washed with water (2 mL). The crude product was purified by preparative HPLC (Varian, Acidic (0.1% Formic acid), Waters X-Select Prep-C18, 5 μm, 19×50 mm column, 25-80% MeCN in Water) to afford the title compound (23 mg) as a colourless solid.

1H NMR (400 MHz, DMSO-d6) δ 9.49 (s, 1H), 9.10 (s, 1H), 8.81 (s, 1H), 8.41 (m, 2H), 8.05 (d, 1H), 7.92 (m, 2H), 7.82 (m, 1H), 7.60 (m, 2H), 7.40 (d, 1H), 7.14 (s, 1H), 7.04 (d, 1H), 6.96 (s, 1H), 6.87 (m, 1H), 6.55 (d, 1H), 6.44 (m, 2H), 3.95 (s, 3H), 3.88 (m, 2H), 3.66 (t, 2H), 3.51 (m, 6H), 3.40 (m, 2H), 3.21 (s, 3H), 1.29 (s, 9H).

LCMS m/z 763 (M+H)$^+$ (ES$^+$)

Example 5

3-(4-((4-(3-(3-(tert-Butyl)-1-(6-methoxypyridin-3-yl)-1H-pyrazol-5-yl)ureido)naphthalen-1-yl)oxy)pyrimidin-2-yl)amino)phenyl carbamate

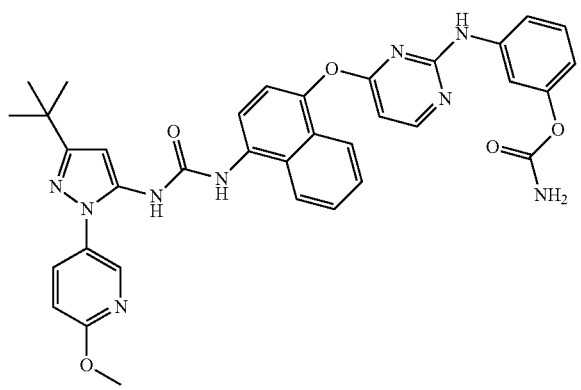 [SMILES: COc1ccc(-n2nc(C(C)(C)C)cc2NC(=O)Nc2ccc(Oc3ccnc(Nc4cccc(OC(N)=O)c4)n3)c3ccccc23)cn1]

(i) 3-Nitrophenyl carbamate

Potassium cyanate (1.166 g, 14.38 mmol) was added to a stirred solution of 3-nitrophenol (1 g, 7.19 mmol) in DCM (10 mL) at 35° C. in a sealed tube. After stirring for 5 minutes, trifluoroacetic acid (1.135 mL, 14.74 mmol) was added dropwise via a syringe. The reaction mixture was stirred at 35° C. overnight. The mixture was diluted with DCM (20 mL) then washed with water (3×30 mL). The solvent was removed under reduced pressure and the residue was purified by chromatography on the Companion (40 g column, 0-50% EtOAc/Hexanes) to afford 3-nitrophenyl carbamate (239 mg) as a white glass.

1H NMR (400 MHz; DMSO-d6) δ 8.08 (ddd, 1H), 7.97 (dd, 1H), 7.68 (dd, 1H), 7.62 (dd, 1H), 7.46 (br s, 1H), 7.18 (br s, 1H).

(ii) 3-Aminophenyl carbamate

The product from step (i) above (235 mg, 1.290 mmol) and 10% Pd/C (34.3 mg, 0.032 mmol) were stirred in ethanol under a balloon of hydrogen overnight. The catalyst was removed by filtration and the filtrate was concentrated under reduced pressure. The residue was purified by chromatography on the Companion (4 g column, 0-100% EtOAc/Hexanes) to afford the sub-title compound (45 mg) as a glass.

1H NMR (400 MHz; DMSO-d6) δ 7.01 (br s, 1H), 6.96 (t, 1H), 6.74 (br s, 1H), 6.37 (dd, 1H), 6.26 (dd, 1H), 6.19 (dd, 1H), 5.16 (s, 2H).

(iii) 3-(4-((4-(3-(3-(tert-Butyl)-1-(6-methoxypyridin-3-yl)-1H-pyrazol-5-yl)ureido)-naphthalen-1-yl)oxy)pyrimidin-2-yl)amino)phenyl carbamate A mixture of 1-(3-(tert-butyl)-1-(6-methoxypyridin-3-yl)-1H-pyrazol-5-yl)-3-(4-((2-chloropyrimidin-4-yl)oxy)naphthalen-1-yl)urea (see Example 1(ii) above; 150 mg, 0.276 mmol), the product from step (ii) above (44.1 mg, 0.290 mmol) and p-TSA monohydrate (26.2 mg, 0.138 mmol) in DMF (2 mL) was heated at 70° C. (bath temperature) for 18 h. Water (4 mL) was added followed by saturated sodium hydrogen carbonate solution (4 mL). The mixture was extracted with ethyl acetate (3×5 mL) and the combined organic phases were concentrated onto silica gel. The silica gel mixture was purified by chromatography on the Companion (40 g column, 0-8% CH₃OH:CH₂Cl₂) to afford an off white solid. The solid was purified by preparative HPLC (Gilson, Acidic (0.1% Formic acid), Agilent Prep C-18, 5 μm, 21.2×50 mm column, 5-95% MeCN in Water) to afford the title compound (12 mg) as an off white solid.

1H NMR (400 MHz; DMSO-d6) δ 9.35 (s, 1H), 8.85 (s, 1H), 8.55 (s, 1H), 8.16-8.09 (m, 2H), 7.82 (d, 1H), 7.68 (dd, 1H), 7.67 (d, 1H), 7.58 (d, 1H), 7.42-7.36 (m, 1H), 7.36-7.29 (m, 1H), 7.17 (d, 1H), 7.06-6.99 (m, 1H), 6.99-6.91 (m, 1H), 6.88-6.73 (m, 1H), 6.79 (dd, 1H), 6.73-6.65 (m, 1H), 6.64-6.53 (m, 1H), 6.33 (d, 1H), 6.32 (dd, 1H), 6.20 (s, 1H), 3.71 (s, 3H), 1.06 (s, 9H).

LCMS m/z 660 (M+H)⁺ (ES⁺); 615 (M-C(O)NH2)⁻ (ES⁻)

Example 6

1-(3-(tert-Butyl)-1-(6-methoxypyridin-3-yl)-1H-pyrazol-5-yl)-3-(4-((2-((3-(2-hydroxyethyl)-thio)phenyl)amino)pyrimidin-4-yl)oxy)naphthalen-1-yl)urea

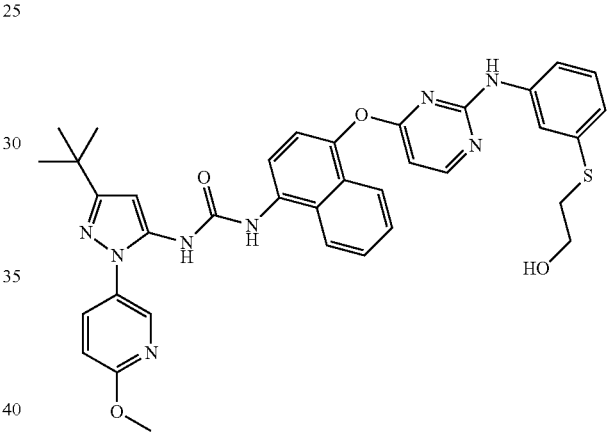

1-(3-(tert-butyl)-1-(6-methoxypyridin-3-yl)-1H-pyrazol-5-yl)-3-(4-((2-chloropyrimidin-4-yl)-oxy)naphthalen-1-yl)urea (see Example 1(ii) above; 150 mg, 0.276 mmol) was dissolved in DMF (1.5 mL) and added to 2-((3-aminophenyl)thio)ethanol (93 mg, 0.551 mmol) and p-TSA monohydrate (26.2 mg, 0.138 mmol). Stirred at 70° C. (block temperature) for 4 h then poured into saturated NaHCO₃ solution (10 mL). The product was extracted with EtOAc (2×20 mL), organics separated and bulked then washed with 20% w/w NaCl solution. The organic layer separated, dried (MgSO₄), filtered and solvent evaporated to give a brown gum. The crude product was purified by chromatography on the Companion (40 g column, 30% EtOAc:isohexane to 100%) to afford the product as a colourless solid which was purified by preparative HPLC (Varian, Acidic (0.1% Formic acid), Waters X-Select Prep-C18, 5 μm, 19×50 mm column, 25-80% MeCN in Water) to afford the title compound (95 mg) as a colourless solid.

1H NMR (400 MHz, DMSO-d6) δ 9.52 (s, 1H), 9.25 (s, 1H), 8.99 (s, 1H), 8.40 (m, 2H), 8.07 (d, 1H), 7.91 (m, 2H), 7.80 (m, 1H), 7.58 (m, 2H), 7.43 (s, 1H), 7.39 (d, 1H), 7.17 (s, 1H), 7.02 (dd, 1H), 6.89 (t, 1H), 6.77 (d, 1H), 6.58 (d, 1H), 6.43 (s, 1H), 4.89 (t, 1H), 3.93 (s, 3H), 3.50 (dd, 2H), 2.90 (t, 2H), 1.29 (s, 9H).

LCMS m/z 677 (M+H)⁺ (ES⁺); 675 (M-H)⁻ (ES⁻)

Example 7

1-(3-(tert-Butyl)-1-(6-methoxypyridin-3-yl)-1H-pyrazol-5-yl)-3-(4-((2-((3-(cyclopropyl-sulfinyl)phenyl)amino)pyrimidin-4-yl)oxy)naphthalen-1-yl)urea

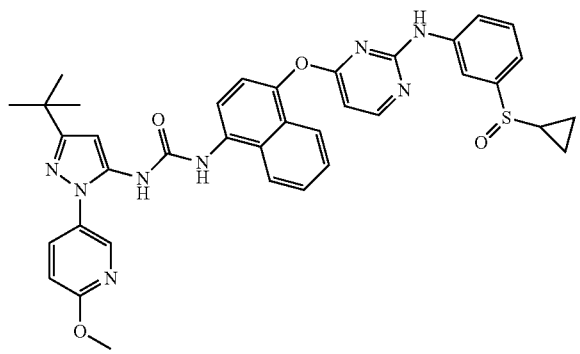 [SMILES: COc1ccc(-n2nc(C(C)(C)C)cc2NC(=O)Nc2ccc(Oc3ccnc(Nc4cccc(S(=O)C5CC5)c4)n3)c3ccccc23)cn1]

(i) 3-(Cyclopropylthio)aniline

3-Aminobenzenethiol (0.899 mL, 8.47 mmol) was dissolved in DMF (10 mL) and NaH, 60% w/w (0.356 g, 8.89 mmol) added portionwise. Stirred for 60 min before addition of cyclopropyl bromide (0.712 mL, 8.89 mmol). Heated to 100° C. for 4 h then the reaction mixture was poured into 1N HCl (50 mL) and extracted with ethyl acetate (50 mL). Aqueous layer separated and basified with NaHCO$_3$ to pH 8. Product extracted with ethyl acetate (2×50 mL), organics bulked, dried MgSO$_4$, filtered and solvents evaporated to give a brown oil. The crude product was purified by chromatography on silica gel (40 g column, 1% MeOH:DCM) to afford the sub-title compound (700 mg) as a pale yellow oil.

1H NMR (400 MHz, DMSO-d6) δ 6.94 (t, 1H), 6.57 (t, 1H), 6.48 (ddd, 1H), 6.35 (ddd, 1H), 5.11 (s, 2H), 2.17 (tt, 1H), 1.04 (m, 2H), 0.55 (dt, 2H).

LCMS m/z 166 (M+H)$^+$ (ES$^+$)

(ii) 1-(3-(tert-Butyl)-1-(6-methoxypyridin-3-yl)-1H-pyrazol-5-yl)-3-(4-((2-((3-(cyclopropylthio)phenyl)amino)pyrimidin-4-yl)oxy)naphthalen-1-yl)urea 1-(3-(tert-Butyl)-1-(6-methoxypyridin-3-yl)-1H-pyrazol-5-yl)-3-(4-((2-chloropyrimidin-4-yl)oxy)naphthalen-1-yl)urea (see Example 1(ii) above; 150 mg, 0.276 mmol) was dissolved in DMF (1.5 mL) and added to p-TSA monohydrate (26.2 mg, 0.138 mmol) and the product from step (i) above (91 mg, 0.551 mmol). Stirred at 70° C. (block temperature) for 4 h then poured into saturated NaHCO$_3$ solution (10 mL). The solid was filtered off and washed with water (2 mL). The crude product was purified by chromatography on the Companion (40 g column, 20% EtOAc/isohexane to 100%) to afford product as a pale tan solid. Triturated with MeCN (4 mL) to afford the sub-title compound (147 mg) as a colourless solid.

1H NMR (400 MHz, DMSO-d6) δ 9.55 (s, 1H), 9.10 (s, 1H), 8.81 (s, 1H), 8.41 (m, 2H), 8.07 (d, 1H), 7.93 (m, 2H), 7.81 (m, 1H), 7.60 (m, 2H), 7.50 (s, 1H), 7.40 (d, 1H), 7.14 (d, 1H), 7.04 (d, 1H), 6.92 (t, 1H), 6.82 (d, 1H), 6.58 (d, 1H), 6.44 (s, 1H), 3.95 (s, 3H), 2.09 (td, 1H), 1.30 (s, 9H), 1.02 (m, 2H), 0.52 (m, 2H).

LCMS m/z 673 (M+H)$^+$ (ES$^+$)

(iii) 1-(3-(tert-Butyl)-1-(6-methoxypyridin-3-yl)-1H-pyrazol-5-yl)-3-(4-((2-((3-(cyclopropylsulfinyl)phenyl)amino)pyrimidin-4-yl)oxy)naphthalen-1-yl)urea A solution of mCPBA (38.5 mg, 0.156 mmol) in DCM (1 mL) was added to a stirred solution of the product from step (ii) above (70 mg, 0.104 mmol) in DCM (1 mL) and MeOH (0.1 mL) at 0-5° C. under N$_2$. The mixture was warmed to rt and stirred for 18 h. A further portion of mCPBA (10 mg) was added, stirred for 4 h then evaporated under reduced pressure. The crude product was purified by preparative HPLC (Waters, Acidic (0.1% Formic acid), Waters X-Select Prep-C18, 5 μm, 19×50 mm column, 40-60% MeCN in Water) then by chromatography on silica gel (4 g column, 0-4% MeOH/DCM) to afford the title compound (9 mg) as a solid.

1H NMR (DMSO-d6) 400 MHz, δ: 9.82 (s, 1H), 9.12 (s, 1H), 8.84 (s, 1H), 8.46-8.41 (m, 2H), 8.08 (d, 1H), 7.97 (d, 1H), 7.93 (dd, 1H), 7.82 (d, 1H), 7.71 (br s, 1H), 7.65-7.55 (m, 2H), 7.44 (br s, 1H), 7.42 (d, 1H), 7.19-7.15 (m, 1H), 7.10 (d, 1H), 7.04 (d, 1H), 6.66 (d, 1H), 6.45 (s, 1H), 3.95 (s, 3H), 2.20-2.13 (m, 1H), 1.30 (s, 9H), 0.94-0.72 (m, 4H).

LCMS m/z 689 (M+H)$^+$ (ES$^+$); 592 (M−H)$^-$ (ES$^-$)

Example 8

1-(3-(tert-Butyl)-1-(6-methoxypyridin-3-yl)-1H-pyrazol-5-yl)-3-(4-((2-((3-(cyclopropyl-sulfonyl)phenyl)amino)pyrimidin-4-yl)oxy)naphthalen-1-yl)urea

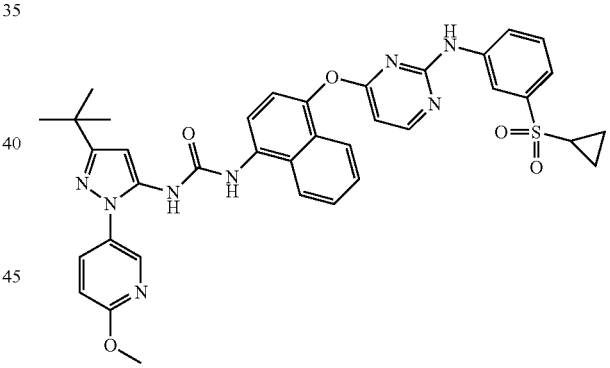

A solution of mCPBA (38.5 mg, 0.156 mmol) in DCM (1 mL) was added to a stirred solution of 1-(3-(tert-butyl)-1-(6-methoxypyridin-3-yl)-1H-pyrazol-5-yl)-3-(4-((2-((3-(cyclopropylthio)phenyl)amino)pyrimidin-4-yl)oxy)naphthalen-1-yl)urea (see Example 7(ii) above; 70 mg, 0.104 mmol) in DCM (1 mL) and MeOH (0.1 mL) at 0-5° C. under N$_2$. The mixture was warmed to rt and stirred for 18 h. A further portion of mCPBA (10 mg) was added, stirred for 4 h then evaporated under reduced pressure. The crude product was purified by preparative HPLC (Waters, Acidic (0.1% Formic acid), Waters X-Select Prep-C18, 5 μm, 19×50 mm column, 40-60% MeCN in Water) then by chromatography on silica gel (4 g column, 0-3% MeOH/DCM) to afford the title compound (13 mg) as a solid.

1H NMR (DMSO-d6) 400 MHz, δ: 9.88 (s, 1H), 9.10 (s, 1H), 8.79 (s, 1H), 8.46 (d, 1H), 8.42 (d, 1H), 8.07-8.05 (m, 2H), 7.94-7.90 (m, 2H), 7.82 (d, 1H), 7.68-7.55 (m, 3H), 7.42 (d, 1H), 7.32 (d, 1H), 7.23-7.19 (m, 1H), 7.04 (d, 1H), 6.66 (d, 1H), 6.44 (s, 1H), 3.95 (s, 3H), 2.72-2.66 (m, 1H), 1.30 (s, 9H), 1.08-0.98 (m, 4H).

LCMS m/z 705 (M+H)+ (ES+)

Example 9

1-(3-Isopropyl-1-(P-tolyl)-1H-pyrazol-5-yl)-3-(4-((2-((3-(2-(2-(2-methoxyethoxy)ethoxy)-ethoxy) phenyl)amino)pyrimidin-4-yl)oxy)naphthalen-1-yl) urea

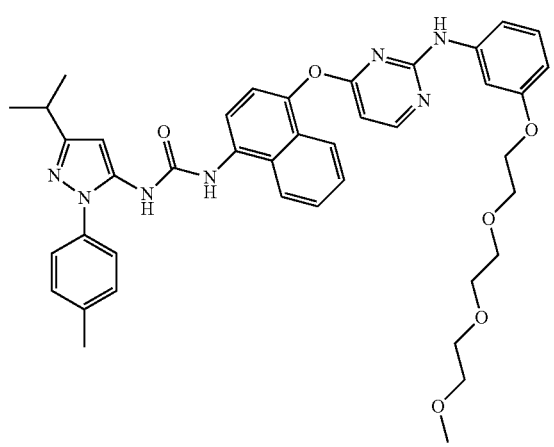 [SMILES: COCCOCCOCCOc1cccc(Nc2nccc(Oc3ccc(NC(=O)Nc4cc(C(C)C)nn4-c4ccc(C)cc4)c4ccccc34)n2)c1]

(i) 1-(4-((2-Chloropyrimidin-4-yl)oxy)naphthalen-1-yl)-3-(3-isopropyl-1-(p-tolyl)-1H-pyrazol-5-yl)urea DMAP (0.187 g, 1.531 mmol) was added to a solution of phenyl (4-((2-chloropyrimidin-4-yl)oxy)naphthalen-1-yl) carbamate (see Example 1(i) above; 3 g, 7.66 mmol) and 3-isopropyl-1-(p-tolyl)-1H-pyrazol-5-amine (1.731 g, 8.04 mmol) in THF (45 mL) and the reaction heated at reflux for 16 h. Cooled and solvent evaporated. The residue was triturated with diethyl ether (50 mL). The resultant precipitate was filtered to give a brown solid. The crude product was preabsorbed on silica and purified by chromatography on the Companion (80 g column, 20% EtOAc/isohexane to 100%) to afford the sub-title compound (2.1 g) as a colourless solid.

1H NMR (400 MHz, DMSO-d6) δ 9.14 (s, 1H), 8.81 (s, 1H), 8.66 (d, 1H), 8.09 (d, 1H), 7.96 (d, 1H), 7.80 (d, 1H), 7.63 (m, 2H), 7.43 (m, 5H), 7.27 (d, 1H), 6.38 (s, 1H), 2.90 (hept, 1H), 2.41 (s, 3H), 1.25 (d, 6H).

LCMS m/z 513/515 (M+H)+ (ES+)

(ii) 1-(3-Isopropyl-1-(P-tolyl)-1H-pyrazol-5-yl)-3-(4-((2-((3-(2-(2-(2-methoxyethoxy)ethoxy) ethoxy) phenyl)amino)pyrimidin-4-yl)oxy)naphthalen-1-yl) urea The product from step (i) above (150 mg, 0.292 mmol) was dissolved in DMF (1.5 mL) and added to p-TSA monohydrate (27.8 mg, 0.146 mmol) and 3-(2-(2-(2-methoxyethoxyl)ethoxy)ethoxy)aniline (see Example 4(ii) above; 149 mg, 0.585 mmol). Stirred at 70° C. (block temperature) for 4 h then poured into saturated NaHCO3 solution (20 mL) and the product extracted with EtOAc (2×20 mL). Organics bulked and washed with 20% w/w brine solution (20 mL), dried (MgSO4), filtered and evaporated to a brown solid. The crude product was preabsorbed onto silica (4 g) and then purified by chromatography on the Companion (40 g column, 20% EtOAc/isohexane to 100%) to afford the product as a pale brown solid (130 mg). This was further purified by preparative HPLC (Varian, Acidic (0.1% Formic acid), Agilent Prep C-18, 5 µm, 21.2×50 mm column, 25-80% MeCN in Water) to afford the title compound (25 mg) as a colourless solid.

1H NMR (400 MHz, DMSO-d6) δ 9.47 (s, 1H), 9.23 (s, 1H), 8.90 (s, 1H), 8.40 (d, 1H), 8.09 (d, 1H), 7.93 (d, 1H), 7.82 (dd, 1H), 7.59 (m, 2H), 7.48 (m, 2H), 7.39 (t, 3H), 7.16 (s, 1H), 6.98 (d, 1H), 6.89 (t, 1H), 6.55 (d, 1H), 6.42 (m, 1H), 6.37 (s, 1H), 3.90 (t, 2H), 3.67 (t, 2H), 3.52 (m, 6H), 3.41 (m, 2H), 3.22 (s, 3H), 2.91 (hept, 1H), 2.40 (s, 3H), 1.25 (d, 6H).

LCMS m/z 732 (M+H)+ (ES+); 730 (M−H)− (ES−)

Example 10

1-(4-((2-((3-Ethynylphenyl)amino)pyrimidin-4-yl) oxy)naphthalen-1-yl)-3-(3-isopropyl-1-(p-tolyl)-1H-pyrazol-5-yl)urea

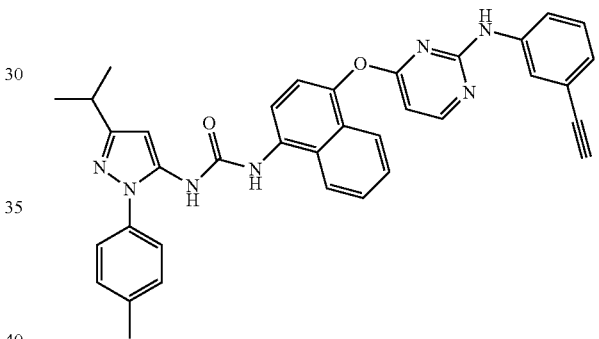

(i) Phenyl (3-isopropyl-1-(p-tolyl)-1H-pyrazol-5-yl) carbamate

The sub-title compound can be prepared according to or by analogy with procedures known to those skilled in the art and/or described herein. For example, the following procedure can be used.

To a biphasic mixture of isopropyl acetate (300 mL) and a solution of Na2CO3 (15.0 g, 142 mmol) in water (100 mL) was added isopropyl-1-(p-tolyl)-1H-pyrazol-5-amine (see, for example Ito, K. et al., WO 2010/067130, 17 Jun. 2010; 25.0 g, 116 mmol). The resulting suspension was stirred at RT until all solids had dissolved (ca. 10 mins) and was then treated with phenyl chloroformate (16.0 mL, 128 mmol) and the mixture stirred at RT for 2 hr. Water (200 mL) was added and the layers were separated. The organic phase was washed with water (2×100 mL) and with brine (100 mL) and then dried and concentrated in vacuo. The resultant thick yellow oil was triturated with 5% diethylether in iso-hexanes (ca. 250 mL) and the solid so produced was collected by filtration and washed with isohexane (50 mL) to afford the sub-title compound as a white powder (28.4 g, 72%).

1H NMR δ: 1.23 (6H, d), 2.37 (3H, s), 2.91 (1H, sept), 6.29 (1H, s), 7.05-7.45 (9H, overlapping m), 9.95 (1H, s) m/z 336 (M+H)+ (ES+)

(ii) 1-(4-(2-Chloropyrimidin-4-yloxy)naphthalen-1-yl)-3-(3-isopropyl-1-p-tolyl-1H-pyrazol-5-yl)urea The sub-title compound can be prepared according to or by analogy with procedures known to those skilled in the art and/or described herein. For example, the following procedure can be used.

To a solution of 4-((2-chloropyrimidin-4-yl)oxy)naphthalen-1-amine (see, for example, Cirillo, P. F. et al., WO 2002/92576, 21 Nov. 2000; 5.00 g, 18.4 mmol) in a mixture of isopropyl acetate (50 mL) and anhydrous THF (50 mL) was added portion-wise the product from step (i) above (7.72 g, 23.0 mmol) followed by triethylamine (0.64 mL, 4.6 mmol) and the reaction mixture maintained at RT for 18 hr. During this interval a thick purple precipitate formed which was collected by filtration and then washed with a mixture of isopropyl acetate and THF (1:1 v/v, 3×40 mL). The solid was purified by flash column chromatography (SiO$_2$, 330 g, 0-5% MeOH in DCM, gradient elution) to afford the title compound, Intermediate C1 as a pale purple solid (5.72 g, 47%).

m/z 513 (M+H)$^+$ (ES$^+$).

(iii) 1-(4-((2-((3-Ethynylphenyl)amino)pyrimidin-4-yl)oxy)naphthalen-1-yl)-3-(3-isopropyl-1-(p-tolyl)-1H-pyrazol-5-yl)urea 1-(4-((2-chloropyrimidin-4-yl)oxy)naphthalen-1-yl)-3-(3-isopropyl-1-(p-tolyl)-1H-pyrazol-5-yl)-urea (see step (ii) above; 150 mg, 0.292 mmol) was dissolved in DMF (1.5 mL) and added to p-TSA monohydrate (27.8 mg, 0.146 mmol) and 3-ethynylaniline (65.9 µL, 0.585 mmol). Stirred at 70° C. (block temperature) for 4 h then poured into saturated NaHCO$_3$ solution (10 mL), and the product extracted with EtOAc (2×20 mL). Organics bulked and washed with 20% w/w brine solution (20 mL), dried (MgSO$_4$), filtered and evaporated to a brown solid. The crude product was preabsorbed onto silica (4 g) and then purified by chromatography on the Companion (40 g column, 20% EtOAc:isohexane to 100%) to afford the product as a pale brown solid (70 mg) which was purified by preparative HPLC (Varian, Acidic (0.1% Formic acid), Agilent Prep C-18, 5 µm, 21.2×50 mm column, 25-80% MeCN in Water) to afford the title compound (23 mg) as a pale brown solid.

1H NMR (400 MHz, DMSO-d6) δ 9.63 (s, 1H), 9.24 (s, 1H), 8.92 (s, 1H), 8.43 (d, 1H), 8.09 (d, 1H), 7.93 (d, 1H), 7.81 (d, 1H), 7.59 (m, 3H), 7.48 (m, 2H), 7.38 (m, 4H), 6.98 (t, 1H), 6.92 (m, 1H), 6.60 (d, 1H), 6.37 (s, 1H), 4.03 (s, 1H), 2.91 (hept, 1H), 2.40 (s, 3H), 1.25 (d, 6H).

LCMS m/z 594 (M+H)$^+$ (ES$^+$)

Example 11

3-(4-((4-(3-(3-Isopropyl-1-(p-tolyl)-1H-pyrazol-5-yl)ureido)naphthalen-1-yl)oxy)pyrimidin-2-yl)amino)phenyl methanesulfonate

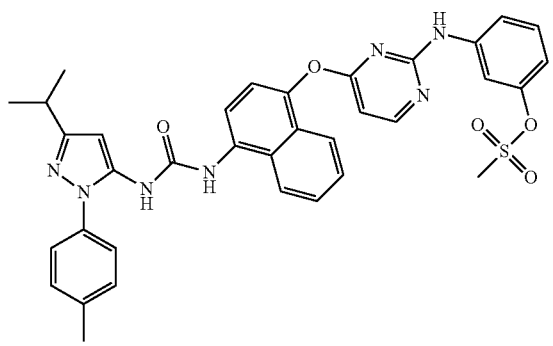 [SMILES: Cc1ccc(-n2nc(C(C)C)cc2NC(=O)Nc2ccc(Oc3ccnc(Nc4cccc(OS(C)(=O)=O)c4)n3)c3ccccc23)cc1]

1-(4-((2-chloropyrimidin-4-yl)oxy)naphthalen-1-yl)-3-(3-isopropyl-1-(p-tolyl)-1H-pyrazol-5-yl)urea (see Example 10(ii) above; 150 mg, 0.292 mmol) was dissolved in DMF (1.5 mL) and added to p-TSA monohydrate (27.8 mg, 0.146 mmol) and 3-aminophenyl methanesulfonate (109 mg, 0.585 mmol). Stirred at 70° C. (block temperature) for 4 h then poured into saturated NaHCO$_3$ solution (10 mL), and the product extracted with EtOAc (2×20 mL). Organics bulked and washed with 20% w/w brine solution (20 mL), dried (MgSO$_4$), filtered and evaporated to a brown solid. The crude product was preabsorbed onto silica (4 g) and then purified by chromatography on the Companion (40 g column, 20% EtOAc:isohexane to 100%) to afford the product as a pale brown solid (130 mg) which was purified by preparative HPLC (Varian, Acidic (0.1% Formic acid), Agilent Prep C-18, 5 µm, 21.2×50 mm column, 25-80%) to afford the title compound (54 mg) as a pale tan solid.

1H NMR (400 MHz, DMSO-d6) δ 9.74 (s, 1H), 9.32 (s, 1H), 9.01 (s, 1H), 8.44 (d, 1H), 8.10 (d, 1H), 7.92 (d, 1H), 7.81 (d, 1H), 7.55 (m, 5H), 7.39 (m, 4H), 7.08 (t, 1H), 6.81 (dd, 1H), 6.63 (d, 1H), 6.36 (s, 1H), 3.29 (s, 3H), 2.91 (hept, 1H), 2.40 (s, 3H), 1.25 (d, 6H).

LCMS m/z 664 (M+H)$^+$ (ES$^+$); 662 (M−H)$^-$ (ES$^-$)

Example 12

3-((4-((4-(3-(3-Isopropyl-1-(p-tolyl)-1H-pyrazol-5-yl)ureido)naphthalen-1-yl)oxy)pyrimidin-2-yl)amino)-5-methoxyphenyl methanesulfonate

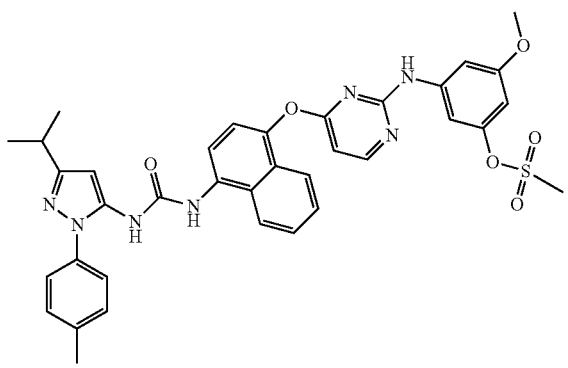 [SMILES: COc1cc(Nc2nccc(Oc3ccc(NC(=O)Nc4cc(C(C)C)nn4-c4ccc(C)cc4)c4ccccc34)n2)cc(OS(C)(=O)=O)c1]

(i) Methyl 3-methoxy-5-((methylsulfonyl)oxy)benzoate

Methyl 3-hydroxy-5-methoxybenzoate (460 mg, 2.53 mmol) and triethylamine (422 µL, 3.03 mmol) were stirred in DCM (10 mL). Methanesulfonyl chloride (216 µL, 2.78 mmol) was added and the mixture was stirred at rt for 18 h. The mixture was diluted with DCM (20 mL), washed with 1M HCl solution (10 mL), water (10 mL), saturated NaHCO$_3$ solution (10 mL) and water (10 mL). The organic phase was dried (MgSO$_4$) and concentrated to yield a white solid. The crude product was purified by chromatography on the Companion (12 g column, CH$_2$Cl$_2$) to afford the sub-title compound (650 mg) as a white solid.

1H NMR (DMSO-d6) 400 MHz, δ: 7.45 (m, 2H), 7.25 (dd, 1H), 3.88 (s, 3H), 3.87 (s, 3H), 4.44 (s, 3H).

LCMS m/z 261 (M+H)$^+$, 283 (MNa)$^+$ (ES$^+$)

(ii) 3-Methoxy-5-((methylsulfonyl)oxy)benzoic acid

1M NaOH solution (2.5 mL, 2.500 mmol) was added to a solution of the product from step (i) above (0.655 g, 2.52 mmol) in tetrahydrofuran (6 mL) at rt then stirred for 18 h. The mixture was acidified with 1 M HCl solution (2.5 mL) and extracted with ethyl acetate (3×10 mL). The combined organic phases were washed with saturated brine (10 mL), dried (MgSO$_4$) and concentrated to yield the sub-title compound (640 mg).

1H NMR (DMSO-d6) 400 MHz, δ: 13.40 (br s, 1H), 7.44 (dd, 1H), 7.43 (dd, 1H), 7.20 (dd, 1H), 3.85 (s, 3H), 3.42 (s, 3H).

LCMS m/z 247 (M+H)$^+$, 269 (MNa)$^+$ (ES$^+$); 245 (M−H)$^−$ (ES$^−$)

(iii) 3-((tert-Butoxycarbonyl)amino)-5-methoxyphenyl methanesulfonate

DPPA (0.241 mL, 1.117 mmol) was added to a stirred solution of the product from step (ii) above (275 mg, 1.117 mmol) and triethylamine (0.389 mL, 2.79 mmol) in toluene (10 mL) under N$_2$ at rt and stirred for 2 h. 2-Methylpropan-2-ol (5 mL, 1.117 mmol) was added and the mixture was heated to reflux for 4 h. The mixture was cooled, then water (15 mL) was added and extracted with ethyl acetate (3×15 mL). The combined organic phases were washed with saturated brine (15 mL), dried (MgSO$_4$) and concentrated under reduced pressure. The crude product was purified by chromatography on the Companion (12 g column, 0-30% EtOAc:iso-hexane) to afford the sub-title compound (302 mg) as a clear colourless oil which crystallised on standing.

1H NMR (DMSO-d6) 400 MHz, δ: 9.57 (s, 1H), 7.12 (dd, 1H), 7.06 (dd, 1H), 6.56 (dd, 1H), 3.74 (s, 3H), 3.37 (s, 3H), 1.48 (s, 9H).

LCMS m/z 318 (M+H)$^+$, 262 (M-$^t$Bu)$^+$ (ES$^+$)

(iv) 3-Amino-5-methoxyphenyl methanesulfonate

Trifluoroacetic acid (733 µL, 9.52 mmol) was added to a stirred solution of the product from step (iii) above (302 mg, 0.952 mmol) in DCM (1 mL) at rt. The resulting mixture was stirred for 1 h at rt. The mixture was diluted with water (5 mL) and 1 M sodium carbonate solution (5 mL) was added before extracting with DCM (3×10 mL). The combined organic phases were washed with saturated brine (10 mL), dried (MgSO$_4$) and concentrated under reduced pressure to yield the sub-title compound (187 mg) as a tan oil which crystallised on standing.

LCMS m/z 218 (M+H)$^+$ (ES$^+$)

(v) 3-((4-((4-(3-(3-Isopropyl-1-(p-tolyl)-1H-pyrazol-5-yl)ureido)naphthalen-1-yl)oxy)-pyrimidin-2-yl)amino)-5-methoxyphenyl methanesulfonate A mixture of 1-(4-((2-chloropyrimidin-4-yl)oxy)naphthalen-1-yl)-3-(3-isopropyl-1-(p-tolyl)-1H-pyrazol-5-yl)urea (see Example 10(ii) above; 150 mg, 0.292 mmol), the product from step (iv) above (127 mg, 0.585 mmol) and p-TSA monohydrate (27.8 mg, 0.146 mmol) was heated to 70° C. (bath temperature) for 10 h. The mixture was diluted with water (5 mL) and saturated NaHCO$_3$ solution (5 mL), then extracted with ethyl acetate (3×10 mL). The combined organic phases were washed with saturated brine (10 mL), dried (MgSO$_4$) and concentrated under reduced pressure. The crude product was purified by chromatography on the Companion (40 g column, 0-100% EtOAc/iso-hexanes) to afford a brown solid. The solid was triturated in acetonitrile to yield the title compound (100 mg) as a pale orange glass.

1H NMR (DMSO-d6) 400 MHz, δ: 9.69 (s, 1H), 9.09 (s, 1H), 8.79 (s, 1H), 8.44 (d, 1H), 8.06 (d, 1H), 7.96 (d, 1H), 7.82 (d, 1H), 7.67-7.60 (m, 1H), 7.60-7.54 (m, 1H), 7.51-7.44 (m, 2H), 7.43-7.34 (m, 3H), 7.24-7.12 (m, 2H), 6.61 (d, 1H), 6.44 (t, 1H), 6.37 (s, 1H), 3.56 (s, 3H), 3.30 (s, 3H), 2.90 (hept, 1H), 2.41 (s, 3H), 1.25 (d, 6H).

LCMS m/z 694 (M+H)$^+$ (ES$^+$); 692 (M−H)$^−$ (ES$^−$)

Example 13

1-(3-Isopropyl-1-(p-tolyl)-1H-pyrazol-5-yl)-3-(4-((2-((3-methoxy-5-(2-(2-(2-methoxy-ethoxy)ethoxy)ethoxy)phenyl)amino)pyrimidin-4-yl)oxy)naphthalen-1-yl)urea

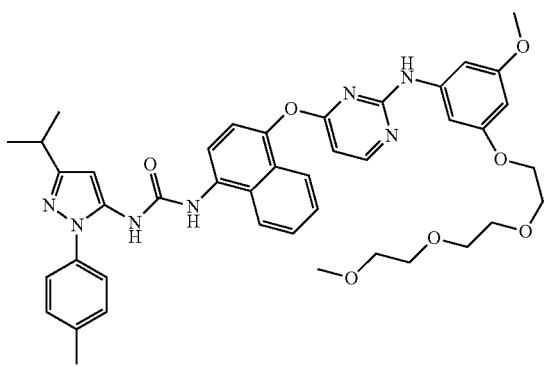 [SMILES: COCCOCCOCCOc1cc(Nc2nccc(Oc3ccc(NC(=O)Nc4cc(C(C)C)nn4-c4ccc(C)cc4)c4ccccc34)n2)cc(OC)c1]

(i) 3-Methoxy-5-(2-(2-(2-methoxyethoxy)ethoxy)ethoxy)aniline

3-Amino-5-methoxyphenol (230 mg, 1.653 mmol) and pyridine (134 µL, 1.653 mmol) were stirred in N,N-dimethylformamide:pyridine (3:1, 2 mL) at rt. 1-Bromo-2-(2-(2-methoxyethoxyl)ethoxy)ethane (375 mg, 1.653 mmol) was added and the mixture was heated to 60° C. overnight. The mixture was concentrated under reduced pressure then resuspended in ethyl acetate (10 mL). The solids were removed by filtration and the filtrate was concentrated under reduced pressure. The crude product was purified by chromatography on the Companion (40 g column, 50-100% EtOAc/iso-hexane) to afford the sub-title compound (133 mg) as a brown oil.

1H NMR (DMSO-d6) 400 MHz, δ: 5.77-5.73 (m, 2H), 5.68 (dd, 1H), 5.05 (br s, 2H), 3.98-3.91 (m, 2H), 3.72-3.66 (m, 2H), 3.63 (s, 3H), 3.60-3.49 (m, 6H), 3.46-3.41 (m, 2H), 3.24 (s, 3H).

(ii) 1-(3-Isopropyl-1-(p-tolyl)-1H-pyrazol-5-yl)-3-(4-((2-((3-methoxy-5-(2-(2-(2-methoxy-ethoxy)ethoxy)ethoxy)phenyl)amino)pyrimidin-4-yl)oxy)naphthalen-1-yl)urea A mixture of 1-(4-((2-chloropyrimidin-4-yl)oxy)naphthalen-1-yl)-3-(3-isopropyl-1-(p-tolyl)-1H-pyrazol-5-yl)urea (see Example 10(ii) above; 150 mg, 0.292 mmol), the product from step (i) above (129 mg, 0.453 mmol) and p-TSA monohydrate (27.8 mg, 0.146 mmol) was heated to 70° C. (bath temperature) for 10 h. The mixture was diluted with water (5 mL) and saturated NaHCO₃ solution (5 mL) and extracted with ethyl acetate (3×10 mL). The combined organic phases were washed with saturated brine (10 mL), dried (MgSO₄) and concentrated under reduced pressure. The crude product was purified by chromatography on the Companion (40 g column, EtOAc:iso-hexanes) to afford a brown oil. The oil was triturated in acetonitrile to yield the title compound (76 mg) as a pale cream solid.

1H NMR (DMSO-d6) 400 MHz, δ: 9.42 (s, 1H), 9.09 (s, 1H), 8.78 (s, 1H), 8.41 (d, 1H), 8.07 (d, 1H), 7.95 (d, 1H), 7.83 (d, 1H), 7.67-7.60 (m, 1H), 7.60-7.54 (m, 1H), 7.50-7.44 (m, 2H), 7.43-7.35 (m, 3H), 6.81 (m, 2H), 6.53 (d, 1H), 6.38 (s, 1H), 6.04 (s, 1H), 3.91-3.82 (m, 2H), 3.68-3.63 (m, 2H), 3.58-3.53 (m, 2H), 3.53-3.47 (m, 7H), 3.43-3.40 (m, 2H), 3.32 (s, 3H), 2.90 (hept, 1H), 2.41 (s, 3H), 1.24 (d, 6H).

LCMS m/z 762 (M+H)⁺ (ES⁺); 760 (M−H)⁻ (ES⁻)

Example 14

3-(4-((4-(3-(3-Isopropyl-1-(p-tolyl)-1H-pyrazol-5-yl)ureido)naphthalen-1-yl)oxy)pyrimidin-2-yl)amino)phenyl-S,S-dimethyl-N-phenyl sulfoximine

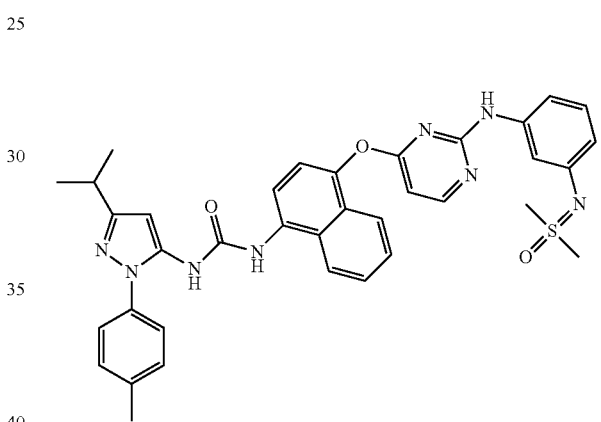

1-(4-((2-Chloropyrimidin-4-yl)oxy)naphthalen-1-yl)-3-(3-isopropyl-1-(p-tolyl)-1H-pyrazol-5-yl)urea (see Example 10(ii) above; 150 mg, 0.292 mmol) was dissolved in DMF (1.5 mL) and added to p-TSA monohydrate (27.8 mg, 0.146 mmol) and S,S-dimethyl-N-(3-aminophenyl)-sulfoximine (108 mg, 0.585 mmol). Stirred at 70° C. (block temperature) for 4 h, then poured into saturated NaHCO₃ solution (20 mL) and the product extracted with EtOAc (2×20 mL). Organics bulked and washed with 20% w/w brine solution (20 mL), dried (MgSO4), filtered and evaporated to a brown solid. The crude product was purified by chromatography on the Companion (40 g column, 2% MeOH:DCM to 8%) to afford the title compound (134 mg) as a pale pink glass.

1H NMR (400 MHz, DMSO-d6) δ 9.34 (s, 1H), 9.12 (s, 1H), 8.76 (s, 1H), 8.36 (d, 1H), 8.07 (d, 1H), 7.94 (d, 1H), 7.82 (d, 1H), 7.60 (m, 2H), 7.47 (m, 2H), 7.39 (m, 3H), 7.09 (s, 1H), 6.93 (d, 1H), 6.77 (t, 1H), 6.48 (m, 2H), 6.38 (s, 1H), 3.17 (s, 6H), 2.91 (hept, 1H), 2.41 (s, 3H), 1.25 (d, 6H).

LCMS m/z 661 (M+H)⁺ (ES⁺)

Example 15

1-(4-((2-((3-Ethynyl-5-methoxyphenyl)amino)pyrimidin-4-yl)oxy)naphthalen-1-yl)-3-(3-isopropyl-1-(p-tolyl)-1H-pyrazol-5-yl)urea

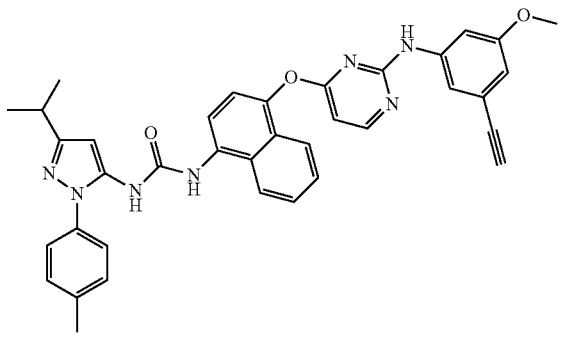 [SMILES: C#Cc1cc(Nc2nccc(Oc3ccc(NC(=O)Nc4cc(C(C)C)nn4-c4ccc(C)cc4)c4ccccc34)n2)cc(OC)c1]

(i) 3-Methoxy-5-((triisopropylsilyl)ethynyl)aniline

Pd(PPh$_3$)$_4$ (286 mg, 0.247 mmol) was added to a degassed suspension of 3-bromo-5-methoxyaniline (500 mg, 2.475 mmol), Cu(I) iodide (47.1 mg, 0.247 mmol), and ethynyltriisopropylsilane (0.833 mL, 3.71 mmol) in TEA (3 mL) and DMF (3 mL). Heated at 80° C. (block temp.) for 1 h then partitioned between ethyl acetate (20 mL) and saturated NH$_4$Cl solution (20 mL). The organics were separated, and washed with 20% w/w NaCl solution, separated, dried (MgSO$_4$) filtered and solvents evaporated. The crude product was purified by chromatography on the Companion (12 g column, 10% EtOAc:isohexane to 40%) to afford the sub-title compound (430 mg) as a clear brown oil.

1H NMR (400 MHz, CDCl$_3$) δ 6.44 (s, 1H), 6.43 (s, 1H), 6.20 (t, 1H), 3.76 (s, 3H), 3.68 (s, 2H), 1.12 (s, 21H).

LCMS m/z 304 (M+H)$^+$ (ES$^+$)

(ii) 3-Ethynyl-5-methoxyaniline

The product from step (i) above (430 mg, 1.417 mmol) was dissolved in THF (5 mL) and 1M TBAF in THF (1558 µL, 1.558 mmol) added. The mixture was partitioned between ethyl acetate (20 mL) and water (20 mL) organics separated, dried (MgSO$_4$) filtered and evaporated to a brown oil. The crude product was purified by chromatography on the Companion (12 g column, 10% EtOAc:isohexane to 50%) to afford the sub-title compound (160 mg) as a clear brown oil.

1H NMR (400 MHz, CDCl$_3$) δ 6.45 (m, 2H), 6.23 (t, 1H), 3.75 (s, 3H), 3.68 (s, 2H), 2.99 (s, 1H).

LCMS m/z 148 (M+H)$^+$ (ES$^+$)

(iii) 1-(4-((2-((3-Ethynyl-5-methoxyphenyl)amino)pyrimidin-4-yl)oxy)naphthalen-1-yl)-3-(3-isopropyl-1-(p-tolyl)-1H-pyrazol-5-yl)urea 1-(4-((2-Chloropyrimidin-4-yl)oxy)naphthalen-1-yl)-3-(3-isopropyl-1-(p-tolyl)-1H-pyrazol-5-yl)urea (see Example 10(ii) above; 150 mg, 0.292 mmol) was dissolved in DMF (1.5 mL) and added to p-TSA monohydrate (27.8 mg, 0.146 mmol) and the product from step (ii) above (86 mg, 0.585 mmol). Stirred at 70° C. (block temperature) for 4 h then poured into saturated NaHCO$_3$ solution (20 mL) and the product extracted with EtOAc (2×20 mL). Organics bulked and washed with 20% w/w brine solution (20 mL), dried (MgSO$_4$), filtered and evaporated to a brown solid. The crude product was purified by chromatography on the Companion (40 g column, 20% EtOAc:isohexane to 80%) to afford the product as a brown solid. Trituration with MeCN (2 mL) then MeOH gave the title compound (19 mg) as a pale brown solid.

1H NMR (400 MHz, DMSO-d6) δ 9.59 (s, 1H), 9.10 (s, 1H), 8.80 (s, 1H), 8.43 (d, 1H), 8.08 (d, 1H), 7.96 (d, 1H), 7.82 (m, 1H), 7.60 (m, 2H), 7.47 (m, 2H), 7.39 (t, 3H), 7.25 (d, 2H), 6.58 (d, 1H), 6.51 (dd, 1H), 6.37 (s, 1H), 4.01 (s, 1H), 3.56 (s, 3H), 2.91 (hept, 1H), 2.40 (s, 3H), 1.25 (d, 6H).

LCMS m/z 624 (M+H)$^+$ (ES$^+$)

Example 16

3-(5-Methoxy((4-((4-(3-(3-isopropyl-1-(p-tolyl)-1H-pyrazol-5-yl)ureido)naphthalen-1-yl)-oxy)pyrimidin-2-yl)amino))phenyl-S,S-dimethyl-N-phenyl sulfoximine

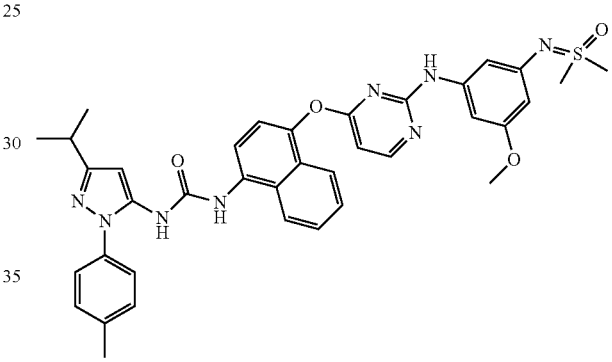

(i) S,S-Dimethyl-N-(3-methoxy-5-nitrophenyl)-sulfoximine

A solution of DMSO (2.110 mL, 29.7 mmol) in DCM (10 mL) was added slowly to a stirred solution of tert-butyl hypochlorite (0.775 g, 7.14 mmol) in DCM (20 mL) at −60° C. under N$_2$. The mixture was stirred for 1 h before a mixture of 3-methoxy-5-nitroaniline (1 g, 5.95 mmol) in DCM (20 mL) was added. After stirring for 6 h at −50° C., a solution of Et$_3$N (4.14 mL, 29.7 mmol) in DCM (10 mL) was added and the mixture allowed to warm to rt. The solvent was evaporated under reduced pressure and the residue partitioned between EtOAc (200 mL) and water (200 mL). The organic layer was separated, washed with brine, dried (MgSO$_4$) and evaporated under reduced pressure. The crude product was purified by chromatography on silica gel (40 g column, 0-100% EtOAc/isohexane) to afford the sub-title compound (101 mg) as a tan solid.

LCMS m/z 245 (M+H)$^+$ (ES$^+$)

(ii) S,S-Dimethyl-N-(3-amino-5-methoxyphenyl)-sulfoximine

Nitrogen was bubbled through a stirred mixture of the product from step (i) above (100 mg, 0.409 mmol) and 10% Pd/C (30 mg) in EtOH (3 mL). The mixture was then hydrogenated under a balloon of hydrogen for 2 h, filtered and evaporated under reduced pressure to afford the sub-title compound (83 mg) as a gum.

1H NMR (CDCl$_3$) 400 MHz, δ: 6.11-6.10 (m, 1H), 6.08-6.07 (m, 1H), 5.94-5.93 (m, 1H), 3.73 (s, 3H), 3.15 (s, 6H).

LCMS m/z 215 (M+H)$^+$ (ES$^+$)

(iii) 3-(5-Methoxy((4-((4-(3-(3-isopropyl-1-(p-tolyl)-1H-pyrazol-5-yl)ureido)naphthalen-1-yl)oxy) pyrimidin-2-yl)amino))phenyl-S,S-dimethyl-N-phenyl sulfoximine A mixture of 1-(4-((2-chloropyrimidin-4-yl)oxy)naphthalen-1-yl)-3-(3-isopropyl-1-(p-tolyl)-1H-pyrazol-5-yl)urea (see Example 10(ii) above; 150 mg, 0.292 mmol), the product from step (ii) above (80 mg, 0.370 mmol) and p-TSA monohydrate (70 mg, 0.368 mmol) in DMF was heated at 65° C. for 6 h. The mixture was partitioned between EtOAc (60 mL) and aqueous NaHCO$_3$ solution (40 mL), the organic layer separated, washed with brine (30 mL), dried (MgSO$_4$) and evaporated under reduced pressure. The crude product was purified by chromatography on silica gel (40 g column, 0-5% MeOH/DCM) then by preparative HPLC (Waters, Acidic (0.1% Formic acid), Waters X-Select Prep-C18, 5 μm, 19×50 mm column, 40-60% MeCN in Water) to afford the title compound (51 mg) as a solid.

1H NMR (400 MHz; DMSO-d6) δ 9.31 (s, 1H), 9.14 (s, 1H), 8.83 (s, 1H), 8.36 (d, 1H), 8.07 (d, 1H), 7.94 (d, 1H), 7.82 (d, 1H), 7.64-7.55 (m, 2H), 7.47 (d, 2H), 7.40-7.37 (m, 3H), 6.80 (brs, 1H), 6.78 (brs, 1H), 6.46 (d, 1H), 6.37 (s, 1H), 6.05 (s, 1H), 3.44 (s, 3H), 3.17 (s, 6H), 2.90 (septet, 1H), 2.4 (s, 3H), 1.25 (d, 6H).

LCMS m/z 691 (M+H)$^+$ (ES$^+$); 689 (M−H)$^-$ (ES$^-$)

Example 17

1-(3-Isopropyl-1-(P-tolyl)-1H-pyrazol-5-yl)-3-(4-((2-((3-methoxy-5-(2-morpholinoethoxy)-phenyl) amino)pyrimidin-4-yl)oxy)naphthalen-1-yl)urea stirred at 60° C. for 18 h, then 4-(2-chloroethyl)morpholine (0.113 g, 0.755 mmol) was added and heating was continued for a further 4 h. Water (10 mL) was added and the mixture was extracted with ethyl acetate (3×20 mL). The combined organic phases were washed with saturated brine (50 mL), dried (MgSO$_4$) and concentrated under reduced pressure to yield the sub-title compound (876 mg).

LCMS m/z 296 (M+H)$^+$ (ES$^+$)

(ii) 3-Methoxy-5-(2-morpholinoethoxyl)benzoic acid, hydrochloride

1 M NaOH solution (2.97 mL, 2.97 mmol) was added to a solution of the product from step (i) above (0.876 g, 2.97 mmol) in tetrahydrofuran (10 mL) at rt then stirred for 18 h. 1 M HCl solution (2.9 mL) was added and the mixture was concentrated under reduced pressure. The residue was resuspended in ethyl acetate:methanol (50 mL, 9:1), dried (MgSO$_4$) and filtered. The filtrate was concentrated under reduced pressure to yield the sub-title compound (700 mg).

LCMS m/z 282 (M+H)$^+$ (ES$^+$); 280 (M−H)$^-$ (ES$^-$)

(iii) tert-Butyl (3-methoxy-5-(2-morpholinoethoxyl) phenyl)carbamate

DPPA (0.529 mL, 2.453 mmol) was added to a stirred solution of the product from step (ii) above (690 mg, 2.453 mmol) and triethylamine (1.368 mL, 9.81 mmol) in toluene (15 mL) under N$_2$ at 0° C. The mixture was allowed to warm to rt and stir for 2 h. 2-Methylpropan-2-ol (10 mL, 2.453 mmol) was added and the mixture was heated to reflux for 6 h. Water (15 mL) and saturated NaHCO$_3$ (10 mL) were added and extracted with ethyl acetate (3×15 mL). The combined organic phases were washed with saturated brine (5 mL), dried (MgSO$_4$) and concentrated under reduced pressure. The crude product was purified by chromatogra-

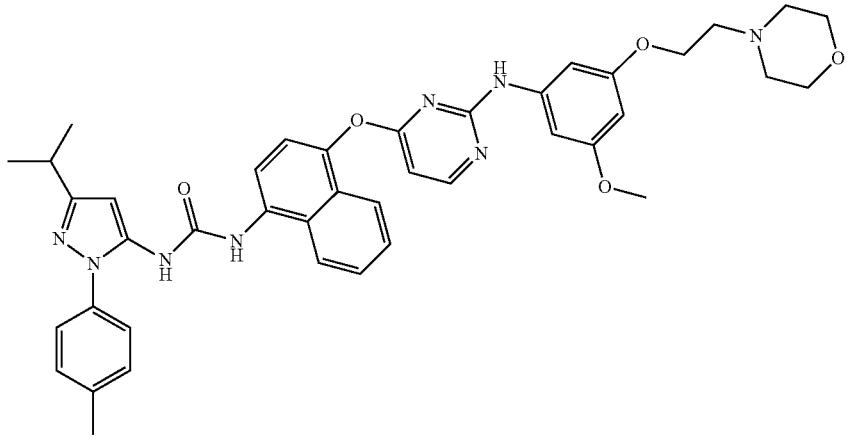 [SMILES: COc1cc(Nc2nccc(Oc3ccc(NC(=O)Nc4cc(C(C)C)nn4-c4ccc(C)cc4)c4ccccc34)n2)cc(OCCN2CCOCC2)c1]

(i) Methyl 3-methoxy-5-(2-morpholinoethoxy)benzoate 4-(2-Chloroethyl)morpholine (0.452 g, 3.02 mmol) was added portionwise to a stirred suspension of methyl 3-hydroxy-5-methoxybenzoate (0.55 g, 3.02 mmol) and K$_2$CO$_3$ (0.835 g, 6.04 mmol) in DMF (5 mL). The mixture was phy on the Companion (40 g column, 0-10% NH$_4$OH in CH$_3$OH(1:9)/CH$_2$Cl$_2$) to afford the sub-title compound (437 mg) as a clear, colourless oil. 1H NMR (DMSO-d6) 400 MHz, δ: 9.25 (s, 1H), 6.72-6.68 (m, 2H), 6.14 (t, 1H), 4.00 (t, 2H), 3.68 (s, 3H), 3.61-3.55 (m, 4H), 2.66 (t, 2H), 2.49-2.43 (m, 4H), 1.47 (s, 9H). LCMS m/z 353 (M+H)$^+$ (ES$^+$)

(iv) 3-Methoxy-5-(2-morpholinoethoxy)aniline, hydrochloride

5M HCl in 2-propanol (2.469 mL, 12.34 mmol) was added to a stirred solution the product from step (iii) above (0.435 g, 1.234 mmol) in 2-propanol (0.5 mL) at rt. The resulting mixture was stirred over the weekend. The solvents were removed under reduced pressure and the residue was co-evaporated with toluene (3×25 mL), then acetonitrile (2×10 mL) to yield the sub-title compound (394 mg) as a sticky, off-white solid.

LCMS m/z 253 (M+H)$^+$ (ES$^+$)

(v) 1-(3-Isopropyl-1-(p-tolyl)-1H-pyrazol-5-yl)-3-(4-((2-((3-methoxy-5-(2-morpholino-ethoxy)phenyl)amino)pyrimidin-4-yl)oxy)naphthalen-1-yl)urea A mixture of 1-(4-((2-chloropyrimidin-4-yl)oxy)naphthalen-1-yl)-3-(3-isopropyl-1-(p-tolyl)-1H-pyrazol-5-yl)urea (see Example 10(ii) above; 150 mg, 0.292 mmol), the product from step (iv) above (131 mg, 0.453 mmol) and p-TSA monohydrate (27.8 mg, 0.146 mmol) was heated to 70° C. in DMF (2 mL) for 18 h. The mixture was diluted with water (5 mL) and saturated NaHCO$_3$ solution (5 mL). The precipitate was collected by filtration and washed with water (5 mL) to yield a dark solid. The crude product was purified by chromatography on the Companion (40 g column, EtOAc, then CH$_2$Cl$_2$:CH$_3$OH:NH$_4$OH 90:9:1) to afford a dark solid. The solid was triturated in acetonitrile to yield the title compound (60 mg) as a tan solid.

1H NMR (DMSO-d6) 400 MHz, δ: 9.40 (s, 1H), 9.10 (s, 1H), 8.79 (s, 1H), 8.40 (d, 1H), 8.07 (d, 1H), 7.97 (d, 1H), 7.85-7.79 (m, 1H), 7.66-7.60 (m, 1H), 7.60-7.54 (m, 1H), 7.50-7.43 (m, 2H), 7.42-7.34 (m, 3H), 6.84-6.74 (m, 2H), 6.54 (d, 1H), 6.38 (s, 1H), 6.04 (t, 1H), 3.89 (t, 2H), 3.58-3.52 (m, 4H), 3.50 (s, 3H), 2.90 (hept, 1H), 2.60 (t, 2H), 2.45-2.37 (m, 4H), 2.41 (s, 3H), 1.25 (d, 6H).

LCMS m/z 729 (M+H)$^+$ (ES$^+$); 727 (M−H)$^-$ (ES$^-$)

Example 18

1-(4-((2-((3-(Cyclopropylsulfonyl)-5-methoxyphenyl)amino)pyrimidin-4-yl)oxy)naphthalen-1-yl)-3-(3-isopropyl-1-(p-tolyl)-1H-pyrazol-5-yl)urea

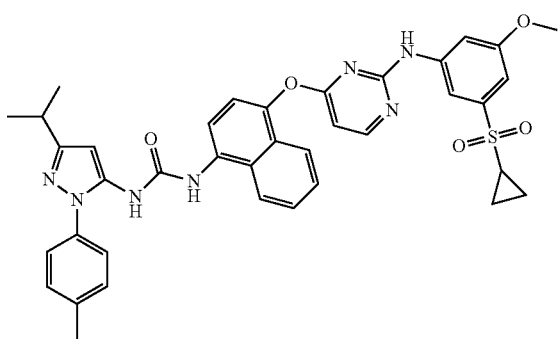 [SMILES: COc1cc(Nc2nccc(Oc3ccc(NC(=O)Nc4cc(C(C)C)nn4-c4ccc(C)cc4)c4ccccc34)n2)cc(S(=O)(=O)C2CC2)c1]

(i) 1-(Cyclopropylsulfonyl)-3-methoxy-5-nitrobenzene

A mixture of 1-bromo-3-methoxy-5-nitrobenzene (302 mg, 1.301 mmol), sodium cyclopropanesulfinate (200 mg, 1.561 mmol), Cu(I) iodide (25 mg, 0.131 mmol), L-proline (30.0 mg, 0.260 mmol) and NaOH (10.41 mg, 0.260 mmol) in DMSO (2 mL) was heated at 95° C. for 18 h. The mixture was partitioned between EtOAc (50 mL) and water (50 mL), the organic layer separated, washed with water (50 mL), dried (MgSO$_4$) and evaporated under reduced pressure. The crude product was purified by chromatography on silica gel (40 g column, 0-40% EtOAc/isohexane) to afford the sub-title compound (135 mg) as a solid.

1H NMR (400 MHz; CDCl$_3$) δ 8.31 (s, 1H), 7.97 (s, 1H), 7.72 (s, 1H), 3.98 (s, 3H), 2.55-2.48 (m, 1H), 1.44-1.39 (m, 2H), 1.15-1.09 (m, 2H).

LCMS m/z 258 (M+H)$^+$ (ES$^+$) weak ionisation

(ii) 3-(Cyclopropylsulfonyl)-5-methoxyaniline

The product from step (i) above (130 mg, 0.505 mmol) was dissolved in EtOH (2 mL) and Pd—C, 10% w/w (13 mg, 0.012 mmol) added. The resulting mixture was stirred under hydrogen for 3 h, then filtered and the solvent evaporated to afford the sub-title compound (105 mg) as a pale green solid.

1H NMR (400 MHz, DMSO-d6) δ 6.66 (t, 1H), 6.49 (t, 1H), 6.39 (t, 1H), 5.67 (s, 2H), 3.74 (s, 3H), 2.75 (tt, 1H), 1.03 (m, 4H).

LCMS m/z 228 (M+H)$^+$ (ES$^+$)

(iii) 1-(4-((2-((3-(Cyclopropylsulfonyl)-5-methoxyphenyl)amino)pyrimidin-4-yl)oxy)-naphthalen-1-yl)-3-(3-isopropyl-1-(p-tolyl)-1H-pyrazol-5-yl)urea 1-(4-((2-Chloropyrimidin-4-yl)oxy)naphthalen-1-yl)-3-(3-isopropyl-1-(p-tolyl)-1H-pyrazol-5-yl)urea (see Example 10(ii) above; 150 mg, 0.292 mmol) was dissolved in DMF (1.5 mL) and added to p-TSA monohydrate (27.8 mg, 0.146 mmol) and the product from step (ii) above (133 mg, 0.585 mmol). Stirred at 70° C. (block temperature) for 6 h then poured into saturated NaHCO$_3$ solution (20 mL) and the product extracted with EtOAc (2×20 mL). Organics bulked and washed with 20% w/w brine solution (20 mL), dried (MgSO$_4$) then filtered and evaporated to a brown solid. The crude product was purified by chromatography on the Companion (40 g column, 20% EtOAc:isohexane to 80%) to afford the product as a colourless solid. Triturated with MeCN (4 mL) to give the title compound (105 mg)

1H NMR (400 MHz, DMSO-d6) δ 9.86 (s, 1H), 9.12 (s, 1H), 8.81 (s, 1H), 8.47 (d, 1H), 8.08 (d, 1H), 7.96 (d, 1H), 7.82 (m, 1H), 7.73 (s, 1H), 7.60 (m, 2H), 7.43 (m, 6H), 6.86 (s, 1H), 6.64 (d, 1H), 6.38 (s, 1H), 3.63 (s, 3H), 2.90 (hept, 1H), 2.73 (m, 1H), 2.40 (s, 3H), 1.25 (d, 6H), 1.03 (m, 4H).

LCMS m/z 704 (M+H)$^+$ (ES$^+$)

Example 19

1-(4-((2-((3-(2-(2-(2-Hydroxyethoxy)ethoxy)ethoxy)phenyl)amino)pyrimidin-4-yl)oxy)-naphthalen-1-yl)-3-(3-isopropyl-1-(p-tolyl)-1H-pyrazol-5-yl)urea

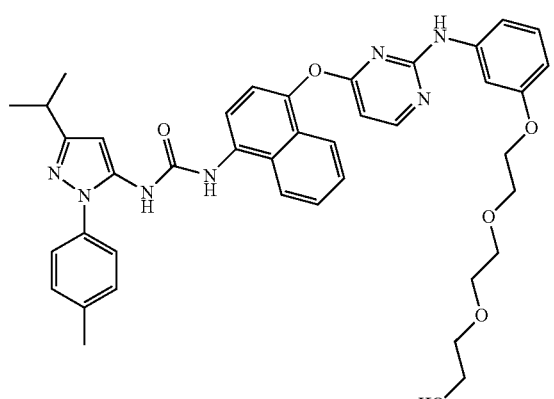

(i) 2-(2-(2-(3-Nitrophenoxy)ethoxy)ethoxy)ethanol

3-Nitrophenol (500 mg, 3.59 mmol), 2-(2-(2-chloroethoxy)ethoxy)ethanol (575 μL, 3.95 mmol), $K_2CO_3$ (1490 mg, 10.78 mmol) and KI (59.7 mg, 0.359 mmol) were suspended in acetone (20 mL) and heated at reflux overnight. 2-(2-(2-Chloroethoxyl)ethoxy)ethanol (100 μL) was added and heating continued for a further 16 h. Filtered and solvents evaporated. The crude product was purified by chromatography on the Companion (40 g column, 30% EtOAc:isohexane to 100%) to afford the sub-title compound (650 mg) as a pale yellow gum.

1H NMR (400 MHz, DMSO-d6) δ 7.82 (ddd, 1H), 7.73 (t, 1H), 7.58 (t, 1H), 7.44 (ddd, 1H), 4.57 (t, 1H), 4.24 (m, 2H), 3.78 (m, 2H), 3.60 (m, 2H), 3.55 (m, 2H), 3.48 (m, 2H), 3.42 (m, 2H).

LCMS m/z 272 (M+H)$^+$ (ES$^+$)

(ii) 2-(2-(2-(3-Aminophenoxyl)ethoxy)ethoxy)ethanol

The product from step (i) above (650 mg, 2.396 mmol) was dissolved in EtOH (5 mL) and Pd—C, 10% w/w (255 mg, 0.240 mmol) added. Stirred under hydrogen for 16 h. Filtered and solvent evaporated to afford the sub-title compound (581 mg).

1H NMR (400 MHz, DMSO-d6) δ 6.89 (t, 1H), 6.11 (m, 3H), 5.02 (s, 2H), 4.58 (t, 1H), 3.97 (m, 2H), 3.70 (m, 2H), 3.54 (m, 6H), 3.43 (m, 2H).

LCMS m/z 242 (M+H)$^+$ (ES$^+$)

(iii) 1-(4-((2-((3-(2-(2-(2-Hydroxyethoxy)ethoxy)ethoxy)phenyl)amino)pyrimidin-4-yl)oxy)-naphthalen-1-yl)-3-(3-isopropyl-1-(p-tolyl)-1H-pyrazol-5-yl)urea 1-(4-((2-Chloropyrimidin-4-yl)oxy)naphthalen-1-yl)-3-(3-isopropyl-1-(p-tolyl)-1H-pyrazol-5-yl)urea (see Example 10(ii) above; 150 mg, 0.292 mmol) was dissolved in DMF (1.5 mL) and added to the product from step (ii) above (141 mg, 0.585 mmol) and p-TSA monohydrate (27.8 mg, 0.146 mmol). Stirred at 70° C. (block temperature) for 6 h then poured into saturated $NaHCO_3$ solution (20 mL) and the product extracted with EtOAc (2×20 mL). Organics bulked and washed with 20% w/w brine solution (20 mL), dried ($MgSO_4$), filtered and evaporated to a brown solid. The crude product was purified by chromatography on the Companion (40 g column, 2% MeOH:DCM to 8%) to afford the product as a colourless solid. Triturated with MeCN (4 mL) to afford the title compound (123 mg).

1H NMR (400 MHz, DMSO-d6) δ 9.48 (s, 1H), 9.13 (s, 1H), 8.78 (s, 1H), 8.40 (d, 1H), 8.07 (d, 1H), 7.94 (d, 1H), 7.82 (d, 1H), 7.60 (m, 2H), 7.47 (m, 2H), 7.40 (m, 3H), 7.15 (s, 1H), 6.97 (s, 1H), 6.88 (t, 1H), 6.55 (d, 1H), 6.42 (m, 1H), 6.38 (s, 1H), 4.59 (t, 1H), 3.89 (t, 2H), 3.67 (dd, 2H), 3.51 (m, 6H), 3.41 (m, 2H), 2.90 (hept, 1H), 2.41 (s, 3H), 1.25 (d, 6H).

LCMS m/z 718 (M+H)$^+$ (ES$^+$)

Example 20

1-(4-((2-(((3-(2-(2-(2-Hydroxyethoxy)ethoxy)ethoxy)-5-methoxyphenyl)amino)pyrimidin-4-yl)oxy)naphthalen-1-yl)-3-(3-isopropyl-1-(P-tolyl)-1H-pyrazol-5-yl)urea

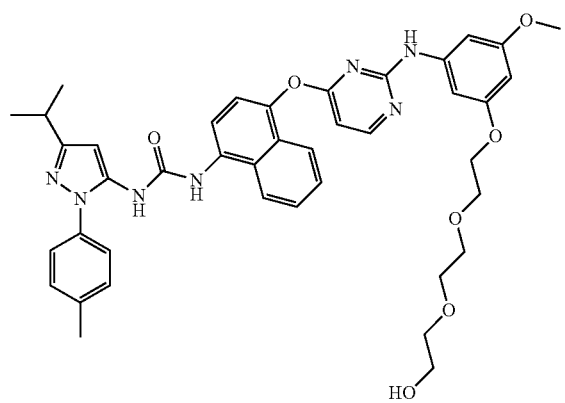 [SMILES: COc1cc(Nc2nccc(Oc3ccc(NC(=O)Nc4cc(C(C)C)nn4-c4ccc(C)cc4)c4ccccc34)n2)cc(OCCOCCOCCO)c1]

(i) 2-(2-(2-(3-Amino-5-methoxyphenoxy)ethoxy)ethoxy)ethanol

3-Amino-5-methoxyphenol (510 mg, 3.67 mmol), and $Cs_2CO_3$ (1433 mg, 4.40 mmol) were stirred vigorously in DMF (12 mL) for 30 min before addition of 2-(2-(2-chloroethoxyl)ethoxy)ethanol (586 μL, 4.03 mmol) and KI (60.8 mg, 0.367 mmol). The mixture was placed in a preheated block at 65° C. and stirring continued for 4 h. Cooled and filtered then partitioned between EtOAc (50 mL) and water (100 mL). Organic layer was separated then washed with 20% w/w NaCl solution (100 mL), dried ($MgSO_4$), filtered and solvent evaporated to give a dark brown oil. The crude product was purified by chromatography on the Companion (40 g column, 50% EtOAc:isohexane to 100% then 2.5% MeOH:EtOAc) to afford the sub-title compound (310 mg) as a clear brown oil.

1H NMR (400 MHz, DMSO-d6) δ 5.76 (m, 2H), 5.69 (t, 1H), 5.06 (s, 2H), 4.58 (s, 1H), 3.95 (m, 2H), 3.69 (m, 2H), 3.63 (s, 3H), 3.56 (m, 4H), 3.49 (s, 2H), 3.43 (m, 2H).

LCMS m/z 272 (M+H)$^+$ (ES$^+$)

(ii) 1-(4-((2-((3-(2-(2-(2-Hydroxyethoxy)
ethoxy)-5-methoxyphenyl)amino)-pyrimidin-4-yl)
oxy)naphthalen-1-yl)-3-(3-isopropyl-1-(p-tolyl)-1H-
pyrazol-5-yl)urea 1-(4-((2-Chloropyrimidin-4-yl)oxy)naphthalen-1-yl)-3-(3-isopropyl-1-(p-tolyl)-1H-pyrazol-5-yl)urea (see Example 10(ii) above; 150 mg, 0.292 mmol) was dissolved in DMF (1.5 mL) and added to the product from step (i) above (159 mg, 0.585 mmol) and p-TSA monohydrate (27.8 mg, 0.146 mmol). Stirred at 70° C. (block temperature) for 6 h then poured into saturated NaHCO$_3$ solution (20 mL) and the product extracted with EtOAc (2×20 mL). Organics bulked then washed with 20% w/w brine solution (20 mL), dried (MgSO$_4$), filtered and evaporated to a brown solid. The crude product was purified by chromatography on the Companion (40 g column, 2% MeOH:DCM to 8%) to afford the product as a colourless solid. Triturated with MeCN (4 mL) to give the title compound (83 mg).

1H NMR (400 MHz, DMSO-d6) δ 9.43 (s, 1H), 9.10 (s, 1H), 8.80 (s, 1H), 8.41 (d, 1H), 8.07 (d, 1H), 7.95 (d, 1H), 7.83 (d, 1H), 7.60 (m, 2H), 7.47 (m, 2H), 7.39 (dd, 3H), 6.81 (s, 2H), 6.54 (d, 1H), 6.38 (s, 1H), 6.04 (t, 1H), 4.59 (t, 1H), 3.87 (t, 2H), 3.65 (m, 2H), 3.50 (m, 10H), 3.41 (m, 1H), 2.90 (m, 1H), 2.41 (s, 3H), 1.25 (d, 6H).

LCMS m/z 748 (M+H)$^+$ (ES$^+$)

Example 21

1-(2,3-Dichloro-4-((2-((3-methoxy-5-(2-morpholinoethoxy)phenyl)amino)pyrimidin-4-yl)-oxy)phenyl)-3-(3-isopropyl-1-(p-tolyl)-1H-pyrazol-5-yl)urea

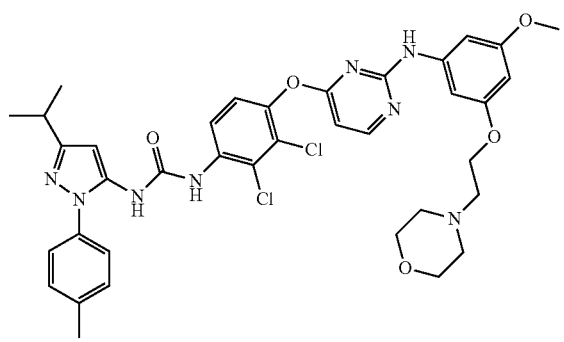 [SMILES: COc1cc(Nc2nccc(Oc3ccc(NC(=O)Nc4cc(C(C)C)nn4-c4ccc(C)cc4)c(Cl)c3Cl)n2)cc(OCCN2CCOCC2)c1]

(i) 2,3-Dichloro-4-((2-chloropyrimidin-4-yl)oxy)
aniline

DBU (11.85 mL, 79 mmol) was added over 5 min to a stirred mixture of 4-amino-2,3-dichlorophenol (10 g, 56.2 mmol) in MeCN (150 mL) at 0-5° C. After stirring for 5 min, 2,4-dichloropyrimidine (8.95 g, 60.1 mmol) was added portionwise over 5 min then the mixture warmed to rt and stirred for 2 h. The solvent was evaporated under reduced pressure and the residue partitioned between ether (200 mL) and water (200 mL). The aqueous layer was extracted with ether (200 mL) then the combined organic layers washed with brine (200 mL), dried (MgSO$_4$), filtered through a pad of silica and evaporated under reduced pressure. The residue was triturated with ether-isohexane, filtered and dried to afford the sub-title compound (14.403 g) as a light brown solid.

1H NMR (CDCl$_3$) 400 MHz, δ: 8.45 (d, 1H), 6.96 (d, 1H), 6.84 (d, 1H), 6.73 (d, 1H), 4.22 (s, 2H).

LCMS m/z 290/2/4 (M+H)$^+$ (ES$^+$)

(ii) Phenyl (3-isopropyl-1-(p-tolyl)-1H-pyrazol-5-yl)
carbamate

Phenyl chloroformate (0.320 mL, 2.55 mmol) was added to a stirred mixture of 3-isopropyl-1-(p-tolyl)-1H-pyrazol-5-amine (see, for example Ito, K. et al., WO 2010/067130, 17 Jun. 2010; 0.5 g, 2.322 mmol) and NaHCO$_3$ (0.390 g, 4.64 mmol) in DCM (10 mL) and THF (4 mL) at rt. The mixture was stirred for 2 h, partitioned between DCM (100 mL) and water (100 mL). The organic layer was separated, dried (MgSO$_4$) and evaporated under reduced pressure to give the sub-title compound (0.8 g) as an oil, which was used crude in the next step.

LCMS m/z 336 (M+H)$^+$ (ES$^+$)

(iii) 1-(2,3-Dichloro-4-((2-chloropyrimidin-4-yl)
oxy)phenyl)-3-(3-isopropyl-1-(p-tolyl)-1H-pyrazol-
5-yl)urea Et$_3$N (0.05 mL, 0.359 mmol) was added to a mixture of the product from step (ii) above (779 mg, 2.322 mmol) and the product from step (i) above (675 mg, 2.322 mmol) in iPrOAc (15 mL) and heated at 60° C. for 6 h. The precipitate was filtered, washed with iPrOAc (20 mL) and dried to afford the sub-title compound. 0.25Et$_3$NHCl (443 mg) as a white solid.

1H NMR (400 MHz; DMSO-d6) δ 9.23 (s, 1H), 8.88 (s, 1H), 8.70 (d, 1H), 8.15 (d, 1H), 7.46 (d, 1H), 7.42 (d, 2H), 7.37-7.35 (m, 3H), 6.34 (s, 1H), 2.89 (septet, 1H), 2.39 (s, 3H), 1.22 (d, 6H).

LCMS m/z 531/3 (M+H)$^+$ (ES$^+$)

(iv) 3-Methoxy-5-(2-morpholinoethoxy)aniline

To a stirred suspension of 3-amino-5-methoxyphenol (1.400 g, 10.06 mmol) and K$_2$CO$_3$ (6.95 g, 50.3 mmol) in pyridine/DMF (18 mL, 1:3) was added 4-(2-chloroethyl)morpholine hydrochloride (1.872 g, 10.06 mmol). The resulting mixture was heated at 60° C. overnight. The reaction was cooled to rt, filtered and concentrated in vacuo to afford a brown oil. The crude product was purified by chromatography on silica gel (40 g column, 0-10% MeOH in DCM) to afford the sub-title compound (1700 mg) as a sticky, orange oil.

1H NMR (DMSO-d6) 400 MHz, δ: 5.75-5.73 (m, 2H) 5.67 (t, 1H) 5.05 (s, 2H) 3.94 (t, 2H) 3.61 (s, 3H) 3.58-3.55 (m, 4H) 2.62 (t, 2H) 2.45-2.43 (m, 4H).

LCMS m/z 253 (M+H)+ (ES+)

(v) 1-(2,3-Dichloro-4-((2-((3-methoxy-5-(2-morpholinoethoxy)phenyl)amino)pyrimidin-4-yl)oxy)
phenyl)-3-(3-isopropyl-1-(p-tolyl)-1H-pyrazol-5-yl)
urea The product from step (iii) above (200 mg, 0.376 mmol) was dissolved in DMF (1.5 mL) and added to the product from step (iv) above (190 mg, 0.752 mmol) and p-TSA monohydrate (179 mg, 0.940 mmol). Stirred at 70° C. (block temperature) for 4 h then poured into saturated NaHCO$_3$ solution (20 mL) and the product extracted with EtOAc (2×20 mL). Organics bulked then washed with 20% w/w brine solution (20 mL), dried (MgSO$_4$), filtered and evaporated to a brown solid. The crude product was purified by chromatography on the Companion (40 g column, 2% MeOH:DCM to 8%), triturated with MeCN (4 mL) then purified by preparative HPLC (Varian, Acidic (0.1% Formic acid), Waters X-Select Prep-C18, 5 μm, 19×50 mm column, 25-70% MeCN in Water) to afford the title compound. 0.2HCO₂H (55 mg) as a colourless solid.

1H NMR (400 MHz, DMSO-d6) δ 9.52 (s, 1H), 9.35 (s, 1H), 8.92 (s, 1H), 8.41 (d, 1H), 8.17 (d, 1H), 7.40 (m, 5H), 6.74 (d, 2H), 6.58 (d, 1H), 6.35 (s, 1H), 6.08 (t, 1H), 3.95 (t, 2H), 3.58 (s, 3H), 3.55 (s, 4H), 2.89 (hept, 1H), 2.62 (t, 2H), 2.43 (s, 4H), 2.39 (s, 3H), 1.23 (d, 6H).

LCMS m/z 746/748(M+H)⁺ (ES⁺); 744/746 (M−H)⁻ (ES⁻)

Example 22

1-(4-((2-((3-(2-Hydroxyethyl)thio)-5-methoxyphenyl)amino)pyrimidin-4-yl)oxy)-naphthalen-1-yl)-3-(3-isopropyl-1-(p-tolyl)-1H-pyrazol-5-yl)urea

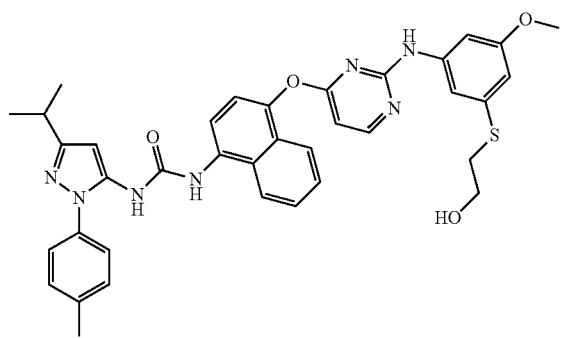 [SMILES: COc1cc(Nc2nccc(Oc3ccc(NC(=O)Nc4cc(C(C)C)nn4-c4ccc(C)cc4)c4ccccc34)n2)cc(SCCO)c1]

(i) 2-((3-Amino-5-methoxyphenyl)thio)ethanol

3-Bromo-5-methoxyaniline (500 mg, 2.475 mmol), Pd₂(dba)₃ (113 mg, 0.124 mmol) and xantphos (143 mg, 0.247 mmol) were added to a degassed solution of DIPEA (1297 μL, 7.42 mmol) and 2-mercaptoethanol (173 μL, 2.475 mmol) in 1,4-dioxane (10 mL). Heated under nitrogen at 100° C. for 16 h then the reaction mixture was filtered through Celite and residue washed with DCM (5 mL). Solvents evaporated to give a brown gum. The crude product was purified by chromatography on the Companion (40 g column, 2% MeOH:DCM to 8%) to afford the sub-title compound (377 mg) as a dark brown oil.

1H NMR (400 MHz, DMSO-d6) δ 6.13 (t, 1H), 6.03 (t, 1H), 5.95 (t, 1H), 5.17 (s, 2H), 4.92 (t, 1H), 3.64 (s, 3H), 3.60-3.49 (m, 2H), 2.93 (t, 2H).

LCMS m/z 200 (M+H)⁺ (ES⁺)

(ii) 1-(4-((2-((3-(2-Hydroxyethyl)thio)-5-methoxyphenyl)amino)pyrimidin-4-yl)oxy)-naphthalen-1-yl)-3-(3-isopropyl-1-(p-tolyl)-1H-pyrazol-5-yl)urea 1-(4-((2-Chloropyrimidin-4-yl)oxy)naphthalen-1-yl)-3-(3-isopropyl-1-(p-tolyl)-1H-pyrazol-5-yl)urea (see Example 10(ii) above; 150 mg, 0.292 mmol) was dissolved in DMF (1.5 mL) and added to the product from step (i) above (117 mg, 0.585 mmol) and p-TSA monohydrate (27.8 mg, 0.146 mmol). Stirred at 70° C. (block temperature) for 6 h then poured into saturated NaHCO₃ solution (20 mL) and the product extracted with EtOAc (2×20 mL). Organics bulked and washed with 20% w/w brine solution (20 mL), dried (MgSO₄), filtered and evaporated to a brown solid. The crude product was purified by chromatography on the Companion (40 g column, 2% MeOH:DCM to 8%) to afford the product as a colourless solid. Triturated with MeCN (4 mL) to afford the title compound (125 mg).

1H NMR (400 MHz, DMSO-d6) δ 9.50 (s, 1H), 9.10 (s, 1H), 8.81 (s, 1H), 8.42 (d, 1H), 8.07 (d, 1H), 7.97 (d, 1H), 7.81 (d, 1H), 7.68-7.53 (m, 2H), 7.52-7.43 (m, 2H), 7.43-7.33 (m, 3H), 7.09 (s, 1H), 7.01 (s, 1H), 6.57 (d, 1H), 6.38 (s, 2H), 4.91 (t, 1H), 3.57-3.45 (m, 5H), 2.96-2.85 (m, 3H), 2.41 (s, 3H), 1.25 (d, 6H).

LCMS m/z 676 (M+H)⁺ (ES⁺)

Example 23

1-(2,3-Dichloro-4-((2-((3-(cyclopropylsulfonyl)-5-methoxyphenyl)amino)pyrimidin-4-yl)-oxy)phenyl)-3-(3-isopropyl-1-(p-tolyl)-1H-pyrazol-5-yl)urea

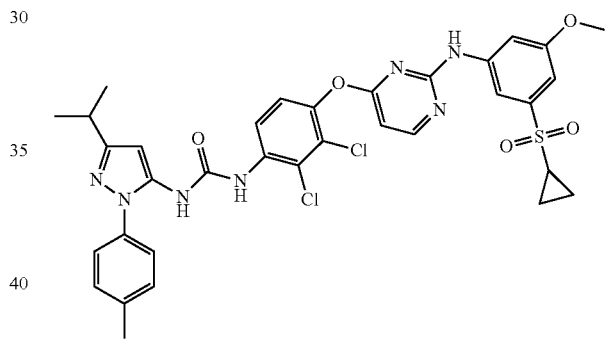

1-(2,3-Dichloro-4-((2-chloropyrimidin-4-yl)oxy)phenyl)-3-(3-isopropyl-1-(p-tolyl)-1H-pyrazol-5-yl)urea (see Example 21(iii) above; 150 mg, 0.282 mmol) was dissolved in DMF (2 mL) and added to 3-(cyclopropylsulfonyl)-5-methoxyaniline (see Example 18(ii) above; 128 mg, 0.564 mmol) and p-TSA monohydrate (26.8 mg, 0.141 mmol). Stirred at 70° C. (block temperature) for 4 h then poured into saturated NaHCO₃ solution (20 mL) and the product extracted with EtOAc (2×20 mL). Organics bulked and washed with 20% w/w brine solution (20 mL), dried (MgSO₄), filtered and evaporated to a yellow solid. The crude product was purified by chromatography on the Companion (40 g column, 2% MeOH:DCM to 6%) then triturated with MeCN (3×2 mL) to afford the title compound (107 mg) as a colourless solid.

1H NMR (400 MHz, DMSO-d6) δ 9.96 (s, 1H), 9.25 (s, 1H), 8.82 (s, 1H), 8.48 (d, 1H), 8.19 (d, 1H), 7.65 (s, 1H), 7.56-7.25 (m, 6H), 6.90 (dd, 1H), 6.68 (d, 1H), 6.35 (s, 1H), 3.71 (s, 3H), 2.90 (hept, 1H), 2.75 (tt, 1H), 2.40 (s, 3H), 1.24 (d, 6H), 1.12-0.97 (m, 4H)

LCMS m/z 722/724 (M+H)⁺ (ES⁺)

Example 24

1-(2,3-Dichloro-4-((2-((3-(cyclopropylsulfonyl)phenyl)amino)pyrimidin-4-yl)oxy)phenyl)-3-(3-isopropyl-1-(p-tolyl)-1H-pyrazol-5-yl)urea

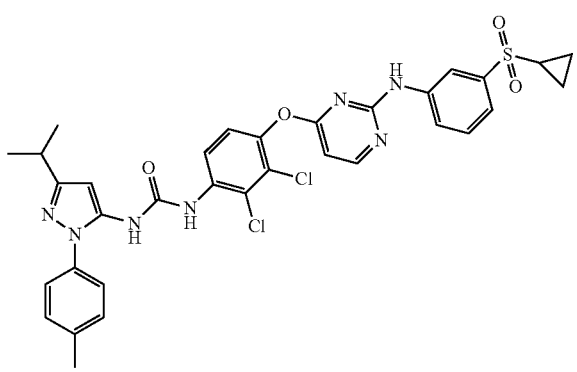 [SMILES: Cc1ccc(-n2nc(C(C)C)cc2NC(=O)Nc2ccc(Oc3ccnc(Nc4cccc(S(=O)(=O)C5CC5)c4)n3)c(Cl)c2Cl)cc1]

(i) 3-(Cyclopropylsulfonyl)aniline

A mixture of 3-bromoaniline (615 mg, 3.58 mmol), sodium cyclopropanesulfinate (550 mg, 4.29 mmol), copper (I) iodide (70 mg, 0.368 mmol), L-proline (82 mg, 0.715 mmol) and NaOH (29 mg, 0.725 mmol) in DMSO (5 mL) was heated at 95° C. for 18 h. The mixture was partitioned between EtOAc (100 mL) and water (100 mL), the organic layer separated, washed with water (100 mL), dried (MgSO₄) and evaporated under reduced pressure. The crude product was purified by chromatography on silica gel (40 g column, 0-80% EtOAc/isohexane) to afford the sub-title compound (212 mg) as a solid.

1H NMR (400 MHz; CDCl₃) δ 7.29-7.22 (m, 2H), 7.16 (s, 1H), 6.85-6.82 (m, 1H), 3.83 (s, 2H), 2.45-2.38 (m, 1H), 1.32-1.28 (m, 2H), 0.99-0.94 (m, 2H).

LCMS m/z 198 (M+H)⁺ (ES⁺)

(ii) Dichloro-4-((2-((3-(cyclopropylsulfonyl)phenyl)amino)pyrimidin-4-yl)oxy)phenyl)-3-(3-isopropyl-1-(p-tolyl)-1H-pyrazol-5-yl)urea A mixture of 1-(2,3-dichloro-4-((2-chloropyrimidin-4-yl)oxy)phenyl)-3-(3-isopropyl-1-(p-tolyl)-1H-pyrazol-5-yl)urea (150 mg, 0.282 mmol), the product from step (i) above (83 mg, 0.423 mmol) and p-TSA monohydrate (26.8 mg, 0.141 mmol) was heated to 70° C. in DMF (2 mL) for 18 h. The mixture was diluted with water (5 mL) and saturated NaHCO₃ solution (5 mL). The precipitate was collected by filtration and washed with water (5 mL) to yield a grey solid. The crude product was purified by chromatography on the Companion (40 g column, 0-100% EtOAc/iso-hexanes) to afford a solid which was purified by preparative HPLC (Varian, Acidic (0.1% Formic acid), Waters X-Select Prep-C18, 5 µm, 19×50 mm column, 5-95% MeCN in Water) to afford the title compound (18 mg) as a white solid.

1H NMR (DMSO-d6) 400 MHz, δ: 10.00 (s, 1H), 9.20 (s, 1H), 8.88 (s, 1H), 8.48 (d, 1H), 8.12 (d, 1H), 8.11 (s, 1H), 7.83 (d, 1H), 7.48-7.40 (m, 3H), 7.40-7.29 (m, 4H), 6.67 (d, 1H), 6.36 (s, 1H), 2.90 (hept, 1H), 2.76-2.66 (m, 1H), 2.39 (s, 3H), 1.24 (d, 6H), 1.13-0.97 (m, 4H).

LCMS m/z 692, 694 (M+H)⁺ (ES⁺)

Example 25

1-(2,3-Difluoro-4-((2-((3-methoxy-5-(2-morpholinoethoxy)phenyl)amino)pyrimidin-4-yl)oxy)phenyl)-3-(3-isopropyl-1-(p-tolyl)-1H-pyrazol-5-yl)urea

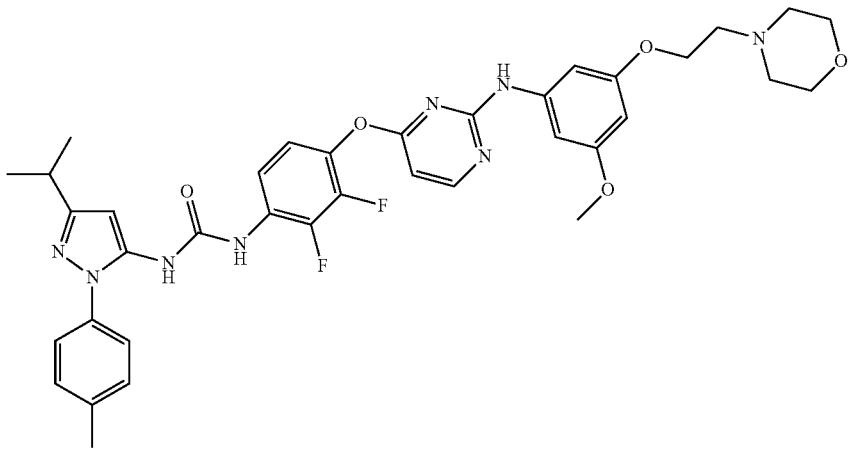 [SMILES: COc1cc(Nc2nccc(Oc3ccc(NC(=O)Nc4cc(C(C)C)nn4-c4ccc(C)cc4)c(F)c3F)n2)cc(OCCN2CCOCC2)c1]

(i) 4((2-Chloropyrimidin-4-yl)oxy)-2,3-difluoroaniline

DBU (7.27 mL, 48.2 mmol) was added over 5 min to a stirred mixture of 4-amino-2,3-difluorophenol (5 g, 34.5 mmol) in MeCN (100 mL) at 0-5° C. After stirring for 5 min, 2,4-dichloropyrimidine (5.49 g, 36.9 mmol) was added portionwise over 5 min then the mixture warmed to rt and stirred for 2 h. The solvent was evaporated under reduced pressure and the residue partitioned between ether (200 mL) and water (200 mL). The aqueous layer was extracted with ether (200 mL) then the combined organic layers washed with brine (200 mL), dried (MgSO₄) and evaporated under reduced pressure. The crude product was purified by chromatography on silica gel (120 g column, 0-40% EtOAc/isohexane) to afford the sub-title compound (4.827 g) as a solid.

1H NMR (400 MHz; CDCl₃) δ 8.46 (d, 1H), 6.89 (d, 1H), 6.81-6.77 (m, 1H), 6.58-6.53 (m, 1H), 3.85 (s, 2H)

LCMS m/z 258/260 (M+H)⁺ (ES⁺).

(ii) 1-(4-((2-Chloropyrimidin-4-yl)oxy)-2,3-difluorophenyl)-3-(3-isopropyl-1-(p-tolyl)-1H-pyrazol-5-yl)urea Et₃N (0.1 mL, 0.717 mmol) was added to a mixture of phenyl (3-isopropyl-1-(p-tolyl)-1H-pyrazol-5-yl)carbamate (see Example 21(ii) above; 1.556 g, 4.64 mmol) and the product from step (i) above (1.195 g, 4.64 mmol) in iPrOAc (30 mL) and heated at 60° C. for 7 h. The mixture was partitioned between EtOAc (200 mL) and brine (100 mL), the organic layer separated, washed with water, dried (MgSO₄) and evaporated under reduced pressure. The residue was triturated with ether/isohexane, filtered and dried to afford the sub-title compound (1.708 g) as a light tan solid.

1H NMR (400 MHz; CDCl₃) δ 8.48 (d, 1H), 7.94-7.89 (m, 1H), 7.54 (s, 1H), 7.26 (d, 2H), 7.19 (d, 2H), 6.97-6.92 (m, 3H), 6.34 (s, 1H), 2.97 (septet, 1H), 2.34 (s, 3H), 1.29 (d, 6H).

LCMS m/z 499/501 (M+H)⁺ (ES⁺)

(iii) 1-(2,3-Difluoro-4-((2-((3-methoxy-5-(2-morpholinoethoxy)phenyl)amino)pyrimidin-4-yl)oxy)phenyl)-3-(3-isopropyl-1-(p-tolyl)-1H-pyrazol-5-yl)urea p-TSA monohydrate (86 mg, 0.451 mmol) was added to a stirred solution of the product from step (ii) above (150 mg, 0.301 mmol) and 3-methoxy-5-(2-morpholinoethoxy)aniline (see Example 21(iv) above; 114 mg, 0.451 mmol) in THF/DMF (4 mL, 1:1). The resulting mixture was heated at 60° C. overnight. The reaction was cooled to rt and partitioned between EtOAc (30 mL) and saturated aqueous NaHCO₃ (20 mL). The aqueous layer was extracted with EtOAc (2×30 mL). The combined organic extracts were washed with water (3×40 mL), brine (50 mL), dried (MgSO₄), filtered and concentrated in vacuo to afford a beige foam (217 mg) at 65% purity. The crude product was purified by chromatography on silica gel (40 g column, 0-10% MeOH in DCM) then purified by preparative HPLC (Waters, Acidic (0.1% Formic acid), Waters X-Select Prep-C18, 5 μm, 19×50 mm column, 20-50% MeCN in Water) to afford the title compound (85 mg) as a white solid (0.3HCO₂H present).

1H NMR (DMSO-d6) 400 MHz, δ: 9.54 (s, 1H) 9.17 (s, 1H) 8.89 (s, 1H) 8.41 (d, 1H) 8.02-7.98 (m, 1H) 7.41-7.35 (m, 4H) 7.21-7.17 (m, 1H) 6.75-6.72 (m, 2H) 6.60 (d, 1H) 6.35 (s, 1H) 6.09-6.08 (m, 1H) 3.96-3.94 (m, 2H) 3.59 (s, 3H) 3.56-3.54 (br m, 4H) 2.92-2.85 (m, 1H) 2.73-2.57 (br m, 2H) 2.49-2.41 (br m, 4H) 2.39 (s, 3H) 1.23 (d, 6H).

LCMS m/z 715 (M+H)⁺ (ES⁺); 713 (M−H)⁻ (ES⁻)

Example 26

S,S-Dimethyl-N-(3-(4-(2,3-dichloro-4-(3-(3-isopropyl-1-(p-tolyl)-1H-pyrazol-5-yl)ureido)-phenoxy)pyrimidin-2-yl)amino)-5-methoxyphenyl)sulfoximine

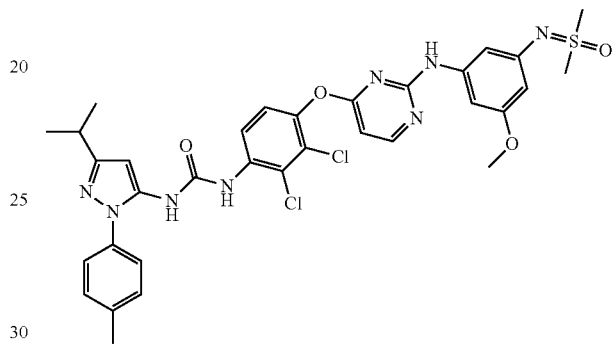

1-(2,3-Dichloro-4-((2-chloropyrimidin-4-yl)oxy)phenyl)-3-(3-isopropyl-1-(p-tolyl)-1H-pyrazol-5-yl)urea (see Example 21(iii) above; 150 mg, 0.282 mmol) was dissolved in DMF (2 mL) and added to S,S-dimethyl-N-(3-amino-5-methoxyphenyl)-sulfoximine (see Example 16(ii) above; 121 mg, 0.564 mmol) and p-TSA monohydrate (26.8 mg, 0.141 mmol). Stirred at 70° C. (block temperature) for 4 h then poured into saturated NaHCO₃ solution (20 mL) and the product extracted with EtOAc (2×20 mL). Organics bulked and washed with 20% w/w brine solution (20 mL), dried (MgSO₄), filtered and evaporated to a yellow gum. The crude product was purified by chromatography on silica gel (40 g column, 2% MeOH:DCM to 8%) to give a colourless solid 146 mg. Recrystallised from MeCN (1 mL) to afford the title compound (65 mg).

1H NMR (400 MHz, DMSO-d6) δ 9.42 (s, 1H), 9.23 (s, 1H), 8.82 (s, 1H), 8.38 (d, 1H), 8.17 (d, 1H), 7.48-7.28 (m, 5H), 6.78 (s, 1H), 6.69 (s, 1H), 6.53 (d, 1H), 6.35 (s, 1H), 6.07 (t, 1H), 3.52 (s, 3H), 3.19 (s, 6H), 2.89 (hept, 1H), 2.39 (s, 3H), 1.24 (d, 6H).

LCMS m/z 709/711 (M+H)⁺ (ES⁺)

Example 27

1-(3-Isopropyl-1-(P-tolyl)-1H-pyrazol-5-yl)-3-(5-((2-((3-methoxy-5-(2-(2-(2-methoxy-ethoxy)ethoxy)ethoxy)phenyl)amino)pyrimidin-4-yl)oxy)quinolin-8-yl)urea

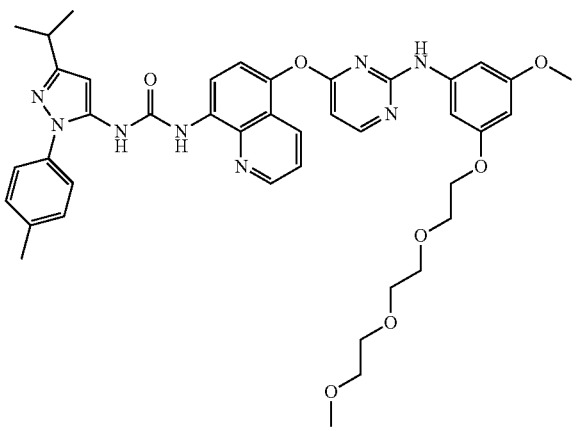 [SMILES: COCCOCCOCCOc1cc(Nc2nccc(Oc3ccc(NC(=O)Nc4cc(C(C)C)nn4-c4ccc(C)cc4)c4ncccc34)n2)cc(OC)c1]

(i) 5-((2-Chloropyrimidin-4-yl)oxy)-8-nitroquinoline

DBU (1.110 mL, 7.36 mmol) was added over 5 min to a stirred mixture of 8-nitroquinolin-5-ol (1 g, 5.26 mmol) in MeCN (20 mL) at 0-5° C. After stirring for 10 min, 2,4-dichloropyrimidine (0.838 g, 5.63 mmol) was added, the mixture stirred at rt for 2 h then heated at 60° C. for 2 h. A further portion of DBU (1.110 mL, 7.36 mmol) and 2,4-dichloropyrimidine (0.838 g, 5.63 mmol) were added, heated at 60° C. for a further 2 h then partitioned between ether (100 mL) and water (100 mL). The organic layer was separated, washed with water, dried (MgSO₄) and evaporated under reduced pressure. The crude product was purified by chromatography on silica gel (40 g column, 0-100% EtOAc/isohexane) to afford the sub-title compound (880 mg) as a yellow solid.

1H NMR (DMSO-d6) 400 MHz, δ: 9.13 (dd, 1H), 8.76 (d, 1H), 8.50 (dd, 1H), 8.44 (d, 1H), 7.80-7.76 (m, 2H), 7.48 (d, 1H).

LCMS m/z 303/305 (M+H)⁺ (ES⁺)

(ii) 5-((2-Chloropyrimidin-4-yl)oxy)quinolin-8-amine

To a partially dissolved suspension of ammonium chloride (68.5 mg, 1.280 mmol) in IPA (90 mL) was added the product from step (i) above (775 mg, 2.56 mmol) and a mixture of iron powder (1430 mg, 25.6 mmol) in water (5 mL). The mixture was heated at reflux for 16 h after which time the mixture was filtered and then the crude product was purified by chromatography on the Companion (40 g column, 0-5% methanol in DCM) to afford the sub-title compound (700 mg) as a pale yellow-brown powder.

1H NMR (400 MHz; DMSO-d6) δ: 8.80 (dd, 1H), 8.60 (d, 1H), 8.03 (dd, 1H), 7.50 (dd, 1H), 7.25 (d, 1H), 7.14 (d, 1H), 6.87 (d, 1H), 6.06 (br.s, 2H).

LCMS m/z 272, 274 (M+H)⁺ (ES⁺); 270, 272 (M−H)⁻ (ES⁻)

(iii) 1-(5-((2-Chloropyrimidin-4-yl)oxy)quinolin-8-yl)-3-(3-isopropyl-1-(p-tolyl)-1H-pyrazol-5-yl)urea To a mixture of phenyl (3-isopropyl-1-(p-tolyl)-1H-pyrazol-5-yl)carbamate (see Example 21(ii) above; 420 mg, 1.127 mmol) and the product from step (ii) above (292 mg, 1.071 mmol) in isopropyl acetate (10 mL) was added triethylamine (23.56 µL, 0.169 mmol) and the mixture heated at 70° C. for 3 h. After this time, isohexanes (6 mL) was added to the warm solution which was then allowed to cool whereupon a precipitate formed. The solid was filtered, washed with ether (10 mL) and dried at 40° C. under vacuum to afford the sub-title compound (297 mg) as a yellow powder.

1H NMR (400 MHz; DMSO-d6) δ: 10.02 (s, 1H), 9.58 (s, 1H), 8.95 (dd, 1H), 8.66 (d, 1H), 8.57 (d, 1H), 8.25 (dd, 1H), 7.65 (dd, 1H), 7.51 (d, 1H), 7.44-7.40 (m, 2H), 7.36-7.31 (m, 2H), 7.28 (d, 1H), 6.38 (s, 1H), 2.95-2.85 (m, 1H), 2.37 (s, 3H), 1.25 (d, 6H).

LCMS m/z 515 (M+H)⁺ (ES⁺); 513 (M−H)⁻ (ES⁻)

(iv) 1-(3-Isopropyl-1-(p-tolyl)-1H-pyrazol-5-yl)-3-(5-((2-((3-methoxy-5-(2-(2-(2-methoxy-ethoxy)ethoxy)ethoxy)phenyl)amino)pyrimidin-4-yl)oxy)quinolin-8-yl)urea To a solution of the product from step (iii) above (142 mg, 0.276 mmol), p-TSA monohydrate (116 mg, 0.608 mmol) and 3-methoxy-5-(2-(2-(2-methoxyethoxyl)ethoxy)-ethoxy)aniline (see Example 13(i) above; 118 mg, 0.414 mmol) in DMF (2 mL) was added THF (1 mL) and the mixture stirred at 70° C. for 10 h. The reaction was cooled to ambient temperature and then partitioned between ethyl acetate (20 mL) and saturated aqueous sodium bicarbonate (10 mL), organic layer washed with further saturated aqueous sodium bicarbonate (2×10 mL), water (5 mL) and brine (5 mL), dried over sodium sulfate, filtered and evaporated to afford crude product as a yellow oil (210 mg). The crude product was purified by chromatography on the Companion (12 g column, 0-3% MeOH in DCM) and then columned a second time on silica (12 g column, 10-50% ethyl acetate in toluene) to afford the title compound (120 mg) as a pale cream solid.

1H NMR (400 MHz; DMSO-d6) δ: 9.98 (s, 1H), 9.56 (s, 1H), 9.40 (br.s, 1H), 8.92 (dd, 1H), 8.56 (d, 1H), 8.41 (d, 1H), 8.21 (dd, 1H), 7.62 (dd, 1H), 7.46 (d, 1H), 7.44-7.40 (m, 2H), 7.36-7.32 (m, 2H), 6.67 (br.d, 2H), 6.59 (d, 1H), 6.38 (s, 1H), 6.00 (t, 1H), 3.85-3.79 (m, 2H), 3.66-3.60 (m, 2H), 3.55-3.44 (m, 9H), 3.42-3.38 (m, 2H), 3.21 (s, 3H), 2.95-2.86 (m, 1H), 2.38 (s, 3H), 1.25 (d, 6H)

LCMS m/z 763 (M+H)⁺ (ES⁺); 761 (M−H)⁻ (ES⁻)

Example 28

1-(3-Isopropyl-1-(P-tolyl)-1H-pyrazol-5-yl)-3-(5-((2-((3-methoxy-5-(2-morpholinoethoxy)-phenyl)amino)pyrimidin-4-yl)oxy)quinolin-8-yl)urea

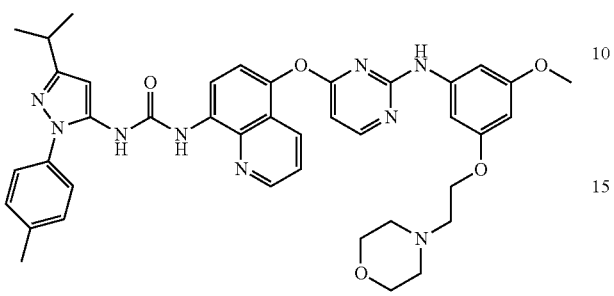

To a solution of 1-(5-((2-chloropyrimidin-4-yl)oxy)quinolin-8-yl)-3-(3-isopropyl-1-(p-tolyl)-1H-pyrazol-5-yl)urea (see Example 27(iii) above; 150 mg, 0.292 mmol), p-TSA monohydrate (122 mg, 0.642 mmol) and 3-methoxy-5-(2-morpholinoethoxy)aniline (see Example 21(iv) above; 110 mg, 0.438 mmol) in DMF (2 mL) was added THF (1 mL) and the mixture stirred at 70° C. After this time the reaction was partitioned between ethyl acetate (20 mL) and saturated aqueous sodium bicarbonate (10 mL). The organic was washed with water (5 mL), brine (2×5 mL) and dried over MgSO₄, filtered and evaporated. The crude product was purified by chromatography on the Companion (12 g column, 0-10% 0.7 M NH₃/MeOH in DCM) then purified by preparative HPLC (Waters, Acidic (0.1% Formic acid), Waters X-Select Prep-C18, 5 µm, 19×50 mm column, 25-60% MeCN in Water) to afford the title compound (70 mg) as a pale cream solid.

1H NMR (400 MHz; DMSO-d6) δ: 9.99 (s, 1H), 9.57 (s, 1H), 9.39 (br.s, 1H), 8.92 (dd, 1H), 8.56 (d, 1H), 8.41 (d, 1H), 8.21 (dd, 1H), 7.62 (dd, 1H), 7.46 (d, 1H), 7.44-7.41 (m, 2H), 7.36-7.32 (m, 2H), 6.66 (br.d, 2H), 6.59 (d, 1H), 6.38 (s, 1H), 5.99 (t, 1H), 3.84 (t, 2H), 3.55-3.51 (m, 4H), 3.47 (s, 3H), 2.95-2.86 (m, 1H), 2.57 (t, 2H), 2.42-2.37 (m, 7H), 1.25 (d, 6H).

LCMS m/z 730 (M+H)⁺ (ES⁺); 728 (M−H)⁻ (ES⁻)

Example 29

1-(4-((2-((3-(2,5,8,11-Tetraoxatridecan-13-yloxy)-5-methoxyphenyl)amino)pyrimidin-4-yl)oxy)naphthalen-1-yl)-3-(3-isopropyl-1-(p-tolyl)-1H-pyrazol-5-yl)urea

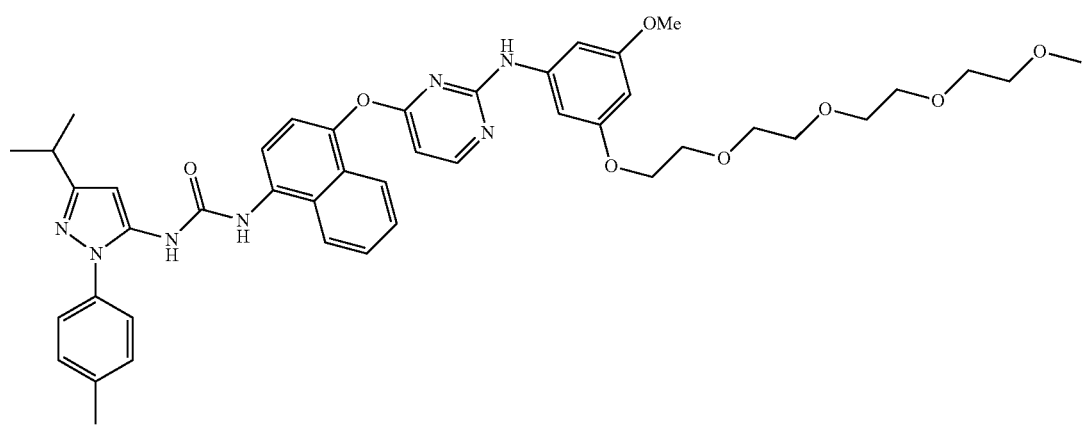 [SMILES: COCCOCCOCCOCCOc1cc(Nc2nccc(Oc3ccc(NC(=O)Nc4cc(C(C)C)nn4-c4ccc(C)cc4)c4ccccc34)n2)cc(OC)c1]

(i) 3-(2,5,8,11-Tetraoxatridecan-13-yloxy)-5-methoxyaniline

3-Amino-5-methoxyphenol (500 mg, 3.59 mmol) and K₂CO₃ (2483 mg, 17.97 mmol) were stirred in N,N-dimethylformamide:pyridine (3:1, 5 mL) at rt. 13-Bromo-2,5,8,11-tetraoxatridecane (1120 mg, 4.13 mmol) was added and the mixture was heated to 60° C. overnight. Sodium iodide (539 mg, 3.59 mmol) was added and the mixture was heated to 90° C. for 2 h. The mixture was diluted with water (75 mL) and extracted with ethyl acetate (3×50 mL). The combined organic phases were washed with saturated brine (3×50 mL), dried (MgSO₄) and concentrated under reduced pressure. The crude product was purified by chromatography on the Companion (40 g column, Et₂O, then EtOAc) to afford the sub-title compound (820 mg) as a brown oil.

1H NMR (DMSO-d6) 400 MHz, δ: 5.77-5.73 (m, 2H), 5.69 (t, 1H), 5.05 (s, 2H), 3.97-3.91 (m, 2H), 3.71-3.66 (m, 2H), 3.63 (s, 3H), 3.60-3.49 (m, 10H), 3.46-3.41 (m, 2H), 3.24 (s, 3H).

(ii) 1-(4-((2-((3-(2,5,8,11-Tetraoxatridecan-13-yloxy)-5-methoxyphenyl)amino)pyrimidin-4-yl)oxy)naphthalen-1-yl)-3-(3-isopropyl-1-(p-tolyl)-1H-pyrazol-5-yl)urea To a solution of 1-(4-((2-chloropyrimidin-4-yl)oxy)naphthalen-1-yl)-3-(3-isopropyl-1-(p-tolyl)-1H-pyrazol-5-yl)urea (see Example 10(ii) above; 150 mg, 0.292 mmol) and the product from step (i) above (120 mg, 0.364 mmol) in DMF (2 mL) was added THF (1 mL) and p-TSA monohydrate (139 mg, 0.731 mmol) and the resulting solution stirred at 70° C. for 16 h. After this time the reaction mixture was diluted with ethyl acetate (30 mL) and washed with saturated aqueous sodium bicarbonate (10 mL), half-saturated brine (10 mL) and brine (10 mL) and then dried over sodium sulfate, filtered and evaporated to afford a brown oil. The crude product was purified by chromatography on the Companion (12 g column, 0-10% (0.7 N NH$_3$ in MeOH) in DCM) to afford a pale brown oil which was further purified by preparative HPLC (Waters, Acidic (0.1% Formic acid), Waters X-Select Prep-C18, 5 μm, 19×50 mm column, 45-70% MeCN in Water) to afford the title compound (20 mg) as a pale orange solid.

1H NMR (400 MHz; DMSO-d6) δ: 9.42 (s, 1H), 9.13 (s, 1H), 8.83 (s, 1H), 8.40 (d, 1H), 8.07 (d, 1H), 7.94 (d, 1H), 7.82 (dd, 1H), 7.65-7.59 (m, 1H), 7.59-7.53 (m, 1H), 7.49-7.44 (2H), 7.41-7.35 (m, 3H), 6.80 (br.d, 2H), 6.53 (d, 1H), 6.37 (s, 1H), 6.03 (t, 1H), 3.89-3.83 (m, 2H), 3.67-3.63 (m, 2H), 3.56-3.46 (m, 13H), 3.41-3.37 (m, 2H), 3.21 (s, 3H), 2.95-2.84 (m, 1H), 2.40 (s, 3H), 1.24 (d, 6H).

LCMS m/z 806 (M+H)$^+$ (ES$^+$); 804 (M−H)$^-$ (ES$^-$)

Example 30

1-(4-((2-((3-(2,5,8,11,14-Pentaoxahexadecan-16-yloxy)-5-methoxyphenyl)amino)-pyrimidin-4-yl)oxy)naphthalen-1-yl)-3-(3-isopropyl-1-(p-tolyl)-1H-pyrazol-5-yl)urea (i) 3-(2,5,8,11,14-Pentaoxahexadecan-16-yloxy)-5-methoxyaniline DIAD (419 μL, 2.156 mmol) added to a suspension of 3-amino-5-methoxyphenol (200 mg, 1.437 mmol), PPh$_3$ (565 mg, 2.156 mmol) and 2,5,8,11,14-pentaoxahexadecan-16-ol (504 μL, 2.156 mmol) in THF (5 mL). Stirred at rt for 16 h. Cooled and partitioned between water (20 mL) and ethyl acetate (20 mL). Organic layer was separated, dried (MgSO$_4$) filtered and solvent evaporated to give a brown oil. The crude product was purified by chromatography on silica gel (40 g column, 1% MeOH:DCM to 5%) then purified further by chromatography on silica gel (12 g column, 50% EtOAc:isohexane to 100%) to afford the sub-title compound (350 mg) as a clear colourless oil.

1H NMR (400 MHz, CDCl$_3$) δ 5.93 (t, 1H), 5.89 (t, 1H), 5.86 (t, 1H), 4.11-4.02 (m, 2H), 3.86-3.77 (m, 2H), 3.76-3.60 (m, 17H), 3.57-3.52 (m, 2H), 3.38 (s, 3H).

(ii) 1-(4-((2-((3-(2,5,8,11,14-Pentaoxahexadecan-16-yloxy)-5-methoxyphenyl)amino)-pyrimidin-4-yl)oxy)naphthalen-1-yl)-3-(3-isopropyl-1-(p-tolyl)-1H-pyrazol-5-yl)urea To a solution of the product from step (i) above (109 mg, 0.292 mmol) and 1-(4-((2-chloropyrimidin-4-yl)oxy)naphthalen-1-yl)-3-(3-isopropyl-1-(p-tolyl)-1H-pyrazol-5-yl)urea (see Example 10(ii) above; 150 mg, 0.292 mmol) in DMF (2 mL) was added p-TSA monohydrate (111 mg, 0.585 mmol) and then THF (1 mL) and the reaction heated at 70° C. over 16 h. After this time the reaction mixture was diluted with ethyl acetate (30 mL) and washed with saturated aqueous sodium bicarbonate (10 mL), half saturated brine (10 mL) and brine (10 mL) and then dried over sodium sulfate, filtered and evaporated to afford a brown oil. The crude product was purified by chromatography on the Companion (12 g column, 0-10% (0.7N NH3 in MeOH) in DCM) to afford a pale brown oil which was further purified by preparative HPLC (Waters, Acidic (0.1% Formic acid), Waters X-Select Prep-C18, 5 μm, 19×50 mm column, 40-70% MeCN in Water) to afford the title compound (9 mg) as a pale orange solid.

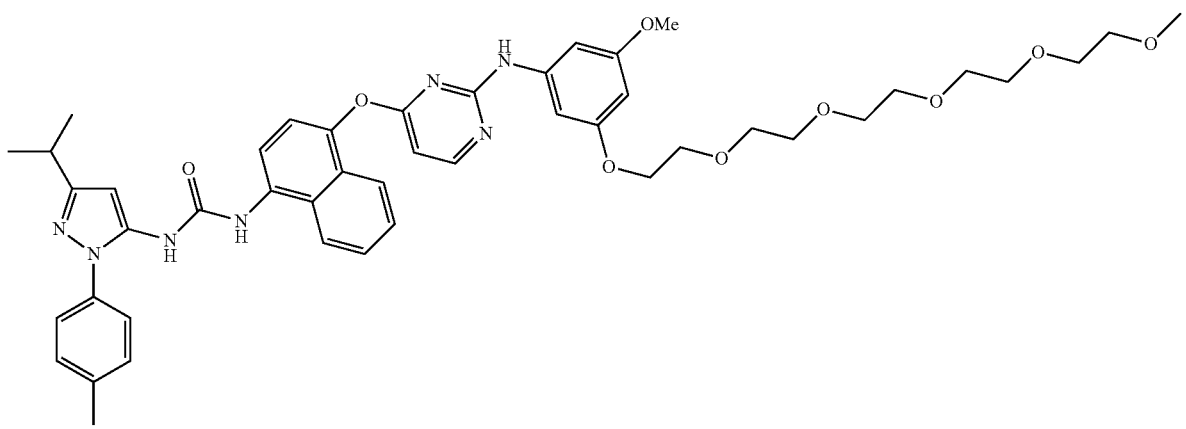 [SMILES: COCCOCCOCCOCCOCCOc1cc(Nc2nccc(Oc3ccc(NC(=O)Nc4cc(C(C)C)nn4-c4ccc(C)cc4)c4ccccc34)n2)cc(OC)c1]

1H NMR (400 MHz; DMSO-d6) δ: 9.42 (s, 1H), 9.18 (s, 1H), 8.89 (s, 1H), 8.40 (d, 1H), 8.07 (d, 1H), 7.94 (d, 1H), 7.81 (dd, 1H), 7.65-7.59 (m, 1H), 7.59-7.53 (m, 1H), 7.49-7.44 (m, 2H), 7.41-7.35 (m, 3H), 6.80 (br.d, 2H), 6.53 (d, 1H), 6.36 (s, 1H), 6.03 (t, 1H), 3.89-3.83 (m, 2H), 3.67-3.63 (m, 2H), 3.56-3.45 (m, 17H), 3.41-3.37 (m, 2H), 3.21 (s, 3H), 2.95-2.84 (m, 1H), 2.39 (s, 3H), 1.24 (d, 6H).

LCMS m/z 850 (M+H)+ (ES+); 848 (M−H)− (ES−)

Example 31

1-(3-Isopropyl-1-(P-tolyl)-1H-pyrazol-5-yl)-3-(4-((2-((3-methoxy-5-((2-(2-(2-methoxy-ethoxy)ethoxy)ethyl)thio)phenyl)amino)pyrimidin-4-yl)oxy)naphthalen-1-yl)urea

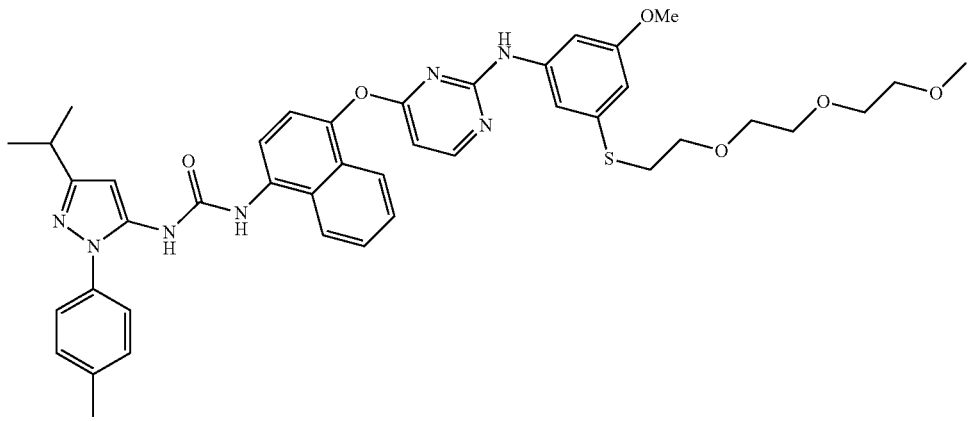 [SMILES: COCCOCCOCCSc1cc(Nc2nccc(Oc3ccc(NC(=O)Nc4cc(C(C)C)nn4-c4ccc(C)cc4)c4ccccc34)n2)cc(OC)c1]

(i) 2-((3-Methoxy-5-nitrophenyl)thio)ethanol

1-Bromo-3-methoxy-5-nitrobenzene (1 g, 4.31 mmol), Pd$_2$(dba)$_3$ (0.197 g, 0.215 mmol) and xantphos (0.249 g, 0.431 mmol) were added to a degassed solution of DIPEA (2.258 mL, 12.93 mmol) and 2-mercaptoethanol (0.302 mL, 4.31 mmol) in 1,4-dioxane (10 mL). Heated under nitrogen at 100° C. for 16 h. The reaction mixture was filtered through Celite and residue partitioned between EtOAc (20 mL) and 20% w/w NaCl solution. Organic layer separated, dried (MgSO$_4$) filtered and solvents evaporated. The crude product was purified by chromatography on the Companion (40 g column, 10% EtOAc:isohexane to 30%) to afford the sub-title compound (925 mg) as a yellow solid.

1H NMR (400 MHz, DMSO-d6) δ 7.69 (t, 1H), 7.49 (t, 1H), 7.33 (dd, 1H), 5.05 (t, 1H), 3.88 (s, 3H), 3.67-3.58 (m, 2H), 3.18 (t, 2H).

(ii) (3-Methoxy-5-nitrophenyl)(2-(2-(2-methoxy-ethoxy)ethoxy)ethyl)sulfane

The product from step (i) above (524 mg, 2.286 mmol) was dissolved in dry DMF (10 mL) under N$_2$ and NaH (96 mg, 2.400 mmol, 60% wt) added. Stirred for 10 min then 1-bromo-2-(2-methoxyethoxy)ethane (323 μL, 2.400 mmol) and NaI (34.3 mg, 0.229 mmol) added. Stirred at rt for 2.5 h, charged again with NaH (96 mg, 2.400 mmol) and 1-bromo-2-(2-methoxyethoxy)ethane (323 μL, 2.400 mmol) and stirred for a further 1 h. The mixture was partitioned between NH$_4$Cl solution (20 mL) and ethyl acetate (20 mL). Organic layer was separated, washed with 20% NaCl solution (20 mL), dried (MgSO$_4$), filtered and solvent evaporated. The crude product was purified by chromatography on silica gel (40 g column, 30% EtOAc: isohexane to 50%) to afford the sub-title compound (380 mg) as a clear yellow oil.

1H NMR (400 MHz, CDCl$_3$) δ 7.78 (t, 1H), 7.51 (t, 1H), 7.16 (dd, 1H), 3.88 (s, 3H), 3.73 (t, 2H), 3.68-3.61 (m, 6H), 3.59-3.51 (m, 2H), 3.38 (s, 3H), 3.20 (t, 2H).

(iii) ethoxy-5-((2-(2-(2-methoxyethoxy)ethoxy)ethyl)thio)aniline

Ammonium chloride (242 mg, 4.53 mmol) was dissolved in ethanol (2 mL) and iron powder (253 mg, 4.53 mmol) added followed by the product from step (ii) above (150 mg, 0.453 mmol) in water (1 mL). Sonicated at 60° C. (bath temperature) for 1 h, then filtered on Celite and solvents evaporated. Partitioned between 1 N HCl (2 mL) and ethyl acetate (2 mL), aqueous layer separated and basified to pH 8 with NaHCO$_3$, then the product was extracted with ethyl acetate (2×5 mL). Organics bulked, dried (MgSO$_4$), and filtered. Solvent evaporated to give the crude product which was purified by chromatography on silica gel (12 g column, 0-100% EtOAc/isohexane) to afford the sub-title compound (67 mg) as an oil.

LCMS m/z 302 (M+H)+ (ES+)

(iv) 1-(3-Isopropyl-1-(p-tolyl)-1H-pyrazol-5-yl)-3-(4-((2-((3-methoxy-5-((2-(2-(2-Methoxy-ethoxy)ethoxy)ethyl)thio)phenyl)amino)pyrimidin- 4-yl)oxy)naphthalen-1-yl)urea To a solution of the product from step (iii) above (61.7 mg, 0.205 mmol) and 1-(4-((2-chloropyrimidin-4-yl)oxy)naphthalen-1-yl)-3-(3-isopropyl-1-(p-tolyl)-1H-pyrazol-5-yl)urea (see Example 10(ii) above; 105 mg, 0.205 mmol) in DMF (2 mL) was added p-TSA monohydrate (78 mg, 0.409 mmol) and then THF (1 mL) and the reaction heated at 70° C. over 16 h. After this time the reaction mixture was diluted with ethyl acetate (30 mL) and washed with saturated aqueous sodium bicarbonate (10 mL), half-saturated brine (10 mL) and brine (10 mL) and then dried over sodium sulfate, filtered and evaporated to afford a brown oil. The crude product was purified by chromatography on the Companion (12 g column, 0-10% (0.7 N NH$_3$ in MeOH) in DCM) to afford a pale brown oil which was further purified by preparative HPLC (Waters, Acidic (0.1% Formic acid), Waters X-Select Prep-C18, 5 µm, 19×50 mm column, 40-80% MeCN in Water) to afford the title compound (9 mg) as a cream solid.

1H NMR (400 MHz; DMSO-d6) δ: 9.49 (s, 1H), 9.14 (s, 1H), 8.86 (s, 1H), 8.41 (d, 1H), 8.07 (d, 1H), 7.96 (d, 1H), 7.81 (dd, 1H), 7.65-7.59 (m, 1H), 7.59-7.53 (m, 1H), 7.49-7.44 (2H), 7.40-7.35 (m, 3H), 7.10 (br.s, 1H), 7.00 (br.s, 1H), 6.56 (d, 1H), 6.39-6.35 (m, 2H), 3.54-3.43 (m, 11H), 3.40-3.36 (m, 2H), 3.20 (s, 3H), 3.00 (t, 2H), 2.94-2.84 (m, 1H), 2.40 (s, 3H), 1.24 (d, 6H).

LCMS m/z 778 (M+H)+ (ES+); 776 (M−H) (ES−)

Example 32

1-(4-((2-((3-(2,5,8,11,14,17,20-Heptaoxadocosan-22-yloxy)-5-methoxyphenyl)amino)-pyrimidin-4-yl)oxy)naphthalen-1-yl)-3-(3-isopropyl-1-(p-tolyl)-1H-pyrazol-5-yl)urea 1H NMR (400 MHz, DMSO-d6) δ 5.77-5.73 (m, 2H), 5.68 (dd, 1H), 5.05 (br s, 2H), 3.97-3.92 (m, 2H), 3.72-3.66 (m, 2H), 3.63 (s, 3H), 3.60-3.48 (m, 22H), 3.45-3.40 (m, 2H), 3.24 (s, 3H).

LCMS m/z 462 (M+H)+ (ES+)

(ii) 1-(4-((2-((3-(2,5,8,11,14,17,20-Heptaoxadocosan-22-yloxy)-5-methoxyphenyl)amino)pyrimidin-4-yl)oxy)naphthalen-1-yl)-3-(3-isopropyl-1-(p-tolyl)-1H-pyrazol-5-yl)urea A mixture of 1-(4-((2-chloropyrimidin-4-yl)oxy)naphthalen-1-yl)-3-(3-isopropyl-1-(p-tolyl)-1H-pyrazol-5-yl)urea (150 mg, 0.278 mmol), the product from step (i) above (135 mg, 0.292 mmol) and p-TSA monohydrate (26.4 mg, 0.139 mmol) was heated to 70° C. in DMF (2 mL) for 18 h. The mixture was cooled, diluted with water (10 mL) and

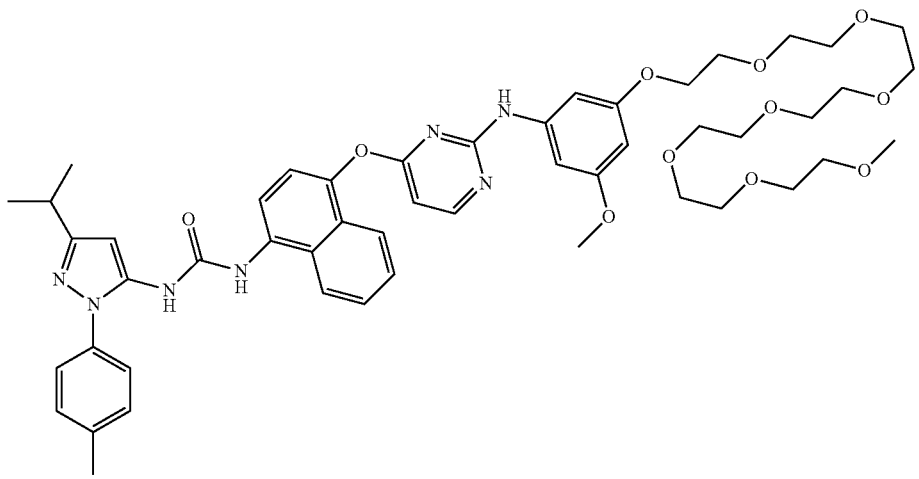 [SMILES: COCCOCCOCCOCCOCCOCCOCCOc1cc(Nc2nccc(Oc3ccc(NC(=O)Nc4cc(C(C)C)nn4-c4ccc(C)cc4)c4ccccc34)n2)cc(OC)c1]

(i) 3-(2,5,8,11,14,17,20-Heptaoxadocosan-22-yloxy)-5-methoxyaniline

DIAD (576 µL, 2.96 mmol) was added to a suspension of 3-amino-5-methoxyphenol (275 mg, 1.976 mmol), PPh3 (778 mg, 2.96 mmol) and O-methylheptaethylene glycol (1009 mg, 2.96 mmol) in THF (5 mL) and the resulting mixture was stirred at rt for 18 h. The mixture was cooled and partitioned between water (20 mL) and ethyl acetate (20 mL). The organic layer was separated, dried (MgSO4), filtered and concentrated under reduced pressure to give a brown oil. The crude product was purified by chromatography on silica gel (40 g column, 0-10% MeOH/EtOAc) to afford a clear brown oil. The oil was further purified by chromatography on the Companion (80 g column, 0-50% acetone/toluene) to afford the sub-title compound (292 mg) as a pale yellow oil.

extracted with ethyl acetate (3×10 mL). The combined organic phases were washed with saturated brine (10 mL), dried (MgSO4) and concentrated under reduced pressure. The crude product was purified by chromatography on the Companion (40 g column, 0-75% acetone/toluene) to afford a brown gum. The gum was triturated in diethyl ether to yield the title compound (43 mg) as a pale pink waxy solid.

1H NMR (DMSO-d6) 400 MHz, δ: 9.43 (s, 1H), 9.10 (s, 1H), 8.79 (s, 1H), 8.41 (d, 1H), 8.07 (d, 1H), 7.96 (d, 1H), 7.83 (dd, 1H), 7.67-7.53 (m, 2H), 7.51-7.43 (m, 2H), 7.43-7.34 (m, 3H), 6.85-6.75 (m, 2H), 6.54 (d, 1H), 6.38 (s, 1H), 6.04 (t, 1H), 3.92-3.83 (m, 2H), 3.70-3.61 (m, 2H), 3.59-3.44 (m, 25H), 3.44-3.37 (m, 2H), 3.23 (s, 3H), 2.90 (hept, 1H), 2.41 (s, 3H), 1.25 (d, 6H).

LCMS m/z 939 (M+H)+ (ES+)

Example 33

1-(3-Isopropyl-1-(p-tolyl)-1H-pyrazol-5-yl)-3-(4-((2-((3-(2-(2-(2-methoxyethoxyl)ethoxy)-ethoxy)-5-(trifluoromethoxy)phenyl)amino)pyrimidin-4-yl)oxy)naphthalen-1-yl)urea

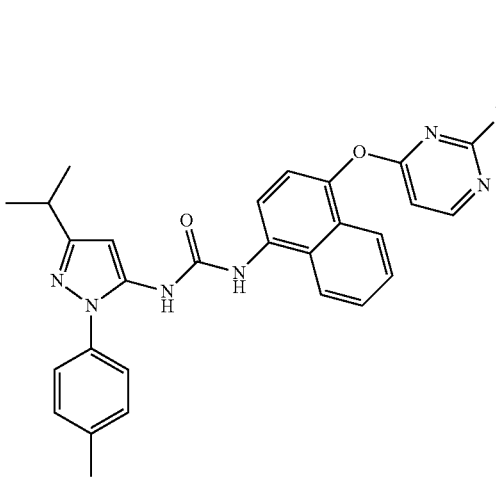
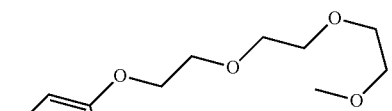

(i) Methyl 3-hydroxy-5-(trifluoromethoxy)benzoate

To a solution of 3-hydroxy-5-(trifluoromethoxy)benzoic acid (2.13 g, 9.59 mmol) in methanol (50 mL) was added TMS-Cl (2.451 ml, 19.18 mmol) and the reaction heated at reflux over 3 h. The volatiles were removed under reduced pressure and the residue was purified by chromatography on the Companion (40 g column, 0-50% Et$_2$O/isohexanes) to afford the sub-title compound (1.80 g) as a white solid.
LCMS m/z 237 (M+H)+ (ES+); 235 (M−H)− (ES−)

(ii) Methyl 3-(2-(2-(2-methoxyethoxyl)ethoxy)ethoxy)-5-(trifluoromethoxy)benzoate The product from step (i) above (1.8 g, 7.62 mmol), K$_2$CO$_3$ (1.580 g, 11.43 mmol) and sodium iodide (0.114 g, 0.762 mmol) were stirred in acetonitrile (15 mL) at room temperature. 1-Bromo-2-(2-(2-methoxyethoxyl)ethoxy)ethane (2.250 g, 9.91 mmol) was added and the mixture was heated to reflux for 6 h. The mixture was cooled, the inorganic solids were removed by filtration and the filtrate was concentrated under reduced pressure. The residue was purified by chromatography on the Companion (40 g column, 50-100% Et$_2$O/isohexanes) to afford the sub-title compound (2.53 g) as a clear colourless oil.
1H NMR (DMSO-d6) 400 MHz, δ: 7.52-7.48 (m, 1H), 7.44-7.39 (m, 1H), 7.33-7.28 (m, 1H), 4.26-4.19 (m, 2H), 3.88 (s, 3H), 3.79-3.73 (m, 2H), 2.62-3.56 (m, 2H), 3.56-3.48 (m, 4H), 3.45-3.39 (m, 2H), 3.23 (s, 3H).
LCMS m/z 383 (M+H)+ (ES+)

(iii) 3-(2-(2-(2-Methoxyethoxyl)ethoxy)ethoxy)-5-(trifluoromethoxy)benzoic acid A solution of the product from step (ii) above (2.53 g, 6.48 mmol) in THF (1 mL) and 1M sodium hydroxide solution (6.48 ml, 6.48 mmol) were stirred at rt for 2 h. The mixture was diluted with water (30 mL) and washed with diethyl ether (3×30 mL). The aqueous phase was treated with 1 M HCl (6.3 mL) to give a pH~4 and extracted with ethyl acetate (3×40 mL). The combined organic phases were washed with saturated brine (50 mL), dried (MgSO$_4$) and concentrated under reduced pressure to give the sub-title compound (2.252 g) as a clear, colourless oil.
1H NMR (DMSO-d6) 400 MHz, δ: 13.47 (br s, 1H), 7.50-7.46 (m, 1H), 7.42-7.37 (m, 1H), 7.28-7.23 (m, 1H), 4.25-4.18 (m, 2H), 3.80-3.72 (m, 2H), 3.62-3.56 (m, 2H), 3.56-3.48 (m, 4H), 3.45-3.39 (m, 2H), 3.23 (s, 3H).
LCMS m/z 369 (M+H)+ (ES+); 367 (M−H) (ES−)

(iv) tert-Butyl (3-(2-(2-(2-methoxyethoxyl)ethoxy)ethoxy)-5-(trifluoromethoxy)phenyl) carbamate DPPA (0.946 ml, 4.39 mmol) was added to a stirred solution of the product from step (iii) above (1100 mg, 2.93 mmol) and triethylamine (0.612 ml, 4.39 mmol) in tert-butanol (20 mL) and heated to reflux for 18 h. The mixture was cooled, water (50 mL) added and extracted with ethyl acetate (3×50 mL). The combined organic phases were washed with saturated brine (25 mL), dried (MgSO$_4$) and concentrated under reduced pressure. The crude product was purified by chromatography on the Companion (40 g column, 20-80% Et$_2$O/isohexane) to afford the sub-title compound (918 mg).
1H NMR (DMSO-d6) 400 MHz, δ: 9.62 (s, 1H), 7.17-7.14 (m, 1H), 7.08-7.02 (m, 1H), 6.57-6.52 (m, 1H), 4.10-4.03 (m, 2H), 3.76-3.69 (m, 2H), 3.61-3.55 (m, 2H), 3.55-3.49 (m, 4H), 3.46-3.41 (m, 2H), 3.24 (s, 3H), 1.48 (s, 9H).
LCMS m/z 462 (M+Na)+(ES+); 438 (M−H)− (ES−)

(v) 3-(2-(2-(2-Methoxyethoxy)ethoxy)ethoxy)-5-(trifluoromethoxy)aniline

The product from step (iv) above (0.915 g, 1.978 mmol) was stirred in 4M HCl in 2-propanol (10 mL, 40.0 mmol) at rt for 5 h. The volatiles were removed under reduced pressure and the residue was co-evaporated with DCM (75 mL) and triethylamine (1 mL). The crude product was purified by chromatography on the Companion (40 g column, 20-80% EtOAc/isohexane) to afford the sub-title compound (0.540 g) as a brown oil.

1H NMR (DMSO-d6) 400 MHz, δ: 6.14-6.07 (m, 2H), 6.04-5.94 (m, 1H), 5.52 (s, 2H), 4.04-3.96 (m, 2H), 3.74-3.66 (m, 2H), 3.62-3.48 (m, 6H), 3.46-3.40 (m, 2H), 3.24 (s, 3H).

LCMS m/z 340 (M+H)$^+$ (ES$^+$)

(vi) 1-(3-Isopropyl-1-(p-tolyl)-1H-pyrazol-5-yl)-3-(4-((2-((3-(2-(2-(2-methoxyethoxy)ethoxy) ethoxy)-5-(trifluoromethoxy)phenyl)amino)pyrimidin-4-yl) oxy)naphthalen-1-yl)urea A mixture of 1-(4-((2-chloropyrimidin-4-yl)oxy)naphthalen-1-yl)-3-(3-isopropyl-1-(p-tolyl)-1H-pyrazol-5-yl)urea (see Example 10(ii) above; 150 mg, 0.278 mmol), the product from step (v) above (118 mg, 0.347 mmol) and p-TSA monohydrate (26.4 mg, 0.139 mmol) was heated to 70° C. in DMF (2 mL) for 18 h. The mixture was diluted with water (10 mL) and extracted with diethyl ether (3×10 mL) then ethyl acetate (3×10 mL). The combined ethyl acetate layers were washed with saturated brine solution, dried (MgSO$_4$) and concentrated under reduced pressure. The crude product was triturated with diethyl ether to yield the title compound (47 mg).

1H NMR (DMSO-d6) 400 MHz, δ: 9.74 (s, 1H), 9.09 (s, 1H), 8.79 (s, 1H), 8.45 (d, 1H), 8.06 (d, 1H), 7.96 (d, 1H), 7.83-7.78 (m, 1H), 7.66-7.59 (m, 1H), 7.59-7.53 (m, 1H), 7.48-7.34 (m, 5H), 7.25-7.17 (m, 2H), 6.62 (d, 1H), 6.41 (s, 1H), 6.36 (s, 1H), 3.97-3.90 (m, 2H), 3.69-3.63 (m, 2H), 3.56-3.46 (m, 6H), 3.42-3.36 (m, 2H), 3.20 (s, 3H), 2.89 (hept, 1H), 2.40 (s, 3H), 1.24 (d, 6H).

LCMS m/z 816 (M+H)$^+$ (ES$^+$)

Example 34

1-(3-Isopropyl-1-(p-tolyl)-1H-pyrazol-5-yl)-3-(4-((2-((3-(2-(2-(2-methoxyethoxy)ethoxy)-ethoxy)-5-(trifluoromethyl)phenylamino)pyrimidin-4-yl)oxy)naphthalen-1-yl)urea

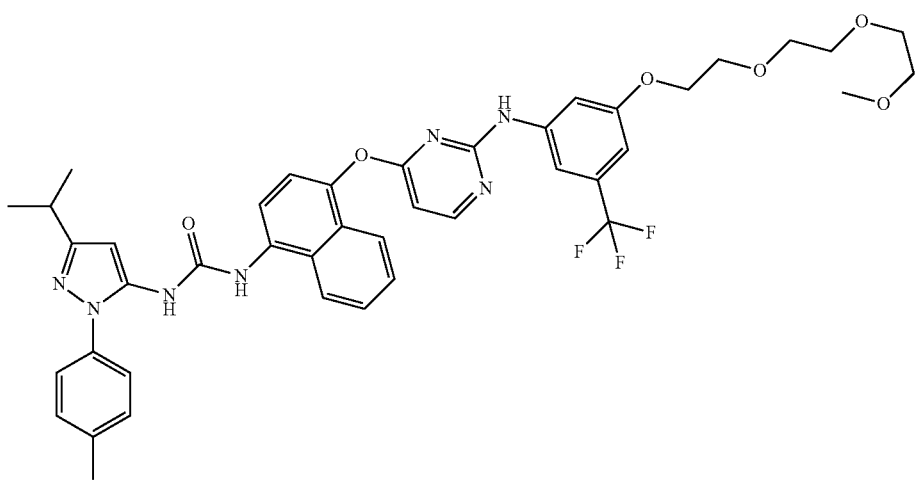 [SMILES: COCCOCCOCCOc1cc(Nc2nccc(Oc3ccc(NC(=O)Nc4cc(C(C)C)nn4-c4ccc(C)cc4)c4ccccc34)n2)cc(C(F)(F)F)c1]

(i) 1-(2-(2-(2-Methoxyethoxy)ethoxy)ethoxy)-3-nitro-5-(trifluoromethyl)benzene

To a stirred suspension of 3-nitro-5-(trifluoromethyl)phenol (1 g, 4.83 mmol) and K$_2$CO$_3$ (1.335 g, 9.66 mmol) in DMF (45 mL) was added 1-bromo-2-(2-(2-methoxyethoxyl) ethoxy) ethane (1.256 ml, 7.24 mmol). The resulting mixture was heated at 60° C. overnight. The reaction was cooled to rt and diluted with water. The mixture was extracted with EtOAc (3×100 mL). The combined organic extracts were washed with water (2×100 mL), brine (100 mL), dried (MgSO$_4$), filtered and concentrated in vacuo to afford an orange liquid. The crude product was purified by chromatography on silica gel (80 g column, 0-100% EtOAc in isohexane) to afford the sub-title compound (1.77 g) as a yellow liquid. The product was used in the next step without further purification.

LCMS m/z 354 (M+H)$^+$ (ES$^+$)

(ii) 3-(2-(2-(2-Methoxyethoxy)ethoxy)ethoxy)-5-(trifluoromethyl)aniline

To a partially dissolved suspension of ammonium chloride (0.133 g, 2.491 mmol) in IPA (150 mL) was added the product from step (i) above (1.76 g, 4.98 mmol) and a mixture of iron powder (2.78 g, 49.8 mmol) in water (10 mL). The mixture was heated at reflux for 4 h then cooled to rt. The reaction mixture was filtered through a pad of Celite and the filtrate concentrated in vacuo. The crude product was purified by chromatography on silica gel (40 g column, 0-10% MeOH in DCM) to afford the sub-title compound (1.27 g) as a dark orange liquid.

1H NMR (DMSO-d6) 400 MHz, δ: 6.46-6.44 (br m, 1H), 6.36-6.34 (br m, 1H), 6.32-6.30 (br m, 1H), 5.57 (s, 2H), 4.05-4.02 (m, 2H), 3.72-3.69 (m, 2H), 3.58-3.56 (m, 2H), 3.54-3.50 (m, 4H), 3.44-3.41 (m, 2H), 3.23 (s, 3H).

LCMS m/z 324 (M+H)$^+$ (ES$^+$)

(iii) 1-(3-Isopropyl-1-(p-tolyl)-1H-pyrazol-5-yl)-3-(4-((2-((3-(2-(2-(2-methoxyethoxy)ethoxy) ethoxy)-5-(trifluoromethyl)phenyl)amino)pyrimidin-4-yl) oxy)naphthalen-1-yl)urea A mixture of 1-(4-((2-chloropyrimidin-4-yl)oxy)naphthalen-1-yl)-3-(3-isopropyl-1-(p-tolyl)-1H-pyrazol-5-yl)urea (see Example 10(ii) above; 150 mg, 0.278 mmol), the product from step (ii) above (112 mg, 0.347 mmol) and p-TSA monohydrate (26.4 mg, 0.139 mmol) was heated to 70° C. in DMF (2 mL) for 18 h. The mixture was diluted with water (5 mL) and saturated sodium hydrogen carbonate solution (5 mL) then extracted with ethyl acetate (3×10 mL).

The combined organic phases were washed with saturated brine solution (10 mL), dried (MgSO$_4$) and concentrated under reduced pressure. The crude product was purified by chromatography on the Companion (40 g column, 0-50% acetone/isohexanes) to afford a red-brown gum. The gum was triturated in diethyl ether to yield the title compound (35 mg) as a pale pink solid.

1H NMR (DMSO-d6) 400 MHz, δ: 9.78 (s, 1H), 9.09 (s, 1H), 8.78 (s, 1H), 8.47 (d, 1H), 8.07 (d, 1H), 7.95 (d, 1H), 7.86-7.79 (m, 1H), 7.67-7.34 (m, 9H), 6.77-6.74 (m, 1H), 6.62 (d, 1H), 6.37 (s, 1H), 4.05-3.95 (m, 2H), 3.74-3.65 (m, 2H), 3.59-3.46 (m, 6H), 3.43-3.37 (m, 2H), 3.21 (s, 3H), 2.91 (hept, 1H), 2.41 (s, 3H), 1.25 (d, 6H).

LCMS m/z 800 (M+H)$^+$ (ES$^+$)

Example 35

1-(2,3-Dichloro-4-((2-((3-methoxy-5-(2-(2-(2-methoxyethoxy)ethoxy)ethoxy)phenyl)-amino)pyrimidin-4-yl)oxy)phenyl)-3-(3-isopropyl-1-(p-tolyl)-1H-pyrazol-5-yl)urea

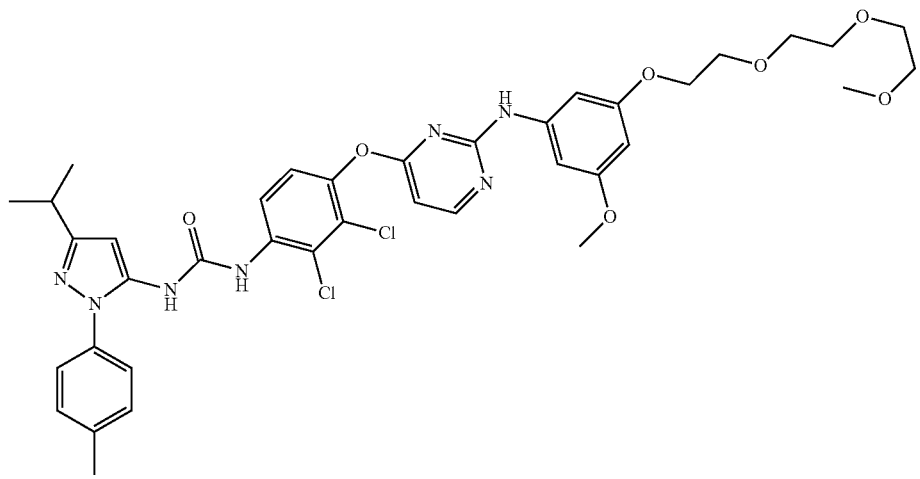 [SMILES: COCCOCCOCCOc1cc(Nc2nccc(Oc3ccc(NC(=O)Nc4cc(C(C)C)nn4-c4ccc(C)cc4)c(Cl)c3Cl)n2)cc(OC)c1]

A mixture of 1-(2,3-dichloro-4-((2-chloropyrimidin-4-yl)oxy)phenyl)-3-(3-isopropyl-1-(p-tolyl)-1H-pyrazol-5-yl)urea (see Example 21(iii) above; 150 mg, 0.282 mmol), 3-methoxy-5-(2-(2-(2-methoxyethoxyl)ethoxy)ethoxy)aniline (see Example 13(i) above; 101 mg, 0.353 mmol) and p-TSA monohydrate (26.8 mg, 0.141 mmol) was heated to 70° C. in DMF (2 mL) for 18 h. The mixture was diluted with water (5 mL) and saturated sodium hydrogen carbonate solution (5 mL) then extracted with ethyl acetate (3×10 mL). The combined organic phases were washed with saturated brine solution (10 mL), dried (MgSO$_4$) and concentrated under reduced pressure. The crude product was purified by chromatography on the Companion (40 g column, 0-50% acetone/isohexanes) to afford a red-brown gum. The gum was triturated in diethyl ether to yield the title compound (35 mg) as a pale pink solid.

1H NMR (DMSO-d6) 400 MHz, δ: 9.51 (s, 1H), 9.22 (s, 1H), 8.81 (s, 1H), 8.41 (d, 1H), 8.17 (d, 1H), 7.46-7.32 (m, 5H), 6.82-6.70 (m, 2H), 6.57 (d, 1H), 6.35 (s, 1H), 6.08 (t, 1H), 4.00-3.90 (m, 2H), 3.73-3.65 (m, 2H), 3.63-3.48 (m, 6H), 3.58 (s, 3H), 3.44-3.39 (m, 2H), 3.23 (s, 3H), 2.90 (hept, 1H), 2.39 (s, 3H), 1.24 (d, 6H).

LCMS m/z 782/780 (M+H)$^+$ (ES$^+$)

Example 36

1-(3-Isopropyl-1-(p-tolyl)-1H-pyrazol-5-yl)-3-(4-((2-((3-methoxy-5-((2-(2-(2-methoxy-ethoxy)ethoxy)ethyl)sulfonyl)phenyl)amino)pyrimidin-4-yl)oxy)naphthalen-1-yl)urea

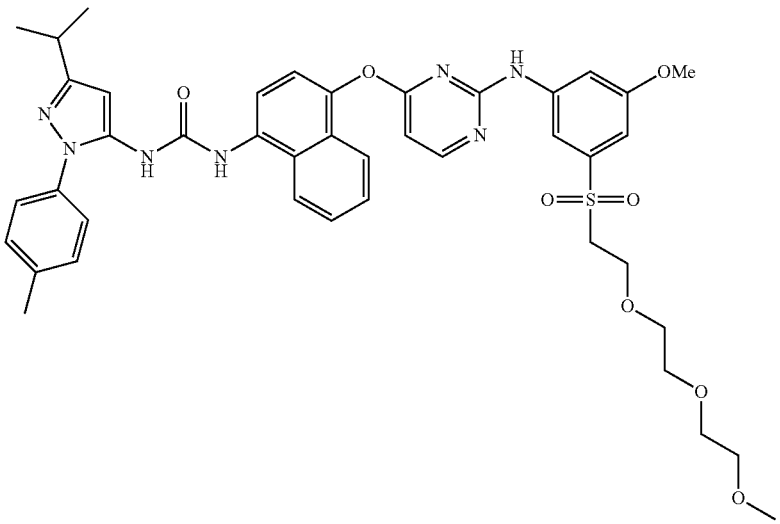 [SMILES: COCCOCCOCCS(=O)(=O)c1cc(Nc2nccc(Oc3ccc(NC(=O)Nc4cc(C(C)C)nn4-c4ccc(C)cc4)c4ccccc34)n2)cc(OC)c1]

(i) 2-((3-Methoxy-5-nitrophenyl)thio)ethanol

1-Bromo-3-methoxy-5-nitrobenzene (1 g, 4.31 mmol), Pd$_2$(dba)$_3$ (0.197 g, 0.215 mmol) and xantphos (0.249 g, 0.431 mmol) were added to a degassed solution of DIPEA (2.258 mL, 12.93 mmol) and 2-mercaptoethanol (0.302 mL, 4.31 mmol) in 1,4-dioxane (10 mL). Heated under nitrogen at 100° C. for 16 h. The reaction mixture was filtered through Celite and residue partitioned between EtOAc (20 mL) and 20% w/w NaCl solution. Organic layer separated, dried (MgSO$_4$) filtered and solvents evaporated. The crude product was purified by chromatography on the Companion (40 g column, 10% EtOAc:isohexane to 30%) to afford the sub-title compound (925 mg) as a yellow solid.

1H NMR (400 MHz, DMSO-d6) δ 7.69 (t, 1H), 7.49 (t, 1H), 7.33 (dd, 1H), 5.05 (t, 1H), 3.88 (s, 3H), 3.67-3.58 (m, 2H), 3.18 (t, 2H).

(ii) (3-Methoxy-5-nitrophenyl)(2-(2-(2-methoxy-ethoxy)ethoxy)ethyl)sulfane

The product from step (i) above (524 mg, 2.286 mmol) was dissolved in dry DMF (10 mL) under nitrogen and NaH (96 mg, 2.400 mmol, 60% Wt) added. Stirred for 10 minutes then 1-bromo-2-(2-methoxyethoxyl)ethane (323 μL, 2.400 mmol) and sodium iodide (34.3 mg, 0.229 mmol) added. Stirred at rt for 2.5 h, then charged again with NaH (96 mg of 60% w/w, 2.400 mmol) and 1-bromo-2-(2-methoxyethoxyl)ethane (323 μL, 2.400 mmol) and stirred for a further 1 h. Partitioned between NH$_4$Cl solution (20 mL) and ethyl acetate (20 mL). The organic layer was separated and washed with 20% NaCl solution (20 mL), dried (MgSO$_4$) filtered and solvent evaporated. The crude product was purified by chromatography on silica gel (40 g column, 30% EtOAc:isohexane to 50%) to afford the sub-title compound (380 mg) as a clear yellow oil.

1H NMR (400 MHz, CDCl$_3$) δ 7.78 (t, 1H), 7.51 (t, 1H), 7.16 (dd, 1H), 3.88 (s, 3H), 3.73 (t, 2H), 3.68-3.61 (m, 6H), 3.59-3.51 (m, 2H), 3.38 (s, 3H), 3.20 (t, 2H).

(iii) 1-Methoxy-3-(2-(2-(2-methoxyethoxyl)ethoxy)ethyl)sulfonyl)-5-nitrobenzene mCPBA (335 mg of ~75% w/w, 1.458 mmol) was added to a stirred solution of the product from step (ii) above (230 mg, 0.694 mmol) in DCM (3 mL) at 0-5° C. The mixture was warmed to rt, stirred for 2 h then partitioned between DCM (30 mL) and aq NaHCO$_3$ solution (20 mL). The organic layer was separated, washed with brine (20 mL), dried (MgSO$_4$) and evaporated under reduced pressure to afford the sub-title compound (251 mg) as a yellow oil.

LCMS m/z 364 (M+H)$^+$ (ES$^+$)

(iv) 3-Methoxy-5-((2-(2-(2-methoxyethoxyl)ethoxy)ethyl)sulfonyl)aniline

A mixture of the product from step (iii) above (250 mg, 0.660 mmol) and 10% Pd—C (50 mg, 0.047 mmol) in EtOH (3 mL) and THF (1 mL) was stirred under a balloon of hydrogen for 4 h. N$_2$ was bubbled through the mixture for 5 min before filtering through Celite. The filtrate was evaporated under reduced pressure and the residue purified by chromatography on silica gel (12 g column, 0-3% MeOH/DCM) to afford the sub-title compound (174 mg) as a gum.

1H NMR (400 MHz; CDCl$_3$) δ 6.82 (dd, 1H), 6.78 (dd, 1H), 6.40 (t, 1H), 3.99 (brs, 2H), 3.82 (t, 2H), 3.81 (s, 3H), 3.61-3.52 (m, 8H), 3.40 (t, 2H), 3.37 (s, 3H).

LCMS m/z 334 (M+H)$^+$ (ES$^+$)

(v) 1-(3-Isopropyl-1-(p-tolyl)-1H-pyrazol-5-yl)-3-(4-((2-((3-methoxy-5-((2-(2-(2-methoxy-ethoxy)ethoxy)ethyl)sulfonyl)phenyl)amino)pyrimidin-4-yl)oxy)naphthalen-1-yl)urea To a solution of 1-(4-((2-chloropyrimidin-4-yl)oxy)naphthalen-1-yl)-3-(3-isopropyl-1-(p-tolyl)-1H-pyrazol-5-yl)

urea (see Example 10(ii) above; 200 mg, 0.390 mmol) and the product from step (iv) above (165 mg, 0.495 mmol) in DMF (2 mL) was added p-TSA monohydrate (74.2 mg, 0.390 mmol) and THF (1 mL) and the resulting solution heated at 70° C. for 20 h. After this time the reaction mixture was diluted with ethyl acetate (30 mL) and washed with saturated aqueous sodium bicarbonate (10 mL), half-saturated brine (10 mL), brine (10 mL) and then dried over sodium sulfate, filtered and evaporated to afford a brown oil. The crude product was purified by chromatography on silica gel (40 g column, 0-5% MeOH/DCM) to afford a brown foam which was triturated with EtOAc/MeCN (5 ml, 10/1) then slurried for 24 h in MeCN (2 mL), filtered and dried to afford the title compound (50 mg) as a white solid.

1H NMR (400 MHz; DMSO-d6) δ 9.85 (s, 1H), 9.11 (s, 1H), 8.81 (s, 1H), 8.47 (d, 1H), 8.08 (d, 1H), 7.97 (d, 1H), 7.82 (d, 1H), 7.73 (brs, 1H), 7.65-7.37 (m, 8H), 6.89 (s, 1H), 6.64 (d, 1H), 6.38 (s, 1H), 3.66-3.64 (m, 5H), 3.49 (t, 2H), 3.35-3.29 (m, 8H, under H$_2$O), 3.17 (s, 3H), 2.90 (septet, 1H), 2.41 (s, 3H), 1.25 (d, 6H).

LCMS m/z 810 (M+H)$^+$ (ES$^+$)

Example 37

1-(3-(tert-Butyl)-1-(p-tolyl)-1H-pyrazol-5-yl)-3-(4-((2-((3-methoxy-5-(2-(2-(2-methoxy-ethoxy)ethoxy)ethoxy)phenyl)amino)pyrimidin-4-yl)oxy)naphthalen-1-yl)urea

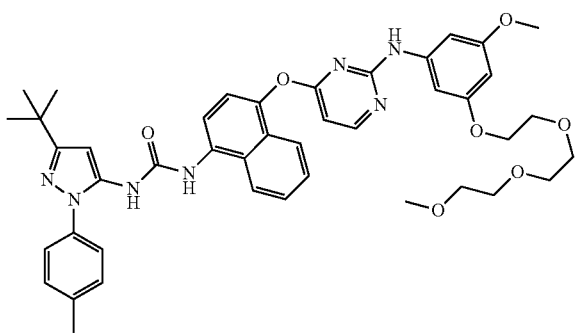 [SMILES: COCCOCCOCCOc1cc(Nc2nccc(Oc3ccc(NC(=O)Nc4cc(C(C)(C)C)nn4-c4ccc(C)cc4)c4ccccc34)n2)cc(OC)c1]

(i) tert-Butyl (4-((2-((3-methoxy-5-(2-(2-(2-methoxyethoxyl)ethoxy)ethoxy)phenyl)amino)pyrimidin-4-yl)oxy)naphthalen-1-yl)carbamate tert-Butyl (4-((2-chloropyrimidin-4-yl)oxy)naphthalen-1-yl)carbamate (see, for example, Ito, K. et al., WO 2010/067130, 17 Jun. 2010; 1 g, 2.69 mmol), 3-methoxy-5-(2-(2-(2-methoxyethoxyl)ethoxy)ethoxy)aniline (see Example 13(i) above; 1.15 g, 4.03 mmol) and p-TSA monohydrate (0.102 g, 0.538 mmol) in DMF (10 mL) was heated at 65° C. (block temperature) for 8 h. The mixture was cooled and partitioned between EtOAc (150 mL) and saturated, aqueous NaHCO$_3$ (50 mL). The organic layer was washed with water (50 mL), dried (MgSO$_4$), filtered and evaporated under reduced pressure. The crude product was purified by chromatography on silica gel (40 g column, 0-5% MeOH/DCM) then further purified by chromatography on silica gel (80 g column, 0-100% EtOAc/isohexane) to afford the sub-title compound (1.01 g) as a foam.

LCMS m/z 621 (M+H)$^+$ (ES$^+$)

(ii) 4-((4-Aminonaphthalen-1-yl)oxy)-N-(3-methoxy-5-(2-(2-(2-methoxyethoxy)ethoxy)-ethoxy)phenyl)pyrimidin-2-amine TFA (3 ml, 38.9 mmol) was added to a stirred solution of the product from step (i) above (1 g, 1.611 mmol) in DCM (12 mL) at rt. The mixture was stirred for 2 h then evaporated under reduced pressure. The residue was partitioned between DCM (100 mL) and saturated, aqueous NaHCO$_3$ solution (50 mL), the organic layer separated, washed with water (50 mL), dried (MgSO$_4$), filtered and evaporated under reduced pressure. MeOH (10 mL) was added and the residue evaporated to afford the sub-title compound (840 mg) as a solid.

1H NMR (400 MHz; DMSO-d6) δ 9.42 (s, 1H), 8.33 (d, 1H), 8.14-8.12 (m, 1H), 7.64-7.62 (m, 1H), 7.46-7.41 (m, 2H), 7.11 (d, 1H), 6.87 (br s, 2H), 6.68 (d, 1H), 6.34 (d, 1H), 6.04 (s, 1H), 5.79 (s, 2H), 3.87-3.85 (m, 2H), 3.68-3.66 (m, 2H), 3.56-3.50 (m, 9H), 3.43-3.41 (m, 2H), 3.22 (s, 3H).

LCMS m/z 521 (M+H)$^+$ (ES$^+$)

(iii) 1-(3-(tert-Butyl)-1-(p-tolyl)-1H-pyrazol-5-yl)-3-(4-((2-((3-methoxy-5-(2-(2-(2-methoxy-ethoxy)ethoxy)ethoxy)phenyl)amino)pyrimidin-4-yl)oxy)naphthalen-1-yl)urea Triethylamine (4 µL, 0.029 mmol) was added to a mixture of phenyl (3-(tert-butyl)-1-(p-tolyl)-1H-pyrazol-5-yl)carbamate (see, for example, Kapadia, S. R. et al., U.S. Pat. No. 6,492,529, 10 Dec. 2002; 50.1 mg, 0.143 mmol) and the product from step (ii) above (75 mg, 0.144 mmol) in isopropyl acetate (2 mL) and the mixture heated at 50° C. for 4 h. Solvent was evaporated and the crude product was purified by chromatography on silica gel (12 g column, 1% MeOH:DCM to 4%) then the resultant solid triturated with Et$_2$O (3×2 mL) to afford the title compound (77 mg) as a colourless solid.

1H NMR (400 MHz, DMSO-d6) δ 9.44 (s, 1H), 9.11 (s, 1H), 8.78 (s, 1H), 8.41 (d, 1H), 8.07 (d, 1H), 7.96 (d, 1H), 7.83 (d, 1H), 7.69-7.51 (m, 2H), 7.52-7.43 (m, 2H), 7.43-7.30 (m, 3H), 6.89-6.69 (m, 2H), 6.54 (d, 1H), 6.42 (s, 1H), 6.04 (t, 1H), 3.97-3.80 (m, 2H), 3.72-3.61 (m, 2H), 3.59-3.45 (m, 9H), 3.46-3.37 (m, 2H), 3.22 (s, 3H), 2.41 (s, 3H), 1.29 (s, 9H).

LCMS m/z 776 (M+H)$^+$ (ES$^+$)

Example 38

1-(3-(tert-Butyl)-1-(6-methoxypyridin-3-yl)-1H-pyrazol-5-yl)-3-(4-((2-((3-methoxy-5-(2-(2-(2-methoxyethoxyl)ethoxy)ethoxy)phenyl)amino)pyrimidin-4-yl)oxy)naphthalen-1-yl)urea

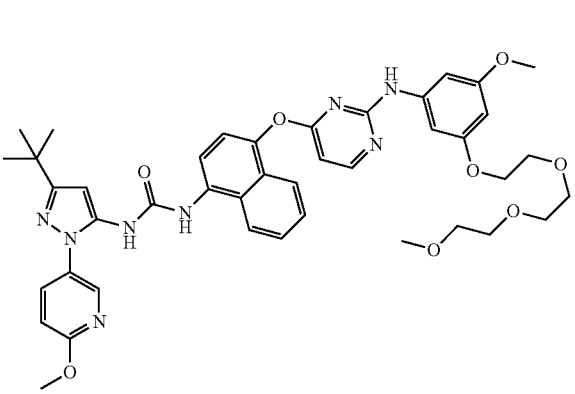 [SMILES: COCCOCCOCCOc1cc(Nc2nccc(Oc3ccc(NC(=O)Nc4cc(C(C)(C)C)nn4-c4ccc(OC)nc4)c4ccccc34)n2)cc(OC)c1]

(i) Phenyl (3-(tert-butyl)-1-(6-methoxypyridin-3-yl)-1H-pyrazol-5-yl)-carbamate The sub-title compound can be prepared according to or by analogy with procedures known to those skilled in the art and/or described herein. For example, the following procedure can be used.

To a stirred suspension of 3-(tert-butyl)-1-(6-methoxypyridin-3-yl)-1H-pyrazol-5-amine (see, for example, Abraham, S. et al., WO 2009/117080, 24 Sep. 2009; 780 mg, 3.17 mmol) and NaHCO$_3$ (532 mg, 6.33 mmol) in DCM (8 mL) and THF (2 mL) was added phenyl chloroformate (481 µL, 3.80 mmol). The resulting mixture was stirred at rt overnight. The reaction mixture was partitioned between DCM (100 mL) and water (100 mL). The aqueous phase was back extracted with DCM (100 mL) and the combined organic extracts were dried (MgSO$_4$), filtered and concentrated in vacuo to afford an oil, which was triturated with a mixture of diethyl ether and isohexane to afford the sub-title compound (736 mg) as a white solid.

1H NMR (DMSO-d6) 400 MHz, δ: 10.12 (s, 1H), 8.32-8.31 (m, 1H), 7.85-7.82 (m, 1H), 7.41-7.37 (m, 2H), 7.24 (t, 1H), 7.10 (br s, 2H), 7.00 (d, 1H), 6.37 (s, 1H), 3.92 (s, 3H), 1.28 (s, 9H).

LCMS m/z 367 (M+H)$^+$ (ES$^+$)

(ii) 1-(3-(tert-Butyl)-1-(6-methoxypyridin-3-yl)-1H-pyrazol-5-yl)-3-(4-((2-((3-methoxy-5-(2-(2-(2-methoxyethoxyl)ethoxy)ethoxy)phenyl)amino)pyrimidin-4-yl)oxy)naphthalen-1-yl)urea Triethylamine (4 µL, 0.029 mmol) was added to a mixture of phenyl (3-(tert-butyl)-1-(6-methoxypyridin-3-yl)-1H-pyrazol-5-yl)carbamate (see step (i) above; 50 mg, 0.136 mmol) and 4-((4-aminonaphthalen-1-yl)oxy)-N-(3-methoxy-5-(2-(2-(2-methoxyethoxyl)ethoxy)-ethoxy)phenyl)pyrimidin-2-amine (see Example 37(ii) above; 70 mg, 0.134 mmol) in isopropyl acetate (2 mL) and the mixture heated at 50° C. for 4 h. The crude product was purified by chromatography on silica gel (12 g column, 1% MeOH to 4%) then the resultant solid triturated with Et$_2$O (3×2 mL) to afford the title compound (49 mg) as a colourless solid.

1H NMR (400 MHz, DMSO-d6) δ 9.43 (s, 1H), 9.08 (s, 1H), 8.81 (s, 1H), 8.45-8.34 (m, 2H), 8.05 (d, 1H), 7.97-7.88 (m, 2H), 7.86-7.80 (m, 1H), 7.69-7.52 (m, 2H), 7.40 (d, 1H), 7.04 (dd, 1H), 6.81 (d, 2H), 6.54 (d, 1H), 6.44 (s, 1H), 6.04 (t, 1H), 3.95 (s, 3H), 3.87 (t, 2H), 3.70-3.60 (m, 2H), 3.57-3.46 (m, 9H), 3.45-3.38 (m, 2H), 3.22 (s, 3H), 1.30 (s, 9H)

LCMS m/z 793 (M+H)$^+$ (ES$^+$)

Example 39

1-(4-((2-((3-Methoxy-5-(2-(2-(2-methoxyethoxyl)ethoxy)ethoxy)phenyl)amino)pyrimidin-4-yl)oxy)naphthalen-1-yl)-3-(3-(perfluoroethyl)-1-(p-tolyl)-1H-pyrazol-5-yl)urea

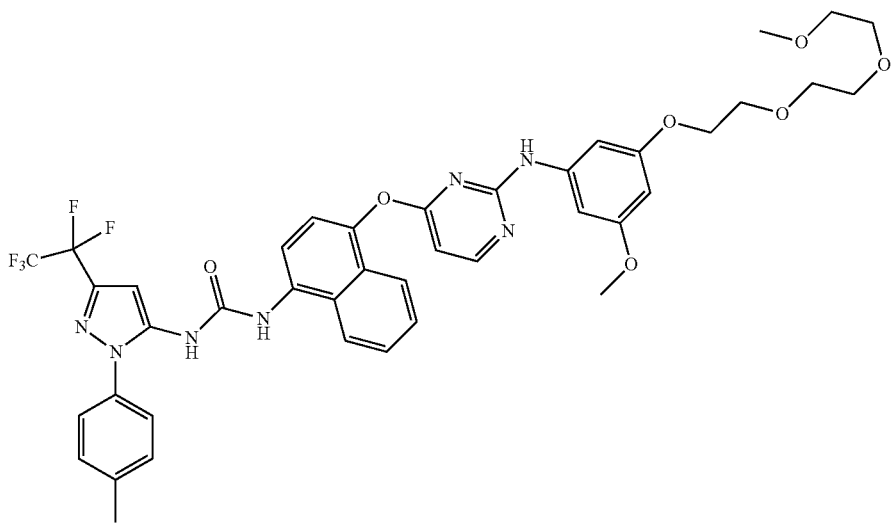 [SMILES: COCCOCCOCCOc1cc(Nc2nccc(Oc3ccc(NC(=O)Nc4cc(C(F)(F)C(F)(F)F)nn4-c4ccc(C)cc4)c4ccccc34)n2)cc(OC)c1]

(i) Phenyl (3-(perfluoroethyl)-1-(p-tolyl)-1H-pyrazol-5-yl)carbamate

To a stirred solution of 3-(perfluoroethyl)-1-(p-tolyl)-1H-pyrazol-5-amine (see, for example, De Dios, A. et al., WO 2007/053346, 10 May 2007; 3.00 g, 10.30 mmol) and sodium bicarbonate (1.70 g, 20.24 mmol) in DCM (25 mL) and THF (10 mL) was added phenyl chloroformate (1.40 mL, 11.14 mmol) and the resulting mixture stirred overnight. An additional 0.2 eq. of phenyl chloroformate was added and stirring continued for a further 60 h. The reaction was diluted with water and DCM, and the mixture passed through a phase separation cartridge. The resulting yellow filtrate was concentrated in vacuo to give an orange oil that solidified to form a pale orange solid upon addition of a small volume of hexane and vigorous scratching. The solid was triturated in isohexane and collected by filtration. The product was washed with further isohexane, providing the sub-title compound (3.86 g) as a white solid.

1H NMR (400 MHz; CDCl$_3$) δ 7.38-7.43 (m, 6H), 7.25-7.29 (m, 1H), 6.89-7.14 (m, 4H), 2.46 (s, 3H).

LCMS m/z 412 (M+H)$^+$ (ES$^+$); 410 (M−H)$^-$ (ES$^-$)

(ii) 1-(4-((2-((3-Methoxy-5-(2-(2-(2-methoxy-ethoxyl)ethoxy)ethoxy)phenyl)amino)-pyrimidin-4-yl)oxy)naphthalen-1-yl)-3-(3-(perfluoroethyl)-1-(p-tolyl)-1H-pyrazol-5-yl)urea Triethylamine (4.00 μL, 0.029 mmol) was added to a mixture of the product from step (i) above (55.3 mg, 0.134 mmol) and 4-((4-aminonaphthalen-1-yl)oxy)-N-(3-methoxy-5-(2-(2-(2-methoxyethoxyl)ethoxy)ethoxy)phenyl)pyrimidin-2-amine (see Example 37(ii) above; 70 mg, 0.134 mmol) in isopropyl acetate (1.5 mL) and the mixture heated at 60° C. for 1 h. The reaction was cooled to rt and diluted with DCM and MeOH (3:1, 15 mL) and the solution concentrated onto silica gel. The crude product was purified by chromatography on the Companion (40 g column, 0-4% MeOH in DCM) to afford the title compound (48 mg) as a pale pink solid.

1H NMR (DMSO-d6) 400 MHz, δ: 9.44 (s, 1H), 9.25 (s, 1H), 9.14 (s, 1H), 8.42 (d, 1H), 8.05 (d, 1H), 7.94 (d, 1H), 7.84 (d, 1H), 7.56-7.66 (m, 4H), 7.48 (d, 2H), 7.42 (d, 1H), 6.94 (s, 1H), 6.80 (d, 2H), 6.55 (d, 1H), 6.04 (s, 1H), 3.86 (t, 2H), 3.65 (t, 2H), 3.48-3.54 (m, 9H), 3.41 (m, 2H), 3.22 (s, 3H), 2.45 (s, 3H).
LCMS m/z 838 (M+H)+ (ES+)

Example 40

1-(4-((2-((3-Methoxy-5-(2-(2-(2-methoxyethoxyl)ethoxy)ethoxy)phenyl)amino)pyrimidin-4-yl)oxy)naphthalen-1-yl)-3-(1-(p-tolyl)-3-(1,1,1-trifluoro-2-methylpropan-2-yl)-1H-pyrazol-5-yl)urea standing. Recrystallisation in cyclohexane (30 mL) followed by washing with iso-hexane (2×30 mL) yielded the sub-title compound (1.75 g) as a colourless crystalline solid.

1H NMR (400 MHz; CDCl3) δ 7.42 (d, 2H), 7.26 (d, 2H), 5.67-5.64 (m, 1H), 3.72 (s, 2H), 2.39 (s, 3H), 1.52 (s, 6H).
LCMS m/z 284 (M+H)+ (ES+)

(ii) Phenyl (1-(p-tolyl)-3-(1,1,1-trifluoro-2-methyl-propan-2-yl)-1H-pyrazol-5-yl)carbamate Phenyl chloroformate (0.85 mL, 6.79 mmol) was added to a stirred mixture of the product from step (i) above (1.75 g, 6.18 mmol) and NaHCO3 (1.05 g, 12.50 mmol) in DCM (20 mL) and THF (15 mL) at rt. The mixture was stirred for 2 h then partitioned between DCM (50 mL) and water (50 mL). The organic layer was separated, dried (MgSO4) and evaporated under reduced pressure to yield a colourless oil. The oil was crystallised from cyclohexane to yield the sub-title compound (2.14 g) as a white solid.

1H NMR (CDCl3) 400 MHz, δ: 7.43-7.31 (m, 6H), 7.30-7.22 (m, 1H), 7.20-7.07 (m, 2H), 7.05-6.88 (m, 1H), 6.68-6.55 (m, 1H), 2.44 (s, 3H), 1.56 (s, 6H).

(iii) 1-(4-((2-((3-Methoxy-5-(2-(2-(2-methoxy-ethoxyl)ethoxy)ethoxy)phenyl)amino)-pyrimidin-4-yl)oxy)naphthalen-1-yl)-3-(1-(p-tolyl)-3-(1,1,1-trifluoro-2-methylpropan-2-yl)-1H-pyrazol-5-yl)urea Triethylamine (5 μL, 0.036 mmol) was added to a mixture of the product from step (ii) above (71 mg, 0.176 mmol) and 4-((4-aminonaphthalen-1-yl)oxy)-N-(3-methoxy-5-(2-(2-(2-methoxyethoxyl)ethoxy)ethoxy)phenyl)pyrimidin-2-amine (see Example 37(ii) above; 100 mg, 0.192 mmol) in

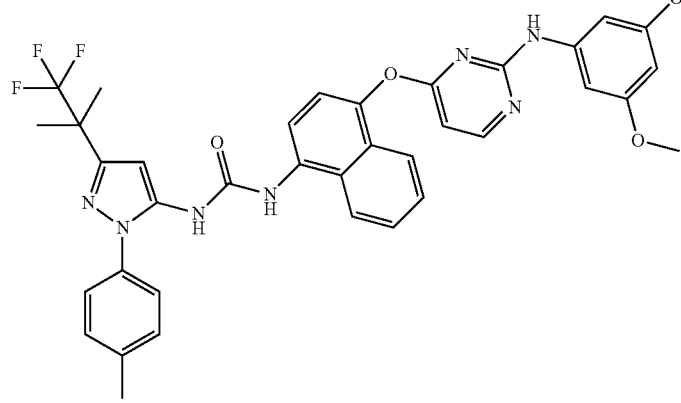

(i) 1-(p-Tolyl)-3-(1,1,1-trifluoro-2-methyl propan-2-yl)-1H-pyrazol-5-amine p-Tolylhydrazine, HCl (3.2 g, 19.97 mmol) and 5,5,5-trifluoro-4,4-dimethyl-3-oxopentane nitrile (4.3 g, 20.40 mmol) were heated to reflux in ethanol (15 mL) for 8 h. The mixture was concentrated under reduced pressure to yield a brown oil. Saturated NaHCO3 solution (50 mL) and water (50 mL) were added and the mixture was extracted with diethyl ether (3×50 mL). The combined organic phases were concentrated and the residue was purified by chromatography on the Companion (40 g column, 0-50% diethyl ether/iso-hexane) to afford an orange oil which crystallised on isopropyl acetate (2 mL) and the mixture heated at 50° C. for 2 h. The mixture was diluted with isohexane and the resulting solid was collected by filtration. The solid was purified by chromatography on the Companion (40 g column, 0-50% acetone/isohexane) to afford the title compound (65 mg) as a pale tan solid.

1H NMR (DMSO-d6) 400 MHz, δ: 9.42 (s, 1H), 9.15 (s, 1H), 8.88 (s, 1H), 8.41 (d, 1H), 8.07 (d, 1H), 7.95 (d, 1H), 7.83 (d, 1H), 7.67-7.60 (m, 1H), 7.60-7.54 (m, 1H), 7.53-7.46 (m, 2H), 7.46-7.36 (m, 3H), 6.86-6.73 (m, 2H), 6.60 (s, 1H), 6.54 (s, 1H), 6.04 (s, 1H), 3.93-3.82 (m, 2H), 3.70-3.62 (m, 2H), 3.58-3.46 (m, 6H), 3.51 (s, 3H), 3.44-3.38 (m, 2H), 3.22 (s, 3H), 2.24 (s, 3H), 1.53 (s, 6H)
LCMS m/z 830 (M+H)+ (ES+); 828 (M−H)− (ES−).

Example 41

1-(3-(tert-Butyl)-1-(p-tolyl)-1H-pyrazol-5-yl)-3-(4-((2-((3-methoxy-5-((2-morpholinoethyl)-thio)phenyl)amino)pyrimidin-4-yl)oxy)naphthalen-1-yl)urea

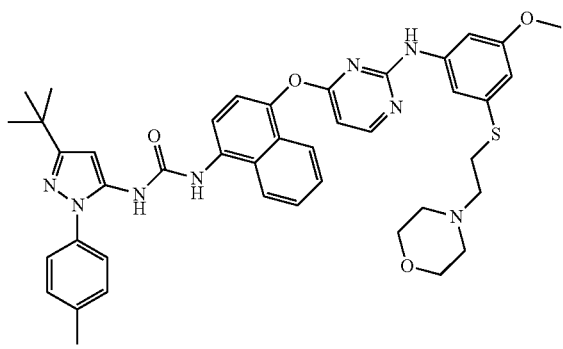 [SMILES: COc1cc(Nc2nccc(Oc3ccc(NC(=O)Nc4cc(C(C)(C)C)nn4-c4ccc(C)cc4)c4ccccc34)n2)cc(SCCN2CCOCC2)c1]

(i) (2-Chloroethyl)(3-methoxy-5-nitrophenyl)sulfane 2,4,6-Trichloro-1,3,5-triazine (350 mg, 1.898 mmol) was added to DMF (500 μL, 6.46 mmol) and the mixture was stirred at rt for 30 minutes, a thick white precipitate formed. To this suspension was added a solution of 2-((3-methoxy-5-nitrophenyl)thio)ethanol (400 mg, 1.745 mmol) in DCM (5 mL) in one portion, the mixture was stirred for 72 h then diluted with EtOAc (20 mL) and filtered. The filtrate was evaporated and the crude product was purified by chromatography on silica gel (40 g column, 0% EtOAc/isohexane to 20%) to afford the sub-title compound (290 mg) as a yellow crystalline solid. 1H NMR (400 MHz, CDCl$_3$) δ 7.79 (t, 1H), 7.57 (t, 1H), 7.18 (dd, 1H), 3.90 (s, 3H), 3.71-3.61 (m, 2H), 3.40-3.28 (m, 2H).

(ii) 4-(2-((3-Methoxy-5-nitrophenyl)thio)ethyl)morpholine

Morpholine (300 μL, 3.44 mmol) was added to a solution of the product from step (ii) above (290 mg, 1.171 mmol) and sodium iodide (18 mg, 0.120 mmol) in acetone (5 mL) then heated at reflux for 16 h. Morpholine (300 μL, 3.44 mmol) and sodium iodide (18 mg, 0.120 mmol) added and heating continued for a further 24 h. The mixture was partitioned between water (10 mL) and EtOAc (20 mL), the aqueous was separated and washed with EtOAc (20 mL). The organics were separated, bulked and washed with 20% w/w NaCl solution. The organic layer was separated, dried (MgSO$_4$) filtered and evaporated. The crude product was purified by chromatography on silica gel (40 g column, 50% EtOAc:isohexane to 100%) to afford the sub-title compound (165 mg) as a thick yellow oil.

1H NMR (400 MHz, CDCl$_3$) δ 7.75 (t, 1H), 7.51 (t, 1H), 7.13 (dd, 1H), 3.88 (s, 3H), 3.79-3.66 (m, 4H), 3.21-3.07 (m, 2H), 2.74-2.64 (m, 2H), 2.56-2.46 (m, 4H).

LCMS m/z 299 (M+H)+ (ES+)

(iii) 3-Methoxy-5-((2-morpholinoethyl)thio)aniline

The product from step (ii) above (165 mg, 0.553 mmol) was dissolved in EtOH (2 mL) and water (400 μL) and ammonium chloride (3 mg, 0.056 mmol) added. When a solution was obtained, iron powder (310 mg, 5.55 mmol) was added and the mixture sonicated at 60° C. (bath temperature) for 1 h. The mixture was filtered and the solvent evaporated. The residue was partitioned between EtOAc (10 mL) and water (10 mL). The aqueous was separated and washed with fresh EtOAc (10 mL). The organics were bulked and washed with 20% w/w NaCl solution (10 mL), separated, dried (MgSO$_4$), filtered and the solvent evaporated to give the sub-title compound (61 mg) as a yellow oil.

1H NMR (400 MHz, DMSO-d$_6$) δ 6.13 (t, 1H), 6.03 (dd, 1H), 5.95 (t, 1H), 5.17 (s, 2H), 3.64 (s, 3H), 3.60-3.51 (m, 4H), 3.06-2.93 (m, 2H), 2.57-2.46 (m, 2H), 2.40 (t, 4H).

LCMS m/z 269 (M+H)+ (ES+)

(iv) 1-(3-(tert-Butyl)-1-(p-tolyl)-1H-pyrazol-5-yl)-3-(4-((2-chloropyrimidin-4-yl)oxy)-naphthalen-1-yl)urea The sub-title compound can be prepared according to or by analogy with procedures known to those skilled in the art and/or described herein. For example, the following procedure can be used.

A stirred suspension of phenyl (3-(tert-butyl)-1-(p-tolyl)-1H-pyrazol-5-yl)carbamate (see, for example, Kapadia, S. R. et al., U.S. Pat. No. 6,492,529, 10 Dec. 2002; 3 g, 8.59 mmol) and 4-((2-chloropyrimidin-4-yl)oxy)naphthalen-1-amine (see, for example, Cirillo, P. F. et al., WO 2002/92576, 21 Nov. 2000; 2.333 g, 8.59 mmol) in isopropyl acetate (100 mL) was treated with triethylamine (0.3 mL, 2.152 mmol) and stirred at 60° C. (bath) for 1 h. The solution was diluted with ethyl acetate (300 mL), washed with water (2×100 mL) followed by brine (100 mL), was dried (Na$_2$SO$_4$) and evaporated. The residue was purified on a 220 g redisep silica cartridge using 5%, for 17 column volumes, and then 40% of acetone in toluene as eluent and then on another 220 g redisep silica cartridge using 0 to 3% MeOH/DCM as eluent to give Intermediate C2 (3.703 g) as a buff foam.

1H NMR (400 MHz, DMSO-d6) δ 9.14 (s, 1H), 8.79 (s, 1H), 8.65 (d, 1H), 8.09 (d, 1H), 7.96 (d, 1H), 7.79 (d, 1H), 7.67-7.64 (m, 1H), 7.60-7.56 (m, 1H), 7.47-7.37 (m, 5H), 7.26 (d, 1H), 6.41 (s, 1H), 2.40 (s, 3H), 1.28 (s, 9H).

LCMS m/z 527/529 (M+H)+ (ES+)

(v) 1-(3-(tert-Butyl)-1-(p-tolyl)-1H-pyrazol-5-yl)-3-(4-((2-((3-methoxy-5-((2-morpholino-ethyl)thio)phenyl)amino)pyrimidin-4-yl)oxy)naphthalen-1-yl)urea 1-(3-(tert-butyl)-1-(p-tolyl)-1H-pyrazol-5-yl)-3-(4-((2-chloropyrimidin-4-yl)oxy)naphthalen-1-yl)urea (see step (iv) above; 90 mg, 0.171 mmol) was dissolved in DMF (2 mL) and added to the product from step (iii) above (60 mg, 0.224 mmol) and p-TSA monohydrate (60 mg, 0.315 mmol) and stirred at 70° C. (block temperature) for 7 h. The mixture was poured into saturated NaHCO$_3$ solution (20 mL) and the product extracted with EtOAc (2×20 mL), washed with 20% NaCl solution (20 mL), separated, dried (MgSO$_4$) filtered and evaporated. The crude product was purified by chromatography on silica gel (40 g column, 1% MeOH:DCM to 7%) to afford a pale yellow solid. Recrystallised from MeCN (3 mL) and solid washed with MeCN (1 mL) to give the title compound (52 mg).

1H NMR (400 MHz, DMSO-d$_6$) δ 9.49 (s, 1H), 9.10 (s, 1H), 8.79 (s, 1H), 8.41 (d, 1H), 8.08 (d, 1H), 8.00 (d, 1H), 7.82 (d, 1H), 7.67-7.53 (m, 2H), 7.47 (d, 2H), 7.43-7.35 (m, 3H), 7.10 (s, 1H), 6.97 (s, 1H), 6.57 (d, 1H), 6.43 (s, 1H), 6.36 (t, 1H), 3.59-3.45 (m, 7H), 3.01-2.89 (m, 2H), 2.50-2.43 (m, 2H), 2.41 (s, 3H), 2.39-2.29 (m, 4H), 1.30 (s, 9H).
LCMS m/z 759 (M+H)+ (ES+)

Example 42

1-(3-(tert-Butyl)-1-(p-tolyl)-1H-pyrazol-5-yl)-3-(4-((2-((3-methoxy-5-((3-morpholinopropyl)-thio)phenyl)amino)pyrimidin-4-yl)oxy)naphthalen-1-yl)urea

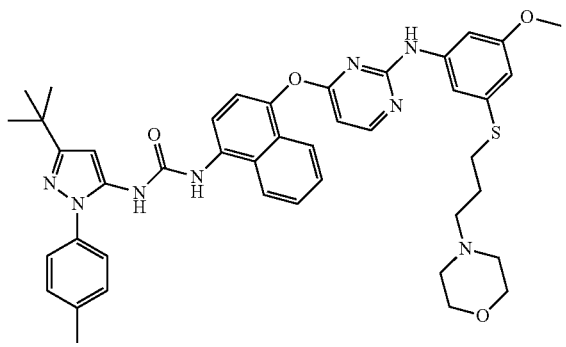 [SMILES: COc1cc(Nc2nccc(Oc3ccc(NC(=O)Nc4cc(C(C)(C)C)nn4-c4ccc(C)cc4)c4ccccc34)n2)cc(SCCCN2CCOCC2)c1]

(i) 3-(3-Methoxy-5-nitrophenyl)thio)propan-1-ol

1-Bromo-3-methoxy-5-nitrobenzene (1 g, 4.31 mmol), Pd$_2$(dba)$_3$ (0.2 g, 0.218 mmol) and xantphos (0.25 g, 0.432 mmol) were added to a degassed solution of DIPEA (2.3 mL, 13.17 mmol) and 3-mercaptopropan-1-ol (0.375 ml, 4.34 mmol) in 1,4-dioxane (10 mL). Heated under nitrogen at 100° C. for 2 h then the reaction mixture was filtered through Celite and the residue partitioned between EtOAc (20 mL) and 20% w/w NaCl solution. Organic layer separated, dried (MgSO$_4$), filtered and solvents evaporated. The crude product was purified by chromatography on the Companion (40 g column, 10% EtOAc:isohexane to 30%) to afford the sub-title compound (950 mg) as a yellow crystalline solid.

1H NMR (400 MHz, DMSO-d$_6$) δ 7.66 (t, 1H), 7.49 (t, 1H), 7.30 (dd, 1H), 4.65 (t, 1H), 3.88 (s, 3H), 3.58-3.44 (m, 2H), 3.21-3.06 (m, 2H), 1.84-1.65 (m, 2H).

(ii) (3-Chloropropyl)(3-methoxy-5-nitrophenyl)sulfane 2,4,6-Trichloro-1,3,5-triazine (350 mg, 1.898 mmol) was added to DMF (500 µL, 6.46 mmol) and stirred at rt for 30 minutes. A thick white precipitate formed. To this suspension was added a solution of the product from step (i) above (400 mg, 1.644 mmol) in DCM (5 mL) in one portion. The mixture was stirred for 72 h then diluted with EtOAc (20 mL) and filtered.

The filtrate was evaporated and the crude product was purified by chromatography on silica gel (40 g column, 0% EtOAc:isohexane to 20%) to afford the sub-title compound (388 mg) as a yellow crystalline solid.

1H NMR (400 MHz, CDCl$_3$) δ 7.74 (t, 1H), 7.52 (t, 1H), 7.14 (dd, 1H), 3.89 (s, 3H), 3.69 (t, 2H), 3.17 (t, 2H), 2.20-2.07 (m, 2H).

(iii) 4-(3-((3-Methoxy-5-nitrophenyl)thio)propyl)morpholine

Morpholine (390 µL, 4.48 mmol) was added to a solution of the product from step (ii) above (388 mg, 1.482 mmol) and sodium iodide (25 mg, 0.167 mmol) in MeCN (5 mL). The mixture was heated at 70° C. overnight. The solvent was evaporated and the residue partitioned between EtOAc (10 mL) and water (10 mL). The aqueous was separated and washed with fresh EtOAc (10 mL). The organics were bulked and washed with 20% w/w NaCl solution (10 mL) separated, dried (MgSO$_4$), filtered and solvent evaporated to give the sub-title compound (425 mg) as a yellow oil.

1H NMR (400 MHz, DMSO-d$_6$) δ 7.65 (t, 1H), 7.50 (t, 1H), 7.30 (dd, 1H), 3.88 (s, 3H), 3.56 (t, 4H), 3.13 (t, 2H), 2.38 (t, 2H), 2.36-2.23 (m, 4H), 1.76 (pent, 2H).
LCMS m/z 313 (M+H)+ (ES+)

(iv) 3-Methoxy-5-((3-morpholinopropyl)thio)aniline

The product from step (iii) above (425 mg, 1.361 mmol) was dissolved in EtOH (4 mL) and water (600 µL) and ammonium chloride (8 mg, 0.150 mmol) added. When a solution was obtained iron powder (760 mg, 13.61 mmol) was added and the mixture sonicated at 60° C. (bath temperature) for 6 h. The mixture was filtered, evaporated and residue partitioned between DCM (20 mL) and water (10 mL). The organic layer was separated, dried (MgSO$_4$), filtered and evaporated. The crude product was purified by chromatography on silica gel (40 g column, 1% MeOH:DCM to 7%) to afford the sub-title compound (293 mg) as a thick yellow oil.

1H NMR (400 MHz, DMSO-d$_6$) δ 6.13 (t, 1H), 6.02 (dd, 1H), 5.96 (t, 1H), 5.15 (s, 2H), 3.64 (s, 3H), 3.61-3.50 (m, 4H), 2.88 (t, 2H), 2.41-2.26 (m, 6H), 1.71 (pent, 2H).

(v) 1-(3-(tert-Butyl)-1-(p-tolyl)-1H-pyrazol-5-yl)-3-(4-((2-((3-methoxy-5-((3-morpholino-propyl)thio)phenyl)amino)pyrimidin-4-yl)oxy)naphthalen-1-yl)urea 1-(3-(tert-Butyl)-1-(p-tolyl)-1H-pyrazol-5-yl)-3-(4-((2-chloropyrimidin-4-yl)oxy)naphthalen-1-yl)urea (see Example 41(iv) above; 150 mg, 0.285 mmol) was dissolved in DMF (2 mL) and added to the product from step (iv) above (130 mg, 0.460 mmol) and p-TSA monohydrate (85 mg, 0.447 mmol) and stirred at 70° C. (block temperature) for 6 h. The mixture was poured into saturated NaHCO$_3$ solution (20 mL) and the product extracted with EtOAc (2×20 mL), washed with 20% NaCl solution (20 mL), separated, dried (MgSO$_4$), filtered and evaporated. The crude product was purified by chromatography on silica gel (40 g column, 1% MeOH:DCM to 7%) to afford a pale yellow solid. Recrystallised from MeCN (5 mL) and solid washed with MeCN (1 mL) to give the title compound (90 mg).

1H NMR (400 MHz, DMSO-d$_6$) δ 9.49 (s, 1H), 9.10 (s, 1H), 8.79 (s, 1H), 8.41 (d, 1H), 8.08 (d, 1H), 7.99 (d, 1H), 7.82 (d, 1H), 7.68-7.53 (m, 2H), 7.51-7.43 (m, 2H), 7.43-7.34 (m, 3H), 7.10 (s, 1H), 6.98 (s, 1H), 6.57 (d, 1H), 6.42 (s, 1H), 6.34 (t, 1H), 3.60-3.43 (m, 7H), 2.83 (t, 2H), 2.41 (s, 3H), 2.36-2.19 (m, 6H), 1.66 (pent, 2H), 1.30 (s, 9H).
LCMS m/z 773 (M+H)+ (ES+)

Example 43

1-(3-(tert-Butyl)-1-(p-tolyl)-1H-pyrazol-5-yl)-3-(4-((2-((3-methoxy-5-((3-morpholinopropyl)-sulfonyl)phenyl)amino)pyrimidin-4-yl)oxy)naphthalen-1-yl)urea

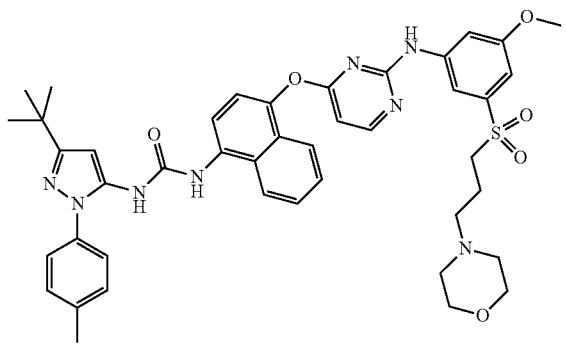 [SMILES: COc1cc(Nc2nccc(Oc3ccc(NC(=O)Nc4cc(C(C)(C)C)nn4-c4ccc(C)cc4)c4ccccc34)n2)cc(S(=O)(=O)CCCN2CCOCC2)c1]

(i) 3-(3-Methoxy-5-nitrophenyl)sulfonyl)propan-1-ol mCPBA, 77% w/w (920 mg, 4.11 mmol) was added to an ice cold solution of 3-((3-methoxy-5-nitrophenyl)thio)propan-1-ol (see Example 42(i) above; 400 mg, 1.644 mmol) in DCM (5 mL) then allowed to warm to rt and stirred for 16 h. The mixture was partitioned between $K_2CO_3$ (1 M, 20 mL) and DCM (20 mL). The organic layer was separated and washed with 20% NaCl solution (20 mL). The organics were separated, dried ($MgSO_4$), filtered and solvents evaporated to give a colourless solid which was purified by chromatography on silica gel (40 g column, 50% EtOAc:isohexane to 100%) to afford the sub-title compound (355 mg) as a colourless crystalline solid.

1H NMR (400 MHz, DMSO-$d_6$) δ 8.17 (t, 1H), 8.06 (t, 1H), 7.85 (dd, 1H), 4.68 (t, 1H), 4.00 (s, 3H), 3.56-3.46 (m, 2H), 3.47-3.38 (m, 2H), 1.82-1.57 (m, 2H).

LCMS m/z 276 (M+H)+ (ES+)

(ii) 1-((3-Chloropropyl)sulfonyl)-3-methoxy-5-nitrobenzene 2,4,6-Trichloro-1,3,5-triazine (235 mg, 1.274 mmol) was added to DMF (400 μL, 5.17 mmol) and the mixture stirred for 30 minutes. A thick white precipitate formed. The product from step (i) above (350 mg, 1.271 mmol) in DCM (5 mL) was added in one portion and the mixture stirred for 16 h. The solvent was evaporated and the residue resuspended in ethyl acetate. The solids were filtered off and filtrate evaporated to a pale yellow oil. The crude product was purified by chromatography on silica gel (40 g column, 10% EtOAc:isohexane to 30%) to afford the sub-title compound (300 mg) as a colourless crystalline solid.

1H NMR (400 MHz, CDCl$_3$) δ 8.34 (dd, 1H), 8.01 (dd, 1H), 7.74 (dd, 1H), 4.00 (s, 3H), 3.75-3.60 (m, 2H), 3.40-3.27 (m, 2H), 2.36-2.18 (m, 2H).

LCMS m/z 294 (M+H)+ (ES+)

(iii) 4-(3-((3-Methoxy-5-nitrophenyl)sulfonyl)propyl)morpholine

Morpholine (265 μL, 3.04 mmol) was added to a solution of the product from step (ii) above (300 mg, 1.021 mmol) and sodium iodide (15 mg, 0.100 mmol) in MeCN (5 mL). The mixture was heated at 70° C. overnight. The solvent was evaporated and the residue partitioned between EtOAc (10 mL) and water (10 mL). The aqueous was separated and washed with fresh EtOAc (10 mL). The organics were bulked and washed with 20% w/w NaCl solution (10 mL), separated, dried (MgSO$_4$), filtered and the solvent evaporated to give a yellow oil. The crude product was purified by chromatography on silica gel (12 g column, 1% MeOH:DCM to 4%) to afford the sub-title compound (260 mg) as a thick yellow oil.

1H NMR (400 MHz, DMSO-$d_6$) δ 8.17 (dd, 1H), 8.10-8.02 (m, 1H), 7.86 (dd, 1H), 4.00 (s, 3H), 3.58-3.45 (m, 6H), 2.37-2.20 (m, 6H), 1.79-1.65 (m, 2H).

LCMS m/z 345 (M+H)+ (ES+)

(iv) 3-Methoxy-5-((3-morpholinopropyl)sulfonyl)aniline

The product from step (iii) above (260 mg, 0.755 mmol) was dissolved in EtOH (4 mL) and water (500 μL) and ammonium chloride (4 mg, 0.075 mmol) added. When a solution was obtained, iron powder (425 mg, 7.61 mmol) was added and the mixture sonicated at 60° C. (bath temperature) for 6 h. The mixture was filtered, evaporated and residue partitioned between DCM (20 mL) and water (10 mL). The organic layer was separated, dried (MgSO$_4$), filtered and evaporated. The crude product was purified by chromatography on silica gel (40 g column, 1% MeOH:DCM to 7%) to afford the sub-title compound (136 mg) as a yellow oil.

1H NMR (400 MHz, DMSO-$d_6$) δ 6.67 (t, 1H), 6.49 (dd, 1H), 6.40 (t, 1H), 5.69 (s, 2H), 3.74 (s, 3H), 3.58-3.47 (m, 4H), 3.28-3.14 (m, 2H), 2.34-2.17 (m, 6H), 1.75-1.59 (m, 2H).

(v) 1-(3-(tert-Butyl)-1-(p-tolyl)-1H-pyrazol-5-yl)-3-(4-((2-((3-methoxy-5-((3-morpholino-propyl)sulfonyl)phenyl)amino)pyrimidin-4-yl)oxy)naphthalen-1-yl)urea 1-(3-(tert-Butyl)-1-(p-tolyl)-1H-pyrazol-5-yl)-3-(4-((2-chloropyrimidin-4-yl)oxy)naphthalen-1-yl)urea (see Example 41(iv) above; 150 mg, 0.285 mmol) was dissolved in DMF (2 mL) and added to the product from step (iv) above (130 mg, 0.413 mmol) and p-TSA monohydrate (85 mg, 0.447 mmol) and stirred at 70° C. (block temperature) for 6 h. The mixture was poured into saturated NaHCO$_3$ solution (20 mL) and the product extracted with EtOAc (2×20 mL), washed with 20% NaCl solution (20 mL), separated, dried (MgSO$_4$) filtered and evaporated. The crude product was purified by chromatography on silica gel (40 g column, 1% MeOH:DCM to 7%) to afford a pale yellow solid. Recrystallised from MeCN (4 mL) and solid washed with MeCN (1 mL) to give the title compound (115 mg).

1H NMR (400 MHz, DMSO-$d_6$) δ 9.85 (s, 1H), 9.11 (s, 1H), 8.78 (s, 1H), 8.47 (d, 1H), 8.08 (d, 1H), 7.97 (d, 1H), 7.82 (d, 1H), 7.73 (s, 1H), 7.68-7.53 (m, 2H), 7.52-7.44 (m, 3H), 7.44-7.34 (m, 3H), 6.88-6.85 (m, 1H), 6.64 (d, 1H), 6.42 (s, 1H), 3.64 (s, 3H), 3.48 (t, 4H), 3.26-3.17 (m, 2H), 2.41 (s, 3H), 2.29-2.15 (m, 6H), 1.65 (pent, 2H), 1.30 (s, 9H)

LCMS m/z 805 (M+H)+ (ES+)

Example 44

1-(3-(tert-Butyl)-1-(4-methoxyphenyl)-1H-pyrazol-5-yl)-3-(4-((2-((3-methoxy-5-(2-(2-(2-methoxyethoxy)ethoxy)ethoxy)phenyl)amino)pyrimidin-4-yl)oxy)naphthalen-1-yl)urea

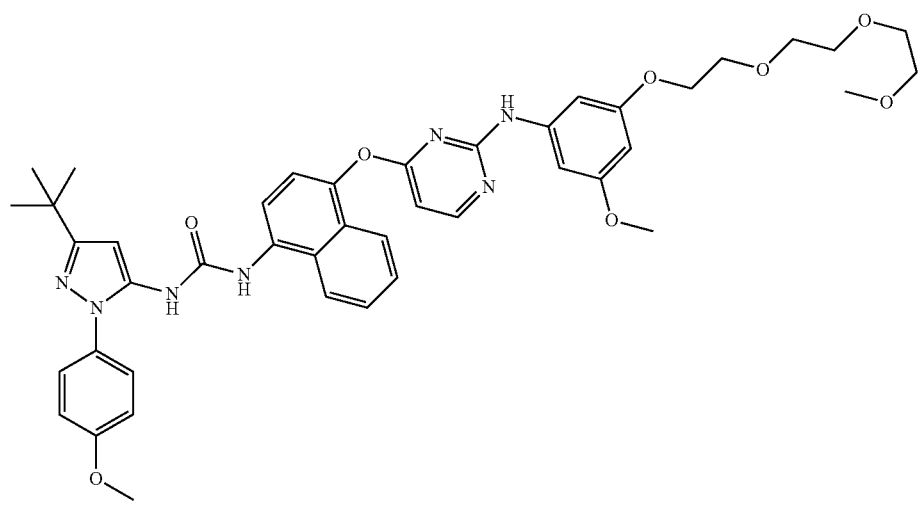 [SMILES: COCCOCCOCCOc1cc(Nc2nccc(Oc3ccc(NC(=O)Nc4cc(C(C)(C)C)nn4-c4ccc(OC)cc4)c4ccccc34)n2)cc(OC)c1]

Triethylamine (5 μL, 0.036 mmol) was added to a mixture of phenyl (3-(tert-butyl)-1-(4-methoxyphenyl)-1H-pyrazol-5-yl)carbamate (see, for example, Abraham, S. et al., WO 2009/117080, 24 Sep. 2009; 70 mg, 0.192 mmol) and 4-((4-aminonaphthalen-1-yl)oxy)-N-(3-methoxy-5-(2-(2-(2-methoxyethoxy)ethoxy)ethoxy)phenyl)pyrimidin-2-amine (see Example 37(ii) above; 109 mg, 0.209 mmol) in isopropyl acetate (2 mL) and the mixture heated at 50° C. for 2 h. The reaction mixture was concentrated under reduced pressure then purified by chromatography on the Companion (80 g column, 0-50% acetone/toluene) to afford a colourless gum. The gum was triturated in diethyl ether to yield the title compound (102 mg) as a white solid.

1H NMR (DMSO-$d_6$) 400 MHz, δ: 9.42 (s, 1H), 9.09 (s, 1H), 8.73 (s, 1H), 8.41 (d, 1H), 8.07 (d, 1H), 7.96 (d, 1H), 7.83 (dd, 1H), 7.66-7.60 (m, 1H), 7.60-7.53 (m, 1H), 7.52-7.45 (m, 2H), 7.39 (d, 1H), 7.16-7.10 (m, 2H), 6.85-6.76 (m, 2H), 6.53 (d, 1H), 6.40 (s, 1H), 6.04 (t, 1H), 3.90-3.84 (m, 2H), 3.85 (s, 3H), 3.68-3.62 (m, 2H), 3.57-3.47 (m, 9H), 3.43-3.39 (m, 2H), 3.22 (s, 3H), 1.29 (s, 9H).

LCMS m/z 792 (M+H)+ (ES+); 790 (M−H)− (ES−)

Example 45

1-(3-(tert-Butyl)-1-(P-tolyl)-1H-pyrazol-5-yl)-3-(4-((2-((3-methoxy-5-(2-morpholinoethoxy)-phenyl)amino)pyrimidin-4-yl)oxy)naphthalen-1-yl)urea

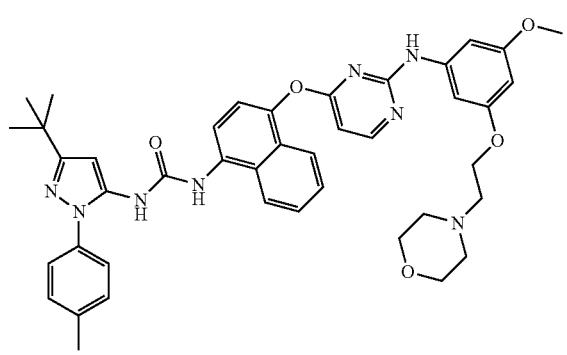 [SMILES: COc1cc(Nc2nccc(Oc3ccc(NC(=O)Nc4cc(C(C)(C)C)nn4-c4ccc(C)cc4)c4ccccc34)n2)cc(OCCN2CCOCC2)c1]

1-(3-(tert-Butyl)-1-(p-tolyl)-1H-pyrazol-5-yl)-3-(4-((2-chloropyrimidin-4-yl)oxy)naphthalen-1-yl)urea (see Example 41(iv) above; 150 mg, 0.285 mmol) was dissolved in DMF (2 mL) and added to 3-methoxy-5-(2-morpholinoethoxy)aniline (see Example 21(iv) above; 145 mg, 0.575 mmol) and p-TSA monohydrate (85 mg, 0.447 mmol) and stirred at 70° C. (block temperature) for 6 h. The mixture was poured into saturated NaHCO₃ solution (20 mL) and the product extracted with EtOAc (2×20 mL), washed with 20% NaCl solution (20 mL), separated, dried (MgSO₄), filtered and evaporated. The crude product was purified by chromatography on silica gel (40 g column, 1% MeOH:DCM to 7%) to afford a pale yellow solid. Recrystallised from MeCN (3 mL) and solid washed with MeCN (1 mL) to afford the title compound (31 mg).

1H NMR (400 MHz, DMSO-d₆) δ 9.40 (s, 1H), 9.11 (s, 1H), 8.78 (s, 1H), 8.41 (d, 1H), 8.08 (d, 1H), 7.97 (d, 1H), 7.83 (d, 1H), 7.70-7.51 (m, 2H), 7.52-7.44 (m, 2H), 7.44-7.33 (m, 3H), 6.80 (s, 1H), 6.78 (s, 1H), 6.54 (d, 1H), 6.42 (s, 1H), 6.04 (t, 1H), 3.89 (t, 2H), 3.59-3.52 (m, 4H), 3.50 (s, 3H), 2.60 (t, 2H), 2.46-2.32 (m, 7H), 1.30 (s, 9H).

LCMS m/z 743 (M+H)+ (ES+)

Example 46

1-(3-(tert-Butyl)-1-(p-tolyl)-1H-pyrazol-5-yl)-3-(4-((2-((3-(cyclopropylsulfonyl)phenyl)-amino)pyrimidin-4-yl)oxy)naphthalen-1-yl)urea

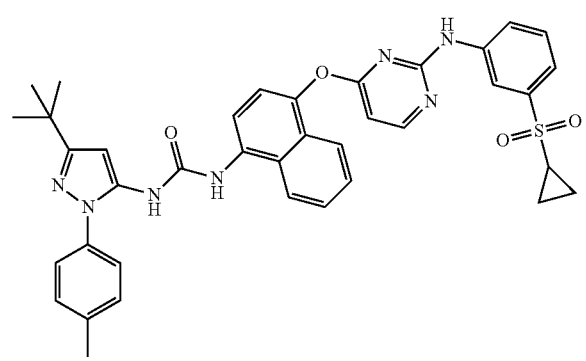 [SMILES: Cc1ccc(-n2nc(C(C)(C)C)cc2NC(=O)Nc2ccc(Oc3ccnc(Nc4cccc(S(=O)(=O)C5CC5)c4)n3)c3ccccc23)cc1]

1-(3-(tert-Butyl)-1-(p-tolyl)-1H-pyrazol-5-yl)-3-(4-((2-chloropyrimidin-4-yl)oxy)naphthalen-1-yl)urea (see Example 41(iv) above; 150 mg, 0.285 mmol) was dissolved in DMF (2 mL) and added to 3-(cyclopropylsulfonyl)aniline (see Example 24(i) above; 100 mg, 0.507 mmol) and p-TSA monohydrate (30 mg, 0.158 mmol) and stirred at 70° C. (block temperature) for 6 h. The mixture was poured into saturated NaHCO₃ solution (20 mL) and the product extracted with EtOAc (2×20 mL). The crude product was purified by chromatography on silica gel (40 g column, 1% MeOH:DCM to 5%) to afford a yellow solid. Recrystallised from MeCN (4 mL) and solid washed with MeCN (1 mL) to afford the title compound (120 mg).

1H NMR (400 MHz, DMSO-d₆) δ 9.89 (s, 1H), 9.14 (s, 1H), 8.76 (s, 1H), 8.46 (d, 1H), 8.15-8.01 (m, 2H), 7.94 (d, 1H), 7.82 (d, 1H), 7.72-7.53 (m, 3H), 7.52-7.45 (m, 2H), 7.46-7.35 (m, 3H), 7.35-7.28 (m, 1H), 7.22 (t, 1H), 6.65 (d, 1H), 6.43 (s, 1H), 2.69 (tt, 1H), 2.41 (s, 3H), 1.30 (s, 9H), 1.11-0.95 (m, 4H).

LCMS m/z 688 (M+H)+ (ES+)

Example 47

1-(3-(tert-Butyl)-1-(p-tolyl)-1H-pyrazol-5-yl)-3-(4-((2-((3-(cyclopropylsulfonyl)-5-methoxy-phenyl)amino)pyrimidin-4-yl)oxy)naphthalen-1-yl)urea

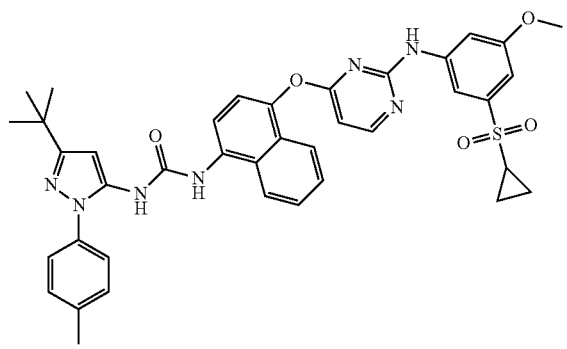 [SMILES: COc1cc(Nc2nccc(Oc3ccc(NC(=O)Nc4cc(C(C)(C)C)nn4-c4ccc(C)cc4)c4ccccc34)n2)cc(S(=O)(=O)C2CC2)c1]

1-(3-(tert-Butyl)-1-(p-tolyl)-1H-pyrazol-5-yl)-3-(4-((2-chloropyrimidin-4-yl)oxy)naphthalen-1-yl)urea (see Example 41(iv) above; 150 mg, 0.285 mmol) was dissolved in DMF (2 mL) and added to 3-(cyclopropylsulfonyl)-5-methoxyaniline (see Example 18(ii) above; 130 mg, 0.572 mmol) and p-TSA monohydrate (30 mg, 0.158 mmol) and stirred at 70° C. (block temperature) for 6 h. The mixture was poured into saturated NaHCO₃ solution (20 mL) and the product extracted with EtOAc (2×20 mL). The crude product was purified by chromatography on silica gel (40 g column, 1% MeOH:DCM to 5%) to afford a yellow solid. Recrystallised from MeCN (4 mL) and solid washed with MeCN (1 mL) to afford the title compound (105 mg).

1H NMR (400 MHz, DMSO-d₆) δ 9.84 (s, 1H), 9.11 (s, 1H), 8.78 (s, 1H), 8.47 (d, 1H), 8.08 (d, 1H), 7.97 (d, 1H), 7.82 (d, 1H), 7.74 (s, 1H), 7.69-7.53 (m, 2H), 7.53-7.44 (m, 3H), 7.44-7.34 (m, 3H), 6.94-6.80 (m, 1H), 6.64 (d, 1H), 6.42 (s, 1H), 3.63 (s, 3H), 2.73 (tt, 1H), 2.41 (s, 3H), 1.30 (s, 9H), 1.12-0.94 (m, 4H).

LCMS m/z 718 (M+H)+ (ES+)

Example 48

1-(3-(tert-Butyl)-1-(p-tolyl)-1H-pyrazol-5-yl)-3-(4-((2-((3-((3-Hydroxypropyl)thio)-5-methoxyphenyl)amino)pyrimidin-4-yl)oxy)naphthalen-1-yl)urea

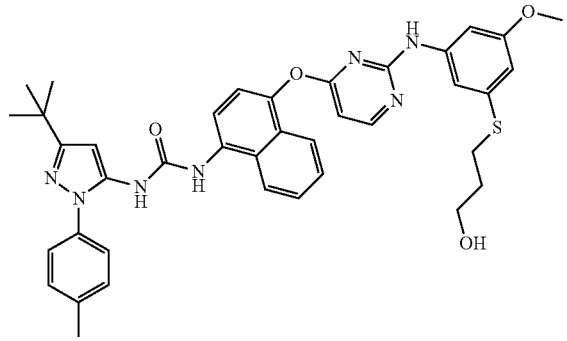 [SMILES: COc1cc(Nc2nccc(Oc3ccc(NC(=O)Nc4cc(C(C)(C)C)nn4-c4ccc(C)cc4)c4ccccc34)n2)cc(SCCCO)c1]

(i) 3-(3-Amino-5-methoxyphenyl)thio)propan-1-ol 3-((3-Methoxy-5-nitrophenyl)thio)propan-1-ol (see Example 42(i) above; 140 mg, 0.575 mmol) was dissolved in EtOH (2 mL) and water (300 μL) and ammonium chloride (3.0 mg, 0.056 mmol) added. When a solution was obtained iron powder (320 mg, 5.73 mmol) was added and the mixture sonicated at 60° C. (bath temperature) for 6 h. The mixture was filtered, evaporated and residue partitioned between DCM (20 mL) and water (10 mL). The organic layer was separated, dried (MgSO$_4$), filtered and evaporated. The crude product was purified by chromatography on silica gel (40 g column, 1% MeOH: DCM to 7%) to afford the sub-title compound (113 mg) as a yellow oil.

1H NMR (400 MHz, DMSO-d$_6$) δ 6.13 (t, 1H), 6.02 (dd, 1H), 5.95 (t, 1H), 5.14 (s, 2H), 4.53 (t, 1H), 3.65 (s, 3H), 3.49 (td, 2H), 2.96-2.81 (m, 2H), 1.76-1.64 (m, 2H).

LCMS m/z 214 (M+H)+ (ES+)

(ii) 1-(3-(tert-Butyl)-1-(p-tolyl)-1H-pyrazol-5-yl)-3-(4-((2-((3-((3-Hydroxypropyl)thio)-5-methoxyphenyl)amino)pyrimidin-4-yl)oxy)naphthalen-1-yl)urea 1-(3-(tert-Butyl)-1-(p-tolyl)-1H-pyrazol-5-yl)-3-(4-((2-chloropyrimidin-4-yl)oxy)naphthalen-1-yl)urea (see Example 41(iv) above; 125 mg, 0.237 mmol) was dissolved in DMF (2 mL) and added to the product from step (i) above (100 mg, 0.469 mmol) and p-TSA monohydrate (30 mg, 0.158 mmol) and stirred at 70° C. (block temperature) for 6 h. The mixture was poured into saturated NaHCO$_3$ solution (20 mL) and the product extracted with EtOAc (2×20 mL), washed with 20% NaCl solution (20 mL), separated, dried (MgSO$_4$) filtered and evaporated. The crude product was purified by chromatography on silica gel (40 g column, 1% MeOH:DCM to 7%) then (12 g column, 50% EtOAc: isohexane to 100%) to afford a pale yellow solid. Recrystallised from MeCN (4 mL) and solid washed with MeCN (1 mL) to afford the title compound (96 mg).

1H NMR (400 MHz, DMSO-d$_6$) δ 9.47 (s, 1H), 9.08 (s, 1H), 8.77 (s, 1H), 8.40 (d, 1H), 8.07 (d, 1H), 7.97 (d, 1H), 7.81 (d, 1H), 7.67-7.51 (m, 2H), 7.50-7.43 (m, 2H), 7.43-7.33 (m, 3H), 7.08 (s, 1H), 7.00 (s, 1H), 6.55 (d, 1H), 6.41 (s, 1H), 6.34 (t, 1H), 4.50 (t, 1H), 3.50 (s, 3H), 3.48-3.40 (m, 2H), 2.86 (t, 2H), 2.40 (s, 3H), 1.76-1.60 (m, 2H), 1.29 (s, 9H).

LCMS m/z 704 (M+H)+ (ES+)

Example 49

1-(3-(tert-Butyl)-1-(p-tolyl)-1H-pyrazol-5-yl)-3-(4-((2-((3-methoxy-5-(3-morpholino-propoxy)phenyl)amino)pyrimidin-4-yl)oxy)naphthalen-1-yl)urea

(i) 3-Methoxy-5-(3-morpholinopropoxy)aniline 4-(3-Chloropropyl)morpholine, HCl (790 mg, 3.95 mmol) was added to a suspension of 3-amino-5-methoxyphenol (500 mg, 3.59 mmol), K$_2$CO$_3$ (2000 mg, 14.47 mmol) and sodium iodide (55 mg, 0.367 mmol) in acetone (50 mL) and heated at reflux with vigorous stirring for 16 h. The reaction mixture was partitioned between EtOAc (10 mL) and 1 N HCl (10 mL). The aqueous layer was separated and basified with NaHCO$_3$ to pH 8. The product was extracted with EtOAc (2×20 mL). The organics were bulked, dried (MgSO$_4$) filtered and evaporated. The crude product was purified by chromatography on silica gel (40 g column, 2% MeOH:DCM to 8%) to afford the sub-title compound (280 mg) as a thick brown oil.

1H NMR (400 MHz, DMSO-d$_6$) δ 5.76-5.70 (m, 2H), 5.66 (t, 1H), 5.06 (s, 2H), 3.86 (t, 2H), 3.62 (s, 3H), 3.57 (t, 4H), 2.44-2.26 (m, 6H), 1.82 (pent, 2H).

LCMS m/z 267 (M+H)+ (ES+)

(ii) 1-(3-(tert-Butyl)-1-(p-tolyl)-1H-pyrazol-5-yl)-3-(4-((2-((3-methoxy-5-(3-morpholino-propoxy)phenyl)amino)pyrimidin-4-yl)oxy)naphthalen-1-yl)urea 1-(3-(tert-Butyl)-1-(p-tolyl)-1H-pyrazol-5-yl)-3-(4-((2-chloropyrimidin-4-yl)oxy)naphthalen-1-yl)urea (see Example 41(iv) above; 165 mg, 0.313 mmol) was dissolved in DMF (2 mL) and added to the product from step (i) above (120 mg, 0.451 mmol) and p-TSA monohydrate (120 mg, 0.631 mmol) and stirred at 70° C. (block temperature) for 6 h. The mixture was poured into saturated NaHCO$_3$ solution (20 mL) and the product extracted with EtOAc (2×20 mL), washed with 20% NaCl solution (20 mL), separated, dried (MgSO$_4$), filtered and evaporated. The crude product was purified by chromatography on silica gel (40 g column, 2% MeOH:DCM to 8%) to afford a pale yellow solid.

Recrystallised from MeCN (4 mL) and solid washed with MeCN (1 mL) to afford the title compound (98 mg).

1H NMR (400 MHz, DMSO-d$_6$) δ 9.41 (s, 1H), 9.11 (s, 1H), 8.78 (s, 1H), 8.41 (d, 1H), 8.08 (d, 1H), 7.98 (d, 1H), 7.83 (d, 1H), 7.68-7.52 (m, 2H), 7.50-7.43 (m, 2H), 7.43-7.35 (m, 3H), 6.79 (s, 1H), 6.77 (s, 1H), 6.55 (d, 1H), 6.42 (s, 1H), 6.00 (t, 1H), 3.77 (t, 2H), 3.54 (t, 4H), 3.50 (s, 3H), 2.41 (s, 3H), 2.38-2.26 (m, 6H), 1.78 (pent, 2H), 1.30 (s, 9H).

LCMS m/z 757 (M+H)+ (ES+)

Example 50

1-(3-(tert-Butyl)-1-(p-tolyl)-1H-pyrazol-5-yl)-3-(4-((2-((3-fluoro-5-(2-(2-(2-methoxyethoxy)-ethoxy)ethoxy)phenyl)amino)pyrimidin-4-yl)oxy)naphthalen-1-yl)urea

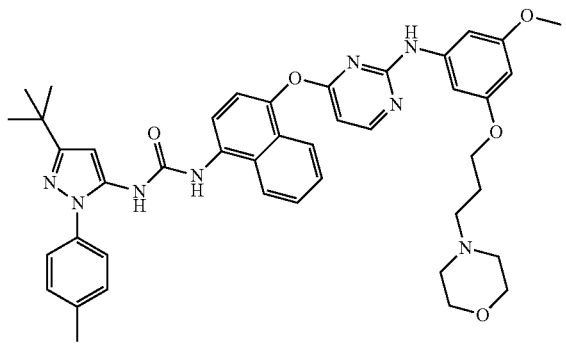

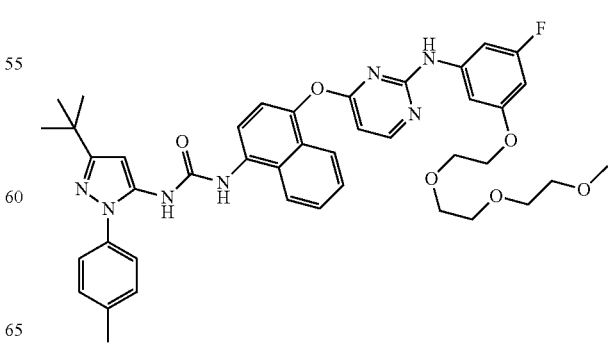

(i) 3-Fluoro-5-(2-(2-(2-methoxyethoxy)ethoxy)ethoxy)aniline

1-Bromo-2-(2-(2-methoxyethoxyl)ethoxy)ethane (430 µL, 2.480 mmol) was added to a suspension of 3-amino-5-fluorophenol (285 mg, 2.242 mmol), K$_2$CO$_3$ (950 mg, 6.87 mmol) and NaI (35 mg, 0.233 mmol) in acetone (5 mL) and heated at reflux for 16 h. The mixture was partitioned between EtOAc (10 mL) and water (10 mL). The organic layer was separated washed with 20% w/w NaCl solution (10 mL), dried (MgSO$_4$), filtered and evaporated. The crude product was purified by chromatography on silica gel (12 g column, 50% EtOAc:isohexane to 100%) to afford the sub-title compound (580 mg) as a pale yellow oil.

1H NMR (400 MHz, DMSO-d$_6$) δ 5.98-5.85 (m, 3H), 5.37 (s, 2H), 4.01-3.93 (m, 2H), 3.74-3.65 (m, 2H), 3.60-3.48 (m, 6H), 3.47-3.39 (m, 2H), 3.24 (s, 3H).

LCMS m/z 274 (M+H)+ (ES+)

(ii) 1-(3-(tert-Butyl)-1-(p-tolyl)-1H-pyrazol-5-yl)-3-(4-((2-((3-fluoro-5-(2-(2-(2-methoxyethoxy)ethoxy)ethoxy)phenyl)amino)pyrimidin-4-yl)oxy)naphthalen-1-yl)urea 1-(3-(tert-Butyl)-1-(p-tolyl)-1H-pyrazol-5-yl)-3-(4-((2-chloropyrimidin-4-yl)oxy)naphthalen-1-yl)urea (see Example 41(iv) above; 150 mg, 0.285 mmol) was dissolved in DMF (2 mL) and added to the compound from step (i) above (135 mg, 0.494 mmol) and p-TSA monohydrate (25 mg, 0.131 mmol) and stirred at 70° C. (block temperature) for 7 h. The mixture was poured into sat. aq. NaHCO$_3$ solution (20 mL) and the product extracted with EtOAc (2×20 mL), washed with 20% w/w NaCl solution (20 mL), separated, dried (MgSO$_4$), filtered and evaporated. The crude product was purified by chromatography on silica gel (40 g column, 1% MeOH:DCM to 7%) to afford a pale yellow solid. Recrystallised from MeCN (4 mL) and the solid washed with MeCN (1 mL) afforded the title compound (70 mg).

1H NMR (400 MHz, DMSO-d$_6$) δ 9.66 (s, 1H), 9.11 (s, 1H), 8.78 (s, 1H), 8.44 (d, 1H), 8.08 (d, 1H), 7.96 (d, 1H), 7.81 (d, 1H), 7.70-7.51 (m, 2H), 7.51-7.43 (m, 2H), 7.43-7.33 (m, 3H), 6.93 (s, 2H), 6.62 (d, 1H), 6.42 (s, 1H), 6.29 (dt, 1H), 3.97-3.88 (m, 2H), 3.72-3.61 (m, 2H), 3.57-3.46 (m, 6H), 3.44-3.37 (m, 2H), 3.22 (s, 3H), 2.41 (s, 3H), 1.30 (s, 9H).

LCMS m/z 764 (M+H)+ (ES+)

Example 51

1-(4-((2-((3-(2,5,8,11,14,17,20-Heptaoxadocosan-22-yloxy)-5-methoxyphenyl)amino)pyrimidin-4-yl)oxy)naphthalen-1-yl)-3-(3-(tert-butyl)-1-(p-tolyl)-1H-pyrazol-5-yl)urea

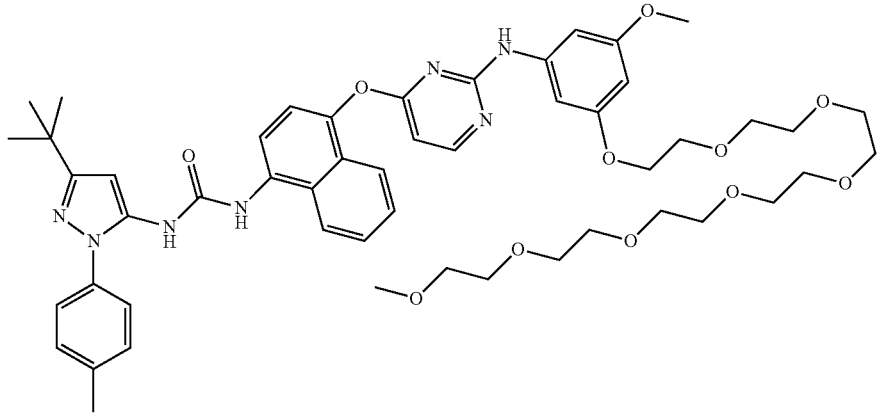 [SMILES: COCCOCCOCCOCCOCCOCCOCCOc1cc(Nc2nccc(Oc3ccc(NC(=O)Nc4cc(C(C)(C)C)nn4-c4ccc(C)cc4)c4ccccc34)n2)cc(OC)c1]

(i) 3-(2,5,8,11,14,17,20-Heptaoxadocosan-22-yloxy)-5-methoxyaniline

DIAD (576 µL, 2.96 mmol) added to a suspension of 3-amino-5-methoxyphenol (275 mg, 1.976 mmol), PPh$_3$ (778 mg, 2.96 mmol) and O-methylheptaethylene glycol (1009 mg, 2.96 mmol) in THF (5 mL) and the resulting mixture was stirred at rt for 18 h. The mixture was cooled and partitioned between water (20 mL) and ethyl acetate (20 mL). The organic layer was separated, dried (MgSO$_4$), filtered and concentrated under reduced pressure to give a brown oil. The crude product was purified by chromatography on silica gel (40 g column, 0-10% MeOH/EtOAc) to afford a clear brown oil. The oil was further purified by chromatography on the Companion (80 g column, 0-50% acetone/toluene) to afford the sub-title compound (292 mg) as a pale yellow oil.

1H NMR (400 MHz, DMSO-d$_6$) δ 5.77-5.73 (m, 2H), 5.68 (dd, 1H), 5.05 (br s, 2H), 3.97-3.92 (m, 2H), 3.72-3.66 (m, 2H), 3.63 (s, 3H), 3.60-3.48 (m, 22H), 3.45-3.40 (m, 2H), 3.24 (s, 3H).

LCMS m/z 462 (M+H)+ (ES+)

(ii) 1-(4-((2-((3-(2,5,8,11,14,17,20-Heptaoxadocosan-22-yloxy)-5-methoxyphenyl)amino)pyrimidin-4-yl)oxy)naphthalen-1-yl)-3-(3-(tert-butyl)-1-(p-tolyl)-1H-pyrazol-5-yl)urea A stirred solution of 1-(3-(tert-butyl)-1-(p-tolyl)-1H-pyrazol-5-yl)-3-(4-((2-chloropyrimidin-4-yl)oxy)naphthalen-1-yl)urea (see Example 41(iv) above; 119 mg, 0.194 mmol) and the product from step (i) above (134 mg, 0.290 mmol) in THF (2 mL) and DMF (4 mL) was treated with p-TSA monohydrate (10 mg, 0.053 mmol) and stirred at 70° C. (bath) overnight. The solution was allowed to cool, poured into saturated aqueous sodium bicarbonate solution (30 mL) and extracted with ethyl acetate (3×40 mL). The combined organic layer were washed with water (2×50 mL) followed by brine (2×50 mL), were dried (Na$_2$SO$_4$) and evaporated. The residue was purified on a 40 g redisep silica cartridge, using a gradient of 0 to 5% MeOH/DCM as eluent to give a brown oil. The oil was further purified on a 40 g redisep silica cartridge, using 40% of acetone in toluene as eluent to give a brown gum. The gum was triturated with ether (5 mL) to give a solid. The ether was removed with a pipette and the residue was dried to give the title compound (54 mg) as a brittle, hygroscopic buff solid.

1H NMR (400 MHz, DMSO-d$_6$) δ 9.40 (s, 1H), 9.09 (s, 1H), 8.76 (s, 1H), 8.40 (d, 1H), 8.06 (d, 1H), 7.95 (d, 1H), 7.82 (m, 1H), 7.64-7.54 (m, 2H), 7.47-7.45 (m, 2H), 7.39-7.37 (m, 3H), 6.80 (d, 2H), 6.53 (d, 1H), 6.41 (s, 1H), 6.03 (t, 1H), 3.86 (t, 2H), 3.70-3.61 (m, 2H), 3.59-3.44 (m, 25H), 3.44-3.38 (m, 2H), 3.22 (s, 3H), 2.40 (s, 3H), 1.29 (s, 9H).

LCMS (m/z) 476.7 (M+2H)$^{2+}$ (ES+)

Example 52

1-(3-(tert-Butyl)-1-(P-tolyl)-1H-pyrazol-5-yl)-3-(4-((2-((3-cyano-5-(2-(2-(2-methoxyethoxy)-ethoxy)ethoxy)phenyl)amino)pyrimidin-4-yl)oxy)naphthalen-1-yl)urea

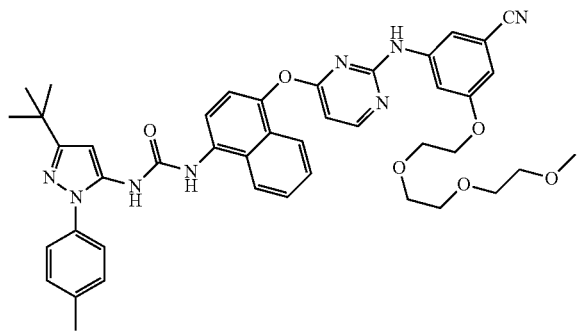 [SMILES: COCCOCCOCCOc1cc(C#N)cc(Nc2nccc(Oc3ccc(NC(=O)Nc4cc(C(C)(C)C)nn4-c4ccc(C)cc4)c4ccccc34)n2)c1]

(i) 3-(2-(2-(2-Methoxyethoxyl)ethoxy)ethoxy)-5-nitrobenzonitrile

3-Hydroxy-5-nitrobenzonitrile (1.0 g, 6.09 mmol), 1-bromo-2-(2-(2-methoxyethoxy)-ethoxy)ethane (1.373 ml, 7.92 mmol) and potassium carbonate were placed in a round bottom flask in MeCN (15 mL) and stirred at reflux under N$_2$ for 6 h. Reaction was stopped and left to cool to rt, inorganic solids were filtered off and washed with MeCN (2×30 mL). Combined organics were concentrated in vacuo and the crude product was purified by chromatography on silica gel (40 g column, EtOAc:Isohexane; 0:100 to 1:1) to afford the sub-title compound (1.74 g) as a clear yellow oil.

Used Crude in Next Step (ii) 3-Amino-5-(2-(2-(2-methoxyethoxyl)ethoxy)ethoxy)benzonitrile In a 100 mL flask, a solution of the product from step (i) above (1.74 g, 5.61 mmol) in EtOH (20 mL) and water (4 mL) was treated with iron powder (3.13 g, 56.1 mmol) and NH$_4$Cl (0.450 g, 8.41 mmol) and the rxn mixture heated to reflux under N$_2$. After 3 h reaction was stopped, left to cool to rt then filtered through celite and the filtrate concentrated in vacuo. The residue was then taken up in EtOAc (100 mL) and washed with saturated NaHCO$_3$ solution (2×50 mL), and saturated brine (1×50 mL). The organics were dried over Na$_2$SO$_4$, filtered and concentrated in vacuo to afford the sub-title compound (1.07 g) as a yellow oil.

1H NMR (CDCl$_3$) 400M Hz; δ 6.55 (s, 1H), 6.52 (s, 1H), 6.43 (s, 1H), 4.10-4.07 (m, 2H), 3.90 (s, 2H), 3.84-3.82 (m, 2H), 3.74-3.64 (m, 6H), 3.57-3.55 (m, 2H), 3.38 (s, 3H).

(iii) 1-(3-(tert-Butyl)-1-(p-tolyl)-1H-pyrazol-5-yl)-3-(4-((2-((3-cyano-5-(2-(2-(2-methoxyethoxyl)ethoxy)ethoxy)phenyl)amino)pyrimidin-4-yl)oxy)naphthalen-1-yl)urea A stirred solution of the product from step (ii) above (112 mg, 0.400 mmol) and 1-(3-(tert-butyl)-1-(p-tolyl)-1H-pyrazol-5-yl)-3-(4-((2-chloropyrimidin-4-yl)oxy)naphthalen-1-yl)urea (see Example 41(iv) above; 123 mg, 0.2 mmol) in DMF (4 mL) and THF (2 mL) was treated with p-TSA monohydrate (10 mg, 0.053 mmol) and stirred at 70° C. (bath) overnight. The solution was treated with more p-TSA monohydrate (10 mg, 0.053 mmol), stirred at 70° C. (bath) for 4 h and allowed to stand overnight. The solution was treated with more p-TSA monohydrate (10 mg, 0.053 mmol) and stirred at 70° C. (bath) overnight. The solution was allowed to cool, poured into saturated aqueous sodium bicarbonate solution (30 mL) and extracted with ethyl acetate (3×40 mL). The combined organic layers were washed with water (2×50 mL) followed by brine (2×50 mL), were dried (Na$_2$SO$_4$) and evaporated. The residue was purified on a 40 g redisep silica cartridge using 20% of acetone in toluene as eluent to give a gum which was triturated with ether (4 mL) to give a brown solution and a pink solid. The mixture was allowed to settle and the solvent was removed with a pipette. The residue was triturated with acetonitrile (2 mL), filtered and washed with acetonitrile (1 mL) followed by ether (2 mL) then dried to afford the title compound (35 mg) as a pale pink solid.

1H NMR (400 MHz, DMSO-d$_6$) δ 9.79 (s, 1H), 9.04 (s, 1H), 8.77 (s, 1H), 8.47 (d, 1H), 8.07 (d, 1H), 7.95 (d, 1H), 7.81 (d, 1H), 7.64-7.36 (mult, 9H), 6.91 (s, 1H), 6.65 (d, 1H), 6.40 (s, 1H), 4.01 (t, 2H), 3.68 (t, 2H), 3.55-3.47 (mult, 6H), 3.41-3.38 (mult, 2H), 3.21 (s, 3H), 2.40 (s, 3H), 1.29 (s, 9H).

LCMS (m/z) 386 (M+2H)$^{2+}$ (ES+); (m/z) 769 (M−H)$^−$ (ES$^−$)

Example 53

1-(3-(tert-Butyl)-1-(p-tolyl)-1H-pyrazol-5-yl)-3-(2,3-dichloro-4-((2-((3-methoxy-5-(2-(2-(2-methoxyethoxyl)ethoxy)ethoxy)phenyl)amino)pyrimidin-4-yl)oxy)phenyl)urea

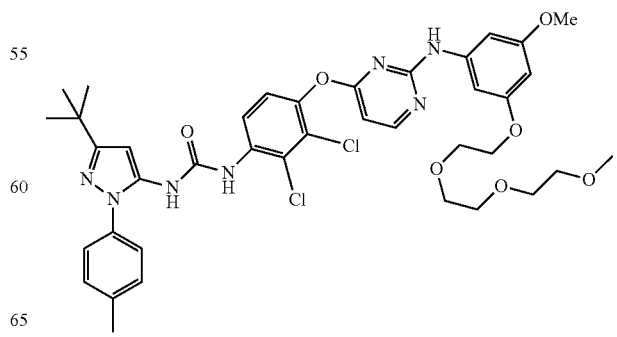

(i) 1-(3-(tert-Butyl)-1-(p-tolyl)-1H-pyrazol-5-yl)-3-(2,3-dichloro-4-((2-chloropyrimidin-4-yl)oxy)phenyl)urea Et₃N (49.0 µL, 0.351 mmol) was added to a stirred solution of phenyl (3-(tert-butyl)-1-(p-tolyl)-1H-pyrazol-5-yl)carbamate (see, for example, Kapadia, S. R. et al., U.S. Pat. No. 6,492,529, December 2002; 800 mg, 2.267 mmol) and 2,3-dichloro-4-((2-chloropyrimidin-4-yl)oxy)aniline (see Example 21(i) above; 693 mg, 2.267 mmol) in i-PrOAc (30 mL). The resulting solution was heated at 70° C. for 3 h. The reaction was cooled to rt and the solvent removed in vacuo. The crude product was purified by chromatography on silica gel (80 g column, 0-100% EtOAc in isohexane) to afford a white foam (720 mg). The compound was purified for a second time by chromatography on silica gel (40 g column, 0-2% MeOH in DCM) to afford the sub-title compound (375 mg) as an off-white solid.

1H NMR (DMSO-d₆) 400 MHz, δ: 9.19 (s, 1H), 8.86 (s, 1H), 8.70 (d, 1H), 8.15 (d, 1H), 7.46 (d, 1H), 7.42-7.40 (m, 2H), 7.36-7.34 (m, 3H), 6.38 (s, 1H), 2.38 (s, 3H), 1.27 (s, 9H).

LCMS m/z 545/547 (M+H)+ (ES+)

(ii) 1-(3-(tert-Butyl)-1-(p-tolyl)-1H-pyrazol-5-yl)-3-(2,3-dichloro-4-((2-((3-methoxy-5-(2-(2-(2-methoxyethoxy)ethoxy)ethoxy)phenyl)amino)pyrimidin-4-yl)oxy)phenyl)urea To a stirred solution of the product from step (i) above (185 mg, 0.288 mmol) and 3-methoxy-5-(2-(2-(2-methoxyethoxyl)ethoxy)ethoxy)aniline (see Example 13(i) above; 180 mg, 0.599 mmol) in THF (6 mL) was added p-TSA monohydrate (82 mg, 0.432 mmol). The resulting mixture was heated at 60° C. overnight. The reaction was cooled to rt and then partitioned between EtOAc (40 mL) and sat. aq. NaHCO₃ (30 mL). The aqueous layer was back extracted with EtOAc (2×40 mL). The combined organic extracts were washed with brine (100 mL), dried (MgSO₄), filtered and concentrated in vacuo to afford a brown oil (298 mg). The crude product was purified by chromatography on silica gel (40 g column, 0-100% EtOAc in isohexane) to afford an off-white foam, which was triturated with diethyl ether to afford the title compound (63 mg) as a pale pink solid.

1H NMR (DMSO-d₆) 400 MHz, δ: 9.53 (s, 1H), 9.22 (s, 1H), 8.82 (s, 1H), 8.41 (d, 1H), 8.17 (d, 1H), 7.42-7.39 (m, 3H), 7.36-7.34 (m, 2H), 6.79-6.70 (br m, 2H), 6.58 (d, 1H), 6.39 (s, 1H), 6.07 (t, 1H), 3.94-3.92 (m, 2H), 3.69-3.67 (m, 2H), 3.57-3.54 (m, 5H), 3.52-3.48 (m, 4H), 3.42-3.39 (m, 2H), 3.21 (s, 3H), 2.38 (s, 3H), 1.27 (s, 9H).

LCMS m/z 794/796 (M+H)+ (ES+); 792 (M−H)− (ES−)

Example 54

1-(3-(tert-Butyl)-1-(p-tolyl)-1H-pyrazol-5-yl)-3-(4-((2-((3-ethynyl-5-(2-(2-(2-methoxyethoxy)ethoxy)ethoxy)phenyl)amino)pyrimidin-4-yl)oxy)naphthalen-1-yl)urea

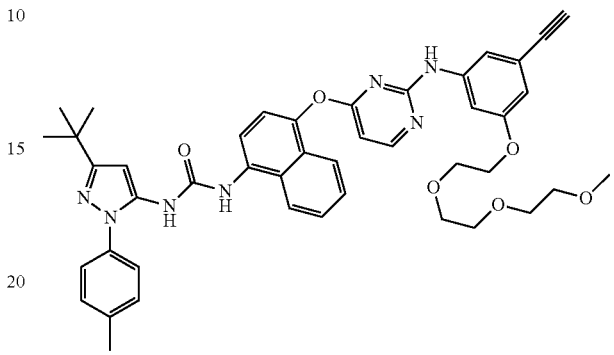

(i) 1-Bromo-3-(2-(2-(2-methoxyethoxy)ethoxy)ethoxy)-5-nitrobenzene

1-Bromo-2-(2-(2-methoxyethoxyl)ethoxy)ethane (1.2 mL, 6.92 mmol) was added to a suspension of 3-bromo-5-nitrophenol (1.27 g, 5.83 mmol), K₂CO₃ (2.5 g, 18.09 mmol) and NaI (0.09 g, 0.600 mmol) in acetone (20 mL) and heated at reflux for 16 h. The mixture was filtered then partitioned between EtOAc (50 mL) and water (50 mL). The organic layer was separated, washed with 20% w/w NaCl solution (50 mL), dried (MgSO₄), filtered and evaporated. The crude product was purified by chromatography on silica gel (40 g column, 20% EtOAc:isohexane to 50%) to afford the sub-title compound (2 g) as a pale yellow oil.

1H NMR (400 MHz, DMSO-d₆) δ 7.95 (t, 1H), 7.75 (t, 1H), 7.69 (dd, 1H), 4.35-4.22 (m, 2H), 3.81-3.72 (m, 2H), 3.64-3.56 (m, 2H), 3.56-3.48 (m, 4H), 3.46-3.38 (m, 2H), 3.23 (s, 3H). c.a. 10% of a ethylene glycol related impurity m/z 364/366 (M+H)+ (ES+)

(ii) Triisopropyl((3-(2-(2-(2-methoxyethoxyl)ethoxy)ethoxy)-5-nitrophenyl)ethynyl)silane Pd(PPh₃)₄ (0.635 g, 0.549 mmol) was added to a degassed suspension of the compound from step (i) above (2 g, 5.49 mmol), CuI (0.052 g, 0.275 mmol), and ethynyltriisopropyl silane (2 mL, 8.92 mmol) in TEA (5 mL) and DMF (15 mL). The mixture was heated at 85° C. (block temp.) for 1 h then cooled and filtered (Whatman glass fibre pad GF/A). The solvent was evaporated and the residue partitioned between EtOAc (100 mL) and 20% w/w NaCl solution (150 mL). The organic layer was separated, dried (MgSO₄), filtered and the solvent evaporated to give a thick yellow oil. The crude product was purified by chromatography on silica gel (40 g column, 0% EtOAc:isohexane to 30%) to afford the sub-title compound (2.25 g) as a thick brown oil.

1H NMR (400 MHz, CDCl₃) δ 7.89 (dd, 1H), 7.71 (t, 1H), 7.31 (dd, 1H), 4.26-4.16 (m, 2H), 3.94-3.84 (m, 2H), 3.77-3.71 (m, 2H), 3.71-3.62 (m, 4H), 3.58-3.51 (m, 2H), 3.38 (s, 3H), 1.22-1.05 (m, 21H).

LCMS m/z 488 (M+Na)+(ES+)

(iii) 1-Ethynyl-3-(2-(2-(2-methoxyethoxy)ethoxy)ethoxy)-5-nitrobenzene

The product from step (ii) above (2.25 g, 4.83 mmol) was dissolved in EtOAc (25 mL) and TBAF, 1M in THF (5 mL, 5.00 mmol) added. The mixture was stirred for 1 h then partitioned between water (100 mL) and EtOAc (100 mL), the aqueous was separated and washed with fresh EtOAc (100 mL). The organics were bulked, dried (MgSO$_4$), filtered and evaporated to a dark brown oil. The crude product was purified by chromatography on silica gel (40 g column, 30% EtOAc:isohexane to 50%) to afford the sub-title compound (1.3 g) as a clear brown oil.

1H NMR (400 MHz, CDCl$_3$) δ 7.92 (dd, 1H), 7.76 (t, 1H), 7.34 (dd, 1H), 4.30-4.13 (m, 2H), 3.95-3.83 (m, 2H), 3.76-3.71 (m, 2H), 3.71-3.63 (m, 4H), 3.58-3.53 (m, 2H), 3.38 (s, 3H), 3.18 (s, 1H)

LCMS m/z 310 (M+H)+ (ES+)

(iv) 3-Ethynyl-5-(2-(2-(2-methoxyethoxy)ethoxy)ethoxy)aniline

Iron powder (4 g, 71.6 mmol) was added to a solution of the product from step (iii) above (1.3 g, 4.20 mmol) in ethanol (20 mL) then NH$_4$Cl (0.4 g, 7.48 mmol) in water (2 mL) added. The mixture was sonicated at 65° C. (bath temperature) for 4 h. The reaction mixture was cooled, filtered (Whatmans glass fibre pad GF/A) and the solvent evaporated. The crude product was purified by chromatography on silica gel (40 g column, 1% MeOH:DCM to 5%) to afford the sub-title compound (0.955 g) as a thick yellow oil.

1H NMR (400 MHz, DMSO-d$_6$) δ 6.27 (t, 1H), 6.17 (t, 2H), 5.24 (s, 2H), 4.02-3.96 (m, 2H), 3.96 (s, 1H), 3.72-3.65 (m, 2H), 3.60-3.48 (m, 6H), 3.46-3.40 (m, 2H), 3.24 (s, 3H).

LCMS m/z 280 (M+H)+ (ES+)

(v) 1-(3-(tert-Butyl)-1-(p-tolyl)-1H-pyrazol-5-yl)-3-(4-((2-((3-ethynyl-5-(2-(2-(2-methoxyethoxy)ethoxy)ethoxy)phenyl)amino)pyrimidin-4-yl)oxy)naphthalen-1-yl)urea 1-(3-(tert-Butyl)-1-(p-tolyl)-1H-pyrazol-5-yl)-3-(4-((2-chloropyrimidin-4-yl)oxy)naphthalen-1-yl)urea (see Example 41(iv) above; 150 mg, 0.285 mmol was dissolved in DMF (2 mL) and added to the product from step (iv) above (140 mg, 0.501 mmol) and p-TSA monohydrate (25 mg, 0.131 mmol) and stirred at 70° C. (block temperature) for 7 h. The mixture was poured into sat. aq. NaHCO$_3$ solution (20 mL) and the product extracted with EtOAc (2×20 mL), washed with 20% w/w NaCl solution (20 mL), separated, dried (MgSO$_4$), filtered and evaporated. The crude product was purified by chromatography on silica gel (40 g column, 1% MeOH:DCM to 6%) to afford a pale yellow solid. Recrystallised from MeCN (4 mL) and solid washed with MeCN (1 mL) to afford the title compound (85 mg).

1H NMR (400 MHz, DMSO-d$_6$) δ 9.59 (s, 1H), 9.09 (s, 1H), 8.77 (s, 1H), 8.44 (d, 1H), 8.07 (d, 1H), 7.95 (d, 1H), 7.82 (d, 1H), 7.69-7.54 (m, 2H), 7.52-7.45 (m, 2H), 7.44-7.35 (m, 3H), 7.32 (s, 2H), 6.63-6.50 (m, 2H), 6.42 (s, 1H), 4.02 (s, 1H), 3.94 (t, 2H), 3.74-3.62 (m, 2H), 3.61-3.45 (m, 6H), 3.45-3.37 (m, 2H), 3.22 (s, 3H), 2.41 (s, 3H), 1.30 (s, 9H).

LCMS m/z 770 (M+H)+ (ES+)

Example 55

1-(3-(tert-Butyl)-1-(p-tolyl)-1H-pyrazol-5-yl)-3-(4-((2-((3-((2-hydroxyethyl)thio)-5-methoxyphenyl)amino)pyrimidin-4-yl)oxy)naphthalen-1-yl)urea

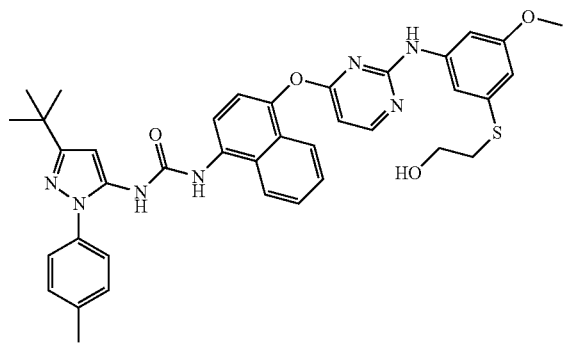 [SMILES: COc1cc(Nc2nccc(Oc3ccc(NC(=O)Nc4cc(C(C)(C)C)nn4-c4ccc(C)cc4)c4ccccc34)n2)cc(SCCO)c1]

(i) 2-((3-Amino-5-methoxyphenyl)thio)ethanol

3-Bromo-5-methoxyaniline (500 mg, 2.475 mmol), Pd$_2$(dba)$_3$ (113 mg, 0.124 mmol) and xantphos (143 mg, 0.247 mmol) were added to a degassed solution of DIPEA (1297 μL, 7.42 mmol) and 2-mercaptoethanol (173 μL, 2.475 mmol) in 1,4-dioxane (10 mL). Heated under nitrogen at 100° C. for 16 h then the reaction mixture was filtered through Celite and residue washed with DCM (5 mL). Solvents evaporated to give a brown gum. The crude product was purified by chromatography on the Companion (40 g column, 2% MeOH:DCM to 8%) to afford the sub-title compound (377 mg) as a dark brown oil.

1H NMR (400 MHz, DMSO-d$_6$) δ 6.13 (t, 1H), 6.03 (t, 1H), 5.95 (t, 1H), 5.17 (s, 2H), 4.92 (t, 1H), 3.64 (s, 3H), 3.60-3.49 (m, 2H), 2.93 (t, 2H).

LCMS m/z 200 (M+H)+ (ES+)

(ii) 1-(3-(tert-Butyl)-1-(p-tolyl)-1H-pyrazol-5-yl)-3-(4-((2-((3-((2-hydroxyethyl)thio)-5-methoxyphenyl)amino)pyrimidin-4-yl)oxy)naphthalen-1-yl)urea 1-(3-(tert-Butyl)-1-(p-tolyl)-1H-pyrazol-5-yl)-3-(4-((2-chloropyrimidin-4-yl)oxy)naphthalen-1-yl)urea (see Example 41(iv) above; 150 mg, 0.285 mmol) was dissolved in DMF (2 mL) and added to the product from step (i) above (120 mg, 0.602 mmol) and p-TSA monohydrate (25 mg, 0.131 mmol) and stirred at 70° C. (block temperature) for 7 h. The mixture was poured into sat. aq. NaHCO$_3$ solution (20 mL) and the product extracted with EtOAc (2×20 mL), washed with 20% w/w NaCl solution (20 mL), separated, dried (MgSO$_4$), filtered and evaporated. The crude product was purified by chromatography on silica gel (40 g column, 2% MeOH:DCM to 8%) to afford a pale yellow solid. Recrystallised from MeCN (4 mL) and solid washed with MeCN (1 mL) to give the title compound (95 mg).

1H NMR (400 MHz, DMSO-d$_6$) δ 9.48 (s, 1H), 9.10 (s, 1H), 8.79 (s, 1H), 8.42 (d, 1H), 8.08 (d, 1H), 7.97 (d, 1H), 7.82 (d, 1H), 7.70-7.53 (m, 2H), 7.52-7.43 (m, 2H), 7.43-7.32 (m, 3H), 7.09 (s, 1H), 7.02 (s, 1H), 6.57 (d, 1H), 6.42 (s, 1H), 6.41-6.32 (m, 1H), 4.89 (t, 1H), 3.57-3.44 (m, 5H), 2.92 (t, 2H), 2.41 (s, 3H), 1.30 (s, 9H).

LCMS m/z 690 (M+H)+ (ES+)

Example 56

1-(3-(tert-Butyl)-1-(p-tolyl)-1H-pyrazol-5-yl)-3-(4-((2-((3-methoxy-5-(2-(2-(2-methoxyethoxy)ethoxy)ethoxy)phenyl)amino)pyridin-4-yl)oxy)naphthalen-1-yl)urea

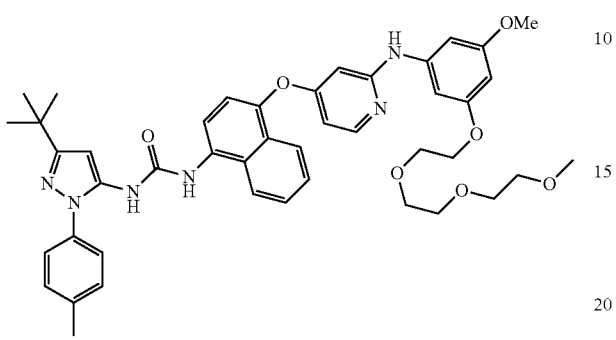

(i) tert-Butyl (4-((2-chloropyridin-4-yl)oxy)naphthalen-1-yl)carbamate

A mixture of 4-((2-chloropyridin-4-yl)oxy)naphthalen-1-amine (see, for example, Ito, K. et al., WO 2010/112936, 7 Oct. 2010; 1000 mg, 3.69 mmol) di-tert-butyl dicarbonate (750 mg, 3.44 mmol) in t-BuOH (10 mL) was stirred at reflux for 18 h. The mixture was diluted with water (15 mL) and collected by filtration. The solid was triturated in diethyl ether to yield the sub-title compound (1002 mg) as a pale grey solid.

1H NMR (DMSO-$d_6$) 400 MHz, δ: 9.37 (s, 1H), 8.28 (d, 1H), 8.16 (d, 1H), 8.82 (dd, 1H), 7.66 (d, 1H), 7.66-7.54 (m, 2H), 7.40 (d, 1H), 7.03 (d, 1H), 6.91 (dd, 1H), 1.52 (s, 9H). LCMS m/z 371 (M+H)+ (ES+); 369 (M–H)– (ES–)

(ii) tert-Butyl (4-((2-((3-methoxy-5-(2-(2-(2-methoxyethoxy)ethoxy)ethoxy)phenyl)amino)-Pyridin-4-yl)oxy)naphthalen-1-yl)carbamate Pd$_2$dba$_3$ (22 mg, 0.024 mmol) and BINAP (30 mg, 0.048 mmol) were stirred in 1,4-dioxane (1 mL) for 10 minutes under N$_2$. In a separate vessel, purged with N$_2$, caesium carbonate (455 mg, 1.396 mmol), 3-methoxy-5-(2-(2-(2-methoxyethoxyl)ethoxy)ethoxy)-aniline (see Example 13(i) above; 265 mg, 0.930 mmol) and the product from step (i) above (345 mg, 0.930 mmol) were stirred in 1,4-dioxane (5 mL). The catalyst solution was added to the main reaction mixture and the whole was heated to 90° C. for 48 h. Pd$_2$dba$_3$ (22 mg, 0.024 mmol) and BINAP (30 mg, 0.048 mmol) were added and the mixture was stirred for a further 18 h. Water was added (15 mL) and the mixture was extracted with ethyl acetate (3×15 mL). The combined organic phases were washed with saturated brine (15 mL), dried (MgSO$_4$) and concentrated under reduced pressure. The crude product was purified by chromatography on the Companion (40 g column, 50-100% EtOAc/isohexane) to afford the sub-title compound (194 mg) as a sticky brown oil.

1H NMR (DMSO-$d_6$) 400 MHz, δ: 9.35 (s, 1H), 8.89 (s, 1H), 8.18-8.08 (m, 2H), 7.84 (d, 1H), 7.67-7.52 (m, 3H), 7.35 (d, 1H), 6.91 (s, 1H), 6.79 (s, 1H), 6.58 (dd, 1H), 6.07-6.02 (m, 2H), 4.01-3.95 (m, 2H), 3.74-6.67 (m, 2H), 3.65 (s, 3H), 3.60-3.48 (m, 6H), 3.46-3.39 (m, 2H), 3.23 (s, 3H), 1.52 (s, 9H).

LCMS m/z 620 (M+H)+ (ES+); 618 (M–H)– (ES–)

(iii) 4-((4-Aminonaphthalen-1-yl)oxy)-N-(3-methoxy-5-(2-(2-(2-methoxyethoxy)ethoxy)-ethoxy)phenyl)pyridin-2-amine A solution of the product from step (ii) above (190 mg, 0.307 mmol) in DCM (0.5 mL) was treated with TFA (500 μL, 6.49 mmol) and stirred at rt for 3 h. The mixture was diluted with water (10 mL) and DCM (10 mL). The mixture was neutralised with saturated sodium hydrogen carbonate and passed through a phase separation cartidge. The organic phase was dried (MgSO$_4$) and concentrated to give the sub-title compound (135 mg) as a brown gum.

1H NMR (DMSO-$d_6$) 400 MHz, δ: 8.08 (s, 1H), 8.20-8.10 (m, 1H), 8.05 (d, 1H), 7.67-7.59 (m, 1H), 7.49-7.39 (m, 2H), 7.09 (d, 1H), 6.89 (s, 1H), 6.76 (s, 1H), 6.71 (d, 1H), 6.52 (dd, 1H), 6.06-5.55 (m, 2H), 5.83 (s, 2H), 4.00-3.90 (m, 2H), 3.74-3.66 (m, 2H), 3.64 (s, 3H), 3.60-3.47 (m, 6H), 3.46-3.38 (m, 2H), 3.23 (s, 3H).

LCMS m/z 520 (M+H)+ (ES+)

(iv) 1-(3-(tert-Butyl)-1-(p-tolyl)-1H-pyrazol-5-yl)-3-(4-((2-((3-methoxy-5-(2-(2-(2-methoxyethoxyl)ethoxy)ethoxy)phenyl)amino)pyridin-4-yl)oxy)naphthalen-1-yl)urea Triethylamine (6 μL, 0.043 mmol) was added to a mixture of phenyl (3-(tert-butyl)-1-(p-tolyl)-1H-pyrazol-5-yl)carbamate (see, for example, Kapadia, S. R. et al., U.S. Pat. No. 6,492,529, 10 Dec. 2002; 75 mg, 0.215 mmol) and the product from step (iii) above (122 mg, 0.234 mmol) in isopropyl acetate (2 mL) and the mixture heated at 50° C. for 2 h. The reaction mixture was concentrated under reduced pressure then purified by chromatography on the Companion (80 g column, 50-100% isohexane/EtOAc) to afford the title compound (135 mg) as a tan glass.

1H NMR (DMSO-$d_6$) 400 MHz, δ: 9.13 (s, 1H), 8.87 (s, 1H), 8.78 (s, 1H), 8.12-8.06 (m, 2H), 8.96 (d, 1H), 7.84 (dd, 1H), 7.69-7.62 (m, 1H), 7.61-7.54 (m, 1H), 7.49-7.43 (m, 2H), 7.41-7.32 (m, 3H), 6.90 (dd, 1H), 6.77 (dd, 1H), 6.55 (dd, 1H), 6.41 (s, 1H), 6.05 (d, 1H), 6.03 (dd, 1H), 4.00-3.93 (m, 2H), 3.73-3.67 (m, 2H), 3.64 (s, 3H), 3.59-3.54 (m, 2H), 3.54-3.48 (m, 4H), 3.44-3.38 (m, 2H), 3.22 (s, 3H), 2.40 (s, 3H), 1.29 (s, 9H).

LCMS m/z 775 (M+H)+ (ES+); 773 (M–H)– (ES–)

Example 57

1-(3-(tert-Butyl)-1-(p-tolyl)-1H-pyrazol-5-yl)-3-(4-((2-((3-(2-(2-(2-(dimethylamino)ethoxy) ethoxy) ethoxy)-5-methoxyphenyl)amino)pyrimidin-4-yl) oxy)naphthalen-1-yl)urea

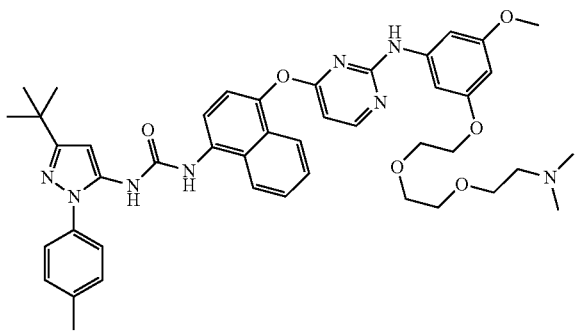 [SMILES: COc1cc(Nc2nccc(Oc3ccc(NC(=O)Nc4cc(C(C)(C)C)nn4-c4ccc(C)cc4)c4ccccc34)n2)cc(OCCOCCOCCN(C)C)c1]

(i) 2-(2-(2-(3-Methoxy-5-nitrophenoxy)ethoxy) ethoxy)-N,N-dimethylethanamine DIAD (480 µL, 2.469 mmol) was added dropwise to a stirred solution of 3-methoxy-5-nitrophenol (350 mg, 2.069 mmol), 2-(2-(2-(dimethylamino)ethoxy)ethoxy)ethanol (440 mg, 2.483 mmol) and PPh₃ (651 mg, 2.483 mmol) in THF (15 mL) at 0-5° C. The mixture was warmed to rt, stirred for 18 h then the solvent evaporated under reduced pressure. The crude product was loaded onto a column of SCX in MeOH. The column was washed with MeOH and then the product was eluted with 7 M ammonia in MeOH. The resultant mixture was concentrated in vacuo and purified by chromatography on silica gel (40 g column, 0-10% MeOH/DCM) to afford the sub-title compound (428 mg) as a yellow oil.

1H NMR (400 MHz; CDCl₃) δ 7.38-7.36 (m, 2H), 6.78 (s, 1H), 4.19-4.17 (m, 2H), 3.89-3.86 (m, 5H), 3.57-3.58 (m, 6H), 2.51 (t, 2H), 2.26 (s, 6H).

LCMS m/z 329 (M+H)+ (ES+)

(ii) 3-(2-(2-(2-(Dimethylamino)ethoxy)ethoxy) ethoxy)-5-methoxyaniline

Pd/C, 10% w/w (50 mg, 0.047 mmol) was added to a solution of the product from step (i) above (420 mg, 1.279 mmol) in EtOH (10 mL) and the mixture stirred under hydrogen (5 bar) for 2 h. The mixture was filtered and the solvent evaporated to give the sub-title compound (380 mg) as a thick yellow oil.

1H NMR (400 MHz, DMSO-d₆) δ 5.79-5.72 (m, 2H), 5.68 (t, 1H), 5.06 (s, 2H), 4.01-3.90 (m, 2H), 3.73-3.65 (m, 2H), 3.62 (s, 3H), 3.59-3.54 (m, 2H), 3.54-3.50 (m, 2H), 3.48 (t, 2H), 2.39 (t, 2H), 2.14 (s, 6H).

LCMS m/z 299 (M+H)+ (ES+)

(iii) 1-(3-(tert-Butyl)-1-(p-tolyl)-1H-pyrazol-5-yl)-3-(4-((2-((3-(2-(2-(2-(dimethylamino)-ethoxy)ethoxy) ethoxy)-5-methoxyphenyl)amino)pyrimidin-4-yl) oxy)naphthalen-1-yl)urea 1-(3-(tert-Butyl)-1-(p-tolyl)-1H-pyrazol-5-yl)-3-(4-((2-chloropyrimidin-4-yl)oxy)naphthalen-1-yl)urea (see Example 41(iv) above; 150 mg, 0.285 mmol) was dissolved in DMF (2 mL) then the product from step (ii) above (135 mg, 0.452 mmol) and p-TSA monohydrate (120 mg, 0.631 mmol) added and the mixture stirred at 70° C. (block temperature) for 7 h. The mixture was poured into sat. aq. NaHCO₃ solution (20 mL) and the product extracted with EtOAc (2×20 mL), washed with 20% w/w NaCl solution (20 mL), separated, dried (MgSO₄), filtered and evaporated. The crude product was purified by chromatography on silica gel (12 g column, 2% 7N NH₃ in MeOH:DCM to 8%) to afford a pale yellow foam. Triturated with Et₂O (2×3 ml) to afford the title compound (100 mg) as a pale tan solid.

1H NMR (400 MHz, DMSO-d₆) δ 9.44 (s, 1H), 9.11 (s, 1H), 8.79 (s, 1H), 8.41 (d, 1H), 8.07 (d, 1H), 7.96 (d, 1H), 7.83 (d, 1H), 7.71-7.52 (m, 2H), 7.52-7.44 (m, 2H), 7.44-7.33 (m, 3H), 6.89-6.71 (m, 2H), 6.54 (d, 1H), 6.42 (s, 1H), 6.03 (t, 1H), 3.95-3.78 (m, 2H), 3.70-3.61 (m, 2H), 3.58-3.41 (m, 9H), 2.41 (s, 3H), 2.35 (t, 2H), 2.11 (s, 6H), 1.29 (s, 9H).

LCMS m/z 789 (M+H)+ (ES+)

Example 58

1-(3-(tert-Butyl)-1-(p-tolyl)-1H-pyrazol-5-yl)-3-(4-((2-((3-methoxy-5-(2-(2-(2-morpholinoethoxy) ethoxy)ethoxy)phenyl)amino)pyrimidin-4-yl)oxy) naphthalen-1-yl)urea

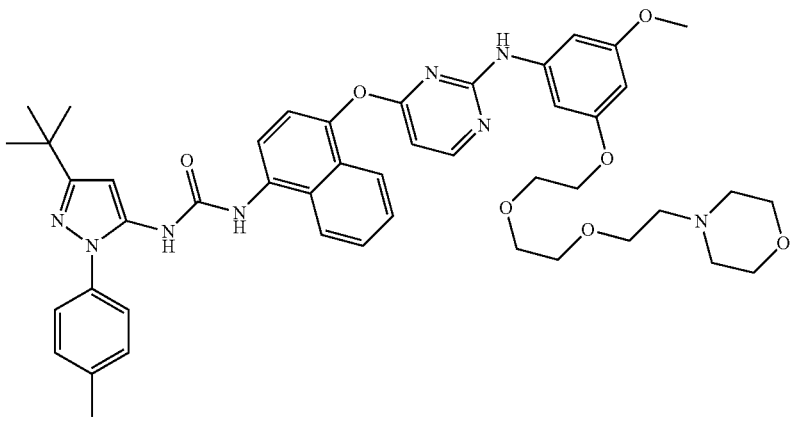 [SMILES: COc1cc(Nc2nccc(Oc3ccc(NC(=O)Nc4cc(C(C)(C)C)nn4-c4ccc(C)cc4)c4ccccc34)n2)cc(OCCOCCOCCN2CCOCC2)c1]

(i) 4-(2-(2-(2-(3-Methoxy-5-nitrophenoxy)ethoxy)ethoxy)ethyl)morpholine

DIAD (530 μL, 2.73 mmol) was added dropwise to a stirred solution of 3-methoxy-5-nitrophenol (386 mg, 2.280 mmol), 2-(2-(2-morpholinoethoxyl)ethoxy)ethanol (600 mg, 2.74 mmol) and PPh₃ (718 mg, 2.74 mmol) in THF (15 mL) at 0-5° C. The mixture was warmed to rt, stirred for 18 h then the solvent evaporated under reduced pressure. The crude product was loaded onto a column of SCX in MeOH. The column was washed with MeOH and then the product was eluted with 7 M ammonia in MeOH. The resultant mixture was concentrated in vacuo and purified by chromatography on silica gel (40 g column, 0-5% MeOH/DCM) to afford the sub-title compound (728 mg) as a yellow oil.

1H NMR (400 MHz; CDCl₃) δ 7.40-7.36 (m, 2H), 6.78 (s, 1H), 4.18 (t, 2H), 3.89-3.96 (m, 5H), 3.73-3.62 (m, 10H), 2.59 (t, 2H), 2.50 (br s, 4H).

LCMS m/z 371 (M+H)+ (ES+)

(ii) 3-Methoxy-5-(2-(2-(2-morpholinoethoxyl)ethoxy)ethoxy)aniline

Pd/C, 10% w/w (100 mg, 0.094 mmol) was added to a solution of the product from step (i) above (720 mg) in EtOH (10 mL) and the mixture stirred under hydrogen (5 bar) for 2 h. The mixture was filtered and the solvent evaporated to give the sub-title compound (650 mg) as a thick yellow oil.

1H NMR (400 MHz, DMSO-d6) δ 5.79-5.71 (m, 2H), 5.68 (t, 1H), 5.06 (s, 2H), 3.98-3.90 (m, 2H), 3.73-3.65 (m, 2H), 3.62 (s, 3H), 3.59-3.48 (m, 10H), 2.45 (t, 2H), 2.42-2.33 (m, 4H).

LCMS m/z 341 (M+H)+ (ES+)

(iii) 1-(3-(tert-Butyl)-1-(p-tolyl)-1H-pyrazol-5-yl)-3-(4-((2-((3-methoxy-5-(2-(2-(2-morpholinoethoxyl)ethoxy)phenyl)amino)pyrimidin-4-yl)oxy)naphthalen-1-yl)urea 1-(3-(tert-Butyl)-1-(p-tolyl)-1H-pyrazol-5-yl)-3-(4-((2-chloropyrimidin-4-yl)oxy)naphthalen-1-yl)urea (see Example 41(iv) above; 150 mg, 0.285 mmol) was dissolved in DMF (2 mL) then the product from step (ii) above (190 mg, 0.558 mmol) and p-TSA monohydrate (150 mg, 0.789 mmol) added and the mixture stirred at 70° C. (block temperature) for 7 h. The mixture was poured into sat. aq. NaHCO₃ solution (20 mL) and the product extracted with EtOAc (2×20 mL), washed with 20% w/w NaCl solution (20 mL), separated, dried (MgSO₄), filtered and evaporated. The crude product was purified by chromatography on silica gel (12 g column, 2% 7N NH₃ in MeOH:DCM to 5%) to afford a pale yellow foam. Triturated with Et₂O (2×3 mL) to give the title compound (115 mg) as a colourless solid 1H NMR (400 MHz, DMSO-d6) δ 9.44 (s, 1H), 9.11 (s, 1H), 8.79 (s, 1H), 8.41 (d, 1H), 8.07 (d, 1H), 7.96 (d, 1H), 7.83 (d, 1H), 7.68-7.53 (m, 2H), 7.52-7.43 (m, 2H), 7.44-7.33 (m, 3H), 6.92-6.71 (m, 2H), 6.54 (d, 1H), 6.42 (s, 1H), 6.03 (t, 1H), 3.92-3.80 (m, 2H), 3.70-3.61 (m, 2H), 3.59-3.44 (m, 13H), 2.47-2.29 (m, 9H), 1.29 (s, 9H).

LCMS m/z 831 (M+H)+ (ES+)

Example 59

1-(3-(tert-Butyl)-1-(p-tolyl)-1H-pyrazol-5-yl)-3-(2,3-dichloro-4-((2-((3-methoxy-5-(2-morpholinoethoxy)phenyl)amino)pyrimidin-4-yl)oxy)phenyl)urea

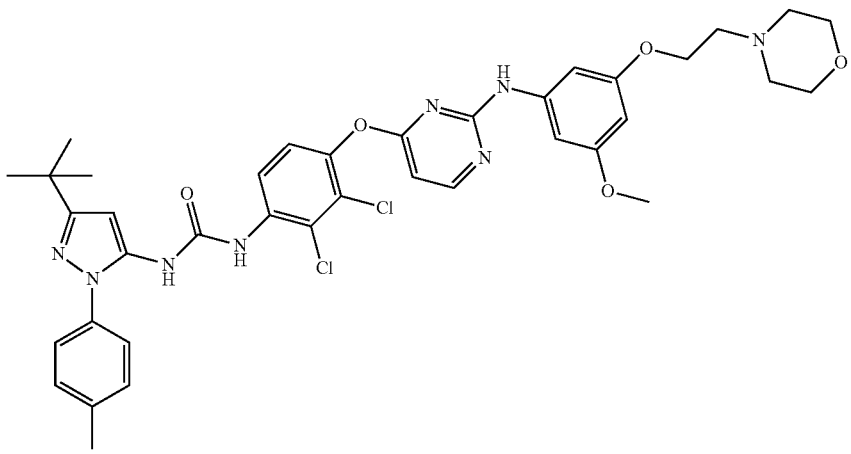 [SMILES: COc1cc(Nc2nccc(Oc3ccc(NC(=O)Nc4cc(C(C)(C)C)nn4-c4ccc(C)cc4)c(Cl)c3Cl)n2)cc(OCCN2CCOCC2)c1]

To a stirred solution of 1-(3-(tert-butyl)-1-(p-tolyl)-1H-pyrazol-5-yl)-3-(2,3-dichloro-4-((2-chloropyrimidin-4-yl)oxy)phenyl)urea (see Example 53(i) above; 185 mg, 0.288 mmol) and 3-methoxy-5-(2-morpholinoethoxy)aniline (see Example 21(iv) above; 135 mg, 0.508 mmol) in THF (6 mL) was added p-TSA monohydrate (82 mg, 0.432 mmol). The resulting mixture was stirred at 60° C. overnight. DMF (2 mL) was added and stirring continued at 60° C. for 72 h. The reaction was cooled to rt then partitioned between EtOAc (40 mL) and sat. aq. NaHCO₃ (30 mL). The aqueous phase was back extracted with EtOAc (40 mL). The combined organic extracts were washed with water (2×50 mL), brine (50 mL), dried (MgSO₄), filtered and concentrated in vacuo to afford a light brown foam. The crude product was purified by chromatography on silica gel (40 g column, 0-5% MeOH in DCM) to afford an off-white foam, which was triturated with a mixture of diethyl ether and isohexane to afford an off-white solid. The crude product was purified by preparative HPLC (Varian, Acidic (0.1% Formic acid), Waters X-Select Prep-C18, 5 μm, 19×50 mm column, 30-60% MeCN in Water) to afford the title compound (62 mg) as a white solid.

1H NMR (DMSO-d6) 400 MHz, δ: 9.51 (s, 1H), 9.26 (s, 1H), 8.85 (s, 1H), 8.41 (d, 1H), 8.18 (d, 1H), 7.43-7.34 (m, 5H), 6.74-6.72 (br m, 2H), 6.58 (d, 1H), 6.39 (s, 1H), 6.07

(t, 1H), 3.94 (t, 2H), 3.58 (s, 3H), 3.55-3.53 (m, 4H), 2.61 (t, 2H), 2.43-2.41 (br m, 4H), 2.39 (s, 3H), 1.27 (s, 9H).

LCMS m/z 381 (M+2H)$^{2+}$ (ES+)

Example 60

1-(3-(tert-Butyl)-1-(p-tolyl)-1H-pyrazol-5-yl)-3-(4-((2-((3-methoxy-5-(2-(2-methoxyethoxy)ethoxy)phenyl)amino)pyrimidin-4-yl)oxy)naphthalen-1-yl)urea

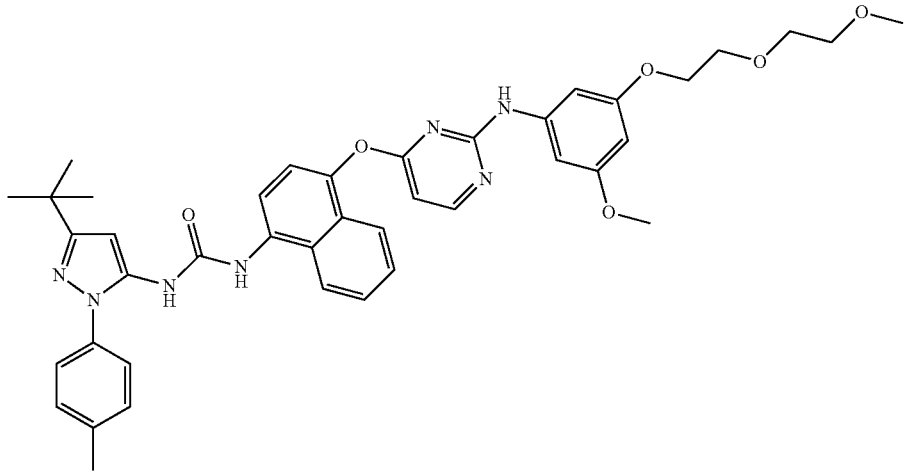 [SMILES: COCCOCCOc1cc(Nc2nccc(Oc3ccc(NC(=O)Nc4cc(C(C)(C)C)nn4-c4ccc(C)cc4)c4ccccc34)n2)cc(OC)c1]

(i) 3-Methoxy-5-(2-(2-methoxyethoxyl)ethoxy)aniline

A stirred suspension of 1-bromo-2-(2-methoxyethoxyl)ethane (145 mg, 0.791 mmol), 3-amino-5-methoxyphenol (100 mg, 0.719 mmol), potassium carbonate (300 mg, 2.171 mmol) and sodium iodide (10 mg, 0.067 mmol) in acetone (3 mL) was heated under reflux overnight. The mixture was evaporated and the residue was partitioned between water (30 mL) and ether (50 mL). The layers were separated and the organic layer was washed with brine (30 mL), dried (Na$_2$SO$_4$) and evaporated. The residue was purified on a 12 g redisep silica cartridge using 50%, then later 100% of ethyl acetate in isohexane as eluent to afford the sub-title compound (66 mg)

1H NMR (400 MHz, DMSO-d6) δ 5.75-5.74 (m, 2H), 5.68-5.67 (m, 1H), 5.04 (s, 2H), 3.94 (m, 2H), 3.67 (m, 2H), 3.62 (s, 3H), 3.60-3.40 (m, 4H), 3.25 (s, 3H). (90% purity)

LCMS m/z 242 (M+H)+ (ES+)

(ii) 1-(3-(tert-Butyl)-1-(p-tolyl)-1H-pyrazol-5-yl)-3-(4-((2-((3-methoxy-5-(2-(2-methoxyethoxyl)ethoxy)phenyl)amino)pyrimidin-4-yl)oxy)naphthalen-1-yl)urea A stirred solution of 1-(3-(tert-butyl)-1-(p-tolyl)-1H-pyrazol-5-yl)-3-(4-((2-chloropyrimidin-4-yl)oxy)naphthalen-1-yl)urea (see Example 41(iv) above; 112 mg, 0.182 mmol) and the product from step (i) above (66 mg, 0.274 mmol) in DMF (4 mL) was treated with p-TSA monohydrate (10 mg, 0.053 mmol) and stirred at 70° C. (bath) overnight. The mixture was allowed to cool and partitioned between ethyl acetate (50 mL) and saturated aq. NaHCO$_3$ solution (50 mL). The layers were separated and the organic layer was washed with brine (40 mL), dried (Na$_2$SO$_4$) and evaporated. The residue was purified on 40 g redisep silica cartridge, using 15% of acetone in toluene as eluent to give a brown glass. The glass was triturated with ether (4 mL) to give a solid which was collected by filtration, washed with ether and dried to afford the title compound (65 mg) as a beige solid.

1H NMR (400 MHz; DMSO-d6) δ 9.43 (s, 1H), 9.10 (s, 1H), 8.78 (s, 1H), 8.41 (d, 1H), 8.06 (d, 1H), 7.95 (d, 1H), 7.82 (d, 1H), 7.64-7.55 (m, 2H), 7.47-7.45 (m, 2H), 7.40-7.37 (m, 3H), 6.80-6.79 (m, 2H), 6.54 (d, 1H), 6.41 (s, 1H), 6.03 (t, 1H), 3.86-3.84 (m, 2H), 3.65-3.63 (m, 2H), 3.55-3.52 (m, 2H), 3.49 (s, 3H), 3.44-3.41 (m, 2H), 3.22 (s, 3H), 2.40 (s, 3H), 1.29 (s, 9H).

LCMS m/z 366.6 (M+2H)$^{2+}$ (ES+)

Example 61

1-(3-(tert-Butyl)-1-(6-methoxypyridin-3-yl)-1H-pyrazol-5-yl)-3-(4-((2-((3-(cyclopropylsulfonyl)-5-methoxyphenyl)amino)pyrimidin-4-yl)oxy)naphthalen-1-yl)urea

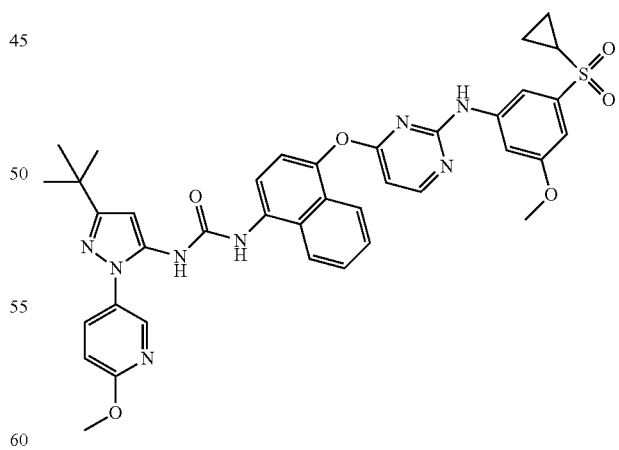

In a 20 mL vial, a mixture of 3-(cyclopropylsulfonyl)-5-methoxyaniline (see Example 18(ii) above; 128 mg, 0.551 mmol) and p-TSA monohydrate (26.2 mg, 0.138 mmol) was treated with a solution of 1-(3-(tert-butyl)-1-(6-methoxypyridin-3-yl)-1H-pyrazol-5-yl)-3-(4-((2-chloropyrimidin-4-yl)oxy)naphthalen-1-yl)urea (see Example 1(ii) above; 150 mg, 0.276 mmol) in DMF (2 mL). The resultant brown solution was heated at 70° C. for 4 h and 47 min and at 50° C. for ~17 h. Poured over saturated NaHCO₃ (aq.) (20 mL) and extracted with EtOAc (2×20 mL). Combined organics were washed with sat. brine solution (20 mL), separated, dried and evaporated to a red solid. The crude product was purified by chromatography on silica gel (80 g column, MeOH in DCM 0-5%) to afford the title compound (50 mg) as an off-white solid.

1H NMR (400 MHz, DMSO-d6) δ 9.84 (s, 1H), 9.08 (s, 1H), 8.82 (s, 1H), 8.46 (d, 1H), 8.40 (d, 1H), 8.05 (d, 1H), 7.96-7.88 (m, 2H), 7.81 (d, 1H), 7.73 (s, 1H), 7.60 (m, 2H), 7.50 (s, 1H), 7.40 (d, 1H), 7.03 (d, 1H), 6.86 (m, 1H), 6.63 (d, 1H), 6.43 (s, 1H), 3.94 (s, 3H), 3.62 (s, 3H), 2.76-2.69 (m, 1H), 1.29 (s, 9H), 1.08-0.96 (m, 4H).

LCMS m/z 735 (M+H)+ (ES+)

Example 62

1-(3-(tert-Butyl)-1-(P-tolyl)-1H-pyrazol-5-yl)-3-(4-((2-((3-(2-(2-(2-hydroxyethoxy)ethoxy) ethoxy)-5-methoxyphenyl)amino)pyrimidin-4-yl)oxy)naphthalen-1-yl)urea

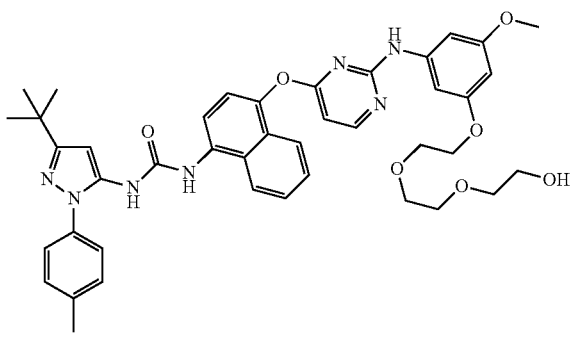 [SMILES: COc1cc(Nc2nccc(Oc3ccc(NC(=O)Nc4cc(C(C)(C)C)nn4-c4ccc(C)cc4)c4ccccc34)n2)cc(OCCOCCOCCO)c1]

(i) 2-(2-(2-(3-Amino-5-methoxyphenoxy)ethoxy)ethoxy)ethanol

3-Amino-5-methoxyphenol (510 mg, 3.67 mmol), and Cs₂CO₃ (1433 mg, 4.40 mmol) were stirred vigorously in DMF (12 mL) for 30 minutes before addition of 2-(2-(2-chloroethoxyl)ethoxy)ethanol (586 μL, 4.03 mmol) and KI (60.8 mg, 0.367 mmol). Placed in a preheated block at 65° C. and stirring continued for 4 h. The mixture was cooled, filtered then partitioned between EtOAc (50 mL) and water (100 mL). Organic layer separated and washed with 20% w/w NaCl solution (100 mL), separated, dried (MgSO₄), filtered and solvent evaporated to give a dark brown oil. The crude product was purified by chromatography on the Companion (40 g column, 50% EtOAc:isohexane to 100% then 2.5% MeOH:EtOAc) to afford the sub-title compound (310 mg) as a clear brown oil.

1H NMR (400 MHz, DMSO-d6) δ 5.76 (m, 2H), 5.69 (t, 1H), 5.06 (s, 2H), 4.58 (s, 1H), 3.95 (m, 2H), 3.69 (m, 2H), 3.63 (s, 3H), 3.56 (m, 4H), 3.49 (s, 2H), 3.43 (m, 2H).

LCMS m/z 272 (M+H)+ (ES+)

(ii) 1-(3-(tert-Butyl)-1-(p-tolyl)-1H-pyrazol-5-yl)-3-(4-((2-((3-(2-(2-(2-Hydroxyethoxy)-ethoxy)ethoxy)-5-methoxyphenyl)amino)pyrimidin-4-yl)oxy)naphthalen-1-yl)urea 1-(3-(tert-Butyl)-1-(p-tolyl)-1H-pyrazol-5-yl)-3-(4-((2-chloropyrimidin-4-yl)oxy)naphthalen-1-yl)urea (see Example 41(iv) above; 150 mg, 0.285 mmol) was dissolved in DMF (2 mL) then the product from step (i) above (140 mg, 0.516 mmol) and p-TSA monohydrate (30 mg, 0.158 mmol) added and the mixture stirred at 70° C. (block temperature) for 7 h. The mixture was poured into sat. NaHCO₃ solution (20 mL) and the product extracted with EtOAc (2×20 mL), washed with 20% w/w NaCl solution (20 mL), separated, dried (MgSO₄), filtered and evaporated. The crude product was purified by chromatography on silica gel (40 g column, 2% MeOH:DCM to 8%) to afford a pale yellow foam which was triturated with Et₂O to give a tan solid. Recrystallisation from MeCN (4 mL) and washing with MeCN (1 mL) afforded the title compound (54 mg).

1H NMR (400 MHz, DMSO-d6) δ 9.43 (s, 1H), 9.11 (s, 1H), 8.79 (s, 1H), 8.41 (d, 1H), 8.07 (d, 1H), 7.96 (d, 1H), 7.83 (d, 1H), 7.70-7.52 (m, 2H), 7.52-7.43 (m, 2H), 7.43-7.31 (m, 3H), 6.96-6.69 (m, 2H), 6.54 (d, 1H), 6.42 (s, 1H), 6.04 (t, 1H), 4.59 (t, 1H), 3.87 (t, 2H), 3.72-3.61 (m, 2H), 3.61-3.45 (m, 9H), 3.45-3.38 (m, 2H), 2.41 (s, 3H), 1.30 (s, 9H).

LCMS m/z 762 (M+H)+ (ES+)

Example 63

1-(3-(tert-Butyl)-1-(4-(dimethylamino)phenyl)-1H-pyrazol-5-yl)-3-(4-((2-((3-methoxy-5-(2-(2-(2-methoxyethoxy)ethoxy)ethoxy)phenyl)amino)pyrimidin-4-yl)oxy)naphthalen-1-yl)urea

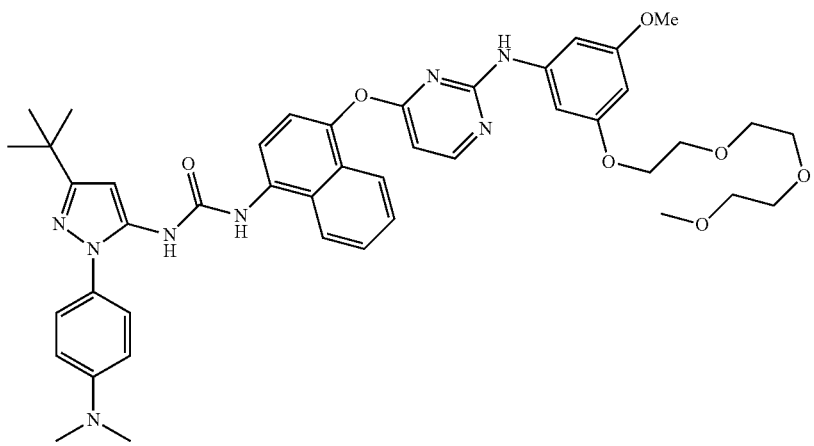 [SMILES: COCCOCCOCCOc1cc(Nc2nccc(Oc3ccc(NC(=O)Nc4cc(C(C)(C)C)nn4-c4ccc(N(C)C)cc4)c4ccccc34)n2)cc(OC)c1]

(i) Ethyl 3-(tert-butyl)-1-(4-(dimethylamino)phenyl)-1H-pyrazole-5-carboxylate Pyridine (350 µL, 4.33 mmol) followed by activated 4A molecular sieves (0.5 g) were added to a stirred mixture of (4-(dimethylamino)phenyl)boronic acid (575 mg, 3.48 mmol), ethyl 3-(tert-butyl)-1H-pyrazole-5-carboxylate (425 mg, 2.166 mmol) and copper (II) acetate (590 mg, 3.25 mmol) in DCM (15 mL) at rt. open to the air. The mixture was stirred for 4 h. A mixture of ether/isohexane (3:1, 300 mL) was added and the solid was filtered off. The filtrate was evaporated under reduced pressure and the residue was purified by chromatography on the Companion (80 g column, 0-60% ether/isohexane) to afford the sub-title compound (464 mg) as a colourless oil.

LCMS m/z 316 (M+H)$^+$ (ES$^+$)

(ii) 3-(tert-Butyl)-1-(4-(dimethylamino)phenyl)-1H-pyrazole-5-carboxylic acid 1 M sodium hydroxide solution (1.5 mL, 1.500 mmol) was added to a stirred solution of the product from step (i) above (0.46 g, 1.458 mmol) in tetrahydrofuran (3 mL) at rt. The mixture was stirred for 3 h at rt then methanol (1 mL) was added and the mixture was stirred for a further 1 h. The mixture was then heated to 40° C. for 1 h, diluted with water (10 mL) and washed with diethyl ether (2×10 mL). The aqueous phase was treated with 1 M HCl (1.5 mL) and extracted with ethyl acetate (3×10 mL). The combined organic phases were washed with saturated brine (10 mL), dried (MgSO$_4$) and concentrated to yield the sub-title compound (395 mg) as an off-white solid.

1H NMR (400 MHz; CDCl$_3$) δ: 7.28-7.22 (m, 2H), 6.91 (s, 1H), 6.74-6.67 (m, 2H), 2.98 (s, 6H), 1.35 (s, 9H).

LCMS m/z 288 (M+H)$^+$ (ES$^+$); 286 (M–H)$^-$ (ES$^-$)

(iii) 1-(3-(tert-Butyl)-1-(4-(dimethylamino)phenyl)-1H-pyrazol-5-yl)-3-(4-((2-((3-methoxy-5-(2-(2-(2-methoxyethoxy)ethoxy)ethoxy)phenyl)amino)pyrimidin-4-yl)oxy)naphthalen-1-yl)urea DPPA (107 µL, 0.496 mmol) was added to a stirred solution of the product from step (ii) above (95 mg, 0.331 mmol) and Et$_3$N (92 µL, 0.661 mmol) in DMF (3 mL) at 0° C. The mixture was allowed to warm to rt and stirred for 45 min. 4-((4-Aminonaphthalen-1-yl)oxy)-N-(3-methoxy-5-(2-(2-(2-methoxyethoxy)ethoxy)ethoxy)phenyl)pyrimidin-2-amine (see Example 37(ii) above; 181 mg, 0.347 mmol) was added and the mixture was heated to 100° C. for 2 h. The mixture was diluted with water (10 mL) and extracted with ethyl acetate (3×10 mL). The combined organic phases were washed with saturated brine (10 mL), dried (MgSO$_4$) and concentrated under reduced pressure. The crude product was purified by chromatography on the Companion (40 g column, EtOAc) to afford a brown gum. The gum was triturated in tert-butyl methyl ether to yield the title compound (64 mg) as a pale tan solid.

1H NMR (DMSO-d6) 400 MHz, δ: 9.42 (s, 1H), 9.13 (s, 1H), 8.67 (s, 1H), 8.41 (d, 1H), 8.08 (d, 1H), 7.98 (d, 1H), 7.83 (d, 1H), 7.66-7.60 (m, 1H), 7.60-7.53 (m, 1H), 7.39 (d, 1H), 7.37-7.30 (m, 2H), 6.93-6.84 (m, 2H), 6.84-6.75 (m, 2H), 6.54 (d, 1H), 6.38 (s, 1H), 6.07-6.00 (m, 1H), 3.91-3.81 (m, 2H), 3.70-3.61 (m, 2H), 3.59-3.45 (m, 6H), 3.50 (s, 3H), 3.45-3.37 (m, 2H), 3.22 (s, 3H), 2.99 (s, 6H), 1.28 (s, 9H).

LCMS m/z 805 (M+H)+ (ES+)

Example 64

1-(3-(tert-Butyl)-1-(p-tolyl)-1H-pyrazol-5-yl)-3-(4-((2-((3-chloro-5-(2-(2-(2-methoxyethoxy)-ethoxy)ethoxy)phenyl)amino)pyrimidin-4-yl)oxy)naphthalen-1-yl)urea

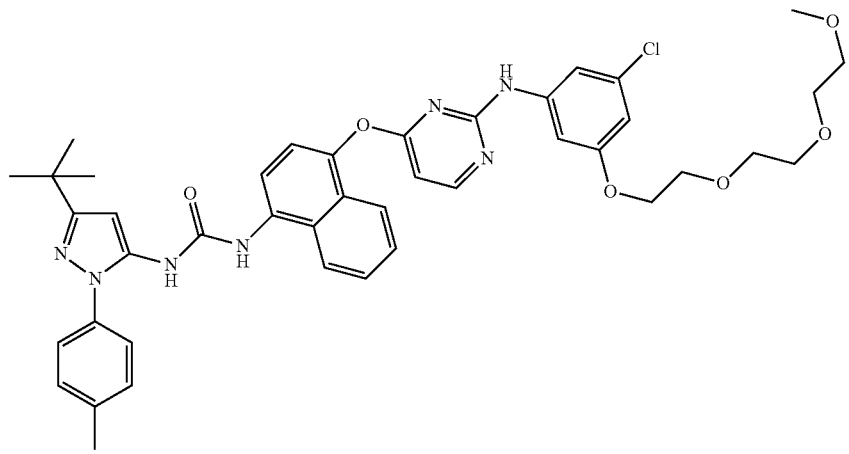 [SMILES: COCCOCCOCCOc1cc(Cl)cc(Nc2nccc(Oc3ccc(NC(=O)Nc4cc(C(C)(C)C)nn4-c4ccc(C)cc4)c4ccccc34)n2)c1]

(i) 1-Chloro-3-(2-(2-(2-methoxyethoxy)ethoxy)ethoxy)-5-nitrobenzene

A stirred solution of 3-chloro-5-nitrophenol (1.0 g, 5.30 mmol), 1-bromo-2-(2-(2-methoxyethoxy)ethoxy)ethane (1.20 mL, 6.92 mmol) and K$_2$CO$_3$ (1.100 g, 7.96 mmol) in MeCN (15 mL) was heated at reflux for 6 h. The reaction was cooled to rt and filtered through celite, washing with MeCN. The filtrate was concentrated in vacuo giving a yellow oil. The crude product was purified by chromatography on the Companion (80 g column, 10-60% EtOAc in hexane) to afford the sub-title compound (1.74 g) as a yellow oil.

1H NMR (DMSO-d6) 400 MHz, δ: 7.86 (t, 1H), 7.73 (t, 1H), 7.59 (t, 1H), 4.27-4.30 (m, 2H), 3.75-3.78 (m, 2H), 3.58-3.60 (m, 2H), 3.50-3.54 (m, 4H), 3.41-3.43 (m, 2H), 3.23 (s, 3H)

LCMS m/z 320 (M+H)+ (ES+)

(ii) 3-Chloro-5-(2-(2-(2-methoxyethoxyl)ethoxy) ethoxy)aniline

To a partially dissolved suspension of ammonium chloride (0.090 g, 1.683 mmol) in IPA (90 ml) was added the product from step (i) above (1.00 g, 3.13 mmol) and a mixture of iron powder (1.75 g, 31.3 mmol) in water (8 mL). The reaction was heated at reflux for 2 h. The reaction was cooled to rt and filtered through Celite. The filtrate was concentrated in vacuo giving a cloudy, pale yellow oil. The crude product was purified by chromatography on the Companion (40 g column, 0-5% MeOH in DCM) to afford the sub-title compound (846 mg) as a yellow oil.

1H NMR (DMSO-d6) 400 MHz, δ: 6.19 (t, 1H), 6.11 (t, 1H), 6.06 (t, 1H), 5.40 (bs, 2H), 3.97-3.99 (m, 2H), 3.68-3.70 (m, 2H), 3.51-3.58 (m, 6H), 3.43 (dd, 2H), 3.24 (s, 3H).
LCMS m/z 290 (M+H)+ (ES+)

(iii) 1-(3-(tert-Butyl)-1-(p-tolyl)-1H-pyrazol-5-yl)-3-(4-((2-((3-chloro-5-(2-(2-(2-methoxyethoxyl)ethoxy) ethoxy)phenyl)amino)pyrimidin-4-yl)oxy)naphthalen-1-yl)urea A suspension of 1-(3-(tert-butyl)-1-(p-tolyl)-1H-pyrazol-5-yl)-3-(4-((2-chloropyrimidin-4-yl)oxy)naphthalen-1-yl)urea (see Example 41(iv) above; 180 mg, 0.307 mmol), the product from step (ii) above (180 mg, 0.621 mmol) and p-TSA monohydrate (11.0 mg, 0.058 mmol) in THF/DMF (6 mL, 1:2) was heated at 60° C. for 40 h. The reaction was cooled to rt and diluted with EtOAc. The organic phase was washed with sat. aq. NaHCO3 solution, water and brine then dried (MgSO4), filtered and concentrated in vacuo onto silica gel. The crude product was purified by chromatography on the Companion (40 g column, 1-5% MeOH in DCM) giving the product as an off white solid. The solid was triturated with MeOH and the resulting solid collected by filtration washing with further MeOH to afford the title compound (73 mg) as a white solid.

1H NMR (DMSO-d6) 400 MHz, δ: 9.67 (s, 1H), 9.09 (s, 1H), 8.77 (s, 1H), 8.46 (d, 1H), 8.08 (d, 1H), 7.98 (d, 1H), 7.81 (d, 1H), 7.54-7.65 (m, 2H), 7.46 (d, 2H), 7.40 (t, 3H), 7.18 (bs, 1H), 7.06 (bs, 1H), 6.64 (d, 1H), 6.49 (s, 1H), 6.42 (s, 1H), 3.94 (t, 2H), 3.66 (t, 2H), 3.48-3.55 (m, 6H), 3.39-3.42 (m, 2H), 3.22 (s, 3H), 2.41 (s, 3H), 1.30 (s, 9H).
LCMS m/z 391 (M+2H)$^{2+}$ (ES+)

Example 65

1-(3-(tert-Butyl)-1-(p-tolyl)-1H-pyrazol-5-yl)-3-(2,3-dichloro-4-((2-((3-methoxy-5-(3-morpholinopropoxyl)phenyl)amino)pyrimidin-4-yl)oxy)phenyl) urea

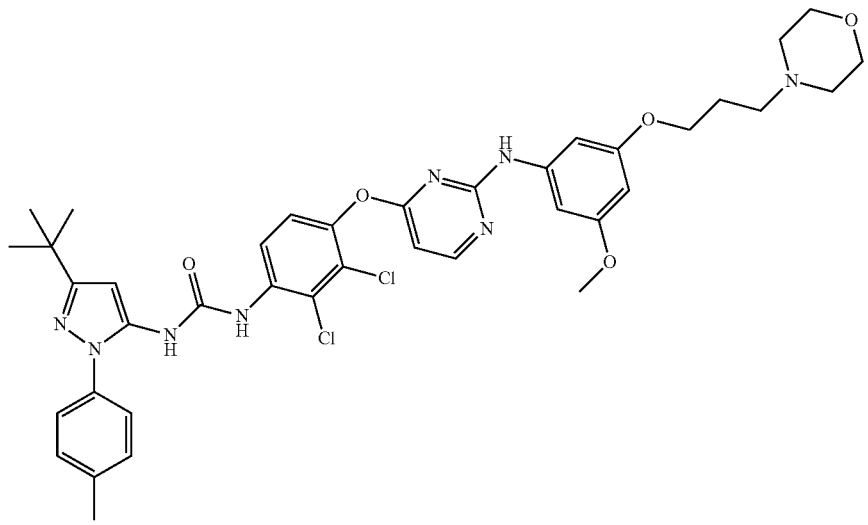 [SMILES: COc1cc(Nc2nccc(Oc3ccc(NC(=O)Nc4cc(C(C)(C)C)nn4-c4ccc(C)cc4)c(Cl)c3Cl)n2)cc(OCCCN2CCOCC2)c1]

In a 20 mL vial, a mixture of 3-methoxy-5-(3-morpholinopropoxy)aniline (see Example 49(i) above; 0.1238 g, 0.451 mmol) and p-TSA monohydrate (0.089 g, 0.470 mmol) was treated with a solution of 1-(3-(tert-butyl)-1-(p-tolyl)-1H-pyrazol-5-yl)-3-(2,3-dichloro-4-((2-chloropyrimidin-4-yl)oxy)phenyl)urea (see Example 53(i) above; 0.171 g, 0.313 mmol) in DMF (2 mL). The resultant brown solution was heated at 70° C. for 20 h. Poured over saturated NaHCO3 (aq.) (20 mL) and extracted with EtOAc (2×20 mL). Combined organics washed with sat. brine solution (20 mL), separated, dried and evaporated to a brown glass (0.227 g). The crude product was purified by chromatography on silica gel (40 g column, MeOH:DCM 0-4%) to afford the title compound (0.1 g) as a clear white solid.

1H NMR (400 MHz, DMSO-d6) δ 9.50 (s, 1H), 9.22 (s, 1H), 8.81 (s, 1H), 8.40 (d, 1H), 8.18 (d, 1H), 7.44-7.33 (m, 5H), 6.72 (d, 2H), 6.57 (d, 1H), 6.39 (s, 1H), 6.03 (t, 1H), 3.84 (t, 2H), 3.60-3.50 (m, 7H), 2.42-2.28 (m, 9H), 1.81 (pent, 2H), 1.28 (s, 9H).
LCMS m/z 775/777 (M+H)+ (ES+); 773/775 (M-H)- (ES-)

Example 66

1-(3-(tert-Butyl)-1-(p-tolyl)-1H-pyrazol-5-yl)-3-(4-((2-((3-(dimethylamino)-5-(2-(2-(2-methoxyethoxy)ethoxy)ethoxy)phenyl)amino)pyrimidin-4-yl)oxy)naphthalen-1-yl)urea

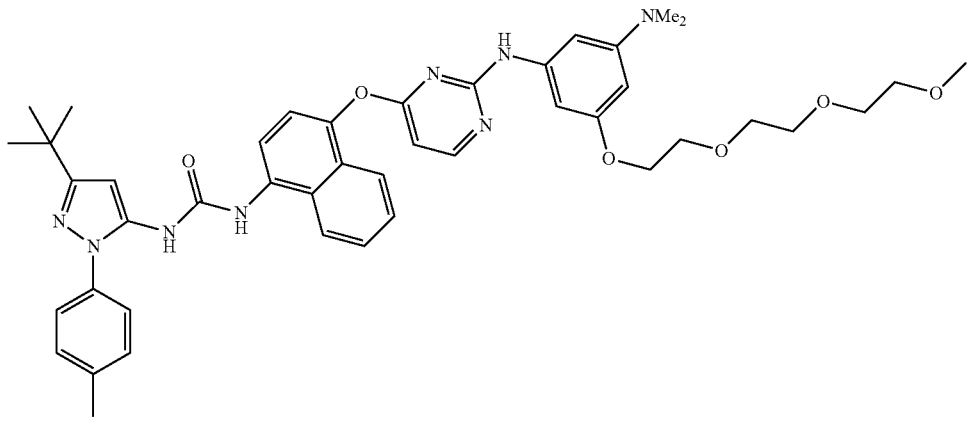 [SMILES: COCCOCCOCCOc1cc(Nc2nccc(Oc3ccc(NC(=O)Nc4cc(C(C)(C)C)nn4-c4ccc(C)cc4)c4ccccc34)n2)cc(N(C)C)c1]

(i) 3-(2-(2-(2-Methoxyethoxyl)ethoxy)ethoxy)-N,N-dimethyl-5-nitroaniline

A stirred suspension of 3-(dimethylamino)-5-nitrophenol (255 mg, 1.400 mmol), 1-bromo-2-(2-(2-methoxyethoxyl)ethoxy)ethane (318 mg, 1.400 mmol) and $K_2CO_3$ (387 mg, 2.80 mmol) in acetone (5 mL) was heated under reflux overnight. The mixture was treated with more 1-bromo-2-(2-(2-methoxyethoxyl)ethoxy)ethane (50 mg, 0.220 mmol) and heated under reflux overnight. The mixture was evaporated and the residue was partitioned between ethyl acetate (50 mL) and water (50 mL) and the layers were separated. The organic phase was washed with brine (50 mL), was dried ($Na_2SO_4$) and evaporated. The residue was purified on a 40 g redisep silica cartridge, using 50% then 75% of ethyl acetate in isohexane as eluent to afford the sub-title compound (471 mg) as a red/orange oil.

1H NMR (400 MHz; DMSO-d6) δ 7.07 (t, 1H), 7.01 (t, 1H), 6.60 (t, 1H), 4.19-4.17 (m, 2H), 3.76-3.73 (m, 2H), 3.60-3.50 (m, 6H), 3.44-3.41 (m, 2H), 3.23 (s, 3H), 2.98 (s, 6H).

LCMS m/z 329 (M+H)+ (ES+)

(ii) 5-(2-(2-(2-M ethoxyethoxy)ethoxy)ethoxy)-N1,N1-dimethyl benzene-1,3-diamine A stirred suspension of the product from step (i) above (471 mg, 1.434 mmol), iron powder (800 mg, 14.33 mmol) and ammonium chloride (40 mg, 0.748 mmol) in propan-2-ol (45 mL) and water (4 mL) was heated under reflux for 1 h and allowed to cool. The mixture was filtered through celite and the pad was washed with propan-2-ol (2×20 mL). The combined filtrates were evaporated and the residue was purified on a 40 g redisep silica cartridge, using a gradient of 0 to 5% of MeOH in DCM as eluent to afford the sub-title compound (349 mg) as an orange oil.

1H NMR (400 MHz; DMSO-d6) δ 5.62 (t, 1H), 5.59 (t, 1H), 5.55 (t, 1H), 5.23 (br s, 2H), 3.95-3.93 (m, 2H), 3.69-3.66 (m, 2H), 3.57-3.51 (m, 6H), 3.44-3.42 (m, 2H), 3.24 (s, 3H), 2.79 (s, 6H). (90% purity)

LCMS m/z 299 (M+H)+ (ES+)

(iii) 1-(3-(tert-Butyl)-1-(p-tolyl)-1H-pyrazol-5-yl)-3-(4-((2-((3-(dimethylamino)-5-(2-(2-(2-methoxyethoxyl)ethoxy)ethoxy)phenyl)amino)pyrimidin-4-yl)oxy)naphthalen-1-yl)urea A stirred solution of 1-(3-(tert-butyl)-1-(p-tolyl)-1H-pyrazol-5-yl)-3-(4-((2-chloropyrimidin-4-yl)oxy)naphthalen-1-yl)urea (see Example 41(iv) above; 150 mg, 0.285 mmol) and the product from step (ii) above (170 mg, 0.569 mmol) in DMF (4 mL) was treated with p-TSA monohydrate (10 mg, 0.053 mmol) and stirred at 50° C. for 4 h, treated with more p-TSA monohydrate (54 mg, 0.284 mmol) and stirred at 50° C. overnight. The mixture was allowed to stand overnight and partitioned between ethyl acetate (50 mL) and saturated aqueous $Na_2CO_3$ solution (50 mL). The layers were separated and the organic layer was washed with brine (40 mL), was dried ($Na_2SO_4$) and evaporated. The residue was purified on 40 g redisep silica cartridge, using 20% of acetone in toluene as eluent to give a gum. The gum was purified on a 40 g redisep silica cartridge using 2% of MeOH in DCM as eluent to give a cream foam. The foam was further purified by reversed phase preparative HPLC on a Waters XBridge 19×50 mm C18 5µ OBD column using a gradient of acetonitrile in 10 mMol aqueous ammonium bicarbonate solution to afford the title compound (115 mg) as a cream foam.

1H NMR (400 MHz; DMSO-d6) δ 9.20 (s, 1H), 9.09 (s, 1H), 8.75 (s, 1H), 8.38 (d, 1H), 8.06 (d, 1H), 7.93 (d, 1H), 7.83 (d, 1H), 7.63-7.55 (m, 2H), 7.47-7.45 (m, 2H), 7.39-7.37 (m, 3H), 6.67 (s, 1H), 6.57 (s, 1H), 6.48 (d, 1H), 6.41 (s, 1H), 5.81 (t, 1H), 3.82-3.80 (m, 2H), 3.64-3.62 (m, 2H), 3.55-3.48 (m, 6H), 3.42-3.39 (m, 2H), 3.21 (s, 3H), 2.68 (s, 6H), 2.40 (s, 3H), 1.29 (s, 9H).

LCMS m/z 789 (M+H)+ (ES+); 787 (M-H)- (ES-)

Example 67

1-(3-(tert-Butyl)-1-(p-tolyl)-1H-pyrazol-5-yl)-3-(4-((2-((3-methoxy-5-((2-(2-(2-methoxy ethoxy)ethoxy)ethyl)(methyl)amino)phenyl)amino)pyrimidin-4-yl)oxy)naphthalen-1-yl)urea

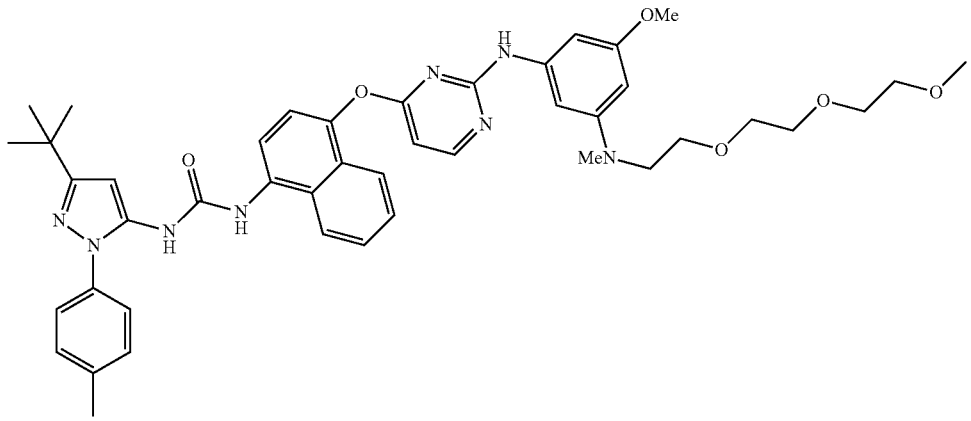 [SMILES: COCCOCCOCCN(C)c1cc(Nc2nccc(Oc3ccc(NC(=O)Nc4cc(C(C)(C)C)nn4-c4ccc(C)cc4)c4ccccc34)n2)cc(OC)c1]

(i) 3-Methoxy-N-methyl-5-nitroaniline

A stirred solution of 3-methoxy-5-nitroaniline (1 g, 5.95 mmol) in DMF (5 mL) was treated with sodium hydride, 60% dispersion in oil (0.238 g, 5.95 mmol) and stirred for 15 mins. The solution was treated with methyl iodide (0.37 mL, 5.95 mmol) and stirred overnight. The mixture was treated with more sodium hydride, 60% dispersion in oil (60 mg, 1.500 mmol), stirred for 15 mins and treated with more methyl iodide (0.094 mL, 1.5 mmol) and stirred for 4 h. The mixture was treated with more sodium hydride, 60% dispersion in oil (60 mg, 1.500 mmol), stirred for 15 mins and treated with more methyl iodide (0.094 mL, 1.5 mmol) and stirred overnight. The mixture was quenched with water (50 mL) and extracted with ether (50 mL). The ether extract was washed with water (5×50 mL) followed by brine (50 mL), was dried ($Na_2SO_4$) and evaporated. The residue was purified on a 80 g redisep silica cartridge, using a gradient of 0 to 20% of ethyl acetate in isohexane as eluent to afford the sub-title compound (223 mg) as a solid.

1H NMR (400 MHz; DMSO-d6) δ 6.97 (t, 1H), 6.88 (t, 1H), 6.44 (t, 1H), 6.44-6.41 (m, 1H), 3.79 (s, 3H), 2.72 (d, 3H).

LCMS, m/z 183 (M+H)+ (ES+)

(ii) 3-Methoxy-N-(2-(2-(2-methoxyethoxy)ethoxy)ethyl)-N-methyl-5-nitroaniline

A stirred suspension of the product from step (i) above (223 mg, 1.224 mmol), 1-bromo-2-(2-(2-methoxyethoxy)ethoxy)ethane (278 mg, 1.224 mmol) and $K_2CO_3$ (338 mg, 2.448 mmol) in acetone (10 mL) was heated under reflux for 3 h. The mixture was evaporated, the residue was partitioned between ether (50 mL) and water (50 mL) and the layers were separated. The organic layer was washed with brine (50 mL), was dried ($Na_2SO_4$) and evaporated. The residue was taken up in DMF (5 mL), stirred and treated with sodium hydride, 60% dispersion in oil (49.0 mg, 1.224 mmol) and stirred for 2 days. The mixture was treated with more sodium hydride, 60% dispersion in oil (49.0 mg, 1.224 mmol), stirred for 2 h, treated with more 1-bromo-2-(2-(2-methoxyethoxy)ethoxy)-ethane (278 mg, 1.224 mmol) and stirred for 2 h. The mixture was treated with more sodium hydride, 60% dispersion in oil (49.0 mg, 1.224 mmol) and stirred overnight. The mixture was stirred at 40° C. for 4 h, allowed to cool, quenched with iced-water (40 mL) and extracted with ether (40 mL). The extract was washed with water (6×40 mL), was dried ($Na_2SO_4$) and evaporated to give a black tar. The aqueous layer was extracted with DCM (100 mL) and the dried ($Na_2SO_4$) extract was evaporated. The residue was taken up in toluene (2×50 mL) and evaporated. The residue was combined with the black tar and purified on 40 g redisep silica cartridge, using 25%, then later 50% of ethyl acetate in isohexane as eluent to afford the sub-title compound (177 mg) as a dark red oil.

1H NMR (400 MHz; DMSO-d6) δ 7.11 (t, 1H), 6.97 (t, 1H), 6.60 (t, 1H), 3.82 (s, 3H), 3.58-3.56 (m, 4H), 3.50-3.45 (m, 6H), 3.39-3.36 (m, 2H), 3.21 (s, 3H), 2.98 (s, 3H).

LCMS m/z 329 (M+H)+ (ES+)

(iii) 5-Methoxy-N1-(2-(2-(2-methoxyethoxy)ethoxy)ethyl)-N1-methyl benzene-1,3-diamine A stirred suspension of the product from step (ii) above (177 mg, 0.539 mmol), iron powder (300 mg, 5.37 mmol) and ammonium chloride (15 mg, 0.280 mmol) in propan-2-ol (20 mL) and water (2 mL) was heated under reflux for 1 h and allowed to cool. The mixture was filtered through celite and the pad was washed with propan-2-ol (3×10 mL). The combined filtrates were evaporated and the residue was purified on a 12 g redisep silica cartridge, using a gradient of 0 to 5% of MeOH in DCM as eluent to afford the sub-title compound (138 mg) as a brown oil.

1H NMR (400 MHz; DMSO-d6) δ 5.56 (t, 1H), 5.52 (t, 1H), 5.47 (t, 1H), 4.79 (br s, 2H), 3.60 (s, 3H), 3.52-3.49 (m, 8H), 3.43-3.40 (m, 2H), 3.37-3.34 (m, 2H), 3.23 (s, 3H), 2.81 (s, 3H). LCMS m/z 299 (M+H)+ (ES+)

(iv) 1-(3-(tert-Butyl)-1-(p-tolyl)-1H-pyrazol-5-yl)-3-(4-((2-((3-methoxy-54(2-(2-(2-methoxy ethoxy)ethoxy)ethyl)(methyl)amino)phenyl)amino)pyrimidin-4-yl)oxy)naphthalen-1-yl)urea A stirred solution of 1-(3-(tert-butyl)-1-(p-tolyl)-1H-pyrazol-5-yl)-3-(4-((2-chloropyrimidin-4-yl)oxy)naphthalen-1-yl)urea (see Example 41(iv) above; 125 mg, 0.215 mmol) and the product from step (iii) above (134 mg, 0.429 mmol) in DMF (4 mL) was treated with p-TSA monohydrate (10 mg, 0.053 mmol) and stirred at 50° C. for 4 h. The mixture was treated with more p-TSA monohydrate (40 mg, 0.210 mmol) and stirred at 50° C. overnight. The mixture was allowed to stand overnight and partitioned between ethyl acetate (50 mL) and saturated aqueous $Na_2CO_3$ solution (50 mL). The layers were separated and the organic layer was washed with brine (40 mL), was dried ($Na_2SO_4$) and evaporated. The residue was purified on 40 g redisep silica cartridge, using 40%, then later 50% of ethyl acetate in toluene as eluent to give a yellow foam. The foam was triturated with ether and evaporated to give a red/brown foam. The foam was further purified by reversed phase preparative HPLC on a Waters XBridge 19×50 mm C18 5μ OBD column using a gradient of acetonitrile in 10 mMol aqueous ammonium bicarbonate solution to the title compound (85 mg) as a charcoal grey solid.

1H NMR (400 MHz; DMSO-d6) δ 9.19 (s, 1H), 9.09 (s, 1H), 8.76 (s, 1H), 8.37 (d, 1H), 8.06 (d, 1H), 7.93 (d, 1H), 7.83 (d, 1H), 7.64-7.55 (m, 2H), 7.47-7.45 (m, 2H), 7.39-7.35 (m, 3H), 6.60 (s, 1H), 6.52 (s, 1H), 6.49 (d, 1H), 6.41 (s, 1H), 5.76 (t, 1H), 3.47-3.36 (m, 12H), 3.20 (s, 3H), 2.73 (s, 3H), 2.40 (s, 3H), 1.29 (s, 9H).

LCMS m/z 789 (M+H)+ (ES+); 787 (M–H)– (ES–)

Example 68

1-(3-(tert-Butyl)-1-(p-tolyl)-1H-pyrazol-5-yl)-3-(2,3-dichloro-4-((2-((3-(cyclopropylsulfonyl)-5-methoxyphenyl)amino)pyrimidin-4-yl)oxy)phenyl)urea

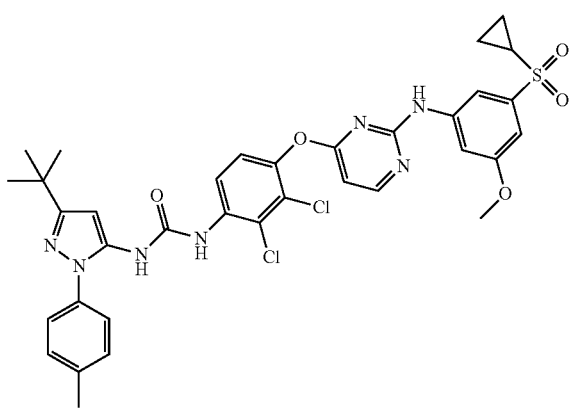 [SMILES: COc1cc(Nc2nccc(Oc3ccc(NC(=O)Nc4cc(C(C)(C)C)nn4-c4ccc(C)cc4)c(Cl)c3Cl)n2)cc(S(=O)(=O)C2CC2)c1]

In a 20 mL vial, a mixture of 3-(cyclopropylsulfonyl)-5-methoxyaniline (see Example 18(ii) above; 127 mg, 0.550 mmol) and p-TSA monohydrate (26.1 mg, 0.137 mmol) was treated with a solution of 1-(3-(tert-butyl)-1-(p-tolyl)-1H-pyrazol-5-yl)-3-(2,3-dichloro-4-((2-chloropyrimidin-4-yl)oxy)phenyl)urea (see Example 53(i) above; 150 mg, 0.275 mmol) in DMF (2 mL). The resultant yellow solution was heated at 70° C. for 4 h and 47 min and at 50° C. for ~17 h. Poured over saturated $NaHCO_3$ (aq.) (20 mL) and extracted with EtOAc (2×20 mL). Combined organics washed with sat. brine solution (20 mL), separated, dried and evaporated to a light-yellow glass (0.266 g, crude). The crude product was purified by preparative HPLC (Varian, Acidic (0.1% Formic acid), Waters X-Select Prep-C18, 5 μm, 19×50 mm column, 40-80% MeCN in Water) to afford the title compound (30 mg) as a clear white crystalline solid.

1H NMR (400 MHz, DMSO-d6) δ 9.95 (s, 1H), 9.24 (s, 1H), 8.82 (s, 1H), 8.47 (d, 1H), 8.18 (d, 1H), 7.64 (s, 1H), 7.47 (s, 1H), 7.44-7.38 (m, 3H), 7.35 (d, 2H), 6.91-6.86 (m, 1H), 6.67 (d, 1H), 6.38 (s, 1H), 3.70 (s, 3H), 2.78-2.70 (m, 1H), 2.39 (s, 3H), 1.28 (s, 9H), 1.08-0.99 (m, 4H).

LCMS m/z 737 (M+H)+ (ES+)

Example 69

1-(3-(tert-Butyl)-1-(p-tolyl)-1H-pyrazol-5-yl)-3-(4-((2-((2-methoxy-6-(2-(2-(2-methoxyethoxy)ethoxy)ethoxy)pyridin-4-yl)amino)pyrimidin-4-yl)oxy)naphthalen-1-yl)urea

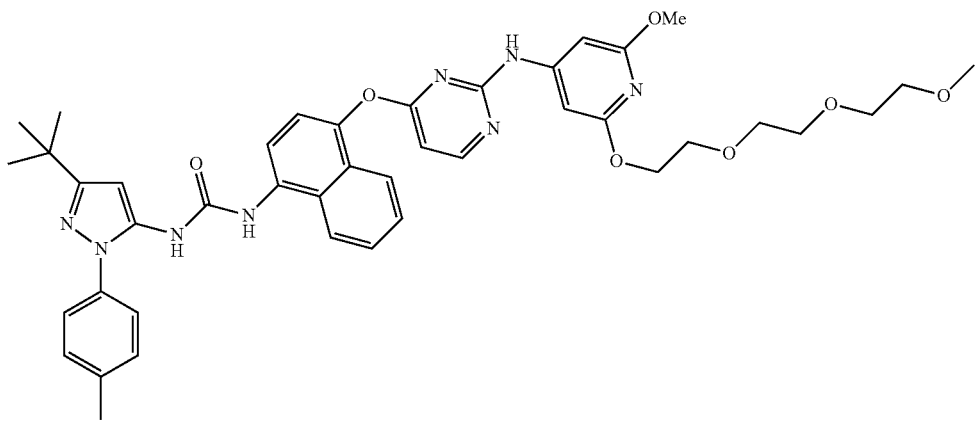 [SMILES: COCCOCCOCCOc1cc(Nc2nccc(Oc3ccc(NC(=O)Nc4cc(C(C)(C)C)nn4-c4ccc(C)cc4)c4ccccc34)n2)cc(OC)n1]

(i) 2-Methoxy-6-(2-(2-(2-methoxyethoxy)ethoxy)ethoxy)pyridin-4-amine

NaH (675 mg, 16.89 mmol), 60% Wt in oil, was added portionwise to a stirred solution of 2-(2-(2-methoxyethoxyl)ethoxy)ethanol (2.7 ml, 16.87 mmol) in dioxane (30 mL) at 0° C.-5° C. under $N_2$. The mixture was stirred for 30 min then a solution of 2-fluoro-6-methoxypyridin-4-amine (800 mg, 5.63 mmol) in dioxane (10 mL) was added and the mixture heated at 90° C. for 3 h. The mixture was cooled and partitioned between EtOAc (100 mL) and water (100 mL). The organic layer was washed with brine (100 mL), dried ($MgSO_4$), filtered and evaporated under reduced pressure. The crude product was purified by chromatography on silica gel (40 g column, 0-100% EtOAc/isohexane) to afford the sub-title compound (1.162 g) as an oil.

1H NMR (400 MHz; $CDCl_3$) δ 5.64 (d, 1H), 5.59 (d, 1H), 4.41-4.39 (m, 2H), 4.02 (s, 2H), 3.82 (s, 3H), 3.82-3.80 (m, 2H), 3.72-3.64 (m, 6H), 3.56-5.54 (m, 2H), 3.38 (s, 3H). LCMS m/z 287 (M+H)+ (ES+)

(ii) tert-Butyl (4-((2-((2-methoxy-6-(2-(2-(2-methoxyethoxy)ethoxy)ethoxy)pyridin-4-yl)amino)pyrimidin-4-yl)oxy)naphthalen-1-yl)carbamate $Pd_2dba_3$ (0.091 g, 0.100 mmol), BINAP (0.124 g, 0.200 mmol), the product from step (i) above (1.1 g, 3.84 mmol), tert-butyl (4-((2-chloropyrimidin-4-yl)oxy)naphthalen-1-yl)carbamate (see, for example, Ito, K. et al., WO 2010/067130, 17 Jun. 2010; 1.43 g, 3.85 mmol) and $Cs_2CO_3$ (1.9 g, 5.83 mmol) were stirred in 1,4-dioxane (20 mL) for 10 minutes under $N_2$ then heated at 90° C. for 18 h. The mixture was cooled and partitioned between EtOAc (150 mL) and water (150 mL). The organic layer was separated, dried ($MgSO_4$), filtered and evaporated under reduced pressure. The crude product was purified by chromatography on silica gel (40 g column, 0-100% EtOAc/isohexane) to afford the product which was purified further by chromatography on silica gel (40 g column, 0-5% MeOH/DCM) to afford the sub-title compound (1.542 g) as a brown oil at ~50% purity
LCMS m/z 622 (M+H)+ (ES+)

(iii) 4((4-aminonaphthalen-1-yl)oxy)-N-(2-methoxy-6-(2-(2-(2-methoxyethoxy)ethoxy)-ethoxy)pyridin-4-yl)pyrimidin-2-amine A mixture of the product from step (ii) above (1.54 g) and TFA (2 mL, 26.0 mmol) in DCM (10 mL) was stirred at rt for 18 h. The mixture was evaporated under reduced pressure and the residue partitioned between DCM (100 mL) and sat. aq. $NaHCO_3$ solution (100 mL). The organic layer was separated, dried ($MgSO_4$), filtered and evaporated under reduced pressure. The crude product was purified by chromatography on silica gel (40 g column, 0-80% EtOAc/isohexane) to afford the sub-title compound (884 mg) as a solid.

1H NMR (400 MHz; DMSO-d6) δ 9.82 (d, 1H), 8.40 (d, 1H), 8.15-8.13 (m, 1H), 7.62-7.60 (m, 1H), 7.44-7.42 (m, 2H), 7.12 (d, 1H), 6.71-6.67 (m, 3H), 6.45 (d, 1H), 5.80 (s, 2H), 4.25-4.22 (m, 2H), 3.70 (s, 3H), 3.70-3.68 (m, 2H), 3.58-3.41 (m, 8H), 3.22 (s, 3H).
LCMS m/z 522 (M+H)+ (ES+)

(iv) 1-(3-(tert-Butyl)-1-(p-tolyl)-1H-pyrazol-5-yl)-3-(4-((2-((2-methoxy-6-(2-(2-(2-methoxyethoxy)ethoxy)ethoxy)pyridin-4-yl)amino)pyrimidin-4-yl)oxy)naphthalen-1-yl)urea A mixture of phenyl (3-(tert-butyl)-1-(p-tolyl)-1H-pyrazol-5-yl)carbamate (see, for example, Kapadia, S. R. et al., U.S. Pat. No. 6,492,529, 10 Dec. 2002; 150 mg, 0.429 mmol), the product from step (iii) above (204 mg, 0.390 mmol) and $Et_3N$ (11 μL, 0.079 mmol) in iPrOAc (5 mL) was heated at 60° C. for 3 h. The mixture was filtered, the solid slurried with MeCN (4 mL) for 2 h, ether (6 mL) added and the solid filtered and dried to afford the title compound (93 mg).

1H NMR (400 MHz; DMSO-d6) δ 9.82 (s, 1H), 9.10 (s, 1H), 8.78 (s, 1H), 8.48 (d, 1H), 8.09 (d, 1H), 7.99 (d, 1H), 7.80 (d, 1H), 7.65-7.54 (m, 2H), 7.47 (d, 2H), 7.42-7.37 (m, 3H), 6.66 (d, 1H), 6.58 (s, 1H), 6.55 (s, 1H), 6.42 (s, 1H), 4.23 (t, 2H), 3.68 (s, 3H), 3.68-3.66 (m, 2H), 3.55-3.48 (m, 6H), 3.42-3.39 (m, 2H), 3.21 (s, 3H), 2.40 (s, 3H), 1.30 (s, 9H).
LCMS m/z 777 (M+H)+ (ES+); 775 (M-H)- (ES-)

Example 70

1-(3-(tert-Butyl)-1-(4-methoxyphenyl)-1H-pyrazol-5-yl)-3-(4-((2-((3-(cyclopropylsulfonyl)-5-methoxyphenyl)amino)pyrimidin-4-yl)oxy)naphthalen-1-yl)urea

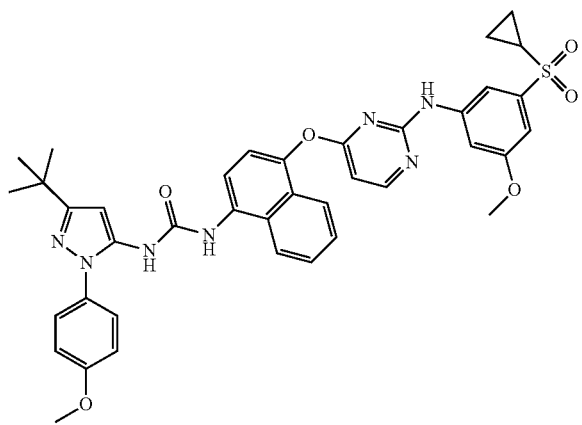 [SMILES: COc1ccc(-n2nc(C(C)(C)C)cc2NC(=O)Nc2ccc(Oc3ccnc(Nc4cc(OC)cc(S(=O)(=O)C5CC5)c4)n3)c3ccccc23)cc1]

(i) 1-(3-(tert-Butyl)-1-(4-methoxyphenyl)-1H-pyrazol-5-yl)-3-(4-((2-chloropyrimidin-4-yl)oxy)naphthalen-1-yl)urea In a 100 mL flask, a solution of phenyl (3-(tert-butyl)-1-(4-methoxyphenyl)-1H-pyrazol-5-yl)carbamate (see, for example, Abraham, S. et al., WO 2009/117080, 24 Sep. 2009; 1917 mg, 5.24 mmol) and 4-((2-chloropyrimidin-4-yl)oxy)naphthalen-1-amine (see, for example, Cirillo, P. F. et al., WO 2002/92576, 21 Nov. 2000; 1500 mg, 5.24 mmol) in isopropyl acetate (58 mL) was treated with $Et_3N$ (113 μL, 0.813 mmol). The resultant brown solution was heated at 70° C. for 2 h and solvent removed in vacuo to afford a brown thick oil. The crude product was purified by chromatography on silica gel (120 g column, EtOAc 0-15% in DCM) to afford the sub-title compound (2.169 g) as a white crystalline solid.

1H NMR (400 MHz, DMSO-d6) δ 9.14 (s, 1H), 8.75 (s, 1H), 8.66 (d, 1H), 8.09 (d, 1H), 7.97 (d, 1H), 7.82-7.77 (m, 1H), 7.69-7.62 (m, 1H), 7.58 (ddd, 1H), 7.51-7.46 (m, 2H), 7.43 (d, 1H), 7.27 (d, 1H), 7.15-7.10 (m, 2H), 6.40 (s, 1H), 3.84 (s, 3H), 1.29 (s, 9H).
LCMS m/z 544 (M+H)+ (ES+)

(ii) 1-(3-(tert-Butyl)-1-(4-methoxyphenyl)-1H-pyra-zol-5-yl)-3-(4-((2-((3-(cyclopropylsulfonyl)-5-methoxyphenyl)amino)pyrimidin-4-yl)oxy)naphthalen-1-yl)urea In a 20 mL flask, a mixture of 3-(cyclopropylsulfonyl)-5-methoxyaniline (see Example 18(ii) above; 128 mg, 0.552 mmol) and p-TSA monohydrate (35.0 mg, 0.184 mmol) was treated with a solution of the product from step (i) above (202 mg, 0.368 mmol) in DMF (2 mL). The resultant yellow solution was heated at 70° C. for 18 h. Poured over saturated NaHCO$_3$ (aq.) (20 mL) and extracted with EtOAc (2×20 mL). Combined organics washed with sat. brine solution (20 mL), separated, dried and evaporated to afford a red residue. The crude product was purified by chromatography on silica gel (80 g column, MeOH in DCM 0-5%) then purified by preparative HPLC (Gilson, Basic (0.1% Ammonium Bicarbonate), Waters X-Bridge Prep-C18, 5 μm, 19×50 mm column, 40-70 MeCN in Water) to afford the title compound (70 mg) as a white solid.

1H NMR (400 MHz, DMSO-d6) δ 9.84 (s, 1H), 9.11 (s, 1H), 8.74 (s, 1H), 8.46 (d, 1H), 8.07 (d, 1H), 7.96 (d, 1H), 7.84-7.79 (m, 1H), 7.73 (s, 1H), 7.66-7.59 (m, 1H), 7.59-7.53 (m, 1H), 7.52-7.45 (m, 3H), 7.40 (d, 1H), 7.15-7.09 (m, 2H), 6.89-6.84 (m, 1H), 6.63 (d, 1H), 6.39 (s, 1H), 3.84 (s, 3H), 3.62 (s, 3H), 2.77-2.67 (m, 1H), 1.28 (s, 9H), 1.09-0.96 (m, 4H).

LCMS m/z 734 (M+H)+ (ES+); 732 (M−H)− (ES−)

Example 71

1-(3-(tert-Butyl)-1-(p-tolyl)-1H-pyrazol-5-yl)-3-(2,3-dichloro-4-((2-((3-(2-(2-(2-hydroxyethoxyl)ethoxy)ethoxy)-5-methoxyphenyl)amino)pyrimidin-4-yl)oxy)phenyl)urea

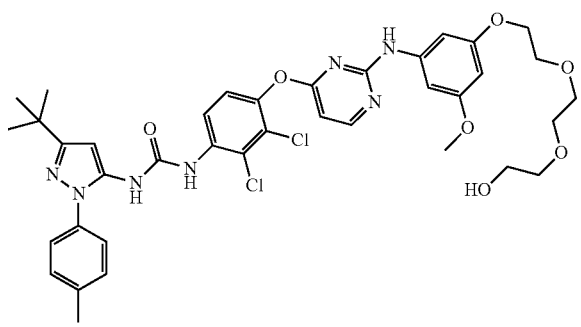 [SMILES: COc1cc(Nc2nccc(Oc3ccc(NC(=O)Nc4cc(C(C)(C)C)nn4-c4ccc(C)cc4)c(Cl)c3Cl)n2)cc(OCCOCCOCCO)c1]

(i) 2-(2-(2-(3-Methoxy-5-nitrophenoxy)ethoxy)ethoxy)ethanol

A stirred suspension of 3-methoxy-5-nitrophenol (0.5 g, 2.93 mmol), 2-(2-(2-chloroethoxyl)ethoxy)ethanol (0.425 ml, 2.93 mmol) and K$_2$CO$_3$ (0.809 g, 5.85 mmol) in acetone (11 mL) was heated under reflux. LCMS after 3 h showed partial conversion to product, thus KI (0.097 g, 0.585 mmol) was added to the reaction mixture after 4 h reaction time. The resultant red suspension was refluxed for 24 h. The solvent was removed in vacuo and residue partitioned between ethyl acetate (25 mL) and water (25 mL). The organic phase was washed with saturated NaHCO$_3$ solution (2×25 mL), water (2×25 mL), and saturated brine (2×25 mL). The organic phase was dried over Na$_2$SO$_4$, filtered and concentrated in vacuo. The crude product was purified by chromatography on silica gel (40 g column, EtOAc in iso-Hexane 0-100%) to afford the sub-title compound (0.6012 g) as a sticky yellow oil (~85% purity).

LCMS m/z 302 (M+H)+ (ES+)

(ii) 2-(2-(2-(3-Amino-5-methoxyphenoxy)ethoxy)ethoxy)ethanol

In a 25 mL flask, a solution of the product from step (i) above (0.6 g, 1.693 mmol) in EtOH (10 mL) was treated with Fe powder (0.945 g, 16.93 mmol) followed by a solution of ammonium chloride (0.905 g, 16.93 mmol) in water (5 mL). The resultant black suspension was heated at 80° C. for 2 h. Filtered on glass fiber pad (Whatman GF/A) and evaporated solvent until an oil separated. The residue was partitioned between water (30 mL) and EtOAc (30 mL). The aqueous phase was extracted with EtOAc (2×25 mL). The organic extracts were combined and washed with water (2×25 mL), brine (25 mL) and then dried over Na$_2$SO$_4$, filtered and concentrated in vacuo to afford the sub-title compound (0.19 g).

1H NMR (400 MHz, DMSO-d6) δ 5.74 (s, 1H), 5.74 (s, 1H), 5.67 (t, 1H), 5.06 (s, 2H), 4.60 (t, 1H), 3.93 (dd, 2H), 3.72-3.65 (m, 2H), 3.62 (s, 3H), 3.59-3.45 (m, 6H), 3.44-3.39 (m, 2H).

LCMS m/z 272 (M+H)+ (ES+)

(iii) 1-(3-(tert-Butyl)-1-(p-tolyl)-1H-pyrazol-5-yl)-3-(2,3-dichloro-4-((2-((3-(2-(2-(2-hydroxyethoxyl)ethoxy)ethoxy)-5-methoxyphenyl)amino)pyrimidin-4-yl)oxy)phenyl)urea In a 20 mL vial, a mixture of the product from step (ii) above (0.1833 g, 0.676 mmol) and p-TSA monohydrate (0.043 g, 0.225 mmol) was treated with a solution of 1-(3-(tert-butyl)-1-(p-tolyl)-1H-pyrazol-5-yl)-3-(2,3-dichloro-4-((2-chloropyrimidin-4-yl)oxy)phenyl)-urea (see Example 53(i) above; 0.246 g, 0.450 mmol) in DMF (2 mL). The resultant pale brown solution was heated at 70° C. for 4 h. The reaction mixture was allowed to cool and poured over saturated NaHCO$_3$ (aq.) (20 mL) and extracted with EtOAc (2×20 mL). Combined organics washed with water (20 mL) and sat. brine solution (20 mL), separated, dried and evaporated to afford a glass. The crude product was purified by chromatography on silica gel (40 g column, MeOH in EtOAc 0-4%) to afford the title compound (0.116 g) as a clear white crystalline solid.

1H NMR (400 MHz, DMSO-d6) δ 9.52 (s, 1H), 9.22 (s, 1H), 8.81 (s, 1H), 8.41 (d, 1H), 8.17 (d, 1H), 7.43-7.38 (m, 3H), 7.35 (d, 2H), 6.75 (d, 2H), 6.57 (d, 1H), 6.39 (s, 1H), 6.08 (t, 1H), 4.58 (t, 1H), 3.97-3.90 (m, 2H), 3.68 (dd, 2H), 3.59-3.54 (m, 5H), 3.53-3.49 (m, 2H), 3.49-3.45 (m, 2H), 3.43-3.39 (m, 2H), 2.39 (s, 3H), 1.28 (s, 9H).

LCMS m/z 781 (M+H)+ (ES+); 779 (M−H)− (ES−)

Example 72

1-(3-(tert-Butyl)-1-(p-tolyl)-1H-pyrazol-5-yl)-3-(4-((2-((4-chloro-3-methoxy-5-(2-(2-(2-methoxyethoxy)ethoxy)ethoxy)phenyl)amino)pyrimidin-4-yl)oxy)naphthalen-1-yl)urea

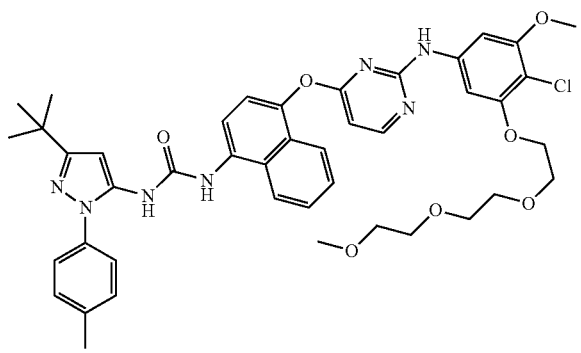 [SMILES: COCCOCCOCCOc1cc(Nc2nccc(Oc3ccc(NC(=O)Nc4cc(C(C)(C)C)nn4-c4ccc(C)cc4)c4ccccc34)n2)cc(OC)c1Cl]

(i) 5-Amino-2-chloro-3-methoxyphenol

BBr$_3$ (1.1 ml, 11.64 mmol) was added dropwise to a solution of 4-chloro-3,5-dimethoxyaniline (2.19 g, 11.67 mmol) in DCM at rt. (precipitate formed). The mixture was stirred for 18 h then heated under reflux for 6 h. A further 1 mL of BBr$_3$ was added and the mixture stirred for 24 h then quenched carefully with MeOH (10 mL). Water (100 mL) was added and the aqueous layer separated then basified with sat aq Na$_2$CO$_3$ to pH 6. The mixture was extracted with DCM (2×100 mL), the organic layers combined, dried (MgSO$_4$), filtered and evaporated under reduced pressure. The residue was triturated with ether/isohexane to afford the sub-title compound (640 mg).

1H NMR (400 MHz; DMSO-d6) δ 9.44 (s, 1H), 5.84 (s, 1H), 5.82 (s, 1H), 5.09 (s, 2H), 3.69 (s, 3H).

LCMS m/z 174/6 (M+H)+ (ES+)

(ii) 4-Chloro-3-methoxy-5-(2-(2-(2-methoxyethoxy)ethoxy)ethoxy)aniline

A mixture of 5-amino-2-chloro-3-methoxyphenol (630 mg, 3.23 mmol), 1-bromo-2-(2-(2-methoxyethoxyl)ethoxy)ethane (907 mg, 3.99 mmol), sodium iodide (54 mg, 0.360 mmol) and K$_2$CO$_3$ (1.5 g, 10.85 mmol) in MeCN (20 mL) was heated at 60° C. for 18 h. The mixture was cooled and partitioned between EtOAc (150 mL) and water (150 mL). The organic layer was separated, dried (MgSO$_4$), filtered and evaporated under reduced pressure. The crude product was purified by chromatography on silica gel (40 g column, 0-100% EtOAc/isohexane) to afford the sub-title compound (860 mg) as an oil.

1H NMR (400 MHz; CDCl$_3$) δ 5.98 (s, 1H), 5.96 (s, 1H), 4.13 (t, 2H), 3.88 (t, 2H), 3.84 (s, 3H), 3.80-3.78 (m, 2H), 3.69-3.66 (m, 4H), 3.57-3.55 (m, 2H), 3.38 (s, 3H).

LCMS m/z 320/2 (M+H)+ (ES+)

(iii) 1-(3-(tert-Butyl)-1-(p-tolyl)-1H-pyrazol-5-yl)-3-(4-((2-((4-chloro-3-methoxy-5-(2-(2-(2-methoxyethoxy)ethoxy)ethoxy)phenyl)amino)pyrimidin-4-yl)oxy)naphthalen-1-yl)urea In a 20 mL vial, a pale brown solution of the product from step (ii) above (132 mg, 0.410 mmol), p-TSA monohydrate (26.0 mg, 0.137 mmol) and 1-(3-(tert-butyl)-1-(p-tolyl)-1H-pyrazol-5-yl)-3-(4-((2-chloropyrimidin-4-yl)oxy)naphthalen-1-yl)urea (see Example 41(iv) above; 150 mg, 0.273 mmol) in DMF (2 mL) was heated at 70° C. for 8 h and at 50° C. for 18 h. The reaction mixture was allowed to cool and poured over saturated NaHCO$_3$ (aq.) (20 mL) and extracted with EtOAc (2×20 mL). Combined organics were washed with water (20 mL) and sat. brine solution (20 mL), separated, dried and evaporated to afford a glass. The crude product was purified by chromatography on silica gel (80 g column, MeOH in EtOAc 0-3%) to afford the title compound (0.1185 g) as an off-white solid.

1H NMR (400 MHz, DMSO-d6) δ 9.56 (s, 1H), 9.12 (s, 1H), 8.77 (s, 1H), 8.45 (d, 1H), 8.06 (d, 1H), 7.93 (d, 1H), 7.83 (d, 1H), 7.63 (ddd, 1H), 7.57 (ddd, 1H), 7.50-7.43 (m, 2H), 7.38 (dd, 3H), 7.05 (d, 2H), 6.63 (d, 1H), 6.42 (s, 1H), 3.81 (s, 2H), 3.70-3.60 (m, 2H), 3.56 (dd, 2H), 3.51-3.45 (m, 4H), 3.44-3.36 (m, 5H), 3.20 (s, 3H), 2.40 (s, 3H), 1.28 (s, 9H).

LCMS m/z 811 (M+H)+ (ES+)

Biological Testing: Experimental Methods

Enzyme Inhibition Assays

The enzyme inhibitory activities of compounds disclosed herein are determined by FRET using synthetic peptides labelled with both donor and acceptor fluorophores (Z-LYTE, Invitrogen Ltd., Paisley, UK).

p38 MAPKα Enzyme Inhibition

The following two assay variants can be used for determination of p38 MAPKα inhibition.

Method 1

The inhibitory activities of test compounds against the p38 MAPKα isoform (MAPK14: Invitrogen), are evaluated indirectly by determining the level of activation/phosphorylation of the down-stream molecule, MAPKAP-K2. The p38 MAPKα protein (80 ng/mL, 2.5 μL) is mixed with the test compound (2.5 μL of either 4 μg/mL, 0.4 μg/mL, 0.04 μg/mL or 0.004 μg/mL) for 2 hr at RT. The mix solution (2.5 μL) of the p38α inactive target MAPKAP-K2 (Invitrogen, 600 ng/mL) and FRET peptide (8 μM; a phosphorylation target for MAPKAP-K2) is then added and the kinase reaction is initiated by adding ATP (40 μM, 2.5 μL). The mixture is incubated for 1 hr at RT. Development reagent (protease, 5 μL) is added for 1 hr prior to detection in a fluorescence microplate reader (Varioskan® Flash, Thermo-Fisher Scientific).

Method 2

This method follows the same steps as Method 1 above, but utilises a higher concentration of the p38 MAPKα protein (2.5 μL of 200 ng/mL protein instead of 2.5 μL of 80 ng/mL protein) for mixing with the test compound.

p38 MAPKγ Enzyme Inhibition

The inhibitory activities of compounds of the invention against p38MAPKγ (MAPK12: Invitrogen), are evaluated in a similar fashion to that described hereinabove. The enzyme (800 ng/mL, 2.5 μL) is incubated with the test compound (2.5 μL at either 4 μg/mL, 0.4 μg/mL, 0.04 μg/mL, or 0.004 μg/mL) for 2 hr at RT. The FRET peptides (8 μM, 2.5 μL), and appropriate ATP solution (2.5 μL, 400 μM) is then added to the enzymes/compound mixtures and incubated for 1 hr. Development reagent (protease, 5 μL) is added for 1 hr prior to detection in a fluorescence microplate reader (Varioskan® Flash, Thermo Scientific).

c-Src and Syk Enzyme Inhibition

The inhibitory activities of compounds of the invention against c-Src and Syk enzymes (Invitrogen), are evaluated in a similar fashion to that described hereinabove. The relevant enzyme (3000 ng/mL or 2000 ng/mL respectively, 2.5 μL) is incubated with the test compound (either 4 µg/mL, 0.4 µg/mL, 0.04 µg/mL, or 0.004 µg/mL, 2.5 µL each) for 2 hr at RT. The FRET peptides (8 µM, 2.5 µL), and appropriate ATP solutions (2.5 µL, 800 µM for c-Src, and 60 µM ATP for Syk) are then added to the enzymes/compound mixtures and incubated for 1 hr. Development reagent (protease, 5 µL) is added for 1 hr prior to detection in a fluorescence microplate reader (Varioskan® Flash, ThermoFisher Scientific).

GSK 3α Enzyme Inhibition

The following two assay variants can be used for determination of GSK 3α inhibition.

Method 1

The inhibitory activities of compounds of the invention against the GSK 3α enzyme isoform (Invitrogen), are evaluated by determining the level of activation/phosphorylation of the target peptide. The GSK3-α protein (500 ng/mL, 2.5 µL) is mixed with the test compound (2.5 µL at either 4 µg/mL, 0.4 µg/mL, 0.04 µg/mL, or 0.004 µg/mL) for 2 hr at RT. The FRET peptide (8 µM, 2.5 µL), which is a phosphorylation target for GSK3α, and ATP (40 µM, 2.5 µL) are then added to the enzyme/compound mixture and the resulting mixture incubated for 1 hr. Development reagent (protease, 5 µL) is added for 1 hr prior to detection in a fluorescence microplate reader (Varioskan® Flash, ThermoFisher Scientific).

In all cases, the site-specific protease cleaves non-phosphorylated peptide only and eliminates the FRET signal. Phosphorylation levels of each reaction are calculated using the ratio of coumarin emission (donor) over fluorescein emission (acceptor), for which high ratios indicate high phosphorylation and low ratios indicate low phosphorylation levels. The percentage inhibition of each reaction is calculated relative to non-inhibited control and the 50% inhibitory concentration ($IC_{50}$ value) is then calculated from the concentration-response curve.

Method 2

This method follows the same steps as Method 1 above, but utilises a shorter period of mixing of the test compound (105 minutes instead of 2 hours) with the GSK3-α protein.

Cellular Assays

The compounds of the invention were studied using one or more of the following assays.

(a) LPS-induced TNFα/IL-8 Release in d-U937 Cells

U937 cells, a human monocytic cell line, are differentiated to macrophage-type cells by incubation with phorbol myristate acetate (PMA; 100 ng/mL) for 48 to 72 hr. Cells are pre-incubated with final concentrations of test compound for 2 hr and are then stimulated with 0.1 µg/mL of LPS (from *E. coli*: O111:B4, Sigma) for 4 hr. The supernatant is collected for determination of TNFα and IL-8 concentrations by sandwich ELISA (Duo-set, R&D systems). The inhibition of TNFα production is calculated as a percentage of that achieved by 10 µg/mL of BIRB796 at each concentration of test compound by comparison against vehicle control. The relative 50% effective concentration ($REC_{50}$) is determined from the resultant concentration-response curve. The inhibition of IL-8 production is calculated at each concentration of test compound by comparison with vehicle control. The 50% inhibitory concentration ($IC_{50}$) is determined from the resultant concentration-response curve.

(b) LPS-Induced TNFα/IL-8 Release in PBMC Cells

Peripheral blood mononuclear cells (PBMCs) from healthy subjects are separated from whole blood using a density gradient (Lymphoprep, Axis-Shield Healthcare). The PBMCs are seeded in 96 well plates and treated with compounds at the desired concentration for 2 hours before addition of 1 ng/mL LPS (*Escherichia Coli* O111:B4 from Sigma Aldrich) for 24 hours under normal tissue culture conditions (37° C., 5% $CO_2$). The supernatant is harvested for determination of IL-8 and TN Fa concentrations by sandwich ELISA (Duo-set, R&D systems) and read on the fluorescence microplate reader (Varioskan® Flash, ThermoFisher Scientific). The concentration at 50% inhibition ($IC_{50}$) of IL-8 and TNFα production is calculated from the dose response curve.

(c) IL-2 and IFN Gamma Release in CD3/CD28 Stimulated PBMC Cells

PBMCs from healthy subjects are separated from whole blood using a density gradient (Lymphoprep, Axis-Shield Healthcare). Cells are added to a 96 well plate pre-coated with a mixture of CD3/CD38 monoclonal antibodies (0.3 µg/mL eBioscience and 3 µg/mL BD Pharmingen respectively). Compound at the desired concentration is then added to the wells and the plate left for 3 days under normal tissue culture conditions. Supernatants are harvested and IL-2 and IFN gamma release determined by Sandwich ELISA (Duo-set, R&D System). The $IC_{50}$ is determined from the dose response curve.

(d) IL-1β-Induced IL-8 Release in HT29 Cells

HT29 cells, a human colon adenocarcinoma cell line, are plated in a 96 well plate (24 hrs) and pre-treated with compounds at the desired concentration for 2 hours before addition of 5 ng/mL of IL-1β (Abcam) for 24 hours. Supernatants are harvested for IL-8 quantification by Sandwich ELISA (Duo-set, R&D System). The $IC_{50}$ is determined from the dose response curve.

(e) LPS-Induced IL-8 and TNFα Release in Primary Macrophages

PBMCs from healthy subjects are separated from whole blood using a density gradient (Lymphoprep, Axis-Shield Healthcare). Cells are incubated for 2 hrs and non-adherent cells removed by washing. To differentiate the cells to macrophages the cells are incubated with 5 ng/mL of GM-CSF (Peprotech) for 7 days under normal tissue culture conditions. Compounds are then added to the cells at the desired concentration for a 2 hour pre-treatment before stimulation with 10 ng/mL LPS for 24 hours. Supernatants are harvested and IL-8 and TNFα release determined by Sandwich ELISA (Duo-set, R&D System). The $IC_{50}$ is determined from the dose response curve.

(f) Poly I:C-Induced ICAM-1 Expression in BEAS2B Cells

Poly I:C is used in these studies as a simple, RNA virus mimic. Poly I:C-Oligofectamine mixture (1 µg/mL Poly I:C, ±2% Oligofectamine, 25 µL; Invivogen Ltd., San Diego, Calif., and Invitrogen, Carlsbad, Calif., respectively) is transfected into BEAS2B cells (human bronchial epithelial cells, ATCC). Cells are pre-incubated with final concentrations of test compounds for 2 hr and the level of ICAM1 expression on the cell surface is determined by cell-based ELISA. At a time point 18 hr after poly I:C transfection, cells are fixed with 4% formaldehyde in PBS and then endogenous peroxidase is quenched by the addition of washing buffer (100 µL, 0.05% Tween in PBS: PBS-Tween) containing 0.1% sodium azide and 1% hydrogen peroxide. Cells are washed with wash-buffer (3×200 µL) and after blocking the wells with 5% milk in PBS-Tween (100 µL) for 1 hr, the cells are incubated with anti-human ICAM-1 antibody (50 µL; Cell Signalling Technology, Danvers, Mass.) in 1% BSA PBS overnight at 4° C.

The cells are washed with PBS-Tween (3×200 µL) and incubated with the secondary antibody (100 µL; HRP-conjugated anti-rabbit IgG, Dako Ltd., Glostrup, Denmark). The cells are then incubated with of substrate (50 µL) for 2-20 min, followed by the addition of stop solution (50 µL, 1N $H_2SO_4$). The ICAM-1 signal is detected by reading the absorbance at 450 nm against a reference wavelength of 655 nm using a spectrophotometer. The cells are then washed with PBS-Tween (3×200 µL) and total cell numbers in each well are determined by reading absorbance at 595 nm after Crystal Violet staining (50 µL of a 2% solution in PBS) and elution by 1% SDS solution (100 µL) in distilled water. The measured OD 450-655 readings are corrected for cell number by dividing with the OD595 reading in each well. The inhibition of ICAM-1 expression is calculated at each concentration of test compound by comparison with vehicle control. The 50% inhibitory concentration ($IC_{50}$) is determined from the resultant concentration-response curve.

(g) Cell Mitosis Assay

Peripheral blood mononucleocytes (PBMCs) from healthy subjects are separated from whole blood (Quintiles, London, UK) using a density gradient (Histopaque®-1077, Sigma-Aldrich, Poole, UK). The PBMCs (3 million cells per sample) are subsequently treated with 2% PHA (phytohaemagglutinin, Sigma-Aldrich, Poole, UK) for 48 hr, followed by a 20 hr exposure to varying concentrations of test compounds. At 2 hr before collection, PBMCs are treated with demecolcine (0.1 µg/mL; Invitrogen, Paisley, UK) to arrest cells in metaphase. To observe mitotic cells, PBMCs are permeabilised and fixed by adding Intraprep (50 µL; Beckman Coulter, France), and stained with anti-phospho-histone 3 (0.26 ng/L; #9701; Cell Signalling, Danvers, Mass.) and propidium iodide (1 mg/mL; Sigma-Aldrich, Poole, UK) as previously described (Muehlbauer P. A. and Schuler M. J., *Mutation Research*, 2003, 537:117-130). Fluorescence is observed using an ATTUNE flow cytometer (Invitrogen, Paisley, UK), gating for lymphocytes. The percentage inhibition of mitosis is calculated for each treatment relative to vehicle (0.5% DMSO) treatment.

(h) Rhinovirus-Induced IL-8 Release and ICAM-1 Expression

Human rhinovirus RV16 is obtained from the American Type Culture Collection (Manassas, Va.). Viral stocks are generated by infecting Hela cells with HRV until 80% of the cells are cytopathic.

BEAS2B cells are infected with HRV at an MOI of 5 and incubated for 2 hr at 33° C. with gentle shaking for to promote absorption. The cells are then washed with PBS, fresh media added and the cells are incubated for a further 72 hr. The supernatant is collected for assay of IL-8 concentrations using a Duoset ELISA development kit (R&D systems, Minneapolis, Minn.).

The level of ICAM1 expressing cell surface is determined by cell-based ELISA. At 72 hr after infection, cells are fixed with 4% formaldehyde in PBS. After quenching endogenous peroxidase by adding 0.1% sodium azide and 1% hydrogen peroxide, wells are washed with wash-buffer (0.05% Tween in PBS: PBS-Tween). After blocking well with 5% milk in PBS-Tween for 1 hr, the cells are incubated with anti-human ICAM-1 antibody in 5% BSA PBS-Tween (1:500) overnight. Wells are washed with PBS-Tween and incubated with the secondary antibody (HRP-conjugated anti-rabbit IgG, Dako Ltd.). The ICAM-1 signal is detected by adding substrate and reading at 450 nm with a reference wavelength of 655 nm using a spectrophotometer. The wells are then washed with PBS-Tween and total cell numbers in each well are determined by reading absorbance at 595 nm after Crystal Violet staining and elution by 1% SDS solution. The measured $OD_{450-655}$ readings are corrected for cell number by dividing with the $OD_{595}$ reading in each well. Compounds are added 2 hr before HRV infection and 2 hr after infection when non-infected HRV is washed out.

(i) Assessment of HRV16 Induced CPE in MRC5

MRC-5 cells are infected with HRV16 at an MOI of 1 in DMEM containing 5% FCS and 1.5 mM $MgCl_2$, followed by incubation for 1 hr at 33° C. to promote adsorption. The supernatants are aspirated, and then fresh media added followed by incubation for 4 days. Where appropriate, cells are pre-incubated with compound or DMSO for 2 hr, and the compounds and DMSO added again after washout of the virus.

Supernatants are aspirated and incubated with methylene blue solution (100 µL, 2% formaldehyde, 10% methanol and 0.175% Methylene Blue) for 2 hr at RT. After washing, 1% SDS in distilled water (100 µL) is added to each well, and the plates are shaken lightly for 1-2 hr prior to reading the absorbance at 660 nm. The percentage inhibition for each well is calculated. The $IC_{50}$ value is calculated from the concentration-response curve generated by the serial dilutions of the test compounds.

(j) In Vitro RSV Virus Load in Primary Bronchial Epithelial Cells

Normal human bronchial epithelial cells (NHBEC) grown in 96 well plates are infected with RSV A2 (Strain A2, HPA, Salisbury, UK) at an MOI of 0.001 in the LHC8 Media: RPMI-1640 (50:50) containing 15 mM magnesium chloride and incubated for 1 hr at 37° C. for adsorption. The cells are then washed with PBS (3×200 µL), fresh media (200 µL) is added and incubation continued for 4 days. Where appropriate, cells are pre-incubated with the compound or DMSO for 2 hr, and then added again after washout of the virus.

The cells are fixed with 4% formaldehyde in PBS solution (50 µL) for 20 min, washed with WB (3×200 µL), (washing buffer, PBS including 0.5% BSA and 0.05% Tween-20) and incubated with blocking solution (5% condensed milk in PBS) for 1 hr. Cells are then washed with WB (3×200 µL) and incubated for 1 hr at RT with anti-RSV (2F7) F-fusion protein antibody (40 µL; mouse monoclonal, lot 798760, Cat. No. ab43812, Abcam) in 5% BSA in PBS-tween. After washing, cells are incubated with an HRP-conjugated secondary antibody solution (50 µL) in 5% BSA in PBS-Tween (lot 00053170, Cat. No. P0447, Dako) and then TMB substrate added (50 µL; substrate reagent pack, lot 269472, Cat. No. DY999, R&D Systems, Inc.). This reaction is stopped by the addition of 2N $H_2SO_4$ (50 µL) and the resultant signal is determined colourimetrically (OD: 450 nm with a reference wavelength of 655 nm) in a microplate reader (Varioskan® Flash, ThermoFisher Scientific).

Cells are then washed and a 2.5% crystal violet solution (50 µL; lot 8656, Cat. No. PL7000, Pro-Lab Diagnostics) is applied for 30 min. After washing with WB, 1% SDS in distilled water (100 µL) is added to each well, and plates are shaken lightly on the shaker for 1 hr prior to reading the absorbance at 595 nm. The measured $OD_{450-655}$ readings are corrected to the cell number by dividing the $OD_{450-655}$ by the $OD_{505}$ readings. The percentage inhibition for each well is calculated and the $IC_{50}$ value is calculated from the concentration-response curve generated from the serial dilutions of compound.

(k) Cell Viability Assay: MTT Assay

Differentiated U937 cells are pre-incubated with each test compound (final concentration 1 µg/mL or 10 µg/mL in 200 µL media indicated below) under two protocols: the first for 4 hr in 5% FCS RPMI1640 media and the second in 10% FCS RPMI1640 media for 24 h. The supernatant is replaced with new media (200 µL) and MTT stock solution (10 µL, 5 mg/mL) is added to each well. After incubation for 1 hr the media are removed, DMSO (200 µL) is added to each well and the plates are shaken lightly for 1 hr prior to reading the absorbance at 550 nm. The percentage loss of cell viability is calculated for each well relative to vehicle (0.5% DMSO) treatment. Consequently an apparent increase in cell viability for drug treatment relative to vehicle is tabulated as a negative percentage.

(l) Human Biopsy Assay

Intestinal mucosa biopsies are obtained from the inflamed regions of the colon of IBD patients. The biopsy material is cut into small pieces (2-3 mm) and placed on steel grids in an organ culture chamber at 37° C. in a 5% $CO_2$/95% $O_2$ atmosphere in serum-free media. DMSO control or test compounds at the desired concentration are added to the tissue and incubated for 24 hr in the organ culture chamber. The supernatant is harvested for determination of IL-6, IL-8, IL-1β and TNFα levels by R&D ELISA. Percentage inhibition of cytokine release by the test compounds is calculated relative to the cytokine release determined for the DMSO control (100%).

(m) Accumulation of β Catenin in d-U937 Cells

U937 cells, a human monocytic cell line, are differentiated into macrophage-type cells by incubation with PMA; (100 ng/mL) for between 48 to 72 hr. The cells are then incubated with either final concentrations of test compound or vehicle for 18 hr. The induction of R-catenin by the test compounds is stopped by replacing the media with 4% formaldehyde solution. Endogenous peroxide activity is neutralised by incubating with quenching buffer (100 µL, 0.1% sodium azide, 1% $H_2O_2$ in PBS with 0.05% Tween-20) for 20 min. The cells are washed with washing buffer (200 µL; PBS containing 0.05% Tween-20) and incubated with blocking solution (200 µL; 5% milk in PBS) for 1 hr, re-washed with washing buffer (200 µL) and then incubated overnight with anti-p-catenin antibody solution (50 µL) in 1% BSA/PBS (BD, Oxford, UK).

After washing with washing buffer (3×200 µL; PBS containing 0.05% Tween-20), cells are incubated with an HRP-conjugated secondary antibody solution (100 µL) in 1% BSA/PBS (Dako, Cambridge, UK) and the resultant signal is determined colourimetrically (OD: 450 nm with a reference wavelength of 655 nm) using TMB substrate (50 µL; R&D Systems, Abingdon, UK). This reaction is stopped by addition of 1N $H_2SO_4$ solution (50 µL). Cells are then washed with washing buffer and 2% crystal violet solution (50 µL) is applied for 30 min. After washing with washing buffer (3×200 µL), 1% SDS (100 µL) is added to each well and the plates are shaken lightly for 1 hr prior to measuring the absorbance at 595 nm (Varioskan® Flash, Thermo-Fisher Scientific).

The measured $OD_{450-655}$ readings are corrected for cell number by dividing the $OD_{450-655}$ by the $OD_{595}$ readings. The percentage induction for each well is calculated relative to vehicle, and the ratio of induction normalised in comparison with the induction produced by a standard control comprising of N-(4-(4-(3-(3-tert-butyl-1-p-tolyl-1H-pyrazol-5-yl)ureido)naphthalen-1-yloxy)pyridin-2-yl)-2-methoxyacetamide (1 µg/m L) which is defined as unity. A signal less than 0.15 of that observed for the standard control is designated as "−ve".

(n) T Cell Proliferation

PBMCs from healthy subjects are separated from whole blood using a density gradient (Lymphoprep, Axis-Shield Healthcare). The lymphocyte fraction is first enriched for CD4+ T cells by negative magnetic cell sorting as per the manufacturer's instructions (Miltenyi Biotec 130-091-155). Naïve CD4+ T cells are then separated using positive magnetic selection of CD45RA+ cells using microbeads as per the manufacturer's instructions (130-045-901). Cells are plated at $2\times10^5$ cells per well in 100 µL RPMI/10% FBS on 96 well flat bottomed plate (Corning Costar). 25 µL of test compound are diluted to the appropriate concentration (8× final conc.) in normal medium and added to duplicate wells on the plate to achieve a dose response range of 0.03 ng/mL 250 ng/mL. DMSO is added as a negative control. Plates are allowed to pre-incubate for 2 hours before stimulation with 1 µg/mL anti-CD3 (OKT3; eBioscience). After 72 h, the medium in each well is replaced with 150 µL of fresh medium containing 10 µM BrdU (Roche). After 16 h, the supernatant is removed, the plate is dried and the cells fixed by adding 100 µL of fix/denature solution to each well for 20 min as per the manufacturer's instructions (Roche). Plates are washed once with PBS before addition of the anti-BrdU detection antibody and incubated for 90 mins at room temperature. Plates are then washed gently 3× with the wash buffer supplied and developed by addition of 100 µL of substrate solution. The reaction is stopped by addition of 50 µL of 1 M $H_2SO_4$, and read for absorbance at 450 nm on a plate reader (Varioskan® Flash, ThermoFisher Scientific). The $IC_{50}$ is determined from the dose response curve.

(o) IL-2 and IFNγ Release in CD3/CD28 Stimulated LPMC Cells from IBD Patients

Lamina propria mononuclear cells (LPMCs) are isolated and purified from inflamed IBD mucosa of surgical specimens or from normal mucosa of surgical specimens as follows: The mucosa is removed from the deeper layers of the surgical specimens with a scalpel and cut in fragments 3-4 mm size. The epithelium is removed by washing the tissue fragments three times with 1 mM EDTA (Sigma-Aldrich, Poole, UK) in HBSS (Sigma-Aldrich) with agitation using a magnetic stirrer, discarding the supernatant after each wash. The sample is subsequently treated with type 1A collagenase (1 mg/mL; Sigma-Aldrich) for 1 h with stirring at 37° C. The resulting cell suspension is then filtered using a 100 µm cell strainer, washed twice, resuspended in RPMI-1640 medium (Sigma-Aldrich) containing 10% fetal calf serum, 100 U/mL penicillin and 100 µg/mL streptomycin, and used for cell culture.

Freshly isolated LPMCs ($2\times10^5$ cells/well) are stimulated with 1 µg/mL a-CD3/a-CD28 for 48 h in the presence of either DMSO control or appropriate concentrations of compound. After 48 h, the supernatant is removed and assayed for the presence of TNFα and IFNγ by R&D ELISA. Percentage inhibition of cytokine release by the test compounds is calculated relative to the cytokine release determined for the DMSO control (100%).

(p) Inhibition of Cytokine Release from Myofibroblasts Isolated from IBD Patients Myofibroblasts from inflamed IBD mucosa are isolated as follows:

The mucosa is dissected and discarded and 1 mm-sized mucosal samples are cultured at 37° C. in a humidified $CO_2$ incubator in Dulbecco's modified Eagle's medium (DMEM, Sigma-Aldrich) supplemented with 20% FBS, 1% non-essential amino acids (Invitrogen, Paisley, UK), 100 U/mL penicillin, 100 µg/mL streptomycin, 50 µg/mL gentamycin, and 1 µg/mL amphotericin (Sigma-Aldrich). Established colonies of myofibroblasts are seeded into 25-cm² culture flasks and cultured in DMEM supplemented with 20% FBS and antibiotics to at least passage 4 to provide a sufficient quantity for use in stimulation experiments.

Subconfluent monolayers of myofibroblasts are then seeded in 12-well plates at $3\times10^5$ cells per well are starved in serum-free medium for 24 h at 37° C., 5% $CO_2$ before being cultured for 24 h in the presence of either DMSO control or appropriate concentrations of compound. After 24 h the supernatant is removed and assayed for the presence of IL-8 and IL-6 by R&D ELISA. Percentage inhibition of cytokine release by the test compounds is calculated relative to the cytokine release determined for the DMSO control (100%).

(q) Human Neutrophil Degranulation

Neutrophils are isolated from human peripheral blood as follows:

Blood is collected by venepuncture and anti-coagulated by addition of 1:1 EDTA: sterile phosphate buffered saline (PBS, no Ca+/Mg+). Dextran (3% w/v) is added (1 part dextran solution to 4 parts blood) and the blood allowed to stand for approximately 20 minutes at rt. The supernatant is carefully layered on a density gradient (Lymphoprep, Axis-Shield Healthcare) and centrifuged (15 mins, 2000 rpm, no brake). The supernatant is aspirated off and the cell pellet is re-suspended in sterile saline (0.2%) for no longer than 60 seconds (to lyse contaminating red blood cells). 10 times volume of PBS is then added and the cells centrifuged (5 mins, 1200 rpm). Cells are re-suspended in HBSS+ (Hanks buffered salt solution (without phenol red) containing cytochalasin B (5 µg/mL) and 1 mM $CaCl_2$) to achieve $5\times10^6$ cells/mL.

$5\times10^4$ cells are added to each well of a V-bottom 96 well plate and incubated (30 mins, 37° C.) with the appropriate concentration of test compound (0.3-1000 ng/mL) or vehicle (DMSO, 0.5% final conc). Degranulation is stimulated by addition of fMLP (final conc 1 µM) which after a further incubation (30 mins, 37° C.) the cells are removed by centrifugation (5 mins, 1500 rpm) and the supernatants transferred to a flat bottom 96 well plate. An equal volume of tetramethylbenzidine (TMB) is added and after 10 mins the reaction terminated by addition of an equal volume of sulphuric acid (0.5 M) and absorbance read at 450 nm (background at 655 nm subtracted). The 50% inhibitory concentration ($IC_{50}$) is determined from the resultant concentration-response curve.

(r) Cell Cytotoxicity Assay $5\times10^4$ TK6 cells (lymphoblastic T cell line) are added to the appropriate number of wells of a 96 well plate in 195 µL of media (RPMI supplemented with 10% foetal bovine serum). 5 µL of DMSO control (final concentration 0.5% v/v) or test compound (final concentration either 5 or 1 µg/mL) is added to the wells and incubated at 37° C., 5% $CO_2$. After 24 hours, the plate is centrifuged at 1300 rpm for 3 minutes and the supernatant discarded. Cells are then resuspended in 7.5 µg/mL propidium iodide (PI) in PBS. After 15 minutes, cells are analysed by flow cytometry (BD accuri). The % viability is calculated as the % of cells that are PI negative in the test wells normalised to the DMSO control.

In Vivo Screening: Pharmacodynamics and Anti-Inflammatory Activity (i) LPS-Induced Neutrophil Accumulation in Mice Non-fasted Balb/c mice are dosed by the intra tracheal route with either vehicle, or the test substance at the indicated times (within the range 2-8 hr) before stimulation of the inflammatory response by application of an LPS challenge. At T=0, mice are placed into an exposure chamber and exposed to LPS (7.0 mL, 0.5 mg/mL solution in PBS) for 30 min. After a further 8 hr the animals are anesthetized, their tracheas cannulated and BALF extracted by infusing and then withdrawing from their lungs 1.0 mL of PBS via the tracheal catheter. Total and differential white cell counts in the BALF samples are measured using a Neubaur haemocytometer. Cytospin smears of the BALF samples are prepared by centrifugation at 200 rpm for 5 min at RT and stained using a DiffQuik stain system (Dade Behring). Cells are counted using oil immersion microscopy. Data for neutrophil numbers in BAL are shown as mean±S.E.M. (standard error of the mean). The percentage inhibition of neutrophil accumulation is calculated for each treatment relative to vehicle treatment.

(ii) Cigarette Smoke Model

A/J mice (males, 5 weeks old) are exposed to cigarette smoke (4% cigarette smoke, diluted with air) for 30 min/day for 11 days using a Tobacco Smoke Inhalation Experiment System for small animals (Model SIS-CS; Sibata Scientific Technology, Tokyo, Japan). Test substances are administered intra-nasally (35 µL of solution in 50% DMSO/PBS) once daily for 3 days after the final cigarette smoke exposure. At 12 hr after the last dosing, each of the animals is anesthetized, the trachea cannulated and bronchoalveolar lavage fluid (BALF) is collected. The numbers of alveolar macrophages and neutrophils are determined by FACS analysis (EPICS® ALTRA II, Beckman Coulter, Inc., Fullerton, Calif., USA) using anti-mouse MOMA2 antibody (macrophage) or anti-mouse 7/4 antibody (neutrophil).

(iii) DSS-Induced Colitis in Mice

Non-fasted, 10-12 week old, male BDF1 mice are dosed by oral gavage twice daily with either vehicle, reference item (5-ASA) or test compound one day before (Day −1) stimulation of the inflammatory response by treatment with dextran sodium sulphate (DSS). On Day 0 of the study DSS (5% w/v) is administered in the drinking water followed by BID dosing of the vehicle (5 mL/kg), reference (100 mg/kg) or test compound (5 mg/kg) for 7 days. The drinking water with DSS is replenished every 3 days. During the study animals are weighed every day and stool observations are made and recorded as a score, based on stool consistency. At the time of sacrifice on Day +6 the large intestine is removed and the length and weight are recorded. Sections of the colon are taken for either MPO analysis to determine neutrophil infiltration or for histopathology scoring to determine disease severity.

(iv) TNBS-Induced Colitis in Mice

Non-fasted, 10-12 week old, male BDF1 mice are dosed by oral gavage twice daily with either vehicle (5 mL/kg), reference item (Budesonide 2.5 mg/kg) or test compound (1 or 5 mg/kg) one day before (Day −1) stimulation of the inflammatory response by treatment with 2,4,6-trinitrobenzenesulphonic add (TNBS) (15 mg/mL in 50% ethanol/50% saline). On Day 0 of the study TNBS (200 µL) is administered intra-colonically via a plastic catheter followed by BID dosing of the vehicle, reference or test compound for 2 or 4 days. During the study animals are weighed every day and stool observations are made and recorded as a score, based on stool consistency. At the time of sacrifice on Day 2 (or Day 4) the large intestine is removed and the length and weight recorded. Sections of the colon are taken for either MPO analysis to determine neutrophil infiltration or for histopathology involving scoring to determine disease severity.

(v) Adoptive Transfer in Mice

On Study day 0, female Balb/C mice are terminated and spleens obtained for $CD45RB^{high}$ cell isolation (Using SCID IBD cell Separation protocol). Approximately $4\times10^5$ cells/mL $CD45RB^{high}$ cells are then injected IP (100 µL/mouse) into female SCID animals. On study day 14, mice are weighed and randomized into treatment groups based on body weight. On Day 21 compounds are administered BID, via oral gavage, in a peanut oil vehicle at the dose levels outlined below and a dose volume of 5 mL/kg. Treatment continues until study day 42, at which point the animals are necropsied 4 hours after am administration. The colon length and weight is recorded and used as a secondary endpoint in the study as a measurement of colon oedema. The colon is then divided into six cross-sections, four of which are used for histopathology scoring (primary endpoint) and two are homogenised for cytokine analysis. Data shown is the % inhibition of the induction window between nave animals and vehicle animals, where higher inhibition implies closer to the non-diseased, nave, phenotype.

Summary of In Vitro and In Vivo Screening Results

TABLE 1

Results from in vitro p38 MAPKα (Method 2), c-Src, Syk and GSK3α (Method 2) inhibition assays

| Test Compound Example No. | IC50 Values for Enzyme Inhibition (nM) | | | |
|---|---|---|---|---|
| | p38 MAPKα | c-Src | Syk | GSK3α |
| 1 | 316 | 28 | 77 | >10000 |
| 2 | 81 | 8 | 15 | 1850 |
| 3 | 28 | 16 | 66 | 2536 |
| 4 | — | — | — | 973 |
| 5 | — | — | — | 306 |
| 6 | — | — | — | 501 |
| 7 | — | — | — | 125 |
| 8 | — | — | — | 258 |
| 9 | 26 | 154 | >1000 | 3724 |
| 10 | — | 137 | 807 | >10000 |
| 11 | 50 | 20 | >622 | 8651 |
| 12 | 422 | 39 | 238 | >10000 |
| 13 | 65 | 10 | 17 | >8917 |
| 14 | — | — | — | 416 |
| 15 | — | >1603 | >1603 | >10000 |
| 16 | — | — | — | 824 |
| 17 | >280 | >383 | >537 | 2666 |
| 18 | 102 | 27 | 358 | 2903 |
| 19 | — | 5 | 20 | 1071 |
| 20 | 26 | 8 | 8 | 3842 |
| 21 | 342 | 61 | 72 | >10000 |
| 22 | 114 | 47 | 134 | 4826 |
| 23 | — | 53 | 289 | 1399 |
| 24 | — | — | — | 117 |
| 25 | — | — | — | 804 |
| 26 | — | — | — | 426 |
| 27 | — | — | — | >10000 |
| 28 | — | — | — | >10000 |
| 29 | 30 | 6 | 16 | >10000 |
| 30 | 32 | 4 | 12 | 7232 |
| 31 | — | — | — | >10000 |
| 32 | 11 | 3 | 7 | 4688 |
| 33 | — | — | — | >10000 |
| 34 | — | — | — | >10000 |
| 35 | 487 | 15 | 30 | >10000 |
| 36 | — | — | — | 596 |
| 37 | 153 | 11 | 36 | 6360 |
| 38 | 132 | 10 | 25 | 5445 |
| 39 | 433 | — | — | 9544 |
| 40 | — | — | — | 8173 |
| 41 | 224 | — | — | 2824 |
| 42 | 291 | 28 | 51 | 1931 |
| 43 | — | — | — | 531 |
| 44 | 103 | 10 | 23 | 4611 |
| 45 | 144 | 12 | 15 | 1489 |
| 46 | — | — | — | 172 |
| 47 | 162 | 46 | 119 | 6829 |
| 48 | 195 | 22 | 37 | 2053 |
| 49 | 175 | 23 | 20 | 7258 |
| 50 | — | — | — | 3027 |
| 51 | 53 | 10 | 18 | 1327 |
| 52 | — | — | — | >12972 |
| 53 | 816 | 23 | 56 | >10000 |
| 54 | — | — | — | >10000 |
| 55 | 200 | 23 | 42 | 1230 |
| 56 | 140 | 28 | 43 | >10000 |
| 57 | — | — | 7 | 8 | 1935 |

TABLE 1-continued

Results from in vitro p38 MAPKα (Method 2), c-Src, Syk and GSK3α (Method 2) inhibition assays

| Test Compound Example No. | IC50 Values for Enzyme Inhibition (nM) | | | |
|---|---|---|---|---|
| | p38 MAPKα | c-Src | Syk | GSK3α |
| 58 | — | 11 | 28 | 2806 |
| 59 | — | — | — | 7365 |
| 60 | — | 17 | 30 | >10000 |
| 61 | 301 | 73 | 120 | 3796 |
| 62 | 95 | 4 | 6 | 1026 |
| 63 | 187 | 13 | 16 | 4817 |
| 64 | — | — | — | >10000 |
| 65 | — | — | — | >10000 |
| 66 | — | — | — | 3387 |
| 67 | — | — | — | 5257 |
| 68 | >1357 | — | — | >10000 |
| 69 | 172 | 14 | 27 | >10000 |
| 70 | 300 | 48 | 62 | 3352 |
| 71 | 740 | 19 | 23 | 7740 |
| 72 | 377 | 39 | 75 | >10000 |

TABLE 2

Results from cellular assays in d-U937 cells, PBMCs and HT29 cells (the protocols for which are described by assays (a) to and (d) above).

| Test Compound Example No. | IC$_{50}$ Values for Inhibition of Cytokine Release (nM) | | | | | | |
|---|---|---|---|---|---|---|---|
| | dU937 cells | | PBMCs | | | | HT29 cells |
| | IL-8 | TNFα | IL-8 | TNFα | IL-2 | IFNγ | IL-8 |
| 1 | 2.1 | 3.6 | 11.5 | — | 39.8 | — | 17.4 |
| 2 | 5.2 | 16.5 | 5.3 | — | 51.1 | — | 18.5 |
| 3 | — | 0.3 | 1.5 | — | 9.9 | 1.2 | 2.2 |
| 4 | — | — | 1.7 | — | — | — | — |
| 5 | — | — | 1.9 | — | — | — | — |
| 6 | — | — | 1.6 | — | — | — | — |
| 7 | — | — | 0.9 | — | — | — | — |
| 8 | — | — | 1.0 | — | — | — | — |
| 9 | 2.8 | 1.5 | 3.1 | — | — | — | 4.5 |
| 10 | — | — | 7.9 | — | — | — | — |
| 11 | 1.4 | 0.9 | 3.6 | — | 151.4 | — | 5.3 |
| 12 | — | 0.4 | 2.8 | — | 24.8 | 4.7 | 4.3 |
| 13 | 1.4 | 4.4 | 2.5 | — | 19.2 | 3.0 | 4.7 |
| 14 | — | — | 2.4 | — | — | — | 7.9 |
| 15 | — | — | 6.1 | — | — | — | — |
| 16 | — | — | 1.7 | — | — | — | — |
| 17 | — | — | 1.1 | — | 20.3 | — | — |
| 18 | — | — | 2.1 | — | 84.6 | — | 6.2 |
| 19 | — | — | 1.2 | — | — | — | — |
| 20 | — | 1.6 | 1.5 | — | 80.8 | — | — |
| 21 | 1.6 | 1.1 | 1.6 | — | 10.7 | 1.9 | — |
| 22 | — | — | 2.3 | — | 30.7 | — | 5.1 |
| 23 | — | — | 2.6 | — | — | — | — |
| 24 | — | — | 3.8 | — | — | — | — |
| 25 | — | — | 2.0 | — | — | — | — |
| 26 | — | — | 3.9 | — | — | — | — |
| 27 | — | — | 24.8 | — | — | — | — |
| 28 | — | — | 24.0 | — | — | — | — |
| 29 | — | — | 2.5 | — | 74.1 | 6.6 | — |
| 30 | — | — | 2.1 | — | 27.3 | 15.2 | — |
| 31 | — | — | 4.4 | — | — | — | — |
| 32 | — | — | 1.4 | — | — | — | — |
| 33 | — | — | 8.7 | — | — | — | — |
| 34 | — | — | 12.2 | — | — | — | — |
| 35 | — | — | 2.1 | — | 9.8 | — | — |
| 36 | — | — | 2.5 | — | — | — | — |
| 37 | 1.7 | — | 1.8 | — | 34.8 | 1.5 | 1.7 |
| 38 | 1.0 | — | 1.5 | — | 40.9 | 1.3 | 1.8 |
| 39 | — | — | 5.5 | — | — | — | — |
| 40 | — | — | 7.2 | — | 174.9 | 1.0 | — |
| 41 | — | — | 4.8 | — | 80.3 | 2.5 | — |
| 42 | — | — | 3.6 | — | 58.5 | 1.0 | — |

TABLE 2-continued

Results from cellular assays in d-U937 cells, PBMCs and HT29 cells (the protocols for which are described by assays (a) to and (d) above).

| Test Compound Example No. | IC$_{50}$ Values for Inhibition of Cytokine Release (nM) | | | | | | HT29 cells |
|---|---|---|---|---|---|---|---|
| | dU937 cells | | PBMCs | | | | |
| | IL-8 | TNFα | IL-8 | TNFα | IL-2 | IFNγ | IL-8 |
| 43 | — | — | 2.9 | — | 78.7 | 2.2 | — |
| 44 | 0.6 | 0.5 | 1.6 | 0.6 | 38.5 | 1.4 | 1.2 |
| 45 | — | — | 3.2 | — | 73.8 | 2.2 | — |
| 46 | — | — | 2.7 | — | — | — | — |
| 47 | 1.2 | 0.6 | 2.6 | — | 95.8 | 1.1 | 1.5 |
| 48 | — | — | 3.0 | — | 49.2 | 2.2 | — |
| 49 | — | — | 1.9 | — | 54.7 | 1.2 | 2.3 |
| 50 | — | — | 8.6 | — | — | — | — |
| 51 | 0.4 | 0.3 | 1.9 | — | 40.7 | 1.8 | 1.6 |
| 52 | — | — | 15.0 | — | — | — | — |
| 53 | — | — | 3.8 | — | 133.0 | 2.1 | 2.4 |
| 54 | — | — | 4.5 | — | — | — | — |
| 55 | — | — | 2.0 | — | 36.8 | 2.0 | 2.4 |
| 56 | 1.4 | 0.8 | 2.4 | 1.6 | 151.8 | 2.7 | 4.5 |
| 57 | — | — | 0.9 | — | 14.6 | 1.4 | — |
| 58 | — | — | 1.1 | — | 39.6 | 1.3 | — |
| 59 | — | — | 4.2 | — | — | — | — |
| 60 | — | — | 2.2 | — | 72.6 | 3.0 | — |
| 61 | — | — | 2.0 | — | 42.4 | 1.9 | 4.8 |
| 62 | — | — | 1.5 | — | 52.9 | 2.1 | 2.5 |
| 63 | 0.6 | 0.4 | 2.0 | — | 76.2 | 1.5 | 2.0 |
| 64 | — | — | 9.5 | — | — | — | — |
| 65 | — | — | 3.5 | — | 37.0 | 2.8 | — |
| 66 | — | — | 2.6 | — | — | — | — |
| 67 | — | — | 3.5 | — | — | — | — |
| 68 | — | — | 5.2 | — | — | — | — |
| 69 | 0.9 | 1.2 | 1.6 | — | 50.3 | 1.4 | 3.1 |
| 70 | 1.9 | 1.1 | 0.9 | — | 73.5 | 1.4 | — |
| 71 | 1.3 | 1.0 | 1.8 | — | 60.8 | 1.1 | — |
| 72 | — | — | 3.9 | — | 35.1 | 3.3 | — |

As illustrated in Table 3 below, the compounds of Examples 13, 18, 22, 44, 47, 51 and 56 were also screened in in vivo assay (iv) above, as conducted over 2 days. Histopathology analysis revealed that the compounds of Examples 13, 18, 22, 44, 47, 51 and 56 displayed significant activity in this in vivo model of colonic inflammation. In particular, these compounds, when dosed orally at either 1 or 5 mg/kg, demonstrated marked improvements in ulcer grade and epithelial repair compared to the vehicle control. In addition, the compounds of Examples 13, 18, 22, 44, 47, 51 and 56 produced a marked reduction in inflammatory cell infiltrate in the reticular and laminar propria zone.

TABLE 3

Summary of results from studies on TNBS-induced colitis in mice.

| Experiment no. | Treatment group | n | TNBS Ulcer grade | LP inflammation |
|---|---|---|---|---|
| 1 | Non-diseased | 6 | 0.0 ± 0.0 | 0.3 ± 0.2 |
| 1 | TNBS + Vehicle | 24 | 3.6 ± 0.3 | 4.0 ± 0.3 |
| 1 | TNBS + Example 13 (1 mg/kg) | 12 | 2.5 ± 0.4 | 2.1 ± 0.3 |
| 1 | TNBS + Example 13 (5 mg/kg) | 12 | 3.1 ± 0.3 | 2.6 ± 0.3 |
| 1 | TNBS + Example 18 (1 mg/kg) | 12 | 3.3 ± 0.4 | 2.8 ± 0.4 |
| 1 | TNBS + Example 18 (5 mg/kg) | 12 | 3.0 ± 0.5 | 2.6 ± 0.3 |
| 1 | TNBS + Example 22 (1 mg/kg) | 12 | 2.8 ± 0.4 | 2.6 ± 0.3 |
| 1 | TNBS + Example 22 (5 mg/kg) | 12 | 3.7 ± 0.4 | 3.8 ± 0.3 |
| 2 | Non-diseased | 6 | 0.0 ± 0.0 | 0.3 ± 0.2 |
| 2 | TNBS + Vehicle | 24 | 3.6 ± 0.4 | 3.9 ± 0.3 |
| 2 | TNBS + Example 47 (1 mg/kg) | 12 | 3.5 ± 0.4 | 2.6 ± 0.3 |
| 2 | TNBS + Example 47 (5 mg/kg) | 12 | 2.8 ± 0.4 | 2.1 ± 0.3 |
| 3 | Non-diseased | 6 | 0.0 ± 0.0 | 0.2 ± 0.2 |
| 3 | TNBS + Vehicle | 24 | 4.0 ± 0.3 | 4.4 ± 0.2 |
| 3 | TNBS + Example 51 (1 mg/kg) | 12 | 2.8 ± 0.5 | 3.1 ± 0.4 |
| 3 | TNBS + Example 51 (5 mg/kg) | 12 | 2.6 ± 0.5 | 2.3 ± 0.4 |
| 3 | TNBS + Example 56 (1 mg/kg) | 12 | 2.3 ± 0.4 | 2.1 ± 0.3 |
| 3 | TNBS + Example 56 (5 mg/kg) | 12 | 3.2 ± 0.4 | 2.4 ± 0.3 |

As illustrated in Table 4 below, the compounds of Examples 13, 44, 47, 51 and 56 were also screened in cellular assay (I), i.e., the ex-vivo human biopsy model described above, where they demonstrated significant anti-inflammatory effects in biopsies from ulcerative colitis (UC) patients. In contrast to healthy volunteers, intestinal mucosal biopsies from UC patients have been shown to spontaneously release pro-inflammatory cytokines in vitro (Onken, J. E. et al., *J Clin Immunol*, 2008, 126(3): 345-352). Thus, the compounds of Examples 13, 44, 47, 51 and 56 significantly inhibited cytokine (IL-1β, IL-6 and IL-8) release compared to the DMSO control when incubated, at 1 μg/mL (and, for the compound of Example 13, also at 0.1 μg/mL (data not shown)), for 24 hours with biopsies from ulcerative colitis patients.

TABLE 4

Summary of results from assays using intestinal mucosa biopsies from the inflamed regions of the colon of various patients suffering from ulcerative colitis (a form of IBD).

| Treatment group | Cytokine release from biopsies of UC patients | | | | | |
|---|---|---|---|---|---|---|
| | n | IL-1β release | n | IL-6 release | n | IL-8 release |
| DMSO control | | 100% | | 100% | | 100% |
| Example 13 (1 μg/ml) | 3 | 10 ± 13 | 5 | 32 ± 64 | 5 | 3 ± 4 |
| Example 44 (1 μg/ml) | 4 | 4 ± 5 | 6 | 25 ± 44 | 6 | 2 ± 2 |
| Example 47 (1 μg/ml) | 2 | 5 ± 6 | 4 | 17 ± 5 | 4 | 26 ± 15 |
| Example 51 (1 μg/ml) | 3 | 4 ± 2 | 3 | 12 ± 15 | 3 | 2 ± 1 |
| Example 56 (1 μg/ml) | 3 | 5 ± 1 | 3 | 19 ± 18 | 3 | 3 ± 3 |

ABBREVIATIONS

AcOH glacial acetic acid
aq aqueous
ATP adenosine-5'-triphosphate
BALF bronchoalveolar lavage fluid
BI NAP 2,2'-bis(diphenylphosphino)-1,1'-binaphthyl
br broad
BSA bovine serum albumin
CatCart® catalytic cartridge
CDI 1,1-carbonyl-diimidazole
COPD chronic obstructive pulmonary disease
d doublet
dba dibenzylideneacetone
DBU 1,8-diazabicyclo[5.4.0]undec-7-ene
DCM dichloromethane
DIAD diisopropyl azodicarboxylate
DIPEA diisopropylethylamine
DMAP 4-dimethylaminopyridine
DMF dimethylformamide
DMSO dimethyl sulfoxide
DPPA diphenylphosphoryl azide d-U937 cells PMA differentiated U-937 cells
(ES+) electrospray ionization, positive mode
Et ethyl
Et₃N triethylamine
EtOAc ethyl acetate
EtOH ethanol
FCS foetal calf serum
FRET fluorescence resonance energy transfer
GSK3α glycogen synthase kinase 3α
HBEC primary human bronchial epithelial cells
HPLC high performance liquid chromatography
hr hour(s)
HRP horseradish peroxidise
HRV human rhinovirus
ICAM-1 inter-cellular adhesion molecule 1
iPrOAc isopropyl acetate
JNK c-Jun N-terminal kinase
LC liquid chromatography
LPS lipopolysaccharide
(M+H)+ protonated molecular ion
MAPK mitogen-activated protein kinase
MAPKAP-K2 mitogen-activated protein kinase-activated protein kinase-2
mCPBA meta-chloroperbenzoic acid
Me methyl
MeCN acetonitrile
MeOH methanol
MHz megahertz
min minute(s)
MMAD mass median aerodynamic diameter
MOI multiplicity of infection
MTT 3-(4,5-dimethylthiazol-2-yl)-2,5-diphenyltetrazolium bromide
MS mass spectrometry
m/z: mass-to-charge ratio
NMP N-methyl pyrrolodinone
NMR nuclear magnetic resonance (spectroscopy)
PBMC peripheral blood mononuclear cell
PBS phosphate buffered saline
Ph phenyl
PHA phytohaemagglutinin
PMA phorbol myristate acetate
p-TsOH 4-methylbenzenesulfonic acid (para-toluenesulfonic acid)
q quartet
rt room temperature
RP HPLC reverse phase high performance liquid chromatography
RSV respiratory syncytical virus
s singlet
sat saturated
SCX solid supported cation exchange (resin)
SDS sodium dodecyl sulfate
S$_N$Ar nucleophilic aromatic substitution
t triplet
TBAF tetrabutylammonium fluoride
TBDMS tert-butyldimethylsilyl
TCID$_{50}$ 50% tissue culture infectious dose
TEA triethylamine
THF tetrahydrofuran
TFA trifluoroacetic acid
TMS-Cl trimethylsilyl chloride
TNFα tumor necrosis factor alpha
Prefixes n-, s-, i-, t- and tert-have their usual meanings: normal, secondary, iso, and tertiary.

What is claimed is:
1. A compound of formula I,

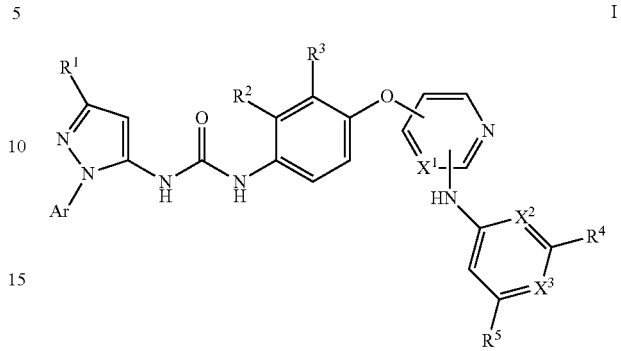

wherein
R$^1$ represents
  C$_{1-6}$ alkyl optionally substituted by one or more substituents selected from the group consisting of halo and hydroxy,
  (C$_{1-2}$ alkylene)$_{0-1}$-C$_{3-8}$ cycloalkyl, which latter group is optionally substituted by one or more substituents selected from the group consisting of C$_{1-3}$ alkyl and C$_{1-3}$ haloalkyl or
  Het$^1$;
Het$^1$ represents a 4- or 5-membered heterocyclic group that is fully saturated, partially unsaturated or fully aromatic, which group contains one or more heteroatoms selected from the group consisting of N, O and S, and which group is optionally substituted by one or more substituents selected from the group consisting of halo, C$_{1-3}$ alkyl and C$_{1-3}$ haloalkyl;
Ar represents phenyl or a 5- or 6-membered heteroaryl group containing one or more heteroatoms selected from the group consisting of N, O and S, wherein Ar is optionally substituted by one to three substituents selected from the group consisting of:
hydroxy, halo,
C$_{1-6}$ alkyl, C$_{1-6}$ alkoxy, which latter two groups are optionally substituted by one or more substituents selected from the group consisting of halo and hydroxy,
NH$_2$, N(H)—C$_{1-6}$ alkyl, N(C$_{1-6}$ alkyl)$_2$,
(C$_{1-6}$ alkylene)$_{0-1}$-Het$^2$ and
(C$_{1-3}$ alkylene)$_{0-1}$-O—(C$_{1-6}$ alkylene)$_{0-1}$-Het$^2$;
Het$^2$ represents a 5- to 10-membered heterocyclic group that is fully saturated, partially unsaturated or fully aromatic, which group is monocyclic or bicyclic and contains one or more heteroatoms selected from the group consisting of N, O and S, and which group is optionally substituted by one or more substituents selected from the group consisting of halo, hydroxy, oxo, C$_{1-3}$ alkyl, C$_{1-3}$ haloalkyl, C$_{1-3}$ alkoxy and C$_{1-3}$ haloalkoxy;
R$^2$ and R$^3$, together with the C-atoms to which they are attached, form a fused phenyl or pyridyl ring, which latter two rings are optionally substituted by one or more substituents selected from the group consisting of C$_{1-3}$ alkyl, C$_{1-3}$ haloalkyl, cyano and halo,
or one of R$^2$ and R$^3$ represents H, halo, cyano, C$_{1-3}$ alkyl or C$_{1-3}$ haloalkyl and the other independently represents halo, cyano, C$_{1-3}$ alkyl or C$_{1-3}$ haloalkyl, or $R^2$ and $R^3$ together combine to form $C_{3-5}$ alkylene or $C_{3-5}$ alkenylene, which latter two groups are optionally substituted by one or more substituents selected from the group consisting of $C_{1-3}$ alkyl, $C_{1-3}$ haloalkyl, cyano and halo;

$X^1$ represents N or CH;

$X^2$ and $X^3$ both represent $C(R^X)$ or one of $X^2$ and $X^3$ represents N and the other represents $C(R^X)$;

$R^X$ represents H, halo, cyano, $C_{1-3}$ alkyl or $C_{1-3}$ alkoxy, which latter two groups are optionally substituted by one or more halo atoms;

$R^4$ represents $-Q^1$-$[CH_2(CH_2)_{0-1}CH_2-O]_{1-12}$-$C_2(CH_2)_{0-1}CH_2$-$R^{6a}$, —$S(O)_nR^{6b}$, -$Q^2$-$CH_2$—$[C_{1-5}$ alkylene$]$-$N(R^{6c})R^{6d}$ —$OS(O)_2R^{6e}$, —$C\equiv C$—$R^{6f}$, —$N=S(O)R^{6g}R^{6h}$ or

—$OC(O)NH_2$;

$R^5$ represents $C_{1-3}$ alkoxy or $C_{1-3}$ alkyl, which latter two groups are optionally substituted by one or more halo atoms, or $R^5$ represents H, $NH_2$, $N(H)$—$C_{1-6}$ alkyl, $N(C_{1-6}$ alkyl$)_2$, cyano, halo or $C_{2-3}$ alkynyl;

$R^{6a}$ represents $OR^{7a}$ or $N(R^{7b})R^{7c}$;

$R^{6b}$ represents $CH_2(CH_2)_{0-1}CH_2$—$OR^{7d}$ or $C_{3-8}$ cycloalkyl, which latter group is optionally substituted by one or more $C_{1-3}$ alkyl substituents;

$R^{7a}$ to $R^{7d}$ independently represent H or $C_{1-4}$ alkyl optionally substituted by one or more halo atoms, or $R^{7b}$ and $R^{7c}$, together with the N-atom to which they are attached, form a 4- to 7-membered heterocyclic group that is fully saturated, partially unsaturated or fully aromatic and which heterocyclic group contains one N atom (the atom to which $R^{7b}$ and $R^{7c}$ are attached) and, optionally, one or more further heteroatoms selected from the group consisting of O, S and N, and which heterocyclic group is optionally substituted by one or more substituents selected from the group consisting of halo, hydroxy, oxo, $C_{1-4}$ alkyl and $C_{1-4}$ alkoxy;

$R^{6c}$ and $R^{6d}$, together with the N-atom to which they are attached, form a 4- to 7-membered heterocyclic group that is fully saturated, partially unsaturated or fully aromatic and which heterocyclic group contains one N atom (the atom to which $R^{6c}$ and $R^{6d}$ are attached) and, optionally, one or more further heteroatoms selected from the group consisting of O, S and N, and which heterocyclic group is optionally substituted by one or more substituents selected from the group consisting of halo, hydroxy, oxo, $C_{1-4}$ alkyl and $C_{1-4}$ alkoxy;

$R^{6e}$, $R^{6f}$, $R^{6g}$, and $R^{6h}$ independently represent $C_{1-4}$ alkyl optionally substituted by one or more halo atoms, or $R^{6f}$ represents H;

$Q^1$ and $Q^2$ independently represent O, $S(O)_p$ or $N(R^{6i})$;

$R^{6i}$ represents H or $C_{1-4}$ alkyl; and n and p independently represent 0, 1 or 2, or a pharmaceutically acceptable salt thereof.

2. A compound as claimed in claim 1 that is a compound of formula Ia or Ib,

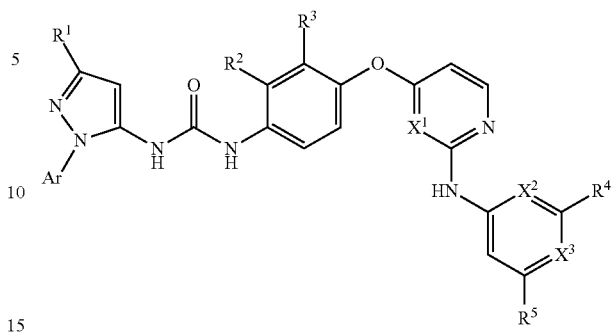

Ia

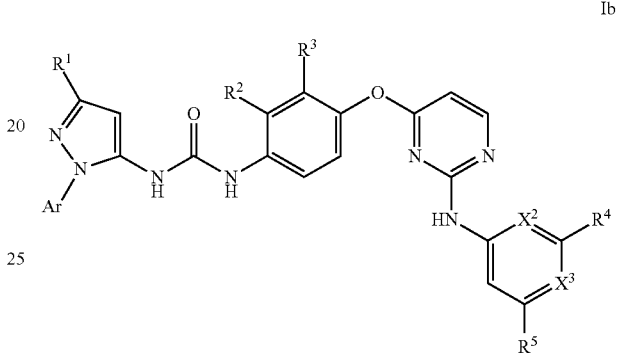

Ib or a pharmaceutically acceptable salt thereof, wherein $R^1$ to $R^5$, Ar and $X^1$ to $X^3$ are as defined in claim 1.

3. A compound as claimed in claim 1, wherein $R^2$ and $R^3$ either independently represent Cl or F, or together with the C-atoms to which they are attached, form a fused phenyl or pyridyl ring, which latter two rings are optionally substituted by one or more substituents selected from the group consisting of $C_{1-3}$ alkyl, $C_{1-3}$ haloalkyl, cyano and halo.

4. A compound as claimed in claim 1, wherein $R^4$ represents

-$Q^1$-$[CH_2CH_2$—$O]_{1-10}$—$CH_2CH_2$—$R^{6a}$,

—$S(O)CH_2CH_2$—$OR^7d$,

—$S(O)_nC_{3-6}$ cycloalkyl,

-$Q_2$-$CH_2(CH_2)_{0-1}CH_2$—$N(R^{6c})R^{6d}$,

—$OS(O)_2R^{6e}$,

—$C\equiv C$—$R^{6f}$,

—$N=S(O)(CH_3)_2$ or

—$OC(O)NH_2$.

5. A compound as claimed in claim 1, wherein $R^5$ represents H, cyano, chloro, fluoro, $C_{2-3}$ alkynyl, $C_{1-2}$ alkyl or $C_{1-2}$ alkoxy, which latter two groups are optionally substituted by one or more fluoro atoms.

6. A compound as claimed in claim 1, wherein $Q^1$ and $Q^2$ independently represent S or O.

7. A compound as claimed in claim 1, wherein $R^{6c}$ and $R^{6d}$, together with the N-atom to which they are attached, form a 5- to 7-membered heterocyclic group that is fully saturated, which heterocyclic group contains one N atom (the atom to which $R^{6c}$ and $R^{6d}$ are attached) and, optionally, one further heteroatom selected from the group consisting of O, S and N, and which heterocyclic group is optionally substituted by one or more substituents selected from the group consisting of halo, hydroxy, oxo, $C_{1-4}$ alkyl and $C_{1-4}$ alkoxy.

8. A compound as claimed in claim 1 that is a compound of formula Ic,

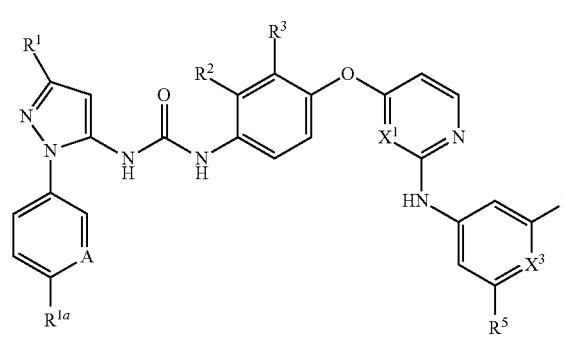

Ic or a pharmaceutically acceptable salt thereof, wherein:
$R^{1a}$ represents
halo,
$C_{1-3}$ alkyl, $C_{1-3}$ alkoxy, which latter two groups are optionally substituted by one or more halo atoms,
$N(C_{1-3}alkyl)_2$ (e.g. $N(CH_3)_2$),
$C_{1-3}$ alkylene-$Het^2$ or
—O—$CH_2$—($C_{1-2}$ alkylene)-$Het^2$
A represents CH or N; and
$R^1$ to $R^5$, $X^1$, $X^3$, $R^X$ and $Het^2$ are as defined in claim 1.

9. A compound as claimed in claim 1, wherein $R^1$ represents tert-butyl.

10. A compound as claimed in claim 1, wherein, when A represents CH or N, $R^{1a}$ represents methyl or methoxy or, when A represents CH, $R^{1a}$ alternatively represents dimethylamino.

11. A compound as claimed in claim 1, wherein $R^2$ and $R^3$ either both represent Cl or, together with the C-atoms to which they are attached, form a fused phenyl ring.

12. A compound as claimed in claim 1, wherein:
$R^4$ represents
—O—$[CH_2CH_2—O]_{2-8}$—$R^{7a}$,
—S—$CH_2CH_2$—OH,
—$S(O)_2$-cyclopropyl,
-$Q^2$-$CH_2(CH_2)_{0-1}CH_2$-(morpholin-1-yl),
—$OS(O)_2CH_3$,
—S—$[CH_2CH_2—O]_{2-8}$—$CH_3$ or
—C≡C—H; and
$R^{7a}$ represents H or $CH_3$.

13. A compound as claimed in claim 1, wherein $R^5$ represents H, ethynyl, methyl, methoxy, trifluoromethyl or trifluoromethoxy.

14. A compound as claimed in claim 1, wherein:
$R^5$ represents methyl, methoxy, trifluoromethyl or trifluoromethoxy or,
when $R^4$ represents -$Q^1$-$[CH_2(CH_2)_{0-1}CH_2$—O$]_{1-12}$—$CH_2(CH_2)_{0-1}CH_2$—$R^{6a}$, —$OS(O)_2R^{6e}$ or —C≡C—$R^{6f}$ (e.g. when $R^4$ represents —$OS(O)_2R^{6e}$), then $R^5$ may alternatively represent H.

15. A compound as claimed in claim 1, wherein $X^3$ represents N, C(H) or C(Cl).

16. A compound as claimed in claim 1, which is a compound selected from the group consisting of:
1-(3-(tert-butyl)-1-(6-methoxypyridin-3-yl)-1H-pyrazol-5-yl)-3-(4-((2-((3-ethynylphenyl)-amino)pyrimidin-4-yl)oxy)naphthalen-1-yl)urea;

S,S-dimethyl-N-(4-((4-((4-(3-(3-(tert-butyl)-1-(6-methoxypyridin-3-yl)-1H-pyrazol-5-yl)-ureido)naphthalen-1-yl)oxy)pyrimidin-2-yl)amino)phenyl sulfoximine;
3-((4-((4-(3-(3-(tert-butyl)-1-(6-methoxypyridin-3-yl)-1H-pyrazol-5-yl)ureido)naphthalen-1-yl)oxy)pyrimidin-2-yl)amino)phenyl methanesulfonate;
1-(3-(tert-butyl)-1-(6-methoxypyridin-3-yl)-1H-pyrazol-5-yl)-3-(4-((2-((3-(2-(2-(2-methoxy-ethoxy)ethoxy)ethoxy)phenyl)amino)pyrimidin-4-yl)oxy)naphthalen-1-yl)urea;
3-((4-((4-(3-(3-(tert-butyl)-1-(6-methoxypyridin-3-yl)-1H-pyrazol-5-yl)ureido)naphthalen-1-yl)oxy)pyrimidin-2-yl)amino)phenyl carbamate;
1-(3-(tert-butyl)-1-(6-methoxypyridin-3-yl)-1H-pyrazol-5-yl)-3-(4-((2-((3-((2-hydroxyethyl)-thio)phenyl)amino)pyrimidin-4-yl)oxy)naphthalen-1-yl)urea;
1-(3-(tert-butyl)-1-(6-methoxypyridin-3-yl)-1H-pyrazol-5-yl)-3-(4-((2-((3-(cyclopropylsulfinyl)phenyl)amino)pyrimidin-4-yl)oxy)naphthalen-1-yl)urea;
1-(3-(tert-butyl)-1-(6-methoxypyridin-3-yl)-1H-pyrazol-5-yl)-3-(4-((2-((3-(cyclopropylsulfonyl) phenyl)amino)pyrimidin-4-yl)oxy)naphthalen-1-yl)urea;
1-(3-isopropyl-1-(p-tolyl)-1H-pyrazol-5-yl)-3-(4-((2-((3-(2-(2-methoxyethoxy)ethoxy)-ethoxy)phenyl)amino)pyrimidin-4-yl)oxy)naphthalen-1-yl)urea;
1-(4-((2-((3-ethynylphenyl)amino)pyrimidin-4-yl)oxy)naphthalen-1-yl)-3-(3-isopropyl-1-(p-tolyl)-1H-pyrazol-5-yl)urea;
3-((4-((4-(3-(3-isopropyl-1-(p-tolyl)-1H-pyrazol-5-yl)ureido)naphthalen-1-yl)oxy)pyrimidin-2-yl)amino)phenyl methanesulfonate;
3-((4-((4-(3-(3-isopropyl-1-(p-tolyl)-1H-pyrazol-5-yl)ureido)naphthalen-1-yl)oxy)pyrimidin-2-yl)amino)-5-methoxyphenyl methanesulfonate;
1-(3-isopropyl-1-(p-tolyl)-1H-pyrazol-5-yl)-3-(4-((2-((3-methoxy-5-(2-(2-(2-methoxy-ethoxy)ethoxy)ethoxy)phenyl)amino)pyrimidin-4-yl)oxy)naphthalen-1-yl)urea;
3-((4-((4-(3-(3-isopropyl-1-(p-tolyl)-1H-pyrazol-5-yl)ureido)naphthalen-1-yl)oxy)pyrimidin-2-yl)amino)pheny-S,S-dimethyl-N-phenyl sulfoximine;
1-(4-((2-((3-ethynyl-5-methoxyphenyl)amino)pyrimidin-4-yl)oxy)naphthalen-1-yl)-3-(3-isopropyl-1-(p-tolyl)-1H-pyrazol-5-yl)urea;
3-(5-methoxy((4-((4-(3-(3-isopropyl-1-(p-tolyl)-1H-pyrazol-5-yl)ureido)naphthalen-1-yl)oxy)pyrimidin-2-yl)amino))phenyl-S,S-dimethyl-N-phenyl sulfoximine;
1-(3-isopropyl-1-(p-tolyl)-1H-pyrazol-5-yl)-3-(4-((2-((3-methoxy-5-(2-morpholinoethoxy)-phenyl)amino)pyrimidin-4-yl)oxy)naphthalen-1-yl)urea;
1-(4-((2-((3-(cyclopropylsulfonyl)-5-methoxyphenyl)amino)pyrimidin-4-yl)oxy)naphthalen-1-yl)-3-(3-isopropyl-1-(p-tolyl)-1H-pyrazol-5-yl)urea;
1-(4-((2-((3-(2-(2-(2-hydroxyethoxy)ethoxy)ethoxy)phenyl)amino)pyrimidin-4-yl)oxy)-naphthalen-1-yl)-3-(3-isopropyl-1-(p-tolyl)-1H-pyrazol-5-yl)urea;
1-(4-((2-((3-(2-(2-(2-hydroxyethoxy)ethoxy)ethoxy)-5-methoxyphenyl)amino)pyrimidin-4-yl)oxy)naphthalen-1-yl)-3-(3-isopropyl-1-(p-tolyl)-1H-pyrazol-5-yl)urea;
1-(2,3-dichloro-4-((2-((3-methoxy-5-(2-morpholinoethoxy)phenyl)amino)pyrimidin-4-yl)oxy)phenyl)-3-(3-isopropyl-1-(p-tolyl)-1H-pyrazol-5-yl)urea;
1-(4-((2-((3-((2-hydroxyethyl)thio)-5-methoxyphenyl)amino)pyrimidin-4-yl)oxy)-naphthalen-1-yl)-3-(3-isopropyl-1-(p-tolyl)-1H-pyrazol-5-yl)urea;

1-(2,3-dichloro-4-((2-((3-(cyclopropylsulfonyl)-5-methoxyphenyl)amino)pyrimidin-4-yl)oxy)phenyl)-3-(3-isopropyl-1-(p-tolyl)-1H-pyrazol-5-yl)urea;

1-(2,3-dichloro-4-((2-((3-(cyclopropylsulfonyl)phenyl)amino)pyrimidin-4-yl)oxy)phenyl)-3-(3-isopropyl-1-(p-tolyl)-1H-pyrazol-5-yl)urea;

1-(2,3-difluoro-4-((2-((3-methoxy-5-(2-morpholinoethoxy)phenyl)amino)pyrimidin-4-yl)oxy)phenyl)-3-(3-isopropyl-1-(p-tolyl)-1H-pyrazol-5-yl)urea;

S,S-dimethyl-N-(3-((4-(2,3-dichloro-4-(3-(3-isopropyl-1-(p-tolyl)-1H-pyrazol-5-yl)ureido) phenoxy)pyrimidin-2-yl)amino)-5-methoxyphenyl)-sulfoximine;

1-(3-isopropyl-1-(p-tolyl)-1H-pyrazol-5-yl)-3-(5-((2-((3-methoxy-5-(2-(2-(2-methoxy-ethoxy)ethoxy)ethoxy)phenyl)amino)pyrimidin-4-yl)oxy)quinolin-8-yl)urea;

1-(3-isopropyl-1-(p-tolyl)-1H-pyrazol-5-yl)-3-(5-((2-((3-methoxy-5-(2-morpholinoethoxy)-phenyl)amino)pyrimidin-4-yl)oxy)quinolin-8-yl)urea;

1-(4-((2-((3-(2,5,8,11-tetraoxatridecan-13-yloxy)-5-methoxyphenyl)amino)pyrimidin-4-yl)oxy)naphthalen-1-yl)-3-(3-isopropyl-1-(p-tolyl)-1H-pyrazol-5-yl)urea;

1-(4-((2-((3-(2,5,8,11,14-pentaoxahexadecan-16-yloxy)-5-methoxyphenyl)amino)-pyrimidin-4-yl)oxy)naphthalen-1-yl)-3-(3-isopropyl-1-(p-tolyl)-1H-pyrazol-5-yl)urea;

1-(3-isopropyl-1-(p-tolyl)-1H-pyrazol-5-yl)-3-(4-((2-((3-methoxy-5-((2-(2-(2-methoxy-ethoxy)ethoxy)ethyl)thio)phenyl)amino)pyrimidin-4-yl)oxy)naphthalen-1-yl)urea;

1-(4-((2-((3-(2,5,8,11,14,17,20-heptaoxadocosan-22-yloxy)-5-methoxyphenyl)amino)-pyrimidin-4-yl)oxy)naphthalen-1-yl)-3-(3-isopropyl-1-(p-tolyl)-1H-pyrazol-5-yl)urea; 1-(3-isopropyl-1-(p-tolyl)-1H-pyrazol-5-yl)-3-(4-((2-((3-(2-(2-(2-methoxyethoxy)ethoxy)-ethoxy)-5-(trifluoromethoxy)phenyl)amino)pyrimidin-4-yl)oxy)naphthalen-1-yl)urea;

1-(3-isopropyl-1-(p-tolyl)-1H-pyrazol-5-yl)-3-(4-((2-((3-(2-(2-(2-methoxyethoxy)ethoxy)-ethoxy)-5-(trifluoromethyl)phenyl)amino)pyrimidin-4-yl)oxy)naphthalen-1-yl)urea;

1-(2,3-dichloro-4-((2-((3-methoxy-5-(2-(2-(2-methoxy-ethoxy)ethoxy)ethoxy)phenyl)-amino)-pyrimidin-4-yl)oxy)phenyl)-3-(3-isopropyl-1-(p-tolyl)-1H-pyrazol-5-yl)urea;

1-(3-isopropyl-1-(p-tolyl)-1H-pyrazol-5-yl)-3-(4-((2-((3-methoxy-5-((2-(2-(2-methoxy-ethoxy)ethoxy)ethyl)sulfonyl)phenyl)amino)pyrimidin-4-yl)oxy)naphthalen-1-yl)urea, 1-(3-(tert-Butyl)-1-(p-tolyl)-1H-pyrazol-5-yl)-3-(4-((2-((3-methoxy-5-(2-(2-(2-methoxy-ethoxy)ethoxy)ethoxy)phenyl)amino)pyrimidin-4-yl)oxy)naphthalen-1-yl)urea;

1-(3-(tert-Butyl)-1-(6-methoxypyridin-3-yl)-1H-pyrazol-5-yl)-3-(4-((2-((3-methoxy-5-(2-(2-(2-methoxyethoxy)ethoxy)ethoxy)phenyl)amino)pyrimidin-4-yl)oxy)naphthalen-1-yl)urea;

1-(4-((2-((3-Methoxy-5-(2-(2-(2-methoxyethoxy)ethoxy)ethoxy)phenyl)amino)pyrimidin-4-yl)oxy)naphthalen-1-yl)-3-(3-(perfluoroethyl)-1-(p-tolyl)-1H-pyrazol-5-yl)urea;

1-(4-((2-((3-Methoxy-5-(2-(2-(2-methoxyethoxy)ethoxy)ethoxy)phenyl)amino)pyrimidin-4-yl)oxy)naphthalen-1-yl)-3-(1-(p-tolyl)-3-(1,1,1-trifluoro-2-methylpropan-2-yl)-1H-pyrazol-5-yl)urea;

1-(3-(tert-Butyl)-1-(p-tolyl)-1H-pyrazol-5-yl)-3-(4-((2-((3-methoxy-5-((2-morpholinoethyl)-thio)phenyl)amino)pyrimidin-4-yl)oxy)naphthalen-1-yl)urea;

1-(3-(tert-Butyl)-1-(p-tolyl)-1H-pyrazol-5-yl)-3-(4-((2-((3-methoxy-5-((3-morpholinopropyl)-thio)phenyl)amino)pyrimidin-4-yl)oxy)naphthalen-1-yl)urea;

1-(3-(tert-Butyl)-1-(p-tolyl)-1H-pyrazol-5-yl)-3-(4-((2-((3-methoxy-5-((3-morpholinopropyl)-sulfonyl)phenyl)amino)pyrimidin-4-yl)oxy)naphthalen-1-yl)urea;

1-(3-(tert-Butyl)-1-(4-methoxyphenyl)-1H-pyrazol-5-yl)-3-(4-((2-((3-methoxy-5-(2-(2-(2-methoxyethoxy)ethoxy)ethoxy)phenyl)amino)pyrimidin-4-yl)oxy)naphthalen-1-yl)urea;

1-(3-(tert-Butyl)-1-(p-tolyl)-1H-pyrazol-5-yl)-3-(4-((2-((3-methoxy-5-(2-morpholinoethoxy)-phenyl)amino)pyrimidin-4-yl)oxy)naphthalen-1-yl)urea;

1-(3-(tert-Butyl)-1-(p-tolyl)-1H-pyrazol-5-yl)-3-(4-((2-((3-(cyclopropylsulfonyl)phenyl)-amino)pyrimidin-4-yl)oxy)naphthalen-1-yl)urea;

1-(3-(tert-Butyl)-1-(p-tolyl)-1H-pyrazol-5-yl)-3-(4-((2-((3-(cyclopropylsulfonyl)-5-methoxy-phenyl)amino)pyrimidin-4-yl)oxy)naphthalen-1-yl)urea;

1-(3-(tert-Butyl)-1-(p-tolyl)-1H-pyrazol-5-yl)-3-(4-((2-((3-((3-hydroxypropyl)thio)-5-methoxyphenyl)amino)pyrimidin-4-yl)oxy)naphthalen-1-yl)urea;

1-(3-(tert-Butyl)-1-(p-tolyl)-1H-pyrazol-5-yl)-3-(4-((2-((3-methoxy-5-(3-morpholino-propoxy)phenyl)amino)pyrimidin-4-yl)oxy)naphthalen-1-yl)urea;

1-(3-(tert-Butyl)-1-(p-tolyl)-1H-pyrazol-5-yl)-3-(4-((2-((3-fluoro-5-(2-(2-(2-methoxyethoxy)-ethoxy)ethoxy)phenyl)amino)pyrimidin-4-yl)oxy)naphthalen-1-yl)urea 1-(4-((2-((3-(2,5,8,11,14,17,20-Heptaoxadocosan-22-yloxy)-5-methoxyphenyl)amino)pyrimidin-4-yl)oxy)naphthalen-1-yl)-3-(3-(tert-butyl)-1-(p-tolyl)-1H-pyrazol-5-yl)urea;

1-(3-(tert-Butyl)-1-(p-tolyl)-1H-pyrazol-5-yl)-3-(4-((2-((3-cyano-5-(2-(2-(2-methoxyethoxy)-ethoxy)ethoxy)phenyl)amino)pyrimidin-4-yl)oxy)naphthalen-1-yl)urea;

1-(3-(tert-Butyl)-1-(p-tolyl)-1H-pyrazol-5-yl)-3-(2,3-dichloro-4-((2-((3-methoxy-5-(2-(2-(2-methoxyethoxy)ethoxy)ethoxy)phenyl)amino)pyrimidin-4-yl)oxy)phenyl)urea;

1-(3-(tert-Butyl)-1-(p-tolyl)-1H-pyrazol-5-yl)-3-(4-((2-((3-ethynyl-5-(2-(2-(2-methoxyethoxy)ethoxy)ethoxy)phenyl)amino)pyrimidin-4-yl)oxy)naphthalen-1-yl)urea;

1-(3-(tert-Butyl)-1-(p-tolyl)-1H-pyrazol-5-yl)-3-(4-((2-((3-((2-hydroxyethyl)thio)-5-methoxyphenyl)amino)pyrimidin-4-yl)oxy)naphthalen-1-yl)urea;

1-(3-(tert-Butyl)-1-(p-tolyl)-1H-pyrazol-5-yl)-3-(4-((2-((3-methoxy-5-(2-(2-(2-methoxyethoxy)ethoxy)ethoxy)phenyl)amino)pyridin-4-yl)oxy)naphthalen-1-yl)urea;

1-(3-(tert-Butyl)-1-(p-tolyl)-1H-pyrazol-5-yl)-3-(4-((2-((3-(2-(2-(2-(dimethylamino)ethoxy)-ethoxy)ethoxy)-5-methoxyphenyl)amino)pyrimidin-4-yl)oxy)naphthalen-1-yl)urea;

1-(3-(tert-Butyl)-1-(p-tolyl)-1H-pyrazol-5-yl)-3-(4-((2-((3-methoxy-5-(2-(2-(2-morpholinoethoxy)ethoxy)ethoxy)phenyl)amino)pyrimidin-4-yl)oxy)naphthalen-1-yl)urea;

1-(3-(tert-Butyl)-1-(p-tolyl)-1H-pyrazol-5-yl)-3-(2,3-dichloro-4-((2-((3-methoxy-5-(2-morpholinoethoxy)phenyl)amino)pyrimidin-4-yl)oxy)phenyl)urea;

1-(3-(tert-Butyl)-1-(p-tolyl)-1H-pyrazol-5-yl)-3-(4-((2-((3-methoxy-5-(2-(2-methoxyethoxy)ethoxy)phenyl)amino)pyrimidin-4-yl)oxy)naphthalen-1-yl)urea;

1-(3-(tert-Butyl)-1-(6-methoxypyridin-3-yl)-1H-pyrazol-5-yl)-3-(4-((2-((3-(cyclopropylsulfonyl)-5-methoxyphenyl)amino)pyrimidin-4-yl)oxy)naphthalen-1-yl)urea;

1-(3-(tert-Butyl)-1-(p-tolyl)-1H-pyrazol-5-yl)-3-(4-((2-((3-(2-(2-(2-hydroxyethoxy)ethoxy)ethoxy)-5-methoxyphenyl)amino)pyrimidin-4-yl)oxy)naphthalen-1-yl)urea;

1-(3-(tert-Butyl)-1-(4-(dimethylamino)phenyl)-1H-pyrazol-5-yl)-3-(4-((2-((3-methoxy-5-(2-(2-(2-methoxyethoxy)ethoxy)ethoxy)phenyl)amino)pyrimidin-4-yl)oxy)naphthalen-1-yl)urea;

1-(3-(tert-Butyl)-1-(p-tolyl)-1H-pyrazol-5-yl)-3-(4-((2-((3-chloro-5-(2-(2-(2-methoxyethoxy)-ethoxy)ethoxy)phenyl)amino)pyrimidin-4-yl)oxy)naphthalen-1-yl)urea;

1-(3-(tert-Butyl)-1-(p-tolyl)-1H-pyrazol-5-yl)-3-(2,3-dichloro-4-((2-((3-methoxy-5-(3-morpholinopropoxy)phenyl)amino)pyrimidin-4-yl)oxy)phenyl)urea;

1-(3-(tert-Butyl)-1-(p-tolyl)-1H-pyrazol-5-yl)-3-(4-((2-((3-(dimethylamino)-5-(2-(2-(2-methoxyethoxy)ethoxy)ethoxy)phenyl)amino)pyrimidin-4-yl)oxy)naphthalen-1-yl)urea;

1-(3-(tert-Butyl)-1-(p-tolyl)-1H-pyrazol-5-yl)-3-(4-((2-((3-methoxy-5-((2-(2-(2-methoxy ethoxy)ethoxy)ethyl)(methyl)amino)phenyl)amino)pyrimidin-4-yl)oxy)naphthalen-1-yl)urea;

1-(3-(tert-Butyl)-1-(p-tolyl)-1H-pyrazol-5-yl)-3-(2,3-dichloro-4-((2-((3-(cyclopropylsulfonyl)-5-methoxyphenyl)amino)pyrimidin-4-yl)oxy)phenyl)urea;

1-(3-(tert-Butyl)-1-(p-tolyl)-1H-pyrazol-5-yl)-3-(4-((2-((2-methoxy-6-(2-(2-(2-methoxyethoxy)ethoxy)ethoxy)pyridin-4-yl)amino)pyrimidin-4-yl)oxy)naphthalen-1-yl)urea;

1-(3-(tert-Butyl)-1-(4-methoxyphenyl)-1H-pyrazol-5-yl)-3-(4-((2-((3-(cyclopropylsulfonyl)-5-methoxyphenyl)amino)pyrimidin-4-yl)oxy)naphthalen-1-yl)urea;

1-(3-(tert-Butyl)-1-(p-tolyl)-1H-pyrazol-5-yl)-3-(2,3-dichloro-4-((2-((3-(2-(2-(2-hydroxyethoxy)ethoxy)-5-methoxyphenyl)amino)pyrimidin-4-yl)oxy)phenyl)urea; and 1-(3-(tert-Butyl)-1-(p-tolyl)-1H-pyrazol-5-yl)-3-(4-((2-((4-chloro-3-methoxy-5-(2-(2-(2-methoxyethoxy)ethoxy)ethoxy)phenyl)amino)pyrimidin-4-yl)oxy)naphthalen-1-yl)urea, and a pharmaceutically acceptable salt thereof.

17. A compound as claimed in claim 1, which is a compound selected from the group consisting of:

1-(3-(tert-Butyl)-1-(4-methoxyphenyl)-1H-pyrazol-5-yl)-3-(4-((2-((3-methoxy-5-(2-(2-(2-methoxyethoxy)ethoxy)phenyl)amino)pyrimidin-4-yl)oxy)naphthalen-1-yl)urea;

1-(3-(tert-Butyl)-1-(p-tolyl)-1H-pyrazol-5-yl)-3-(4-((2-((3-(cyclopropylsulfonyl)-5-methoxy-phenyl)amino)pyrimidin-4-yl)oxy)naphthalen-1-yl)urea;

1-(4-((2-((3-(2,5,8,11,14,17,20-Heptaoxadocosan-22-yloxy)-5-methoxyphenyl)amino)pyrimidin-4-yl)oxy)naphthalen-1-yl)-3-(3-(tert-butyl)-1-(p-tolyl)-1H-pyrazol-5-yl)urea; and 1-(3-(tert-Butyl)-1-(p-tolyl)-1H-pyrazol-5-yl)-3-(4-((2-((3-methoxy-5-(2-(2-(2-methoxyethoxy)ethoxy)ethoxy)phenyl)amino)pyridin-4-yl)oxy)naphthalen-1-yl)urea, and a pharmaceutically acceptable salt thereof.

18. A pharmaceutical formulation comprising a compound as defined in claim 1, or pharmaceutically acceptable salt thereof, in admixture with a pharmaceutically acceptable adjuvant, diluent or carrier.

19. A combination product comprising
(A) a compound as defined in claim 1, or pharmaceutically acceptable salt thereof, and
(B) another therapeutic agent,
wherein each of components (A) and (B) is formulated in admixture with a pharmaceutically-acceptable adjuvant, diluent or carrier.

20. A method of treating inflammation, said method comprising administering to a subject:
an effective amount of a compound as defined in claim 1, or pharmaceutically acceptable salt thereof,
a pharmaceutical formulation comprising a compound as defined in claim 1, or pharmaceutically acceptable salt thereof, in admixture with a pharmaceutically acceptable adjuvant, diluent or carrier, or
a combination product comprising:
(A) a compound as defined in claim 1, or pharmaceutically acceptable salt thereof, and
(B) another therapeutic agent,
wherein each of components (A) and (B) is formulated in admixture with a pharmaceutically-acceptable adjuvant, diluent or carrier,
wherein the inflammation is a component in a disease is selected from the group consisting of COPD, asthma, Crohn's disease and ulcerative colitis.

21. A process for the preparation of a compound of formula I which process comprises:
(a) reaction of a compound of formula II,

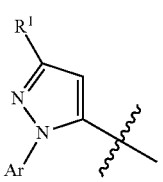

with a compound of formula III, wherein one of $Z^1$ and $Z^2$ is a structural fragment of formula IV and the other of $Z^1$ and $Z^2$ is a structural fragment of formula V

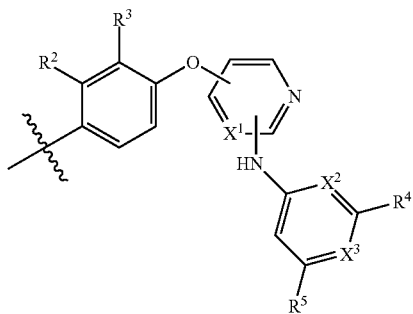

where $R^1$ to $R^5$, Ar and $X^1$ to $X^3$ are as defined in claim 1;

(b) reaction of a compound of formula IIa,

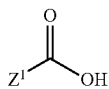

wherein $Z^1$ is as defined above, with a suitable azide-forming agent, which reaction is followed, without isolation, by thermal rearrangement of the intermediate acyl azide (of formula $Z^1$—C(O)—$N_3$) to provide, in situ, a compound of formula II, which compound is then reacted with a compound of formula III as defined above;

(c) reaction of a compound of formula IIb,

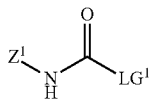

wherein $LG^1$ represents a leaving group and $Z^1$ is as defined above, with a compound of formula III, as defined above;

(d) reaction of a compound of formula VI,

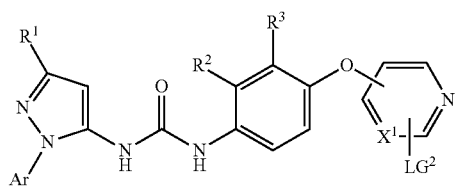

wherein $LG^2$ represents a leaving group and $R^1$ to $R^3$, Ar and $X^1$ are as defined in claim 1, with a compound of formula VII,

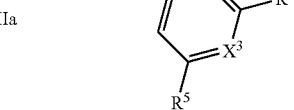

wherein $R^4$, $R^5$, $X^2$ and $X^3$ are as defined in claim 1;

(e) for compounds of formula I in which $R^4$ represents
—S(O)$_{1-2}$—[CH$_2$(CH$_2$)$_{0-1}$CH$_2$—O]$_{1-12}$—CH$_2$(CH$_2$)$_{0-1}$CH$_2$—R$^{6a}$,
—S(O)$_{1-2}$R$^{6b}$,
—S(O)$_{1-2}$—CH$_2$—[C$_{1-5}$ alkylene]-N(R$^{6c}$)R$^{6a}$,
oxidation of a corresponding compound of formula I in which, respectively, $R^4$ represents
—S—[CH$_2$(CH$_2$)$_{0-1}$CH$_2$—O]$_{1-12}$—CH$_2$(CH$_2$)$_{0-1}$CH$_2$—R$^{6a}$,
—S—R$^{6b}$,
—S—CH$_2$—[C$_{1-5}$ alkylene]-N(R$^{6c}$)R$^{6d}$,
wherein $R^{6a}$ to $R^{6d}$ are as defined in claim 1; or (f) deprotection of an protected derivative of a compound of formula I, wherein the protected derivative bears a protecting group on an O- or N-atom of the compound of formula I.

* * * * *